(12) United States Patent
Schwarz et al.

(10) Patent No.: US 11,484,727 B2
(45) Date of Patent: Nov. 1, 2022

(54) AESTHETIC METHOD OF BIOLOGICAL STRUCTURE TREATMENT BY MAGNETIC FIELD

(71) Applicant: BTL Medical Solutions A.S., Prague (CZ)

(72) Inventors: Tomas Schwarz, Prague (CZ); Ondra Prouza, Ricany u Prahy (CZ)

(73) Assignee: BTL Medical Solutions A.S., Prague (CZ)

( * ) Notice: Subject to any disclaimer, the term of this patent is extended or adjusted under 35 U.S.C. 154(b) by 0 days.

(21) Appl. No.: 17/090,560

(22) Filed: Nov. 5, 2020

(65) Prior Publication Data
US 2021/0052913 A1 Feb. 25, 2021

Related U.S. Application Data

(63) Continuation of application No. 16/827,330, filed on Mar. 23, 2020, which is a continuation of application
(Continued)

(51) Int. Cl.
*A61N 2/02* (2006.01)
*A61N 2/00* (2006.01)
(Continued)

(52) U.S. Cl.
CPC .............. *A61N 2/02* (2013.01); *A61F 7/007* (2013.01); *A61F 7/0053* (2013.01); *A61N 2/004* (2013.01);
(Continued)

(58) Field of Classification Search
CPC .......... A61N 2/02; A61N 2/004; A61N 2/006; A61N 5/0616; A61N 2007/0034;
(Continued)

(56) References Cited

U.S. PATENT DOCUMENTS

| 1,973,387 A | 9/1934 | Neymann et al. |
| 2,021,676 A | 11/1935 | Wood et al. |

(Continued)

FOREIGN PATENT DOCUMENTS

| AU | 747678 B2 | 5/2002 |
| AU | 2011265424 B2 | 7/2014 |

(Continued)

OTHER PUBLICATIONS

US 10,398,895 B2, 09/2019, Schwarz (withdrawn)
(Continued)

*Primary Examiner* — Tigist S Demie
(74) *Attorney, Agent, or Firm* — Sterne, Kessler, Goldstein & Fox P.L.L.C.

(57) ABSTRACT

In methods for treating a patient, a time varying magnetic field is applied to a patient's body and causes a muscle contraction. The time-varying magnetic field may be monophasic, biphasic, polyphasic and/or static. The method may reduce adipose tissue, improve metabolism, blood and/or lymph circulation. The method may use combinations of treatments to enhance the visual appearance of the patient.

30 Claims, 27 Drawing Sheets

Related U.S. Application Data

No. 15/601,719, filed on May 22, 2017, now Pat. No. 10,596,386.

(60) Provisional application No. 62/440,905, filed on Dec. 30, 2016, provisional application No. 62/440,922, filed on Dec. 30, 2016, provisional application No. 62/357,679, filed on Jul. 1, 2016.

(51) Int. Cl.
*A61F 7/00* (2006.01)
*A61F 7/02* (2006.01)

(52) U.S. Cl.
CPC .............. *A61F 2007/0056* (2013.01); *A61F 2007/0075* (2013.01); *A61F 2007/029* (2013.01)

(58) Field of Classification Search
CPC .......... A61N 5/062; A61N 7/00; A61N 2/002; A61N 2005/0644; A61N 2005/0661; A61N 2005/067; A61N 2007/0039; A61N 1/40; A61N 2/008; A61N 2005/0659; A61N 2007/0008; A61N 1/06; A61N 5/0625; A61N 2005/0626; A61N 2005/0663; A61N 5/0622; A61N 5/0624; A61N 2005/0649; A61N 2005/0628; A61N 2005/0662; A61N 2/06; A61N 2005/005; A61N 2005/0633; A61N 2005/066; A61N 5/0613; A61N 2005/0643; A61N 2005/0651; A61N 5/025; A61B 18/203; A61B 2018/00452; A61B 2018/00464; A61B 2018/00994; A61B 90/50; A61B 2018/00791; A61B 2017/00106; A61B 2017/00482; A61B 2018/00005; A61B 2018/0047; A61B 2018/00559; A61B 2018/00577; A61B 2018/00589; A61B 2018/00642; A61B 2018/00672; A61B 2018/00678; A61B 2018/00708; A61B 2018/00809; A61B 2018/20351; A61B 18/02; A61B 18/22; A61B 2017/0046; A61B 18/1815; A61B 18/201; A61B 2018/00458; A61B 2018/00714; A61B 2018/00017; A61B 2018/00047; A61B 2018/00476; A61B 2090/064; A61B 90/361; A61B 2017/00154; A61B 2018/00011; A61B 2018/00333; A61B 2018/0066; A61B 2018/00803; A61B 2018/00821; A61B 2018/00827; A61B 2018/00875; A61B 2018/00892; A61B 2018/00898; A61B 2018/20359; A61B 2018/2285; A61B 2090/378; A61B 2017/00057; A61B 2017/00115; A61B 2017/00473; A61B 2017/00747; A61B 2017/00769; A61B 2018/00029; A61B 2018/00208; A61B 2018/00315; A61B 2018/00321; A61B 2018/00761; A61B 2018/00785; A61B 2018/00839; A61B 2018/00869; A61B 2018/00904; A61B 2018/00988; A61B 2018/1807; A61B 2018/2035; A61B 2018/20355; A61B 2018/2266; A61B 2090/062; A61B 2562/0247; A61B 90/06; A61B 90/98; A61B 18/12; A61B 18/1206; A61B 18/14; A61B 18/20; A61B 2018/00863; A61F 2007/0056; A61F 2007/029; A61F 7/00; A61F 7/007; A61F 2007/0075; A61F 7/0053; A61F 2007/0052; A61F 2007/0093; A61F 2007/0054; A61F 2007/0095; A61F 2007/0022; A61F 2007/004; A61F 2007/0041; A61F 2007/0027; A61F 2007/0029; A61F 2007/006; A61F 2007/0086; A61F 2007/0087; A61F 2007/009; A61F 2007/0096; A61F 7/0085; A61F 2007/0064; A61F 2007/0296; A61F 7/10; H01F 7/064; A61H 2201/0207; A61H 2201/0214; A61H 2201/025; A61H 2201/0285; A61H 2201/10; A61H 2201/5061; A61H 2201/5084; A61H 2201/5092; A61H 2230/208; A61H 2230/505; A61H 23/006; A61H 23/008; A61H 23/02; A61H 23/0236; A61H 23/0245; A61H 9/0057

See application file for complete search history.

(56) References Cited

U.S. PATENT DOCUMENTS

| | | |
|---|---|---|
| 3,163,161 A | 12/1964 | Courtin |
| 3,566,877 A | 3/1971 | Smith et al. |
| 3,658,051 A | 4/1972 | MacLean et al. |
| 3,841,306 A | 10/1974 | Hallgren et al. |
| 3,915,151 A | 10/1975 | Kraus et al. |
| 3,946,349 A | 3/1976 | Haldeman, III |
| 3,952,751 A | 4/1976 | Yarger |
| 3,971,387 A | 7/1976 | Mantell |
| 4,068,292 A | 1/1978 | Berry et al. |
| 4,143,661 A | 3/1979 | LaForge et al. |
| 4,197,851 A | 4/1980 | Fellus |
| 4,237,898 A | 12/1980 | Whalley |
| 4,305,115 A | 12/1981 | Armitage |
| 4,315,503 A | 2/1982 | Ryaby et al. |
| 4,392,040 A | 7/1983 | Rand et al. |
| 4,454,883 A | 6/1984 | Fellus |
| 4,456,001 A | 6/1984 | Pescatore |
| 4,550,714 A | 11/1985 | Talish |
| 4,556,056 A | 12/1985 | Fischer et al. |
| 4,665,898 A | 5/1987 | Costa et al. |
| 4,674,482 A | 6/1987 | Waltonen et al. |
| 4,674,505 A | 6/1987 | Pauli et al. |
| 4,723,536 A | 2/1988 | Rauscher et al. |
| 4,850,959 A | 7/1989 | Findl |
| 4,889,526 A | 12/1989 | Rauscher et al. |
| 4,957,480 A | 9/1990 | Morenings |
| 4,989,604 A | 2/1991 | Fang |
| 4,993,413 A | 2/1991 | McLeod et al. |
| 5,061,234 A | 10/1991 | Chaney |
| 5,067,940 A | 11/1991 | Liboff et al. |
| 5,085,626 A | 2/1992 | Frey |
| 5,143,063 A | 9/1992 | Fellner |
| 5,156,587 A * | 10/1992 | Montone .................. A61N 2/02 600/13 |
| 5,181,902 A | 1/1993 | Erickson et al. |
| 5,199,951 A | 4/1993 | Spears |
| 5,334,181 A | 8/1994 | Rubinsky et al. |
| 5,344,384 A | 9/1994 | Ostrow et al. |
| 5,401,233 A | 3/1995 | Erickson et al. |
| 5,415,617 A | 5/1995 | Kraus |
| 5,419,344 A | 5/1995 | Dewitt |
| 5,433,737 A | 7/1995 | Aimone |
| 5,433,740 A | 7/1995 | Yamaguchi |
| 5,584,863 A | 12/1996 | Rauch et al. |
| 5,620,463 A | 4/1997 | Drolet |
| 5,660,836 A | 8/1997 | Knowlton |
| 5,674,218 A | 10/1997 | Rubinsky et al. |
| 5,690,692 A | 11/1997 | Fleming |
| 5,691,873 A | 11/1997 | Masaki |
| 5,718,662 A | 2/1998 | Jalinous |
| 5,725,471 A | 3/1998 | Davey et al. |
| 5,755,753 A | 5/1998 | Knowlton |

(56) References Cited

U.S. PATENT DOCUMENTS

| | | |
|---|---|---|
| 5,766,124 A | 6/1998 | Polson |
| 5,782,743 A | 7/1998 | Russell |
| 5,807,232 A | 9/1998 | Espinoza et al. |
| 5,857,957 A | 1/1999 | Lin |
| 5,908,444 A | 6/1999 | Azure |
| 5,919,219 A | 7/1999 | Knowlton |
| 5,968,527 A | 10/1999 | Litovitz |
| 5,984,854 A | 11/1999 | Ishikawa et al. |
| 6,017,337 A | 1/2000 | Pira |
| 6,032,675 A | 3/2000 | Rubinsky |
| 6,038,485 A | 3/2000 | Axelgaard |
| 6,047,215 A | 4/2000 | McClure et al. |
| 6,063,108 A | 5/2000 | Salansky et al. |
| 6,067,474 A | 5/2000 | Schulman et al. |
| 6,086,525 A | 7/2000 | Davey et al. |
| 6,094,599 A | 7/2000 | Bingham et al. |
| 6,099,459 A | 8/2000 | Jacobson |
| 6,099,523 A | 8/2000 | Kim et al. |
| 6,117,066 A | 9/2000 | Abrams et al. |
| 6,132,361 A | 10/2000 | Epstein et al. |
| 6,141,985 A | 11/2000 | Cluzeau et al. |
| 6,155,966 A | 12/2000 | Parker |
| 6,161,757 A | 12/2000 | Morris |
| 6,179,769 B1 | 1/2001 | Ishikawa et al. |
| 6,179,770 B1 | 1/2001 | Mould |
| 6,179,771 B1 | 1/2001 | Mueller |
| 6,200,259 B1 | 3/2001 | March |
| 6,213,933 B1 | 4/2001 | Lin |
| 6,223,750 B1 | 5/2001 | Ishikawa et al. |
| 6,246,905 B1 | 6/2001 | Mogul |
| 6,255,815 B1 | 7/2001 | Davey |
| 6,261,301 B1 | 7/2001 | Knesch et al. |
| 6,273,862 B1 | 8/2001 | Privitera et al. |
| 6,273,884 B1 | 8/2001 | Altshuler et al. |
| 6,280,376 B1 | 8/2001 | Holcomb |
| 6,282,448 B1 | 8/2001 | Katz et al. |
| D447,806 S | 9/2001 | Davey et al. |
| 6,311,090 B1 | 10/2001 | Knowlton |
| 6,324,430 B1 | 11/2001 | Zarinetchi et al. |
| 6,324,432 B1 | 11/2001 | Rigaux et al. |
| 6,334,069 B1 | 12/2001 | George et al. |
| 6,334,074 B1 | 12/2001 | Spertell |
| 6,350,276 B1 | 2/2002 | Knowlton |
| 6,402,678 B1 | 6/2002 | Fischell et al. |
| 6,413,255 B1 | 7/2002 | Stern |
| 6,418,345 B1 | 7/2002 | Tepper et al. |
| 6,424,864 B1 | 7/2002 | Matsuura |
| 6,425,852 B1 | 7/2002 | Epstein et al. |
| 6,443,883 B1 | 9/2002 | Ostrow et al. |
| 6,445,955 B1 | 9/2002 | Michelson et al. |
| 6,447,440 B1 | 9/2002 | Markoll |
| 6,453,202 B1 | 9/2002 | Knowlton |
| 6,461,375 B1 | 10/2002 | Baudry et al. |
| 6,491,620 B1 | 12/2002 | Davey |
| 6,500,110 B1 | 12/2002 | Davey et al. |
| 6,520,903 B1 | 2/2003 | Yamashiro |
| 6,527,694 B1 | 3/2003 | Ishikawa et al. |
| 6,527,695 B1 | 3/2003 | Davey et al. |
| 6,537,197 B1 | 3/2003 | Ruohonen et al. |
| 6,569,078 B2 | 5/2003 | Ishikawa et al. |
| 6,605,080 B1 | 8/2003 | Altshuler et al. |
| 6,635,053 B1 | 10/2003 | Lalonde et al. |
| 6,658,301 B2 | 12/2003 | Loeb et al. |
| 6,662,054 B2 | 12/2003 | Kreindel et al. |
| 6,663,556 B2 | 12/2003 | Barker |
| 6,663,659 B2 | 12/2003 | McDaniel |
| 6,701,185 B2 | 3/2004 | Burnett et al. |
| 6,735,481 B1 | 5/2004 | Bingham et al. |
| 6,738,667 B2 | 5/2004 | Deno et al. |
| 6,749,624 B2 | 6/2004 | Knowlton |
| 6,827,681 B2 | 12/2004 | Tanner et al. |
| 6,849,040 B2 | 2/2005 | Ruohonen et al. |
| 6,860,852 B2 | 3/2005 | Schonenberger et al. |
| 6,871,099 B1 | 3/2005 | Whitehurst et al. |
| 6,879,859 B1 | 4/2005 | Boveja |
| 6,889,090 B2 | 5/2005 | Kreindel |
| 6,920,883 B2 | 7/2005 | Bessette et al. |
| 6,939,287 B1 | 9/2005 | Ardizzone et al. |
| 6,960,202 B2 | 11/2005 | Cluzeau et al. |
| 6,990,427 B2 | 1/2006 | Kirsch et al. |
| 7,024,239 B2 | 4/2006 | George et al. |
| 7,030,764 B2 | 4/2006 | Smith et al. |
| 7,041,100 B2 | 5/2006 | Kreindel |
| 7,083,580 B2 | 8/2006 | Bernabei |
| 7,186,209 B2 | 3/2007 | Jacobson et al. |
| 7,217,265 B2 | 5/2007 | Hennings et al. |
| 7,276,058 B2 | 10/2007 | Altshuler et al. |
| 7,309,309 B2 | 12/2007 | Wang et al. |
| 7,318,821 B2 | 1/2008 | Lalonde et al. |
| 7,351,252 B2 | 4/2008 | Altshuler et al. |
| 7,367,341 B2 | 5/2008 | Anderson et al. |
| 7,369,895 B2 | 5/2008 | Hurtado |
| 7,372,271 B2 | 5/2008 | Roozen et al. |
| 7,376,460 B2 | 5/2008 | Bernabei |
| 7,396,326 B2 | 7/2008 | Ghiron et al. |
| 7,496,401 B2 | 2/2009 | Bernabei |
| 7,520,849 B1 | 4/2009 | Simon |
| 7,520,875 B2 | 4/2009 | Bernabei |
| 7,532,926 B2 | 5/2009 | Bernabei |
| 7,571,003 B2 | 8/2009 | Pozzato |
| 7,591,776 B2 | 9/2009 | Phillips et al. |
| 7,601,115 B2 | 10/2009 | Riehl |
| 7,608,035 B2 | 10/2009 | Farone |
| 7,618,429 B2 | 11/2009 | Mulholland |
| 7,630,774 B2 | 12/2009 | Karni et al. |
| 7,643,883 B2 | 1/2010 | Kreindel |
| 7,697,998 B2 | 4/2010 | Axelgaard |
| 7,699,768 B2 | 4/2010 | Kishawi et al. |
| 7,740,574 B2 | 6/2010 | Pilla et al. |
| 7,744,523 B2 | 6/2010 | Epstein |
| 7,783,348 B2 | 8/2010 | Gill et al. |
| 7,785,358 B2 | 8/2010 | Lach |
| 7,854,754 B2 | 12/2010 | Ting et al. |
| 7,909,786 B2 | 3/2011 | Bonnefin et al. |
| 7,914,469 B2 | 3/2011 | Torbati |
| 7,945,321 B2 | 5/2011 | Bernabei |
| 7,946,973 B2 | 5/2011 | Peterchev |
| 7,953,500 B2 | 5/2011 | Bingham et al. |
| 7,998,053 B2 | 8/2011 | Aho |
| 8,035,385 B2 | 10/2011 | Tomiha et al. |
| RE43,007 E | 12/2011 | Lalonde et al. |
| 8,088,058 B2 | 1/2012 | Juliana et al. |
| 8,128,549 B2 | 3/2012 | Testani et al. |
| 8,133,191 B2 | 3/2012 | Rosenberg et al. |
| 8,137,258 B1 | 3/2012 | Dennis et al. |
| 8,172,835 B2 | 5/2012 | Leyh et al. |
| 8,192,474 B2 | 6/2012 | Levinson |
| 8,204,446 B2 | 6/2012 | Scheer et al. |
| 8,251,986 B2 | 8/2012 | Chornenky et al. |
| 8,265,763 B2 | 9/2012 | Fahey |
| 8,271,090 B1 | 9/2012 | Hartman et al. |
| 8,275,442 B2 | 9/2012 | Allison |
| 8,285,390 B2 | 10/2012 | Levinson et al. |
| 8,335,566 B2 | 12/2012 | Muller et al. |
| 8,337,539 B2 | 12/2012 | Ting et al. |
| 8,366,756 B2 | 2/2013 | Tucek et al. |
| 8,376,825 B2 | 2/2013 | Guinn et al. |
| 8,376,925 B1 | 2/2013 | Dennis et al. |
| 8,454,591 B2 | 6/2013 | Leyh et al. |
| 8,457,751 B2 | 6/2013 | Pozzato |
| 8,475,354 B2 | 7/2013 | Phillips et al. |
| 8,523,927 B2 | 9/2013 | Levinson et al. |
| 8,548,599 B2 | 10/2013 | Zarsky et al. |
| 8,565,888 B2 | 10/2013 | Buhlmann et al. |
| 8,579,953 B1 | 11/2013 | Dunbar et al. |
| 8,588,930 B2 | 11/2013 | DiUbaldi et al. |
| 8,593,245 B2 | 11/2013 | Zeng et al. |
| 8,603,073 B2 | 12/2013 | Allison |
| 8,646,239 B2 | 2/2014 | Rulon |
| 8,666,492 B2 | 3/2014 | Muller et al. |
| 8,676,338 B2 | 3/2014 | Levinson |
| 8,684,901 B1 | 4/2014 | Zabara |
| 8,700,176 B2 | 4/2014 | Azar et al. |
| 8,702,774 B2 | 4/2014 | Baker et al. |

(56) References Cited

U.S. PATENT DOCUMENTS

| | | |
|---|---|---|
| 8,725,270 B2 | 5/2014 | Towe |
| 8,771,326 B2 | 7/2014 | Myeong et al. |
| 8,788,060 B2 | 7/2014 | Nebrigic et al. |
| 8,795,148 B2 | 8/2014 | Schneider et al. |
| 8,834,547 B2 | 9/2014 | Anderson et al. |
| 8,840,608 B2 | 9/2014 | Anderson et al. |
| 8,864,641 B2 | 10/2014 | Riehl et al. |
| 8,868,177 B2 | 10/2014 | Simon et al. |
| 8,906,009 B2 | 12/2014 | Nebrigic et al. |
| 8,915,948 B2 | 12/2014 | Altshuler et al. |
| 8,932,338 B2 | 1/2015 | Lim et al. |
| 8,979,727 B2 | 3/2015 | Ron et al. |
| 8,985,331 B2 | 3/2015 | Guenter et al. |
| 8,998,791 B2 | 4/2015 | Ron et al. |
| 9,002,477 B2 | 4/2015 | Burnett |
| 9,028,469 B2 | 5/2015 | Jones et al. |
| 9,037,247 B2 | 5/2015 | Simon et al. |
| 9,044,595 B2 | 6/2015 | Araya et al. |
| 9,061,128 B2 | 6/2015 | Hall et al. |
| 9,072,891 B1 | 7/2015 | Rao |
| 9,078,634 B2 | 7/2015 | Gonzales et al. |
| 9,089,719 B2 | 7/2015 | Simon et al. |
| 9,101,524 B2 | 8/2015 | Aghion |
| 9,132,031 B2 | 9/2015 | Levinson et al. |
| 9,149,650 B2 | 10/2015 | Shanks et al. |
| 9,168,096 B2 | 10/2015 | Kreindel |
| 9,233,257 B1 | 1/2016 | Zabara |
| 9,254,395 B1 | 2/2016 | Shambayati |
| 9,261,574 B2 | 2/2016 | Boskamp et al. |
| 9,265,690 B2 | 2/2016 | Kriksunov et al. |
| 9,308,120 B2 | 4/2016 | Anderson et al. |
| 9,314,368 B2 | 4/2016 | Allison et al. |
| 9,326,910 B2 | 5/2016 | Eckhouse et al. |
| 9,339,641 B2 | 5/2016 | Rajguru et al. |
| 9,358,068 B2 | 6/2016 | Schomacker et al. |
| 9,358,149 B2 | 6/2016 | Anderson et al. |
| 9,375,345 B2 | 6/2016 | Levinson et al. |
| 9,387,339 B2 | 7/2016 | Sham et al. |
| 9,398,975 B2 | 7/2016 | Müller et al. |
| 9,408,745 B2 | 8/2016 | Levinson et al. |
| 9,414,759 B2 | 8/2016 | Lang et al. |
| 9,433,797 B2 | 9/2016 | Pilla et al. |
| 9,439,805 B2 | 9/2016 | Gonzales et al. |
| 9,446,258 B1 | 9/2016 | Schwarz et al. |
| 9,468,774 B2 | 10/2016 | Zarksy et al. |
| 9,532,832 B2 | 1/2017 | Ron Edoute et al. |
| 9,545,523 B2 | 1/2017 | Nanda |
| 9,561,357 B2 | 2/2017 | Hall et al. |
| 9,586,057 B2 | 3/2017 | Ladman et al. |
| 9,596,920 B2 | 3/2017 | Shalev et al. |
| 9,610,429 B2 | 4/2017 | Harris et al. |
| 9,610,459 B2 | 4/2017 | Burnett et al. |
| 9,615,854 B2 | 4/2017 | Matsushita |
| 9,636,516 B2 | 5/2017 | Schwarz |
| 9,636,519 B2 | 5/2017 | Ladman et al. |
| 9,649,220 B2 | 5/2017 | Anderson et al. |
| 9,655,770 B2 | 5/2017 | Levinson et al. |
| 9,694,194 B2 | 7/2017 | Ron Edoute et al. |
| 9,737,238 B2 | 8/2017 | Wright et al. |
| 9,737,434 B2 | 8/2017 | Allison |
| 9,757,584 B2 | 9/2017 | Burnett |
| 9,782,324 B2 | 10/2017 | Crunick et al. |
| 9,814,897 B2 | 11/2017 | Ron Edoute et al. |
| 9,844,460 B2 | 12/2017 | Weber et al. |
| 9,844,461 B2 | 12/2017 | Levinson et al. |
| 9,855,166 B2 | 1/2018 | Anderson et al. |
| 9,861,421 B2 | 1/2018 | O'Neil et al. |
| 9,861,520 B2 | 1/2018 | Baker et al. |
| 9,867,996 B2 | 1/2018 | Zarsky et al. |
| 9,901,743 B2 | 2/2018 | Ron Edoute et al. |
| 9,919,161 B2 | 3/2018 | Schwarz et al. |
| 9,937,358 B2 | 4/2018 | Schwarz et al. |
| 9,962,553 B2 | 5/2018 | Schwarz et al. |
| 9,968,797 B2 | 5/2018 | Sham et al. |
| 9,974,519 B1 | 5/2018 | Schwarz et al. |
| 9,974,684 B2 | 5/2018 | Anderson et al. |
| 9,980,765 B2 | 5/2018 | Avram et al. |
| 9,981,143 B2 | 5/2018 | Ron Edoute et al. |
| 9,999,780 B2 | 6/2018 | Weyh et al. |
| 10,037,867 B2 | 7/2018 | Godyak |
| 10,039,929 B1 | 8/2018 | Schwarz et al. |
| 10,080,906 B2 | 9/2018 | Schwarz |
| 10,092,346 B2 | 10/2018 | Levinson |
| 10,111,770 B2 | 10/2018 | Harris et al. |
| 10,111,774 B2 | 10/2018 | Gonzales et al. |
| 10,124,187 B2 | 11/2018 | Schwarz et al. |
| 10,183,172 B2 | 1/2019 | Ghiron et al. |
| 10,195,453 B2 | 2/2019 | Schwarz et al. |
| 10,195,454 B2 | 2/2019 | Yamashiro |
| 10,201,380 B2 | 2/2019 | Debenedictis et al. |
| 10,245,439 B1 | 4/2019 | Schwarz et al. |
| 10,271,900 B2 | 4/2019 | Marchitto et al. |
| 10,342,988 B2 | 7/2019 | Midorikawa et al. |
| 10,413,745 B2 | 9/2019 | Riehl |
| 10,463,869 B2 | 11/2019 | Ron Edoute et al. |
| 10,471,269 B2 | 11/2019 | Schwarz et al. |
| 10,478,588 B2 | 11/2019 | Walpole et al. |
| 10,478,633 B2 | 11/2019 | Schwarz et al. |
| 10,478,634 B2 | 11/2019 | Schwarz et al. |
| 10,493,293 B2 | 12/2019 | Schwarz et al. |
| 10,518,098 B2 | 12/2019 | Hong et al. |
| 10,549,109 B2 | 2/2020 | Schwarz et al. |
| 10,549,110 B1 | 2/2020 | Schwarz et al. |
| 10,556,121 B2 | 2/2020 | Gurfein |
| 10,556,122 B1 | 2/2020 | Schwarz et al. |
| 10,569,094 B2 | 2/2020 | Schwarz et al. |
| 10,569,095 B1 | 2/2020 | Schwarz et al. |
| 10,583,287 B2 | 3/2020 | Schwarz |
| 10,596,386 B2 | 3/2020 | Schwarz et al. |
| 10,610,696 B1 | 4/2020 | Peled |
| 10,632,321 B2 | 4/2020 | Schwarz et al. |
| 10,639,490 B2 | 5/2020 | Simon et al. |
| 10,661,093 B2 | 5/2020 | Ron Edoute et al. |
| 10,675,819 B2 | 6/2020 | Li et al. |
| 10,688,310 B2 | 6/2020 | Schwarz et al. |
| 10,695,575 B1 | 6/2020 | Schwarz et al. |
| 10,695,576 B2 | 6/2020 | Schwarz et al. |
| 10,709,894 B2 | 7/2020 | Schwarz et al. |
| 10,709,895 B2 | 7/2020 | Schwarz et al. |
| 10,806,943 B2 | 10/2020 | Sokolowski |
| 10,821,295 B1 | 11/2020 | Schwarz et al. |
| 10,849,784 B2 | 12/2020 | Jurna et al. |
| 2001/0018547 A1 | 8/2001 | Mechlenburg et al. |
| 2001/0031906 A1 | 10/2001 | Ishikawa et al. |
| 2002/0010414 A1 | 1/2002 | Coston et al. |
| 2002/0049483 A1 | 4/2002 | Knowlton |
| 2002/0082466 A1 | 6/2002 | Han |
| 2002/0128686 A1 | 9/2002 | Minogue et al. |
| 2002/0143365 A1 | 10/2002 | Herbst |
| 2002/0160436 A1 | 10/2002 | Markov et al. |
| 2002/0165590 A1 | 11/2002 | Crowe et al. |
| 2003/0028072 A1 | 2/2003 | Fischell et al. |
| 2003/0032900 A1 | 2/2003 | Ella |
| 2003/0032950 A1 | 2/2003 | Altshuler et al. |
| 2003/0050527 A1 | 3/2003 | Fox et al. |
| 2003/0074037 A1 | 4/2003 | Moore et al. |
| 2003/0078646 A1 | 4/2003 | Axelgaard |
| 2003/0093133 A1 | 5/2003 | Crowe et al. |
| 2003/0130711 A1 | 7/2003 | Pearson et al. |
| 2003/0149451 A1 | 8/2003 | Chomenky et al. |
| 2003/0153958 A1 | 8/2003 | Yamazaki et al. |
| 2003/0158585 A1 | 8/2003 | Burnett |
| 2003/0216729 A1 | 11/2003 | Marchitto et al. |
| 2003/0220674 A1 | 11/2003 | Anderson et al. |
| 2003/0236487 A1 | 12/2003 | Knowlton |
| 2004/0015163 A1 | 1/2004 | Buysse et al. |
| 2004/0034346 A1 | 2/2004 | Stern et al. |
| 2004/0039279 A1 | 2/2004 | Ruohonen |
| 2004/0073079 A1 | 4/2004 | Altshuler et al. |
| 2004/0077977 A1 | 4/2004 | Ella et al. |
| 2004/0093042 A1 | 5/2004 | Altshuler et al. |
| 2004/0102768 A1 | 5/2004 | Cluzeau et al. |
| 2004/0162583 A1 | 8/2004 | Bingham et al. |
| 2004/0193003 A1 | 9/2004 | Mechlenburg et al. |

(56) References Cited

U.S. PATENT DOCUMENTS

| | | |
|---|---|---|
| 2004/0206365 A1 | 10/2004 | Knowlton |
| 2004/0210214 A1 | 10/2004 | Knowlton |
| 2004/0210282 A1 | 10/2004 | Flock et al. |
| 2004/0210287 A1 | 10/2004 | Greene |
| 2004/0230226 A1 | 11/2004 | Bingham et al. |
| 2005/0038313 A1 | 2/2005 | Ardizzone |
| 2005/0049543 A1 | 3/2005 | Anderson et al. |
| 2005/0075701 A1 | 4/2005 | Shafer |
| 2005/0075702 A1 | 4/2005 | Shafer |
| 2005/0090814 A1 | 4/2005 | Lalonde et al. |
| 2005/0107656 A1 | 5/2005 | Jang et al. |
| 2005/0134193 A1 | 6/2005 | Myers et al. |
| 2005/0187599 A1 | 8/2005 | Sharkey et al. |
| 2005/0203504 A1 | 9/2005 | Wham et al. |
| 2005/0215987 A1 | 9/2005 | Slatkine |
| 2005/0216062 A1 | 9/2005 | Herbst |
| 2005/0251120 A1 | 11/2005 | Anderson et al. |
| 2006/0004244 A1 | 1/2006 | Phillips et al. |
| 2006/0020236 A1 | 1/2006 | Ben-Nun |
| 2006/0036300 A1 | 2/2006 | Kreindel |
| 2006/0094924 A1 | 5/2006 | Riehl |
| 2006/0106375 A1 | 5/2006 | Werneth et al. |
| 2006/0152301 A1 | 7/2006 | Rohwedder |
| 2006/0184214 A1 | 8/2006 | McDaniel |
| 2006/0187607 A1 | 8/2006 | Mo |
| 2006/0195168 A1 | 8/2006 | Dunbar et al. |
| 2006/0199992 A1 | 9/2006 | Eisenberg et al. |
| 2006/0206103 A1 | 9/2006 | Altshuler et al. |
| 2006/0206180 A1 | 9/2006 | Alcidi |
| 2006/0253176 A1 | 11/2006 | Caruso et al. |
| 2006/0259102 A1 | 11/2006 | Slatkine |
| 2006/0271028 A1 | 11/2006 | Altshuler et al. |
| 2006/0287566 A1 | 12/2006 | Zangen et al. |
| 2006/0293719 A1 | 12/2006 | Naghavi |
| 2007/0010766 A1 | 1/2007 | Gil et al. |
| 2007/0010861 A1 | 1/2007 | Anderson et al. |
| 2007/0016274 A1 | 1/2007 | Boveja et al. |
| 2007/0027411 A1 | 2/2007 | Ella et al. |
| 2007/0083237 A1 | 4/2007 | Teruel |
| 2007/0088413 A1 | 4/2007 | Weber et al. |
| 2007/0088419 A1 | 4/2007 | Fiorina et al. |
| 2007/0135811 A1 | 6/2007 | Hooven |
| 2007/0142886 A1 | 6/2007 | Fischell et al. |
| 2007/0173749 A1 | 7/2007 | Williams et al. |
| 2007/0173805 A1 | 7/2007 | Weinberg et al. |
| 2007/0179534 A1 | 8/2007 | Firlik et al. |
| 2007/0198071 A1 | 8/2007 | Ting et al. |
| 2007/0232966 A1 | 10/2007 | Applebaum et al. |
| 2007/0244530 A1 | 10/2007 | Ren |
| 2007/0255355 A1 | 11/2007 | Altshuler et al. |
| 2007/0255362 A1 | 11/2007 | Levinson et al. |
| 2007/0260107 A1 | 11/2007 | Mishelevich et al. |
| 2007/0270795 A1 | 11/2007 | Francischelli et al. |
| 2007/0270925 A1 | 11/2007 | Levinson |
| 2007/0282156 A1 | 12/2007 | Konings |
| 2007/0293911 A1 | 12/2007 | Crowe et al. |
| 2007/0293918 A1 | 12/2007 | Thompson et al. |
| 2008/0009885 A1 | 1/2008 | Del Giglio |
| 2008/0046053 A1 | 2/2008 | Wagner et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0082094 A1 | 4/2008 | McPherson et al. |
| 2008/0082153 A1 | 4/2008 | Gadsby et al. |
| 2008/0103565 A1 | 5/2008 | Altshuler et al. |
| 2008/0132971 A1 | 6/2008 | Pille et al. |
| 2008/0183251 A1 | 7/2008 | Azar et al. |
| 2008/0188915 A1 | 8/2008 | Mills et al. |
| 2008/0228520 A1 | 9/2008 | Day et al. |
| 2008/0234534 A1 | 9/2008 | Mikas et al. |
| 2008/0249350 A1 | 10/2008 | Marchitto et al. |
| 2008/0255572 A1 | 10/2008 | Zeller et al. |
| 2008/0255637 A1 | 10/2008 | Oishi |
| 2008/0262287 A1 | 10/2008 | Dussau |
| 2008/0262574 A1 | 10/2008 | Briefs et al. |
| 2008/0287839 A1 | 11/2008 | Rosen et al. |
| 2008/0287948 A1 | 11/2008 | Newton et al. |
| 2008/0306325 A1 | 12/2008 | Burnett et al. |
| 2008/0306326 A1 | 12/2008 | Epstein |
| 2008/0312647 A1 | 12/2008 | Knopp et al. |
| 2009/0005631 A1 | 1/2009 | Simenhaus et al. |
| 2009/0018384 A1 | 1/2009 | Boyden et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0018628 A1 | 1/2009 | Burns et al. |
| 2009/0024192 A1 | 1/2009 | Mulholland |
| 2009/0024193 A1 | 1/2009 | Altshuler et al. |
| 2009/0036958 A1 | 2/2009 | Mehta |
| 2009/0043293 A1 | 2/2009 | Pankratov et al. |
| 2009/0099405 A1 | 4/2009 | Schneider et al. |
| 2009/0108969 A1 | 4/2009 | Sims et al. |
| 2009/0118722 A1 | 5/2009 | Ebbers et al. |
| 2009/0118790 A1 | 5/2009 | Van Herk |
| 2009/0149300 A1 | 6/2009 | Chen |
| 2009/0149929 A1 | 6/2009 | Levinson et al. |
| 2009/0149930 A1 | 6/2009 | Schenck |
| 2009/0156958 A1 | 6/2009 | Mehta et al. |
| 2009/0221938 A1 | 9/2009 | Rosenberg et al. |
| 2009/0227831 A1 | 9/2009 | Burnett et al. |
| 2009/0234423 A1 | 9/2009 | Vetanze |
| 2009/0248004 A1 | 10/2009 | Altshuler et al. |
| 2009/0254154 A1 | 10/2009 | De et al. |
| 2009/0270945 A1 | 10/2009 | Markoll et al. |
| 2009/0284339 A1 | 11/2009 | Choi et al. |
| 2009/0306648 A1 | 12/2009 | Podhajsky et al. |
| 2009/0326571 A1 | 12/2009 | Mulholland |
| 2010/0004536 A1 | 1/2010 | Rosenberg |
| 2010/0004715 A1 | 1/2010 | Fahey |
| 2010/0016761 A1 | 1/2010 | Rosenberg |
| 2010/0036191 A1 | 2/2010 | Walter et al. |
| 2010/0036368 A1 | 2/2010 | England et al. |
| 2010/0049188 A1 | 2/2010 | Nelson et al. |
| 2010/0069704 A1 | 3/2010 | Peterchev |
| 2010/0081971 A1 | 4/2010 | Allison |
| 2010/0087699 A1 | 4/2010 | Peterchev |
| 2010/0087816 A1 | 4/2010 | Roy |
| 2010/0121131 A1* | 5/2010 | Mathes ............... A61N 2/02 600/14 |
| 2010/0130945 A1 | 5/2010 | Laniado et al. |
| 2010/0145399 A1 | 6/2010 | Johari et al. |
| 2010/0152522 A1 | 6/2010 | Roth et al. |
| 2010/0152824 A1 | 6/2010 | Allison |
| 2010/0160712 A1 | 6/2010 | Burnett et al. |
| 2010/0168501 A1 | 7/2010 | Burnett et al. |
| 2010/0179372 A1 | 7/2010 | Glassman |
| 2010/0185042 A1 | 7/2010 | Schneider et al. |
| 2010/0217253 A1 | 8/2010 | Mehta |
| 2010/0222629 A1 | 9/2010 | Burnett et al. |
| 2010/0228250 A1 | 9/2010 | Brogna |
| 2010/0256438 A1 | 10/2010 | Mishelevich et al. |
| 2010/0256439 A1 | 10/2010 | Schneider et al. |
| 2010/0261992 A1 | 10/2010 | Axelgaard |
| 2010/0274327 A1 | 10/2010 | Carroll et al. |
| 2010/0274329 A1 | 10/2010 | Bradley et al. |
| 2010/0280582 A1 | 11/2010 | Baker et al. |
| 2010/0286470 A1 | 11/2010 | Schneider et al. |
| 2010/0286691 A1 | 11/2010 | Kerr et al. |
| 2010/0298623 A1 | 11/2010 | Mishelevich et al. |
| 2010/0309689 A1 | 12/2010 | Coulson |
| 2010/0324611 A1 | 12/2010 | Deming et al. |
| 2010/0331602 A1 | 12/2010 | Mishelevich et al. |
| 2010/0331603 A1 | 12/2010 | Szecsi |
| 2011/0004261 A1 | 1/2011 | Sham et al. |
| 2011/0007745 A1 | 1/2011 | Schultz et al. |
| 2011/0009737 A1 | 1/2011 | Manstein |
| 2011/0015464 A1 | 1/2011 | Riehl et al. |
| 2011/0021863 A1 | 1/2011 | Burnett et al. |
| 2011/0046432 A1* | 2/2011 | Simon ............... A61N 2/02 600/14 |
| 2011/0046523 A1 | 2/2011 | Altshuler et al. |
| 2011/0066216 A1 | 3/2011 | Ting et al. |

(56) References Cited

U.S. PATENT DOCUMENTS

| | | |
|---|---|---|
| 2011/0077451 A1 | 3/2011 | Marchitto et al. |
| 2011/0082383 A1 | 4/2011 | Cory et al. |
| 2011/0087312 A1 | 4/2011 | Shanks et al. |
| 2011/0105826 A1 | 5/2011 | Mishelevich et al. |
| 2011/0112520 A1 | 5/2011 | Michael |
| 2011/0118722 A1 | 5/2011 | Lischinsky et al. |
| 2011/0125203 A1 | 5/2011 | Simon et al. |
| 2011/0130618 A1 | 6/2011 | Ron et al. |
| 2011/0130713 A1 | 6/2011 | Dufay |
| 2011/0130796 A1 | 6/2011 | Louise |
| 2011/0152967 A1 | 6/2011 | Simon et al. |
| 2011/0172735 A1 | 7/2011 | Johari |
| 2011/0172752 A1 | 7/2011 | Bingham et al. |
| 2011/0190569 A1 | 8/2011 | Simon et al. |
| 2011/0196438 A1 | 8/2011 | Mnozil et al. |
| 2011/0202058 A1 | 8/2011 | Eder et al. |
| 2011/0218464 A1 | 9/2011 | Iger |
| 2011/0224761 A1 | 9/2011 | Manstein |
| 2011/0237921 A1 | 9/2011 | Askin, III et al. |
| 2011/0238050 A1 | 9/2011 | Allison et al. |
| 2011/0238051 A1 | 9/2011 | Levinson et al. |
| 2011/0245900 A1 | 10/2011 | Turner |
| 2011/0263925 A1 | 10/2011 | Bratton |
| 2011/0273251 A1 | 11/2011 | Mishelevich et al. |
| 2011/0275927 A1 | 11/2011 | Wagner et al. |
| 2011/0276108 A1 | 11/2011 | Crowe et al. |
| 2011/0300079 A1 | 12/2011 | Martens et al. |
| 2011/0306943 A1 | 12/2011 | Dunbar et al. |
| 2011/0319700 A1 | 12/2011 | Schneider |
| 2012/0016359 A1 | 1/2012 | Podhajsky |
| 2012/0022518 A1 | 1/2012 | Levinson |
| 2012/0029394 A1 | 2/2012 | Babaev |
| 2012/0035608 A1 | 2/2012 | Marchitto et al. |
| 2012/0046598 A1 | 2/2012 | Kardos et al. |
| 2012/0046653 A1 | 2/2012 | Welches et al. |
| 2012/0053449 A1 | 3/2012 | Moses et al. |
| 2012/0101326 A1 | 4/2012 | Simon et al. |
| 2012/0108883 A1 | 5/2012 | Peterchev |
| 2012/0108884 A1 | 5/2012 | Bechler et al. |
| 2012/0109241 A1 | 5/2012 | Rauscher |
| 2012/0116271 A1 | 5/2012 | Caruso et al. |
| 2012/0150079 A1 | 6/2012 | Rosenberg |
| 2012/0157747 A1 | 6/2012 | Rybski et al. |
| 2012/0158100 A1 | 6/2012 | Schomacker |
| 2012/0172653 A1 | 7/2012 | Chornenky et al. |
| 2012/0197361 A1 | 8/2012 | Gonzales et al. |
| 2012/0215210 A1 | 8/2012 | Brown et al. |
| 2012/0226272 A1 | 9/2012 | Chernov et al. |
| 2012/0226330 A1 | 9/2012 | Kolen et al. |
| 2012/0239123 A1 | 9/2012 | Weber et al. |
| 2012/0240940 A1 | 9/2012 | Paraschac et al. |
| 2012/0245483 A1 | 9/2012 | Lundqvist |
| 2012/0253098 A1 | 10/2012 | George et al. |
| 2012/0271206 A1 | 10/2012 | Shalev et al. |
| 2012/0271294 A1 | 10/2012 | Barthe et al. |
| 2012/0277587 A1 | 11/2012 | Adanny et al. |
| 2012/0302821 A1 | 11/2012 | Burnett |
| 2012/0303076 A1 | 11/2012 | Fahey |
| 2012/0310033 A1 | 12/2012 | Muntermann |
| 2012/0310035 A1 | 12/2012 | Schneider et al. |
| 2012/0310311 A1 | 12/2012 | Elkah |
| 2012/0330090 A1 | 12/2012 | Sham et al. |
| 2013/0006039 A1 | 1/2013 | Sadler |
| 2013/0012755 A1 | 1/2013 | Slayton |
| 2013/0030239 A1 | 1/2013 | Weyh et al. |
| 2013/0035745 A1 | 2/2013 | Ahmed et al. |
| 2013/0053620 A1 | 2/2013 | Susedik et al. |
| 2013/0066309 A1 | 3/2013 | Levinson |
| 2013/0079684 A1 | 3/2013 | Rosen et al. |
| 2013/0096363 A1 | 4/2013 | Schneider et al. |
| 2013/0103127 A1 | 4/2013 | Muller et al. |
| 2013/0116758 A1 | 5/2013 | Levinson et al. |
| 2013/0116759 A1 | 5/2013 | Levinson et al. |
| 2013/0123568 A1 | 5/2013 | Hamilton et al. |
| 2013/0123629 A1 | 5/2013 | Rosenberg et al. |
| 2013/0123764 A1 | 5/2013 | Zarsky et al. |
| 2013/0123765 A1 | 5/2013 | Zarsky et al. |
| 2013/0131764 A1 | 5/2013 | Grove |
| 2013/0137918 A1 | 5/2013 | Phillips et al. |
| 2013/0144280 A1 | 6/2013 | Eckhouse et al. |
| 2013/0150653 A1 | 6/2013 | Borsody |
| 2013/0158440 A1 | 6/2013 | Allison |
| 2013/0158634 A1 | 6/2013 | Ron et al. |
| 2013/0158636 A1 | 6/2013 | Ting et al. |
| 2013/0178764 A1 | 7/2013 | Eckhouse et al. |
| 2013/0184693 A1 | 7/2013 | Neev |
| 2013/0190744 A1 | 7/2013 | Avram et al. |
| 2013/0238043 A1 | 9/2013 | Beardall et al. |
| 2013/0238061 A1 | 9/2013 | Ron et al. |
| 2013/0238062 A1 | 9/2013 | Ron Edoute et al. |
| 2013/0245731 A1 | 9/2013 | Allison |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0261374 A1 | 10/2013 | Elder |
| 2013/0261683 A1 | 10/2013 | Soikum et al. |
| 2013/0267943 A1 | 10/2013 | Hancock |
| 2013/0289433 A1 | 10/2013 | Jin et al. |
| 2013/0303904 A1 | 11/2013 | Barthe et al. |
| 2013/0304159 A1 | 11/2013 | Simon et al. |
| 2013/0317281 A1 | 11/2013 | Schneider et al. |
| 2013/0317282 A1 | 11/2013 | Ron Edoute et al. |
| 2013/0331637 A1 | 12/2013 | Greff |
| 2014/0005758 A1 | 1/2014 | Ben-Yehuda et al. |
| 2014/0005760 A1 | 1/2014 | Levinson et al. |
| 2014/0012064 A1 | 1/2014 | Riehl et al. |
| 2014/0018767 A1 | 1/2014 | Harris et al. |
| 2014/0025033 A1 | 1/2014 | Mirkov et al. |
| 2014/0025142 A1 | 1/2014 | Zarksy et al. |
| 2014/0046423 A1 | 2/2014 | Rajguru et al. |
| 2014/0066786 A1 | 3/2014 | Naghavi et al. |
| 2014/0067025 A1 | 3/2014 | Levinson et al. |
| 2014/0081359 A1 | 3/2014 | Sand |
| 2014/0148870 A1 | 5/2014 | Burnett |
| 2014/0194958 A1 | 7/2014 | Chabal et al. |
| 2014/0200388 A1 | 7/2014 | Schneider et al. |
| 2014/0221990 A1 | 8/2014 | Kreindel |
| 2014/0235928 A1 | 8/2014 | Zangen et al. |
| 2014/0243933 A1 | 8/2014 | Ginggen |
| 2014/0249355 A1 | 9/2014 | Martinez |
| 2014/0249609 A1 | 9/2014 | Zarsky et al. |
| 2014/0257071 A1 | 9/2014 | Curran et al. |
| 2014/0257443 A1 | 9/2014 | Baker et al. |
| 2014/0276248 A1 | 9/2014 | Hall et al. |
| 2014/0276693 A1 | 9/2014 | Altshuler et al. |
| 2014/0277219 A1 | 9/2014 | Nanda |
| 2014/0277302 A1 | 9/2014 | Weber et al. |
| 2014/0303425 A1 | 10/2014 | Pilla et al. |
| 2014/0303525 A1 | 10/2014 | Sitharaman |
| 2014/0303696 A1 | 10/2014 | Anderson et al. |
| 2014/0303697 A1 | 10/2014 | Anderson et al. |
| 2014/0316393 A1 | 10/2014 | Levinson |
| 2014/0324120 A1 | 10/2014 | Bogie et al. |
| 2014/0330067 A1 | 11/2014 | Jordan |
| 2014/0350438 A1 | 11/2014 | Papirov et al. |
| 2014/0357935 A1 | 12/2014 | Ilmoniemi et al. |
| 2014/0364841 A1 | 12/2014 | Kornstein |
| 2014/0371515 A1 | 12/2014 | John |
| 2014/0378875 A1 | 12/2014 | Ron Edoute et al. |
| 2015/0005569 A1 | 1/2015 | Missoli |
| 2015/0005759 A1 | 1/2015 | Welches et al. |
| 2015/0018667 A1 | 1/2015 | Radman et al. |
| 2015/0025299 A1 | 1/2015 | Ron et al. |
| 2015/0080769 A1 | 3/2015 | Lotsch |
| 2015/0088105 A1 | 3/2015 | Fatemi |
| 2015/0094788 A1 | 4/2015 | Pierenkemper |
| 2015/0112412 A1 | 4/2015 | Anderson et al. |
| 2015/0119849 A1 | 4/2015 | Aronhalt et al. |
| 2015/0123661 A1 | 5/2015 | Yui et al. |
| 2015/0127075 A1 | 5/2015 | Ward et al. |
| 2015/0133717 A1 | 5/2015 | Ghiron et al. |
| 2015/0133718 A1 | 5/2015 | Schneider et al. |

(56) References Cited

U.S. PATENT DOCUMENTS

| | | |
|---|---|---|
| 2015/0141877 A1 | 5/2015 | Feldman |
| 2015/0148858 A1 | 5/2015 | Kaib |
| 2015/0157873 A1* | 6/2015 | Sokolowski ............ A61N 1/40 600/14 |
| 2015/0165226 A1 | 6/2015 | Simon et al. |
| 2015/0165232 A1 | 6/2015 | Altshuler et al. |
| 2015/0165238 A1 | 6/2015 | Slayton et al. |
| 2015/0174002 A1 | 6/2015 | Burbank et al. |
| 2015/0202454 A1 | 7/2015 | Burnett |
| 2015/0216719 A1 | 8/2015 | Debenedictis et al. |
| 2015/0216720 A1 | 8/2015 | Debenedictis et al. |
| 2015/0216816 A1 | 8/2015 | O'Neil et al. |
| 2015/0223975 A1 | 8/2015 | Anderson et al. |
| 2015/0238248 A1 | 8/2015 | Thompson et al. |
| 2015/0238771 A1 | 8/2015 | Zarsk et al. |
| 2015/0272776 A1 | 10/2015 | Gonzales et al. |
| 2015/0283022 A1 | 10/2015 | Lee et al. |
| 2015/0297909 A1 | 10/2015 | Peashock |
| 2015/0314133 A1 | 11/2015 | Yamashiro |
| 2015/0328077 A1 | 11/2015 | Levinson |
| 2015/0328475 A1 | 11/2015 | Kim et al. |
| 2015/0342661 A1 | 12/2015 | Ron Edoute |
| 2015/0342780 A1 | 12/2015 | Levinson et al. |
| 2015/0360045 A1 | 12/2015 | Fischell et al. |
| 2015/0367141 A1 | 12/2015 | Goetz et al. |
| 2015/0375005 A1 | 12/2015 | Segal |
| 2016/0015995 A1 | 1/2016 | Leung |
| 2016/0016013 A1 | 1/2016 | Capelli et al. |
| 2016/0020070 A1 | 1/2016 | Kim et al. |
| 2016/0022349 A1 | 1/2016 | Woloszko et al. |
| 2016/0030763 A1 | 2/2016 | Midorikawa et al. |
| 2016/0045755 A1 | 2/2016 | Chun et al. |
| 2016/0051401 A1 | 2/2016 | Yee et al. |
| 2016/0051827 A1 | 2/2016 | Ron et al. |
| 2016/0066977 A1 | 3/2016 | Neal, II et al. |
| 2016/0066994 A1 | 3/2016 | Shanks |
| 2016/0067516 A1 | 3/2016 | Schneider et al. |
| 2016/0067517 A1 | 3/2016 | Burnett |
| 2016/0089550 A1 | 3/2016 | Debenedictis et al. |
| 2016/0106982 A1 | 4/2016 | Cakmak et al. |
| 2016/0121112 A1 | 5/2016 | Azar |
| 2016/0129273 A1 | 5/2016 | Park |
| 2016/0129274 A1 | 5/2016 | Park |
| 2016/0136462 A1 | 5/2016 | Lewis, Jr. et al. |
| 2016/0150494 A1 | 5/2016 | Tabet et al. |
| 2016/0151637 A1 | 6/2016 | Abe et al. |
| 2016/0158574 A1 | 6/2016 | Eckhouse et al. |
| 2016/0175193 A1 | 6/2016 | Jung |
| 2016/0184601 A1 | 6/2016 | Gleich et al. |
| 2016/0193466 A1 | 7/2016 | Burnett |
| 2016/0213924 A1 | 7/2016 | Coleman et al. |
| 2016/0220834 A1 | 8/2016 | Schwarz |
| 2016/0250494 A1 | 9/2016 | Sakaki et al. |
| 2016/0256702 A1 | 9/2016 | Schwarz et al. |
| 2016/0256703 A1 | 9/2016 | Schwarz et al. |
| 2016/0270951 A1 | 9/2016 | Martins et al. |
| 2016/0317346 A1 | 11/2016 | Kovach |
| 2016/0317827 A1 | 11/2016 | Schwarz et al. |
| 2016/0324684 A1 | 11/2016 | Levinson et al. |
| 2016/0346561 A1 | 12/2016 | Ron Edoute et al. |
| 2016/0354237 A1 | 12/2016 | Gonzales et al. |
| 2017/0001024 A1 | 1/2017 | Prouza |
| 2017/0001025 A1 | 1/2017 | Schwarz et al. |
| 2017/0001026 A1 | 1/2017 | Schwarz et al. |
| 2017/0001027 A1 | 1/2017 | Ladman et al. |
| 2017/0001028 A1 | 1/2017 | Ladman et al. |
| 2017/0001029 A1 | 1/2017 | Pribula et al. |
| 2017/0001030 A1 | 1/2017 | Pribula et al. |
| 2017/0007309 A1 | 1/2017 | Debenedictis et al. |
| 2017/0036019 A1 | 2/2017 | Matsushita |
| 2017/0043177 A1 | 2/2017 | Ron Edoute et al. |
| 2017/0050019 A1 | 2/2017 | Ron Edoute et al. |
| 2017/0072212 A1 | 3/2017 | Ladman et al. |
| 2017/0087373 A1 | 3/2017 | Schwarz |
| 2017/0100585 A1 | 4/2017 | Hall et al. |
| 2017/0105869 A1 | 4/2017 | Frangineas, Jr. |
| 2017/0106201 A1 | 4/2017 | Schwarz et al. |
| 2017/0106203 A1 | 4/2017 | Schneider et al. |
| 2017/0120067 A1 | 5/2017 | Prouza |
| 2017/0143958 A1 | 5/2017 | Shalev et al. |
| 2017/0156907 A1 | 6/2017 | Harris et al. |
| 2017/0173347 A1 | 6/2017 | Schwarz et al. |
| 2017/0182334 A1 | 6/2017 | Altshuler et al. |
| 2017/0182335 A1 | 6/2017 | Altshuler et al. |
| 2017/0189707 A1 | 7/2017 | Zabara |
| 2017/0196731 A1 | 7/2017 | Debenedictis et al. |
| 2017/0209708 A1 | 7/2017 | Schwarz |
| 2017/0239079 A1 | 8/2017 | Root et al. |
| 2017/0239467 A1 | 8/2017 | Shalev et al. |
| 2017/0259077 A1 | 9/2017 | Jin |
| 2017/0280889 A1 | 10/2017 | Koch |
| 2017/0304642 A1 | 10/2017 | Ron Edoute et al. |
| 2017/0319378 A1 | 11/2017 | Anderson et al. |
| 2017/0325992 A1 | 11/2017 | Debenedictis et al. |
| 2017/0325993 A1 | 11/2017 | Jimenez et al. |
| 2017/0326042 A1 | 11/2017 | Zeng et al. |
| 2017/0326346 A1 | 11/2017 | Jimenez et al. |
| 2017/0333705 A1 | 11/2017 | Schwarz |
| 2017/0348143 A1 | 12/2017 | Rosen et al. |
| 2017/0348539 A1 | 12/2017 | Schwarz et al. |
| 2017/0354530 A1 | 12/2017 | Shagdar et al. |
| 2017/0361095 A1 | 12/2017 | Mueller et al. |
| 2018/0000347 A1 | 1/2018 | Perez et al. |
| 2018/0001106 A1 | 1/2018 | Schwarz |
| 2018/0001107 A1 | 1/2018 | Schwarz et al. |
| 2018/0021565 A1 | 1/2018 | Dar et al. |
| 2018/0028831 A1 | 2/2018 | Ron Edoute et al. |
| 2018/0036548 A1 | 2/2018 | Nusse |
| 2018/0043151 A1 | 2/2018 | Ejiri et al. |
| 2018/0071544 A1 | 3/2018 | Ghiron et al. |
| 2018/0103991 A1 | 4/2018 | Linhart et al. |
| 2018/0125416 A1 | 5/2018 | Schwarz et al. |
| 2018/0133498 A1 | 5/2018 | Chornenky et al. |
| 2018/0153736 A1 | 6/2018 | Mills et al. |
| 2018/0153760 A1 | 6/2018 | Rosen et al. |
| 2018/0161197 A1 | 6/2018 | Baker et al. |
| 2018/0177996 A1 | 6/2018 | Gozani et al. |
| 2018/0185081 A1 | 7/2018 | O'Neil et al. |
| 2018/0185189 A1 | 7/2018 | Weber et al. |
| 2018/0214300 A1 | 8/2018 | Anderson et al. |
| 2018/0228646 A1 | 8/2018 | Gonzales et al. |
| 2018/0229048 A1 | 8/2018 | Sikora et al. |
| 2018/0236254 A1 | 8/2018 | Schwarz et al. |
| 2018/0250056 A1 | 9/2018 | Avram et al. |
| 2018/0263677 A1 | 9/2018 | Hilton et al. |
| 2018/0264245 A1 | 9/2018 | Edwards et al. |
| 2018/0271767 A1 | 9/2018 | Jimenez et al. |
| 2018/0296831 A1 | 10/2018 | Matsushita |
| 2018/0310950 A1 | 11/2018 | Yee et al. |
| 2018/0345012 A1 | 12/2018 | Schwarz et al. |
| 2018/0353767 A1 | 12/2018 | Biginton |
| 2019/0000524 A1 | 1/2019 | Rosen et al. |
| 2019/0000529 A1 | 1/2019 | Kothare et al. |
| 2019/0000663 A1 | 1/2019 | Anderson et al. |
| 2019/0029876 A1 | 1/2019 | Anderson et al. |
| 2019/0030356 A1 | 1/2019 | Schwarz |
| 2019/0053941 A1 | 2/2019 | Samson |
| 2019/0111255 A1 | 4/2019 | Errico et al. |
| 2019/0117965 A1 | 4/2019 | Iger et al. |
| 2019/0134414 A1 | 5/2019 | Prouza et al. |
| 2019/0151655 A1 | 5/2019 | Hall et al. |
| 2019/0168012 A1 | 6/2019 | Biginton |
| 2019/0183562 A1 | 6/2019 | Widgerow |
| 2019/0192219 A1 | 6/2019 | Kreindel |
| 2019/0192853 A1 | 6/2019 | Kim et al. |
| 2019/0192872 A1 | 6/2019 | Schwarz et al. |
| 2019/0192873 A1 | 6/2019 | Schwarz et al. |
| 2019/0192875 A1 | 6/2019 | Schwarz et al. |
| 2019/0201705 A1 | 7/2019 | Schwarz et al. |
| 2019/0201706 A1 | 7/2019 | Schwarz et al. |
| 2019/0209836 A1 | 7/2019 | Yakoub et al. |
| 2019/0255346 A1 | 8/2019 | Ghiron |
| 2019/0269909 A1 | 9/2019 | Gozani et al. |
| 2019/0275320 A1 | 9/2019 | Kim et al. |

(56) References Cited

U.S. PATENT DOCUMENTS

| | | | |
|---|---|---|---|
| 2019/0299018 A1 | 10/2019 | Chornenky et al. |
| 2019/0314629 A1 | 10/2019 | Kreindel |
| 2019/0314638 A1 | 10/2019 | Kreindel |
| 2019/0329065 A1 | 10/2019 | Gandel |
| 2019/0336783 A1 | 11/2019 | Sokolowski |
| 2019/0344091 A1 | 11/2019 | Fischer |
| 2019/0350646 A1 | 11/2019 | Kreindel |
| 2019/0365462 A1 | 12/2019 | Casalino et al. |
| 2019/0388698 A1 | 12/2019 | Schwarz et al. |
| 2020/0001103 A1 | 1/2020 | Schwarz et al. |
| 2020/0016422 A1 | 1/2020 | Ron Edoute et al. |
| 2020/0016423 A1 | 1/2020 | Ron Edoute et al. |
| 2020/0054890 A1 | 2/2020 | Schwarz et al. |
| 2020/0061385 A1 | 2/2020 | Schwarz et al. |
| 2020/0061386 A1 | 2/2020 | Schwarz et al. |
| 2020/0094066 A1 | 3/2020 | Heath |
| 2020/0114160 A1 | 4/2020 | Blendermann |
| 2020/0129759 A1 | 4/2020 | Schwarz |
| 2020/0139148 A1 | 5/2020 | Schwarz et al. |
| 2020/0155221 A1 | 5/2020 | Marchitto et al. |
| 2020/0171297 A1 | 6/2020 | Kirson et al. |
| 2020/0197696 A1 | 6/2020 | Nagel et al. |
| 2020/0206524 A1 | 7/2020 | Katznelson et al. |
| 2020/0237424 A1 | 7/2020 | Hunziker et al. |
| 2020/0281642 A1 | 9/2020 | Kreindel |
| 2020/0289838 A1 | 9/2020 | Schwarz et al. |
| 2020/0324133 A1 | 10/2020 | Schwarz et al. |
| 2020/0330782 A1 | 10/2020 | Zabara |
| 2020/0352633 A1 | 11/2020 | Treen et al. |
| 2020/0353244 A1 | 11/2020 | Yamazaki |
| 2020/0353273 A1 | 11/2020 | Zucco |
| 2020/0360681 A1 | 11/2020 | Lay |
| 2021/0008369 A1 | 1/2021 | Crosson |
| 2021/0038894 A1 | 2/2021 | Mowery et al. |
| 2021/0146150 A1 | 5/2021 | Frangineas, Jr. et al. |
| 2021/0275825 A1 | 9/2021 | Kreindel |
| 2021/0283395 A1 | 9/2021 | Kreindel |
| 2021/0361938 A1 | 11/2021 | Gershonowitz |

FOREIGN PATENT DOCUMENTS

| | | |
|---|---|---|
| AU | 2012244313 B2 | 11/2014 |
| AU | 2014203094 B2 | 7/2015 |
| AU | 2013207657 B2 | 11/2015 |
| BR | PI0812502 A2 | 6/2015 |
| CA | 2484880 A1 | 4/2006 |
| CA | 2604112 C | 7/2016 |
| CA | 3019140 A1 | 10/2017 |
| CA | 3019410 A1 | 10/2017 |
| CA | 3023821 A1 | 11/2017 |
| CH | 714113 A2 | 3/2019 |
| CN | 86204070 U | 9/1987 |
| CN | 87203746 U | 12/1987 |
| CN | 87215926 U | 7/1988 |
| CN | 1026953 C | 12/1994 |
| CN | 1027958 C | 3/1995 |
| CN | 2192348 Y | 3/1995 |
| CN | 1206975 C | 6/2005 |
| CN | 101234231 A | 8/2008 |
| CN | 101327358 A | 12/2008 |
| CN | 201906360 U | 7/2011 |
| CN | 102319141 A | 1/2012 |
| CN | 102711706 A | 10/2012 |
| CN | 102847231 A | 1/2013 |
| CN | 202637725 U | 1/2013 |
| CN | 203169831 U | 9/2013 |
| CN | 102319141 B | 8/2014 |
| CN | 106540375 A | 3/2017 |
| CN | 107613914 A | 1/2018 |
| CN | 108882992 A | 11/2018 |
| CN | 109310516 A | 2/2019 |
| CN | 112221015 A | 1/2021 |
| DE | 718637 C | 3/1942 |
| DE | 1118902 B | 12/1961 |
| DE | 2748780 A1 | 5/1978 |
| DE | 3205048 A1 | 8/1983 |
| DE | 3340974 A1 | 5/1985 |
| DE | 3610474 A1 | 10/1986 |
| DE | 3825165 A1 | 1/1990 |
| DE | 3340974 C2 | 7/1994 |
| DE | 69318706 T2 | 1/1999 |
| DE | 10062050 A1 | 4/2002 |
| DE | 102004006192 A1 | 9/2005 |
| DE | 60033756 T2 | 6/2007 |
| DE | 102009023855 A1 | 12/2010 |
| DE | 102009050010 A1 | 5/2011 |
| DE | 102010004307 A1 | 7/2011 |
| DE | 102011014291 A1 | 9/2012 |
| DE | 102013211859 B4 | 7/2015 |
| DE | 102016116399 A1 | 3/2018 |
| DE | 202016008884 U1 | 7/2020 |
| DE | 102010014157 B4 | 2/2021 |
| DK | 0633008 T3 | 3/1999 |
| EA | 000494 B1 | 8/1999 |
| EA | 002087 B1 | 12/2001 |
| EA | 002179 B1 | 2/2002 |
| EA | 003851 B1 | 10/2003 |
| EA | 007347 B1 | 8/2006 |
| EA | 007975 B1 | 2/2007 |
| EP | 0048451 A1 | 3/1982 |
| EP | 0209246 A1 | 1/1987 |
| EP | 0459101 A1 | 12/1991 |
| EP | 0459401 A1 | 12/1991 |
| EP | 0633008 A1 | 1/1995 |
| EP | 0788813 A1 | 8/1997 |
| EP | 0633008 B1 | 5/1998 |
| EP | 0692993 B1 | 9/1999 |
| EP | 1022034 A1 | 7/2000 |
| EP | 1916013 A1 | 4/2008 |
| EP | 2124800 B1 | 11/2010 |
| EP | 1917935 B1 | 1/2011 |
| EP | 2308559 A2 | 4/2011 |
| EP | 2139560 | 5/2012 |
| EP | 2461765 A1 | 6/2012 |
| EP | 2069014 B1 | 6/2013 |
| EP | 2614807 A1 | 7/2013 |
| EP | 2676700 A2 | 12/2013 |
| EP | 2694159 A2 | 2/2014 |
| EP | 2749259 A1 | 7/2014 |
| EP | 2814445 A1 | 12/2014 |
| EP | 2856986 A1 | 4/2015 |
| EP | 3009167 A1 | 4/2016 |
| EP | 2501352 B1 | 7/2016 |
| EP | 3209246 A1 | 8/2017 |
| EP | 3342379 A1 | 7/2018 |
| EP | 3389532 A1 | 10/2018 |
| EP | 3434323 A1 | 1/2019 |
| EP | 3721939 A1 | 10/2020 |
| ES | 2118925 T3 | 10/1998 |
| ES | 2300569 T3 | 6/2008 |
| ES | 2305698 T3 | 11/2008 |
| ES | 2359581 T3 | 5/2011 |
| ES | 2533145 A2 | 4/2015 |
| ES | 2533145 B1 | 7/2016 |
| ES | 2533145 R1 | 10/2018 |
| FR | 3041881 A1 | 4/2017 |
| FR | 3061012 A1 | 6/2018 |
| GB | 260116 A | 10/1926 |
| GB | 304587 A | 3/1930 |
| GB | 390500 A | 4/1933 |
| GB | 871672 A | 6/1961 |
| GB | 2188238 A | 9/1987 |
| GB | 2176009 B | 12/1989 |
| GB | 2261820 A | 6/1993 |
| GB | 2286660 A | 8/1995 |
| GB | 2395907 B | 12/2004 |
| GB | 2504984 A | 2/2014 |
| GB | 2521240 A | 6/2015 |
| GB | 2552004 A | 1/2018 |
| GR | 3027678 T3 | 11/1998 |
| IT | 1217550 B | 3/1990 |
| IT | RE20120010 A1 | 8/2013 |
| IT | UB20159823 A1 | 7/2017 |
| JP | 2003305131 A | 10/2003 |

(56) References Cited

FOREIGN PATENT DOCUMENTS

| | | |
|---|---|---|
| JP | 2006130055 A | 5/2006 |
| JP | 4178762 B2 | 11/2008 |
| JP | 4324673 B2 | 9/2009 |
| JP | 2010207268 A | 9/2010 |
| JP | 2010533054 A | 10/2010 |
| JP | 2011194176 A | 10/2011 |
| JP | 2013063285 A | 4/2013 |
| JP | 2017518857 A | 7/2017 |
| JP | 2018501927 A | 1/2018 |
| JP | 2018018650 A | 2/2018 |
| KR | 20030065126 A | 8/2003 |
| KR | 100484618 B1 | 4/2005 |
| KR | 100491988 B1 | 5/2005 |
| KR | 200407524 Y1 | 1/2006 |
| KR | 100556230 B1 | 3/2006 |
| KR | 200410065 Y1 | 3/2006 |
| KR | 100841596 B1 | 6/2008 |
| KR | 20090063618 A | 6/2009 |
| KR | 20090095143 A | 9/2009 |
| KR | 100936914 B1 | 1/2010 |
| KR | 1020100026107 A | 3/2010 |
| KR | 101022244 B1 | 3/2011 |
| KR | 20110123831 A | 11/2011 |
| KR | 20120037011 A | 4/2012 |
| KR | 101233286 B1 | 2/2013 |
| KR | 101233287 B1 | 2/2013 |
| KR | 20130072244 A | 7/2013 |
| KR | 101292289 B1 | 8/2013 |
| KR | 20130128391 A | 11/2013 |
| KR | 101413022 B1 | 7/2014 |
| KR | 101415141 B1 | 7/2014 |
| KR | 101447532 B1 | 10/2014 |
| KR | 101511444 B1 | 4/2015 |
| KR | 20150058102 A | 5/2015 |
| KR | 101539633 B1 | 7/2015 |
| KR | 20150079619 A | 7/2015 |
| KR | 20150106379 A | 9/2015 |
| KR | 101650155 B1 | 8/2016 |
| KR | 101673182 B1 | 11/2016 |
| KR | 20170090654 A | 8/2017 |
| KR | 20170107603 A | 9/2017 |
| KR | 101794269 B1 | 11/2017 |
| KR | 20180059114 A | 6/2018 |
| KR | 20180092020 A | 8/2018 |
| KR | 101941863 B1 | 1/2019 |
| KR | 20190005981 A | 1/2019 |
| KR | 102000971 B1 | 7/2019 |
| KR | 20190001779 U | 7/2019 |
| KR | 200491572 Y1 | 5/2020 |
| KR | 20200000889 U | 5/2020 |
| KR | 20200052602 A | 5/2020 |
| KR | 20200056692 A | 5/2020 |
| KR | 20200056693 A | 5/2020 |
| KR | 20200056801 A | 5/2020 |
| KR | 20200056802 A | 5/2020 |
| KR | 20200057154 A | 5/2020 |
| KR | 20210002973 A | 1/2021 |
| KR | 20210002974 A | 1/2021 |
| MX | 2012012158 A | 4/2014 |
| NL | 7510644 A | 3/1977 |
| NL | 1037451 B2 | 5/2011 |
| RU | 2212909 C2 | 9/2003 |
| RU | 2226115 C2 | 3/2004 |
| RU | 2281128 C2 | 8/2006 |
| RU | 2373971 C2 | 11/2009 |
| RU | 2392979 C2 | 6/2010 |
| RU | 2395267 C2 | 7/2010 |
| RU | 2496532 C2 | 10/2013 |
| RU | 2529471 C2 | 9/2014 |
| RU | 2596053 C2 | 8/2016 |
| RU | 2637104 C2 | 11/2017 |
| RU | 2645923 C2 | 2/2018 |
| SI | 24921 A | 8/2016 |
| TW | 200423986 A | 11/2004 |
| WO | WO-9312835 A1 | 7/1993 |
| WO | WO-9521655 A1 | 8/1995 |
| WO | WO9527533 A1 | 10/1995 |
| WO | WO-9932191 A1 | 7/1999 |
| WO | WO-0013749 A1 | 3/2000 |
| WO | WO-0044346 A1 | 8/2000 |
| WO | WO-0107111 A2 | 2/2001 |
| WO | WO-0112089 A1 | 2/2001 |
| WO | WO-0193797 A2 | 12/2001 |
| WO | WO-0225675 A1 | 3/2002 |
| WO | WO-03078596 A2 | 9/2003 |
| WO | WO 03079916 A1 | 10/2003 |
| WO | WO-03090863 A1 | 11/2003 |
| WO | WO-03103769 A1 | 12/2003 |
| WO | WO-2004078255 A1 | 9/2004 |
| WO | WO-2004087255 A1 | 10/2004 |
| WO | WO-2004095385 A2 | 11/2004 |
| WO | WO-2004095835 A1 | 11/2004 |
| WO | WO-2004096343 A2 | 11/2004 |
| WO | WO-2004108211 A1 | 12/2004 |
| WO | WO-2005032660 A1 | 4/2005 |
| WO | WO-2005107866 A1 | 11/2005 |
| WO | WO-2006115120 A1 | 11/2006 |
| WO | WO-2007096206 A1 | 8/2007 |
| WO | WO-2007140584 A1 | 12/2007 |
| WO | WO-2008012827 A2 | 1/2008 |
| WO | WO-2008049775 A1 | 5/2008 |
| WO | WO 2008060494 A2 | 5/2008 |
| WO | WO-2008109058 A1 | 9/2008 |
| WO | WO-2008127011 A2 | 10/2008 |
| WO | WO-2008145260 A2 | 12/2008 |
| WO | WO 2009011708 A1 | 1/2009 |
| WO | WO-2009013729 A2 | 1/2009 |
| WO | WO-2009036040 A1 | 3/2009 |
| WO | WO-2009042863 A1 | 4/2009 |
| WO | WO-2009044400 A2 | 4/2009 |
| WO | WO-2009047628 A2 | 4/2009 |
| WO | WO-2009083915 A2 | 7/2009 |
| WO | WO-2010007614 A2 | 1/2010 |
| WO | WO 2010022278 A1 | 2/2010 |
| WO | WO-2010007614 A3 | 5/2010 |
| WO | WO-2010135425 A1 | 11/2010 |
| WO | WO-2010139376 A1 | 12/2010 |
| WO | WO-2011011749 A1 | 1/2011 |
| WO | WO-2011016019 A1 | 2/2011 |
| WO | WO 2011021184 A1 | 2/2011 |
| WO | WO-2011045002 A1 | 4/2011 |
| WO | WO-2011053607 A1 | 5/2011 |
| WO | WO-2011058565 A2 | 5/2011 |
| WO | WO-2011156495 A2 | 12/2011 |
| WO | WO-2012005766 A1 | 1/2012 |
| WO | WO-2012029065 A2 | 3/2012 |
| WO | WO-2012040243 A1 | 3/2012 |
| WO | WO-2012073232 A1 | 6/2012 |
| WO | WO-2012103632 A1 | 8/2012 |
| WO | WO-2012119293 A1 | 9/2012 |
| WO | WO-2012138169 A2 | 10/2012 |
| WO | WO-2013021380 A1 | 2/2013 |
| WO | WO-2013026393 A1 | 2/2013 |
| WO | WO-2013035088 A1 | 3/2013 |
| WO | WO-2013074576 A2 | 5/2013 |
| WO | WO-2013098815 A1 | 7/2013 |
| WO | WO-2013191699 A1 | 12/2013 |
| WO | WO 2014009875 A2 | 1/2014 |
| WO | WO-2014016820 A2 | 1/2014 |
| WO | WO-2014109653 A1 | 7/2014 |
| WO | WO-2014137344 A1 | 9/2014 |
| WO | WO-2014141229 A1 | 9/2014 |
| WO | WO-2014149021 A2 | 9/2014 |
| WO | WO-2014151431 A2 | 9/2014 |
| WO | WO-2014163020 A1 | 10/2014 |
| WO | WO-2014164926 A1 | 10/2014 |
| WO | WO-2015004540 A1 | 1/2015 |
| WO | WO-2015012639 A1 | 1/2015 |
| WO | WO-2015012672 A1 | 1/2015 |
| WO | WO-2015052705 A1 | 4/2015 |
| WO | WO-2015083305 A1 | 6/2015 |
| WO | WO-2015137733 A1 | 9/2015 |
| WO | WO-2015157725 A1 | 10/2015 |
| WO | WO-2015179571 A1 | 11/2015 |

(56) References Cited

FOREIGN PATENT DOCUMENTS

| | | |
|---|---|---|
| WO | WO-2016116747 A1 | 7/2016 |
| WO | WO-2016140871 A1 | 9/2016 |
| WO | WO-2017002065 A1 | 1/2017 |
| WO | WO-2017103923 A1 | 6/2017 |
| WO | WO-2017159959 A1 | 9/2017 |
| WO | WO-2017160097 A2 | 9/2017 |
| WO | WO-2017176621 A1 | 10/2017 |
| WO | WO-2017196548 A1 | 11/2017 |
| WO | WO-2017212253 A1 | 12/2017 |
| WO | WO-2018006086 A1 | 1/2018 |
| WO | WO-2018008023 A1 | 1/2018 |
| WO | WO-2018044825 A1 | 3/2018 |
| WO | WO-2018121998 A2 | 7/2018 |
| WO | WO-2018122535 A1 | 7/2018 |
| WO | WO-2017160097 A3 | 9/2018 |
| WO | WO-2018208992 A1 | 11/2018 |
| WO | WO-2019120420 A1 | 6/2019 |
| WO | WO-2019150378 A1 | 8/2019 |
| WO | WO-2019166965 A1 | 9/2019 |
| WO | WO-2019173866 A1 | 9/2019 |
| WO | WO-2019183622 A1 | 9/2019 |
| WO | WO-2020002801 A1 | 1/2020 |
| WO | WO-2020035852 A2 | 2/2020 |
| WO | WO-2020041502 A1 | 2/2020 |
| WO | WO-2020142470 A1 | 7/2020 |
| WO | WO-2020144486 A1 | 7/2020 |
| WO | WO-2020174444 A1 | 9/2020 |
| WO | WO-2020183508 A1 | 9/2020 |
| WO | WO-2020190514 A1 | 9/2020 |
| WO | WO-2020208590 A1 | 10/2020 |
| WO | WO-2020264263 A1 | 12/2020 |
| WO | WO-2021013654 A1 | 1/2021 |
| WO | WO-2021102365 A1 | 5/2021 |

OTHER PUBLICATIONS

2018 Cutera University, Clinical Forum, Cutera 20, 26 pages.
Abulhasan, J.F., et al., "Peripheral Electrical and Magnetic Stimulation to Augment Resistance Training," Journal of Functional Morphology and Kinesiology, 1(3):328-342, (Sep. 2016).
Accent Radiofrequency System, Operator's Manual, Alma Lasers, Wellbeing Through Technology, 2008, 82 Pages.
Avram, M.M and Harry, R.S., "Cryolipolysis for Subcutaneous Fat Layer Reduction," Lasers in Surgery and Medicine, 41(10):703-708, Wiley-Liss, United States (Dec. 2009).
Bachasson, D., et al., "Quadriceps Function Assessment Using an Incremental Test and Magnetic Neurostimulation: a Reliability Study," Journal of Electromyography and Kinesiology, 23(3):649-658, Elsevier, England, (Jun. 2013).
Baranov, A., Krion, Whole Body Cryotherapy, Russia, 19 Pages.
Barker, A.T, "An Introduction to the Basic Principles of Magnetic Nerve Stimulation," Journal of Clinical Neurophysiology, 8(1):26-37, Lippincott Williams & Wilkins, United States, (Jan. 1991).
Basic Protocol of Salus, Talent with Incontinence Chair, REMED, 1 page.
Behrens, M., et al., "Repetitive Peripheral Magnetic Stimulation (15 Hz RPMS) of the Human Soleus Muscle did not Affect Spinal Excitability," Journal of Sports Science and Medicine, 10(1):39-44, Dept. of Sports Medicine, Medical Faculty of Uludag University, Turkey (Mar. 2011).
Beilin, G., et al., "Electromagnetic Fields Applied to the Reduction of Abdominal Obesity," Journal of Cosmetic & Laser Therapy, 14(1):24-42, Informs Healthcare, England, (Feb. 2012).
Buenos Aires, Oct. 14, 2014, Venus Concept, Provision No. 7246, 56 pages (With Machine Translation).
Burge, S.M and Dawber, R.P., "Hair Follicle Destruction and Regeneration in Guinea Pig Skin After Cutaneous Freeze Injury," Cryobiology, 27(2):153-163, Elsevier, Netherlands (Apr. 1990).
Bustamante, V., et al., "Muscle Training With Repetitive Magnetic Stimulation of the Quadriceps in Severe COPD Patients," Respiratory Medicine, 104(2):237-245, Elsevier, England, (Feb. 2010).

Bustamante, V., et al., "Redox Balance Following Magnetic Stimulation Training in the Quadriceps of Patients With Severe COPD," Free Radical Research, 42(11-12):939-948, Informa Healthcare, England, (Nov. 2008).
Caress, J.B., et al., "A Novel Method of Inducing Muscle Cramps Using Repetitive Magnetic Stimulation," Muscle Nerve, 23(1):126-128, John Wiley & Sons, United States, (Jan. 2000).
Chesterton, L.S., et al., "Skin Temperature Response to Cryotherapy,"Archives of Physical Medicine and Rehabilitation, 83(4):543-549, W.B. Saunders, United States (Apr. 2002).
Clinical Application of Electro Magnetic Stimulation, Salus-Talent, Korea Society of interventional Muscle and Soft Tissue Stimulation Therapy, CR Technology, 141 pages.
Course in Physical Therapy, Presentation, Jan. 4, 2013, 156 pages.
CR Technology, Salus-Talent, Technical File of Electro-magnetic Stimulator, Document No. TF-C05, 2008, 241 pages.
CR Technology, Technology for Health and Business for Human Being, investor relations, 2008, 21 pages.
CryoGenTech GmbH, Company Profile, Creating CRYO, Medica, 9 pages.
CynoSure, SculpSure TM, The New Shape of Energy-Based body Contouring, 2015, Cynosure Inc, 2 pages.
CYNOSURE, Smooth Shapes XV, Now with Smoothshape petite, Transforming non-invasive Body Shaping, Retrieved from the Internet: (http://www.cynosure.com), 2011, Cynosure Inc, 8 pages.
DuoMAG Magnetic Stimulator, Alien Technik User Manuel, Jun. 26, 2012, 48 pages, Version 2.1.
Dybek, T., et al., "Impact of 10 Sessions of Whole Body Cryostimulation on Aerobic and Anaerobic Capacity and on Selected Blood Count Parameters," Biology of Sport, 29(1):39-43 (Jan. 2012).
Effective PEMF Magnetic Fat Reduction Slimming Body Beauty Salon Machine (PEMF Star), Wolfbeauty 1980, PEMF Star, China, Retrieved from the Internet: (URL: https://www.ec21.com/product-details/Effective-PEMF-Magnetic-Fat-Reduction--8928746.html), 2019, 5 pages.
Eliminate Stubborn Fat without Surgery or Downtime and Feel Great From Every Angle, Fear No Mirror®, Consultation Guide, Coolsculpting, 2014, 20 pages.
EndyMed PRO, 3 Deep, 3 Dimensional Control of the Target Zone, A Brilliant RadioFrequency Innovation, Eclipse Aesthetics, 7 Pages.
European Commission, "Neurogenerative Disorders," 10 pages printed Dec. 27, 2016.
European Patent Office, International Search Report and Written Opinion for International Application No. PCT/162016/053930, dated Dec. 12, 2016, 19 pages.
Exilis, Operator's Manual, BTL, 2012, 44 Pages.
FMS Tesla Stym—AKCE, Medila Cenova nabidika, Price offer c. 191, 24 pages.
Fisher, Robert S. et al., "A practical clinical definition of epilepsy", Epilepsia, 55(4): pp. 475-482 (2014).
Goetz, S.M., et al., "Coil Design for Neuromuscular Magnetic Stimulation Based on a Detailed 3-D Thigh Model," IEEE Transactions on Magnetics, 50(6):10, IEEE, (Jun. 2014).
Gorodnichev, R.M., "Magnetic Stimulation of Muscles as New Method to Enhance Their Strength," Velikie Luki State Academy of Physical Culture and Sport, Velikie Luki, 2016, 5 pages.
Hamnegard, C.H., et al., "Quadriceps Strength Assessed by Magnetic Stimulation of the Femoral Nerve in Normal Subjects," Clinical Physiology and Functional Imaging, 24(5):276-280, Blackwell, England, (Sep. 2004).
Han, T.R., et al., "Magnetic Stimulation of the Quadriceps Femoris Muscle: Comparison of Pain With Electrical Stimulation," American Journal of Physical Medicine & Rehabilitation, 85(7):593- 599, Lippincott Williams & Wilkins, United States, (Jul. 2006).
Hasala, O., et al., Case Study of Treating Acute Ankle Distortion Using TMS, Charles University, Faculty of Physical Education and Sports, Prague, Czech Republic, 4 Pages.
Heisel, Jurgen, Physikalische Medizin, Stuttgart: Georg Thieme Verlag KG, 2005. ISBN 3-13-139881-7. p. 159.
Hirvonen, H.E., et al., "Effectiveness of Different Cryotherapies on Pain and Disease Activity in Active Rheumatoid Arthritis. A Randomised

(56) References Cited

OTHER PUBLICATIONS

Single Blinded Controlled Trial," Clinical and Experimental Rheumatology, 24(3):295-301, Clinical and Experimental Rheumatology S.A. S, Italy (May-Jun. 2006).

I-Lipo by Chromo genex, i-Lipo Ultra is the Intelligent, Non-Surgical Alternative to Liposuction, 2011, 2 pages.

Increasing Physiotherapy Presence in Cosmetology, Spa Inspirations, Jan. 2012, pp. 34-35.

Iskra Medical, Magneto System, 2012, 2 pages.

Izumiya, et al., "Fast/Glycolytic Muscle Fiber Growth Reduces Fat Mass and Improves Metabolic Parameters in Obese Mice," Cell Metab. Feb. 2008: 7(2): 159-172.

Jeanrenaud, B., "Lipid components of adipose tissue," Handbook of Physiology, Adipose Tissue, Chapter 15, 8 Pages.

Jutte, L.S., et al., "The Relationship Between Intramuscular Temperature, Skin Temperature, and Adipose Thickness During Cryotherapy and Rewarming," Archives of Physical Medicine and Rehabilitation, 82(6):845-850, W.B. Saunders, United States (Jun. 2001).

Katuscakova, Z.L., et al., High Induction Magnet Therapy in Rehabilitation, Department of Physiactric Rehabilitation, 2012, 72 pages.

Kim, Y.H., et al., "The Effect of Cold Air Application on Intra-Articular and Skin Temperatures in the Knee," Yonsei Medical Journal, 43(5):621-626, Yonsei University, Korea (South) (Oct. 2002).

Korman, P., et al., "Temperature Changes in Rheumatoid Hand Treated With Nitrogen Vapors and Cold Air," Rheumatology International, 32(10):2987-2992, Springer International, Germany (Oct. 2012).

Lampropoulou, S.I., et al., "Magnetic Versus Electrical Stimulation in the Interpolation Twitch Technique of Elbow Flexors," Journal of Sports Science and Medicine, 11(4):709-718, Dept. of Sports Medicine, Medical Faculty of Uludag University, Turkey (Dec. 2012).

Letter from Department of Health and Human Services, Public Health Service, Dec. 19, 2014, 7 pages.

Lin, V.W., et al., "Functional Magnetic Stimulation: A New Modality for Enhancing Systemic Fibrinolysis," Archives of Physical Medicine and Rehabilitation 80(5):545-550, W.B. Saunders, United States (May 1999).

Lin, V.W., et al., "Functional Magnetic Stimulation for Restoring Cough in Patients With Tetraplegia," Archives of Physical Medicine and Rehabilitation, 79(5):517-522, W.B. Saunders, United States, (May 1998).

Lin, V.W., et al., "Functional Magnetic Stimulation of Expiratory Muscles: a Noninvasive and New Method for Restoring Cough," Journal of Applied Physiology (1985), 84(4):1144-1150, American Physiological Society, United States, (Apr. 1998).

Lineham, Christine et al., Brainwave the Irish Epilepsy Assoication, "The Prevalence of Epilepsy in Ireland" Summary Report, pp. 1-8 (May 2009).

Madariaga, V.B., et al., "[Magnetic Stimulation of the Quadriceps: Analysis of 2 Stimulators Used for Diagnostic and Therapeutic Applications]," Archivos De Bronconeumologia, 43(7):411- 417, Elsevier Espana, Spain, (Jul. 2007).

Mag and More Gmbh, Magnetic and Life Science System, Power Mag, 12 Pages.

Mag Expert, 2 pages.

Mag Venture, Magnetic Stimulation, Accessories Catalogue, Accessories Catalogue, 2011, 54 pages.

MagVenture, MagPro® by MagVenture®, Versatility in Magnetic Stimulation, World Leading Transcranial Magnetic Stimulation Systems, 2011, 6 Pages.

Manstein, D., et al., "Selective Cryolysis: A Novel Method of Non-Invasive Fat Removal," Lasers in Surgery and Medicine, 40(9):595-604, Wiley-Liss, United States (Nov. 2008).

MecoTec Freezing Technology, Presentation Cryoair Whole Body Cryotherapy Chambers, Germany, Jul. 2017, 52 pages.

Medline, Body Temperature Norms, 2 pages (Year: 2019).

Mulholland, R.S., Synergistic Multi-polar Radiofrequency and Pulsed Magnetic Fields in the Non-Invasive Treatment of Skin Laxity and Body Contouring, 4 pages.

Nadler, S.F., et al., "The Physiologic Basis and Clinical Applications of Cryotherapy and Thermotherapy for the Pain Practitioner," Pain Physician, 7(3):395-399, American Society of Interventional Pain Physicians, United States (Jul. 2004).

Nassab, R., "The Evidence Behind Noninvasive Body Contouring Devices," Aesthetic Surgery Journal, 35(3):279-293, Oxford University Press, England (Mar. 2015).

National Institute of Neurological Disorders and Stroke, Epilepsy Information Page, www.ninds. iih.gov/disorders/epilepsy/epilepsy. htm, pp. 1-6 (Feb. 1, 2016).

Neuro Star, TMS Therapy, Bringing Hope to Patients with Depression, 2013, 6 Pages.

Neurosoft, Ivanovo, Since 1992, Magnetic Stimulator, NEURO-MS, Technical Manual, Neurosoft Ltd, Ivanovo, Russia, 2006, 67 Pages.

Nexstim NBS System, Navigated Brain Stimulation, Noninvasive, direct cortical mapping, 2012, 5 Pages.

Non Final Office Action dated Jun. 23, 2017, in U.S. Appl. No. 15/473,390, Schwarz, T., et al., filed Mar. 29, 2017.

Obsluze, N.K.,Usage Instructions, User's Manual, Device for high-induction magnetic stimulation of type designation:Saluter Moti, 2016, 88 Pages.

Operating Manual: Magstim $D70^2$ Coil, MOP06-EN, Revision 01, The Magstim Company Limited, Feb. 2012, 14 Pages.

Operating Manual: Magstim Magstim $200^2$, MOP01-EN, Revision 01, The Magstim Company Limited, Sep. 2011, 25 Pages.

Operating Manual: Magstim, Magstim Alpha Coil Range, MOP11-EN, Revision 01, Oct. 2012, 18 Pages.

Operating Manual: Magstim, Magstim $Bistim^2$, MOP02-EN, Revision, The Magstim Company Limited, 01, Sep. 2011, 27 Pages.

Operating Manual, Magstim, Model 200, P/N 3001-01, Double 70mm, Remote Coil, P/N 3190-00, The Magstim Company Limited, 2006, 32 pages.

Operating Manual: Magstim R, 2nd, Generation Coil Family, 3100-23-02, Magstim Coils, The Magstim Company Limited, Nov. 2002, 14 Pages.

Operating Manual, Magstim R Air-Cooled Double 70mm Coil System, 1600-23-04, The Magstim Company Limited, 1999, 18 Pages.

Operating Manual: Magstim R, Bistim System, P/N 3234-23-01, The Magstim Company Limited, Nov. 2004, 30 Pages.

Operating Manual: Magstim R, Coils & Accessories, 1623-23-07, Magstim Coils & Accessories, May 2010, 24 Pages.

Operating Manual: Magstim, RAPID2, P/N 3576-23-09, The Magstim Company Ltd, Nov. 2009, 61 Pages.

Operator's Manual: BTL EMSCULPT, BTL Industries Ltd, United Kingdom, 2018, 35 pages.

Operator'S Manual: BTL, HPM-6000U, BTL Industries Ltd, United Kingdom, Dec. 2016, 36 pages.

Otte, J.S., et al., "Subcutaneous Adipose Tissue Thickness Alters Cooling Time During Cryotherapy," Archives of Physical Medicine and Rehabilitation, 83(11):1501-1505, W.B. Saunders, United States (Nov. 2002).

Papimi, For Scientific Research, Pap Ion Magnetic Inductor, Presentation, Magnetotherapeutic Device, Nov. 2009, 61 Pages.

Periso SA, CTU mega Diamagnetic Pump 20: Device for Diamagnetic Therapy, CTU Mega 20 Manual, dated Aug. 28, 2019, 44 pages, Pazzallo Switzerland.

Physiomed, MAG-Expert, Physiomed Manual, Dec. 19, 2012.

Physiomed, Physiomed Mag-Expert, Physiomed Catalog, pp. 81-83.

Podebradsky.K., et al., Clinical study of high-inductive electromagnetic stimulator SALUS talent, 2010, 8 pages.

Polk, C., "Therapeutic Applications of Low-Frequency Sinusoidal and Pulsed Electric and Magnetic Fields," The Biomedical Engineering Handbook, vol. 1, 2000, Second edition, CRC Press LLC, pp. 1625-1636.

Polkey M.I., et al., "Functional Magnetic Stimulation of the Abdominal Muscles in Humans," American Journal of Respiratory and Critical Care Medicine, 160(2):513-522, American Thoracic Society, United States (Aug. 1999).

(56) References Cited

OTHER PUBLICATIONS

Polkey, M.I., et al., "Quadriceps Strength and Fatigue Assessed by Magnetic Stimulation of the Femoral Nerve in Man," Muscle Nerve, 19(5):549-555, John Wiley & Sons, United States, (May 1996).
Quick Start Manuals, Magstim Super Rapid Plus Quick Start, Aalto TMS Laboratory, Aalto School of Science, 2013, 7 Pages.
Reaction User Manual, Viora, Doc No. MK-004 A, 2008, 53 Pages.
Reshaping the Future of Your Practice, Cool sculpting, A Revolution in Aesthetic Fat Reduction, 2011, 10 Pages.
Salus Talent, a Vertice and Talos, Drott, 6 pages.
Salus Talent, Deep Penetrating Electro-Magnetic Stimulator, CR Technology, 4 pages.
Salus Talent, Deep Penetrating Electro-Magnetic Stimulator, Rehabilitation Medical Company, New choice, new satisfaction, Talent, 4 pages.
Salus Talent, Electro Magnetic Stimulator, CR Technology, 9 Pages.
Salus Talent Pro, Specification, 2 pages.
Salus, Talent Pro, The Birth of Salus Talent Pro inspired by 10 Years of Experience, Specification, Rehabilitation Medical Company, Slimon, 2 pages.
Salus, Talent Pro, The World's 1st Development 3 Tesla, 2Channel Magnetic field Therapy, Slimon, 10 pages.
Salus Talent-A, REMED, User Guide, High Intensity Electro Magnetic Field Therapy, 2017, 37 pages.
Salus Talent-Pop Double, 1 page.
Salus-Talent, Device for Deep Electromagnetic Stimulation, Nowosc, Fizjoterapia, 6 Pages.
Scientific & Clinical Background of (MP)2®—A synergy between Multi polar RF and Pulsed Magnetic Field developed by Venus Concept. Prof. Yeouda Edoute M.D, Ph,D, 2 pages.
Starbelle, PEMF Shape, Webpage, dated Feb. 10, 2020, 3 pages, available at http://www.starbelle.cn/info/PEMFShape.html.
Szecsi, J., et al., "A Comparison of Functional Electrical and Magnetic Stimulation for Propelled Cycling of Paretic Patients," Archives of Physical Medicine and Rehabilitation, 90(4):564-570, W.B. Saunders, United States, (Apr. 2009).
Szecsi, J., et al., "Force-pain Relationship in Functional Magnetic and Electrical Stimulation of Subjects With Paresis and Preserved Sensation," Clinical Neurophysiology, 121(9):1589-1597, Elsevier, Netherlands, (Sep. 2010).
Taylor, J.L, "Magnetic Muscle Stimulation Produces Fatigue Without Effort," Journal of Applied Physiology (1985), 103(3):733-734, American Physiological Society, United States, (Sep. 2007).
Tesla Stym, Iskra Medical, Tone the inner muscle with FMS Functional Magnetic Stimulation, 2013, 4 pages.
The Burn Centre Care, Education, 3 pages, printed from internet Nov. 13, 2017.
Thermi Smooth TM 250, High Power Temperature Controlled Radio Frequency, Thermi Aesthetics, 25 pages.
TSEM Med Swiss SA, Diamagnetic Therapy: A Revolutionary Therapy, CTU Mega 20 Catalogue, dated 2016, 24 pages, Lugano Switzerland.
Ultra Slim Professional, The very best body Contouring, Wardphotonics LLC, 2018, 16 pages.
Unique Multi-Treatment Platform for, Feminine Health, Venus Fiore, 12 pages.
Urban J., "Magnetotherapy and Physiotherapy", 40 pages.
Uro Diagnostic Clinic, Now in Udc, Automated pelvic floor muscle training, Qrs International Ag, 16 pp.. 0.
U.S. Appl. No. 62/331,060, inventor Schwarz, T., filed May 3, 2016 (Not Published).
U.S. Appl. No. 62/331,072, inventor Schwarz, T., filed May 3, 2016 (Not Published).
U.S. Appl. No. 62/331,088, inventor Schwarz, T., filed May 3, 2016 (Not Published).
U.S. Appl. No. 62/333,666, inventor Schwarz, T., filed May 9, 2016 (Not Published).
U.S. Appl. No. 62/357,679, inventor Schwarz, T., filed Jul. 1, 2016 (Not Published).
U.S. Appl. No. 62/440,905, inventors Schwarz, T. et al., filed Dec. 30, 2016 (Not Published).
U.S. Appl. No. 62/440,912, inventors Schwarz, T. et al., filed Dec. 30, 2016 (Not Published).
U.S. Appl. No. 62/440,922, inventor Schwarz, T., filed Dec. 30, 2016 (Not Published).
U.S. Appl. No. 62/440,936, inventor Schwarz, T., filed Dec. 30, 2016 (Not Published).
U.S. Appl. No. 62/440,940, inventor Schwarz, T., filed Dec. 30, 2016 (Not Published).
U.S. Appl. No. 62/441,805, inventor Prouza, O., filed Jan. 3, 2017 (Not Published).
U.S. Appl. No. 62/786,731, inventor Schwarz, T., filed Dec. 31, 2018 (Not Published).
U.S. Appl. No. 62/351,156, inventor Schwarz, T., filed Jun. 16, 2016 (Not Published).
User Guide: Mag Venture, Magpro family, MagPro R30, MagPro R30 with MagOption, MagPro X100, MagPro X100 with MagOption, MagPro software v.5.0, US-edition, MagPro family User Guide, 2010, 52 Pages.
User Guide, Salus Talent Pro, REMED, High Intensity Electro magnetic Field Therapy—2 Channel, 2017, Version M-1.0.0, 45 pages.
User Guide, Salus Talent, REMED, High Intensity Electro magnetic Field Therapy, Version. M-1.0.0, 2017, 40 pages.
User's Manual: BTL-6000, Super Inductive System Elite, BBTL Industries Ltd, United Kingdom, Sep. 2016, 36 pages.
User Manual: Electro-magnetic Stimulator, Salus-Talent, Version 1.00, Rehabilitation Medical Company, 2013, 34 pages.
User Manual: Regenetron PRO, System Information, Regenetron PRO User Manual, Nov. 2014, 7 Pages.
Vanquish Operator's Manual, BTL, 2012, 48 Pages.
Venus Legacy, Featuring LiftFX and SculptFX, Venus Concept, Delivering the Promise, 24 pages.
Venus Legacy, User Manual International, 2009, Venus Concept, 49 pages.
Venus Swan, Experience the Difference, Venus Concept, Delivering the Promise, 2 pages.
VenusFreeze, Experience the Energy, Venus Concept, Delivering the Promise, 2 pages.
Verges S., et al., "Comparison of Electrical and Magnetic Stimulations to Assess Quadriceps Muscle Function," Journal of Applied Physiology (1985), 106(2):701-710, American Physiological Society, United States, (Feb. 2009).
Wasilewski, M.L., Academy of Aesthetic and Anti-Aging Medicine, Application of magnetic fields with deep stimulation in the fight against local obesity of lower limbs, BTL, 2012, 4 pages.
WEB MD, what is normal body temperature? 3 pages, printed Mar. 4, 2019.
Weight to volume aluminum, 2 pages. printed from internet Sep. 25, 2018.
Weight to volume copper, 2 pages printed from internet Sep. 25, 2018.
Z Wave, Instructions for Use, Zimmer Aesthetic Division, Version 5, 44 pages.
Zelickson, B., et al., "Cryolipolysis for Noninvasive Fat Cell Destruction: Initial Results From a Pig Model," Dermatologic Surgery, 35(10)1 462-1470, Hagerstown, MD Lippincott, Williams & Wilkins, United States (Oct. 2009).
ZELTIQ System User Manual- Print and Binding Specifications, ZELTIQ Aesthetics, Inc, Mar. 2011, 88 pages.
Zerona, Reveal your True Shape, Product Fact Sheet, 3 pages.
Zerona R-Z6 by Erchonia, Specifications,Retrieved from the Internet: (http://www.myzerona.com), 2015, 1 page.
Hera Estetik Medikal, "LIPOSTAR" dated Jul. 7, 2014. https://www.youtube.com/watch?v=-R7OnFIK9go, accessed Dec. 15, 2021.
Marek Heinfarth, "LipoStar" dated Jan. 10, 2013. https://www.youtube.com/watch?v=hZurkn8iU_U, accessed Dec. 15, 2021.
Hera Estetik Medikal, "Lipostar Manyetik incelme" https://www.heraestetik.com/en/urun-detay/liposter-manyetik-incelme, accessed Dec. 15, 2021.

(56) References Cited

OTHER PUBLICATIONS

Moon, Chi-Woong "Study on the Pulsed Electromagnetic Fields effect of adipocyte decomposition" Final Report of a middle-grade researcher support project, Inje University, 2017.
501 (k) K030708 Slendertone FLEX Letter from Department of Health and Humane Serivces, Public Health Service, Jun. 25, 2003, 6 pages.
501 (k) K163165 AM-100 Letter from Department of Health and Human Services, Public Health Service, Feb. 16, 2017, 9 pages.
Alma Lasers., "Accent Radiofrequency System, Operator's Manual," Wellbeing Through Technology, 2008, Chapters 1-6, Appendix A.
Arjunan, P.A., et al., "Computation and Evaluation of Features of Surface Electromyogram to Identify the Force of Muscle Contraction and Muscle Fatigue," BioMed research international 2014:197960, Hindawi Pub. Co, United States (2014).
Barker, A.T., et al., "Non-lnvasive Magnetic Stimulation of Human Motor Cortex," Lancet 1(8437):1106-1107, Elsevier, England (May 1985).
Barker, A.T., "The History and Basic Principles of Magnetic Nerve Stimulation," Electroencephalography and Clinical Neurophysiology 51:3-21, Elsevier, Netherlands (1999).
Barrett, J., et al., "Mechanisms of Action Underlying the Effect of Repetitive Transcranial Magnetic Stimulation on Mood: Behavioral and Brain Imaging Studies," Neuropsychopharmacology 29(6):1172-1189, Nature Publishing Group, England (Jun. 1905).
Belanger, A-Y., "Chapter 13: Neuromuscular Electrical Stimulation," in Therapeutic Electrophysical Agents: Evidence Behind Practice, 3rd Edition, Lupash, E., ed., pp. 220-255, Lippincott Williams & Wilkins, United States (2015).
Benton, et al., "Functional Electrical Stimulation- A Practical Clinical Guide," Second Edition, The Professional Staff Association of the Rancho Los Amigos Hospital, Inc. :16 (1981).
Benton, L.A., et al., "Chapter 2: Physiological Basis of Nerve and Muscle Excitation" and "Chapter 4: General Uses of Electrical Stimulation," in Functional Electrical Stimulation: A Practical Guide, 2nd Edition, pp. 11-30 and 53-71, Rancho Los Amigos Rehabilitation Engineering Center, Downey, CA (1981), 42 pages.
Bergh, U., and Ekblom, B., "Influence of Muscle Temperature on Maximal Muscle Strength and Power Output in Human Skeletal Muscles," Acta Physiologica Scandinavica 107(1):33-37, Blackwell Scientific Publications, England (Aug. 1979).
Binder-MacLeod, S.A., et al., "Force Output of Cat Motor Units Stimulated with Trains of Linearly Varying Frequency," Journal of Neurophysiology 61 (1):208-217, American Physiological Society, United States (Jan. 1989).
Binder-MacLeod, S.A., et al., "Use of a Catchlike Property of Human Skeletal Muscle to Reduce Fatigue," Muscle & Nerve 14(9):850-857, John Wiley & Sons, United States (Sep. 1991).
Bio Medical Research Limited., "Slendertone Flex Abdominal Training System, Instructions for Use," All pages (Aug. 2006).
Bio Medical Research Limited., "Slendertone Flex Max Instruction Manual," All pages (Apr. 2006).
Bio-Medical Research Ltd., K010335, 510(k) Summary, Slendertone Flex, All pages (Sep. 2001).
Bio-Medical Research Ltd., K022855 510(k) Summary, Slendertone, 1-6 (Mar. 2003).
Bischoff, C., et al., "Repetitive Magnetic Nerve Stimulation: Technical Considerations and Clinical Use in the Assessment of Neuromuscular Transmission," Electroencephalography and Clinical Neurophysiology 93(1):15-20, Elsevier, Ireland (Feb. 1994).
Bourland, J.D., et al., "Transchest Magnetic (Eddy-Current) Stimulation of the Dog Heart," Medical & Biological Engineering & Computing 28(2):196-198, Springer, United States (Mar. 1990).
BTL Industries, Inc., K163165 510(k) Summary, AM-100, All pages (Feb. 2017).
BTL Industries, Inc., K180813 510(k) Summary, Emsculpt, All pages (Mar. 2018).
*BTL Industries, Inc.v. Allergan Ltd et al.* DDE-1-20-cv-01046, Complaint for Patent Infringement and Exhibits 1-38, 821 pages (Aug. 2020).
*BTL Industries, Inc.v. Allergan Ltd et al.* DDE-1-20-cv-01046, Order Granting Motion to Stay Pending Resolution of Proceedings at the International Trade Commission (Unopposed), 2 pages (Oct. 2020).
Busso, M. and Denkova, R "Efficacy of High Intensity Focused Electro-Magnetic (HIFEM) Field Therapy When Used For Non-lnvasive Buttocks Augmentation and Lifting: A Clinical Study" American Society for Laser Medicine and Surgery Abstracts, 382 (2018).
Callaghan, M.J., et al., "Electric Muscle Stimulation of the Quadriceps in the Treatment of Patellofemoral Pain," Archives of Physical Medicine and Rehabilitation 85(6):956-962, W.B. Saunders, United Staes (Jun. 2004).
Carbonaro, M., et al., "Architectural Changes in Superficial and Deep Compartments of the Tibialis Anterior during Electrical Stimulation over Different Sites," IEEE transactions on Neural Systems and Rehabilitation Engineering 28(11):2557-2565, IEEE, United States (Nov. 2020).
Certain Non-Invasive Aesthetic Body Contouring Devices, Components Thereof, and Methods of Using the Same, Inv. No. 337-TA-1219, BTL's Statement of Suggested Claim Terms to Be Construed Pursuant to Ground Rule 6b, Nov. 4, 2020, 2 pages.
Certain Non-Invasive Aesthetic Body Contouring Devices, Components Thereof, and Methods of Using the Same, Inv. No. 337-TA-1219, Complainant BTL's Proposed Construction of Disputed Claim Terms, Dec. 8, 2020, 19 pages.
Certain Non-Invasive Aesthetic Body Contouring Devices, Components Thereof, and Methods of Using the Same, Inv. No. 337-TA-1219, Complaint, Aug. 5, 2020, 93 pages.
Certain Non-Invasive Aesthetic Body Contouring Devices, Components Thereof, and Methods of Using the Same, Inv. No. 337-TA-1219, Joint Claim Construction Chart, Dec. 14, 2020, 15 pages.
Certain Non-Invasive Aesthetic Body Contouring Devices, Components Thereof, and Methods of Using the Same; Inv. No. 337-TA-1219, Joint Claim Construction Chart, Dec. 18, 2020, 15 pages.
Certain Non-Invasive Aesthetic Body Contouring Devices, Components Thereof, and Methods of Using the Same, Inv. No. 337-TA-1219, Respondents' Allergan Limited, Allergan USA, Inc., Allergan, Inc., Zeltiq Aesthetics, Inc., Zeltiq Ireland Unlimited Company, and Zimmer MedizinSysteme GmbH's Notice of Prior Art, Nov. 20, 2020, 53 pages.
Certain Non-Invasive Aesthetic Body Contouring Devices, Components Thereof, and Methods of Using the Same, Inv. No. 337-TA-1219, Respondents' List of Claim Terms for Construction, Nov. 4, 2020, 8 pages.
Certain Non-Invasive Aesthetic Body Contouring Devices, Components Thereof, and Methods of Using the Same; Inv. No. 337-TA-1219, Respondents' List of Proposed Claim Constructions and Their Intrinsic and Extrinsic Support, filed Dec. 15, 2020, 23 pages.
Certain Non-Invasive Aesthetic Body Contouring Devices, Components Thereof, and Methods of Using the Same, Inv. No. 337-TA-1219, Response of Respondent Zimmer MedizinSysteme GmbH to the Complaint and Notice of Investigation, Oct. 22, 2020, 68 pages.
Certain Non-Invasive Aesthetic Body Contouring Devices, Components Thereof, and Methods of Using the Same, Inv. No. 337-TA-1219, Response of Respondents Allergan Limited, Allergan USA, Inc., Allergan, Inc., Zeltiq Aesthetics, Inc., and Zeltiq IrelandUnlimited Company to the Complaint and Notice of Investigation, Oct. 22, 2020, 69 pages.
Certain Non-Invasive Aesthetic Body-Contouring Devices, Components Thereof, and Methods of Using Same, Notice of Institution of Investigation, Inv. No. 337-TA-1219, Notice of Institution of Investigation, Sep. 2, 2020, 21 pages.
Certain Non-Invasive Aesthetic Body-Contouring Devices, Components Thereof, and Methods of Using the Same, Inv. No. 337-TA-1219, Order No. 21 (Initial Determination), Apr. 28, 2021, 5 pages.
Certain Non-Invasive Aesthetic Body-Contouring Devices, Components Thereof, and Methods of Using the Same, Inv. No. 337-TA-1219, Order No. 17: Amending Procedural Schedule, Apr. 9, 2021, 4 pages.

(56) References Cited

OTHER PUBLICATIONS

Certified English Translation of Belyaev, A.G., "Effect of Magnetic Stimulation on the Strength Capacity of Skeletal Muscles," Ph.D. Thesis Abstract, Smolensk State Academy of Physical Culture, Sport, and Tourism, Dec. 11, 2020, 23 pages.
Certified English Translation of Belyaev, A.G., "Effect of Magnetic Stimulation on the Strength Capacity of Skeletal Muscles," Ph.D. Thesis, Smolensk State Academy of Physical Culture, Sport, and Tourism, Dec. 11, 2020, 117 pages.
Chattanooga Group of Encore Medical, L.P., "Intelect SWD 100 User Manual, Operation & Installation Instructions for Intelect SWD 00—Model 1600," All pages (2009).
Collins, D.F., et al., "Large Involuntary Forces Consistent With Plateau-Like Behavior of Human Motoneurons," Journal of Neuroscience 21 (11):4059-4065, Society for Neuroscience, United States (Jun. 2001).
Colson, S., et al., "Re-Examination of Training Effects by Electrostimulation in the Human Elbow Musculoskeletal System," International Journal of Sports Medicine 21(4):281-288, Stuttgart, Thieme (May 2000).
CR Technologies, "Salus Talent Pop Manual KFDA First Approval Document" (English Translation), Nov. 25, 2011, 47 pages.
CR Technologies, "Notification of medical device manufacturing item permission, Salus Talent Pop KFDA Approval Document" (English Translation), 3 pages (Sep. 2011).
CR Technology Co, Ltd., "Salus-Talent DOUBLE Sales Brochure" 2 pages, (Oct. 2020).
CR Technology Co. Ltd., "Medical Laser Irradiator Salus-Talent-Pop User Manual Version 1.00" (Nov. 2020).
CR Technology Co. Ltd., Salus Talent Pop User Manual, Ver. 1.00, All pages, Approx. 2012.
Currier, D. P., "Effects of Electrical and Electromagnetic Stimulation after Anterior Cruciate Ligament Reconstruction," The Journal of Orthopaedic and Sports Physical Therapy 17(4):177-84, Williams And Wilkins, United States (1993).
Davies, C.T., et al., "Contractile Properties of the Human Triceps Surae With Some Observations on the Effects of Temperature and Exercise," European Journal of Applied Physiology and Occupational Physiology 49(2):255-269, Springer Verlag, Germany (Aug. 1982).
Deng, Z.D., et al., "Electric Field Depth-Focality Tradeoff in Transcranial Magnetic Stimulation: Simulation Comparison of 50 Coil Designs," Brain stimulation 6(1):1-13, Elsevier, New York (Jan. 2013).
Dudley, G. and Stevenson, S., "Use of Electrical Stimulation in Strength and Power Training," Special Problems in Strength and Power Training :426-435 (2003).
Duncan, D., et al., "Noninvasive Induction of Muscle Fiber Hypertrophy and Hyperplasia: Effects of High-Intensity Focused Electromagnetic Field Evaluated in an In-Vivo Porcine Model: A Pilot Study," Aesthetic Surgery Journal 40(5):568-574, Oxford University Press, United States (Apr. 2020).
Dynatronics., "Better Rehab Solutions for Better Outcomes," Rehabilitation Products Guide 2.3, 2017, 52 pages.
Elamed, Magnetic Therapeutic Apparatus for Running Pulse Magfield small-sized ALMAG-01 Manual, All pages.
Energist Ltd—Acquired Chromogenez—Old Account, iLipo—Laser Liposuction (i-Lipo), Video Screenshots, Aug. 10, 2009, 5 pages.
Enoka, R.M., "Muscle Strength and Its Development," Sports Medicine 6:146-168, Springer (Oct. 1988).
Epstein, C., et al., "The Oxford Handbook of Transcranial Stimulation," 773 pages (2008).
Faghri, P.D., et al., "The Effects of Functional Electrical Stimulation on Shoulder Subluxation, Arm Function Recovery, and Shoulder Pain in Hemiplegic Stroke Patients," Archives of Physical Medicine and Rehabilitation 75(1):73-79, W.B. Saunders, United States (Jan. 1994).
Fischer, J., et al., "Precise Subpixel Position Measurement with Linear Interpolation of CMOS Sensor Image Data," The 6th IEEE International Conference on Intelligent Data Acquisition and Advanced Computing Systems, 500-504 (Sep. 2011).
Fujimura, K., et al., "Effects of Repetitive Peripheral Magnetic Stimulation on Shoulder Subluxations Caused by Stroke: A Preliminary Study," Neuromodulation : Journal of the International Neuromodulation Society 23(6):847-851, Wiley-Blackwell, United States (Nov. 2020).
Gaines, M., "Slendertone Abdominal Training System, the First FDA-Cleared Abdominal Belt, Introduced in United States by Compex Technologies on Time for Holiday Gift-Giving," Business Wire 44199 (Oct. 2003).
Geddes, L. A., "History of Magnetic Stimulation of the Nervous System," Journal of Clinical Neurophysiology 8(1):3-9, Lippincott Williams & Wilkins, New York, (Jan. 1991).
Geddes, L.A., "History of Magnetic Stimulation of the Nervous System," Journal of Clinical Neurophysiology 8(1):3-9, Lippincott Williams & Wilkins, United States (Jan. 1991).
Goodman, B.E., "Channels Active in the Excitability of Nerves and Skeletal Muscles Across the Neuromuscular Junction: Basic Function and Pathophysiology," Advances in Physiology Education 32(2):127-135, American Physiological Society, United States (Jun. 2008).
Gorodnichev, R.M., et al., "The Effect of Electromagnetic Stimulation on the Parameters of Muscular Strength," Human Physiology 40:65-69 (2014).
Halaas, Y. and Bernardy, J., "Biochemical Perspective of Fat Physiology after Application of HIFEM Field Technology: Additional Investigation of Fat Disruption Effects in a Porcine Study," American Society for Laser Medicine and Surgery Abstracts, S4 (2019).
Han, B.H., et al., "Development of four-channel magnetic nerve stimulator," 2001 Proceedings of the 23rd Annual EMBS International Conference, pp. 1325-1327, Turkey (2001).
Harkey, M.S., "Disinhibitory Interventions and Voluntary Quadriceps Activation: A Systematic Review," Journal of Athletic Training 49(3):411-421, National Athletic Trainers' Association, United States (2014).
Heidland, A., et al., "Neuromuscular Electrostimulation Techniques: Historical Aspects and Current Possibilities in Treatment of Pain and Muscle Waisting," Clinical Nephrology 79 Suppl 1:S12-S23, Dustri-Verlag Dr. Karl Feistle, Germany (Jan. 2012).
Hill, A., "The Influence of Temperature on the Tension Developed in an Isometric Twitch," Proceeding of the Royal Society B 138:349-354, (Sep. 1951).
Hovey, C. and Jalinous, R., "The Guide to Magnetic Stimulation" Magstim, Pioneers in Nerve Stimulation and Monitoring, pp. 1-44 (2016).
Hovey, C., et al., "The Guide to Magnetic Stimulation," The Magstim Company Limited, 48 pages (Jul. 2006).
Huang, Y.Z., et al., "Theta Burst Stimulation of the Human Motor Cortex," Neuron 45(2):201-206, Cell Press, United States (Jan. 2005).
Irazoqui P.; Post Grant Review of U.S. Pat. No. 10,695,576, PTAB-PGR2021-00024, filed as EX1085, Dec. 14, 2020, 25 pages.
Iskra Medical, "TESLA Stym—Functional Magnetic Stimulation FMS," Nov. 2013, http://ww.iskramedical.eu/magneto-therapy-medical/tesla-stym, 5 pages.
Jacob, C., et al., "High Intensity Focused Electro-Magnetic Technology (HIFEM) for Non-lnvasive Buttock Lifting and Toning of Gluteal Muscles: A Multi-Center Efficacy And Safety Study," Journal of Drugs in Dermatology 17(11):1229-1232, Physicians Continuing Education Corporation, United States (Nov. 2018).
Jacob, C.I., et al., "Safety And Efficacy of a Novel High-Intensity Focused Electromagnetic Technology Device for Noninvasive Abdominal Body Shaping," Journal of Cosmetic Dermatology, 17(5):783-787, Blackwell Science, United States (Oct. 2018).
Jacobm C., and Paskova, "A Novel Non-lnvasive Technology Based on Simultaneous Induction of Changes in Adipose and Muscle Tissues: Safety and Efficacy of a High Intensity Focused Electro-Magnetic (HIFEM) Field Device Used For Abdominal Body Shaping," American Society for Laser Medicine and Surgery, 2018 Electronic Posters (ePosters) Town Hall and ePosters, 369, p. 1, Wiley Periodicals, Inc. (2018).

(56) References Cited

OTHER PUBLICATIONS

Johari Digital Healthcare Ltd., 510(k)—K062439 Powertone Letter from Department of Health and Humane Services Summary, Public Health Service, Jan. 8, 2007, 6 pages.

Johari Digital Healthcare Ltd., "510(k)—K131291 Torc Body Letter from Department of Health and Humane Services", Public Health Service, Jun. 14, 2013, 10 pages.

Johari Digital Healthcare Ltd., K131291 510(k) Summary, TorcBody, All pages (Jun. 2013).

Katz, B., et al., "Changes in Subcutaneous Abdominal Fat Thickness Following High-Intensity Focused Electro-Magnetic (HIFEM) Field Treatments: A Multi Center Ultrasound Study," American Society for Laser Medicine and Surgery Abstracts, 360-361 (2018).

Katz, B., et al., "Ultrasound Assessment of Subcutaneous Abdominal Fat Thickness after Treatments with a High-Intensity Focused Electromagnetic Field Device: A Multicenter Study," Dermatologic Surgery 45(12):1542-1548, Williams & Wilkins, United States (Dec. 2019).

Kavanagh, S., et al., "Use of a Neuromuscular Electrical Stimulation Device for Facial Muscle Toning: A Randomized, Controlled Trial," Journal of Cosmetic Dermatology 11(4):261-266, Blackwell Science, United States (Dec. 2012).

Kent, D., and Jacob C., "Computed Tomography (CT) Based Evidence of Simultaneous Changes in Human Adipose and Muscle Tissues Following a High Intensity Focused Electro-Magnetic Field (HIFEM) Application: A New Method for Non-Invasive Body Sculpting," American Society for Laser Medicine and Surgery Abstracts, p. 370 (2018).

Kent, D,E. and Jacob, C.I., Simultaneous Changes in Abdominal Adipose and Muscle Tissues Following Treatments by High-Intensity Focused Electromagnetic HIFEM Technology-Based Device: Computed Tomography Evaluation, Journal of Drugs in Dermatology 18(11):1098-1102, Physicians Continuing Education Corporation, United States (Nov. 2019).

Kinney, B.M. and Lozanova P., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine 51(1):40-46, Wiley-Liss, United States (Jan. 2019).

Kolin, A., et al., "Stimulation of Irritable Tissues by means of an Alternating Magnetic Field," Proceedings of the Society for Experimental Biology and Medicine 102:251-253, Blackwell Science, United States (Oct. 1959).

Kumar, N. and Agnihotri, R.C., "Effect of Frequency and Amplitude of Fes Pulses on Muscle Fatigue During Toning of Muscles," Journal of Scientific and Industrial Research 67(4):288-290, (Apr. 2008).

Langford, J. and McCarthy, P.W., "Randomised controlled clinical trial of magnet use in chronic low back pain; a pilot study," Clinical Chiropractic 8(1):13-19, Elsevier (Mar. 2005).

Lee, P.B., et al., "Efficacy of Pulsed Electromagnetic Therapy for Chronic Lower Back Pain: a Randomized, Double-blind, Placeb-controlled Study," The Journal of International Medical Research 34(2):160-167, Cambridge Medical Publications, England (Mar.-Apr. 2006).

Leitch, M., et al., "Intramuscular Stimulation of Tibialis Anterior in Human Subjects: The Effects of Discharge Variability on Force Production and Fatigue," Physiological Reports 5(15):e13326, Wiley Periodicals, Inc., United States (Aug. 2017).

Leon-Salas, W.D., et al., "A Dual Mode Pulsed Electro-Magnetic Cell Stimulator Produces Acceleration of Myogenic Differentiation," Recent Patents on Biotechnology 7(1):71-81, Bentham Science Publishers, United Arab Emirates (Apr. 2013).

Lin, V.W., et al., "Functional Magnetic Stimulation for Conditioning of Expiratory Muscles in Patients with Spinal Cord Injury.," Archives of Physical medicine and Rehabilitation 82(2):162-166, W.B. Saunders, United States (Feb. 2001).

Lin, V.W., et al., "Functional Magnetic Stimulation of the Respiratory Muscles in Dogs," Muscle & Nerve 21(8):1048-1057, John Wiley & Sons, United States (Aug. 1998).

Lotz, B.P., et al., "Preferential Activation of Muscle Fibers with Peripheral Magnetic Stimulation of the Limb," Muscle & Nerve, 12(8):636-639, John Wiley & Sons, United States (Aug. 1989).

Maffiuletti, N.A., et al., "Activation of Human Plantar Flexor Muscles Increases After Electromyostimulation Training," Journal of Applied Physiology 92(4):1383-1392, American Physiological Society, United States (Nov. 2001).

Maffiuletti, N.A., et al., "The Effects of Electromyostimulation Training and Basketball Practice on Muscle Strength and Jumping Ability," International journal of sports medicine 21(6):437-443, Thieme, Germany (Aug. 2000).

Magstim Company Limited, K051864 510(k) Summary, Magstim Rapid and Magstim Super Rapid, All pages (Dec. 2005).

Magstim Company US, LLC, K060847 510(k) Summary, Magstim Model 200-2 with Double 70mm Remote Coil, All pages (Sep. 2006).

Magstim Corporation US, K992911 510(k) Summary, Magstim Rapid, All pages (Jan. 2000).

Man, W.D-C., et al., "Magnetic Stimulation for the Measurement of Respiratory and Skeletal Muscle Function," The European Respiratory Journal 24(5):846-60, European Respiratory Society, England (2004).

Mantovani, A., et al., "Applications of Transcranial Magnetic Stimulation to Therapy in Pyschiatry," Psychiatric Times 21(9), Intellisphere, 29 pages (Aug. 2004).

Markov, M.S., "Pulsed Electromagnetic Field Therapy History, State of the Art and Future," Environment Systems and Decisions 27(4):465-475, Springer (Dec. 2007).

Mettler J.A., et al., "Low-Frequency Electrical Stimulation With Variable Intensity Preserves Torque," Journal of Electromyography and Kinesiology : Official Journal of the International Society of Electrophysiological Kinesiology 42:49-56, Oxford:Elsevier, England (Oct. 2018).

Mogyoros, I., et al., "Strength-Duration Properties of Human Peripheral Nerve," Brain 119(Pt 2):439-447, Oxford University Press, England (Apr. 1996).

Morrissey. M., "Electromyostimulation from a Clinical Perspective," Sports Medicine 6(1):29-41, Springer International, New Zealand (Aug. 1988).

Mustafa, B., "Design and Construction of a Low Cost dsPIC Controller Based Repetitive Transcranial Magnetic Stimulator TMS," Journal of medical systems 34(1):15-24, Kluwer Academic/Plenum Publishers, United States (2010).

Neotonus, Inc., K973096 510(k) Summary, Neotonus Model 100 Muscle Stimulator System, All pages (Jun. 1998).

Neotonus, Inc., K973929 510(k) Summary and FDA Correspondence, Neotonus, All pages (May 1998).

Neyroud, D., et al., "Comparison of Electrical Nerve Stimulation, Electrical Muscle Stimulation and Magnetic Nerve Stimulation to Assess the Neuromuscular Function of the Plantar Flexor Muscles," European journal of applied physiology 115(7):1429-1439, Springer-Verlag, Germany (2015).

Nielsen, J.F., et al., "A New High-frequency Magnetic Stimulator With an Oil-cooled Coil," Journal of Clinical Neurophysiology 12(5):460-467, Lippincott Williams & Wilkins, United States (Sep. 1995).

Novickij, V., et al., "Compact Microsecond Pulsed Magnetic Field Generator for Application in Bioelectronics," Elektronika ir Elektrotechnika 19(8):25-28 (Oct. 2013).

Novickij, V., et al., "Design and Optimization of Pulsed Magnetic Field Generator for Cell Magneto-Permeabilization," Elektronika ir Elektrotechnika(Electronics and Electrical Engineering) 23(2):21-25 (Apr. 2017).

Novickij, V., et al., "Magneto-Permeabilization of Viable Cell Membrane Using High Pulsed Magnetic Field," IEEE Transactions on Magnetics 51(9), All pages (Sep. 2015).

Novickij, V., et al., "Programmable Pulsed Magnetic Field System for Biological Applications," IEEE Transactions on Magnetics 50(11):5 (Nov. 2014).

NPF Electroapparat, Amplipulse-5Br Manual, All pages.

Nuerosoft Ltd., "Neurosoft - Neuro-MS Transcranial Magnetic Simulator Technical Manual," All pages (Nov. 2014).

(56) References Cited

OTHER PUBLICATIONS

Oliveira, P.DE., et al., "Neuromuscular Fatigue After Low-and Medium-frequency Electrical Stimulation in Healthy Adults," Muscle & Nerve 58(2):293-299, John Wiley & Sons, United States (Aug. 2018).

Pain Management Technologies, "Pain Management Technologies Product Catalog," (2012).

Photograph, Alleged Photograph of Components of a Salus Talent Pop Double Device with An Aalleged Manufacture date of Nov. 14, 2012, 1 page.

Platil, A., "Magnetopneumography Using Optical Position Reference," Sensor Letters 11 (1):69-73, ResearchGate (2013).

Pohanka, J., et al., "An Embedded Stereovision System: Aspects of Measurement Precision," 12th Biennial Baltic Electronics Conference, pp. 157-160 (Oct. 2010).

Porcari, J.P., et al., "Effects of Electrical Muscle Stimulation on Body Composition, Muscle Strength, and Physical Appearance," Journal of Strength and Conditioning Reasearch 16(2):165-172, Human Kinetics Pub., United States (May 2002).

Porcari, J.P., et al., "The Effects of Neuromuscular Electrical Stimulation Training on Abdominal Strength, Endurance, and Selected Anthropometric Measures," Journal of Sports Science and Medicine 4(1):66-75, Dept. of Sports Medicine, Turkey (Mar. 2005).

Pribula, O. and Fischer, J., "Real Time Precise Position Measurement Based on Low-Cost CMOS Image Sensor," IEEE, 5 pages (2011).

Pribula, O., et al., "cost-effective Image Acquisition System for Precise Pc-based Measurements," Przeglad Elektrotechniczny (Electrical Review), 2011, pp. 259-263.

Pribula, O., et al., "Optical Position Sensor Based on Digital Image Processing: Magnetic Field Mapping Improvement," Radioengineering 20 (1):55-60, (Apr. 2011).

Pribula, O., et al., "Real-Time Video Sequences Matching Spatio-Temporal Fingerprint," IEEE, 911-916 (Jun. 2010).

Prouza, O., et al., "High-Intensity Electromagnetic Stimulation Can Reduce Spasticity in PostStroke Patients," International Journal of Physiotherapy 5(3):87-91 (2018).

Prouza, O., "Targeted Radiofrequency Therapy for Training Induced Muscle Fatigue—Effective or Not?," International Journal of Physiotherapy 3(6):707-710 (Dec. 2016).

PTAB-IPR2021-00296, U.S. Pat. No. 10,493,293, Petition for Inter Partes Review, Dec. 14, 2020, 117 pages.

PTAB-IPR2021-00312, U.S. Pat. No. 10,478,634, Petition for Inter Partes Review, Dec. 14, 2020, 108 pages.

PTAB-PGR2021-00015, U.S. Pat. No. 10,709,895, Petition for Post-Grant Review, Dec. 14, 2020, 140 pages.

PTAB-PGR2021-00016, U.S. Pat. No. 10,709,895, Petition for Post-Grant Review, Dec. 14, 2020, 144 pages.

PTAB-PGR2021-00017, U.S. Pat. No. 10,632,321, Petition for Post-Grant Review, Dec. 14, 2020, 121 pages.

PTAB-PGR2021-00018, U.S. Pat. No. 10,632,321, Petition for Post-Grant Review, Dec. 14, 2020, 140 pages.

PTAB-PGR2021-00020, U.S. Pat. No. 10,695,575, Petition for Post-Grant Review, Dec. 14, 2020, 112 pages.

PTAB-PGR2021-00021, U.S. Pat. No. 10,695,575, Petition for Post-Grant Review, Dec. 14, 2020, 117 pages.

PTAB-PGR2021-00022, U.S. Pat. No. 10,709,894, Petition for Post-Grant Review, Dec. 14, 2020, 119 pages.

PTAB-PGR2021-00023, U.S. Pat. No. 10,709,894, Petition for Post-Grant Review, Dec. 14, 2020, 136 pages.

PTAB-PGR2021-00024, U.S. Pat. No. 10,695,576, Petition for Post-Grant Review, Dec. 14, 2020, 136 pages.

PTAB-PGR2021-00025, U.S. Pat. No. 10,695,576, Petition for Post-Grant Review, Dec. 14, 2020, 135 pages.

Radakovic T. and Radakovic N., "The Effectiveness of the Functional Magnetic Stimulation Therapy in Treating Sciatica Syndrome," Open Journal of Therapy and Rehabilitation 3(3):63-69 (2015).

Riehl., M., "Chapters: TMS Stimulator Design" The Oxford Handbook of Transcranial Stimulation, Wasserman, E.M., ed., pp. 13-23, Oxford University Press, 26 pages, United Kingdom (2008).

Roots, H., and Ranatunga, K.W., "An Analysis of the Temperature Dependence of Force, During Steady Shortening at Different Velocities, in (Mammalian) Fast Muscle Fibres," Journal of Muscle Research and Cell Motility 29(1):9-24, Springer, Netherlands (Jun. 2008).

Salus Talent Pop, The first sales bill, Authorization No. 20120221-41000096-66667961, 2 pages, (Feb. 2012).

Sargeant, A.J., "Effect of Muscle Temperature on Leg Extension Force and Short-term Power Output in Humans," European Journal of Applied Physiology and Occupational Physiology 56(6):693-698, Springer Verlag, Germany (Sep. 1987).

Schaefer, D.J., et al., "Review of Patient Safety in Time-Varying Gradient Fields," Journal of Magnetic Resonance Imaging, 12:20-29, Wiley-Liss, United States (Jul. 2000).

Shimada, Y., et al., "Effects of therapeutic magnetic stimulation on acute muscle atrophy in rats after hindlimb suspension," Biomedical Research 27(1):23-27, Biomedical Research Foundation, Japan (Feb. 2006).

Silinskas, V., et al., "Effect of Electrical Myostimulation on the Function of Lower Leg Muscles," Journal of strength and Conditioning Research 31 (6):1577-1584, Human Kinetics Pub, United States (2017).

Sport-Elec S.A., K061914 510(k) Summary, Sport—Elec, All pages (Jul. 2007).

Sport-Elec S.A., K081026 510(k) Summary, Sport—Elec, All pages (Nov. 2008).

Stedman, T.L., "Aponeurosis—Apparatus," in Stedman's Medical Dictionary, 27th Edition, Pugh, M.B., ed., pp. 113-114, Lippincott Williams & Wilkins, Baltimore, MD (2000).

Struppler, A., et al., "Facilitation of Skilled Finger Movements by Repetitive Peripheral Magnetic Stimulation (RPMS) - A New Approach In Central Paresis.," NeuroRehabilitation 18(1):69-82, IOS Press, Amsterdam (2003).

Struppler, A., et al., "Modulatory Effect of Repetitive Peripheral Magnetic Stimulation on Skeletal Muscle Tone in Healthy Subjects: Stabilization of the Elbow Joint," Experimental Brain Research 157(1):59-66, Springer Verlag, Germany (Feb. 2004).

Suarez-Bagnasco, D., et al., "The Excitation Functional for Magnetic Stimulation of Fibers.," Annual International Conference of the IEEE Engineering in Medicine and Biology Society, IEEE Engineering in Medicine and Biology Society, Annual International Conference, 2010:4829-4833, IEEE, United States (2010).

Swallow, E.B., et al., "A Novel Technique for Nonvolitional Assessment of Quadriceps Muscle Endurance in Humans," Journal of Applied Physiology 103(3):739-746, American Physiological Society, United States (Sep. 2007).

The Magstim Company Ltd, K080499 510(k) Summary, Magstim Double 70mm Air Film Coil, All pages (Dec. 2008).

The Magstim Company Ltd., K130403 510(k) Summary, Magstim D702 coil, All pages (Aug. 2013).

Thermi Launches Arvati, powered by Thermi, with newest advances in True Temperature Controlled Radiofrequency Technology, 5 pages (2018).

Thompson, M.T., "Inductance Calculation Techniques—Part II: Approxmiations and Handbook Methods," Power Control and Intelligent Motion, 11 pages (Dec. 1999) http://www.pcim.com/.

Thompson, M.T., "Inductance Calculation Techniques—Part I: Classical Methods," Power Control and Intelligent Motion, 25(12):40-45, (Dec. 1999) http://www.pcim.com/.

Tomek, J., et al., "Magnetopneumography - Incorporation of optical position reference," Journal of Electrical Engineering, All pages (2012).

Torbergsen, T., "Abstracts of the International Course and Symposium in Single Fibre EMG and Quantitative EMG Analysis. Tromsø, Norway, Jun. 4-8, 1984," Muscle & Nerve 9(6):562-574, John Wiley & Sons, United States (Jul.-Aug. 1986).

Vance, C., et al., "Effects of Transcutaneous Electrical Nerve Stimulation on Pain, Pain Sensitivity, and Function in People with Knee Osteoarthritis," Physical Therapy 92:898-910 (2012).

(56) References Cited

OTHER PUBLICATIONS

Wada, K., et al., "Design and Implementation of Multi-Frequency Magnetic Field Generator Producing Sinusoidal Current Waveform for Biological Researches," IEEE, 9 pages (2016).
Ward, A.R. and Shkuratova, N., "Russian Electrical Stimulation: The Early Experiments," Physical therapy, 82(10):1019-1030, Oxford University Press, United States (2002).
Weiss, R.A., et al., "Induction of Fat Apoptosis by a Non-Thermal Device: Mechanism of Action of Non-lnvasive High-Intensity Electromagnetic Technology in a Porcine Model," Lasers in surgery and medicine 51(1):47-53, Wiley-Liss, United States (Jan. 2019).
Weng, O., "Electromagnetic Activation of the Calf Muscle Pump," UMI Dissertation Publishing (2014).
Yacyshy, A.F., et al., "The Inclusion of Interstimulus Interval Variability Does Not Mitigate Electrically-evoked Fatigue of the Knee Extensors," European Journal of Applied Physiology 120(12):2649-2656, Springer-Verlag, Germany (Sep. 2020).
Zao Okb Ritm, Electroneurostimulants, Transdermal Scenar-NT Instructions, All Pages (Nov. 2013).
Zao Okb Ritm, Percutaneous Electrical Stimulators With Individual Biofeedback Dosing Impact on Reflex Zones, All pages (Jul. 1905).
Zhang, G., et al., "A Method of Nerve Electrical Stimulation by Magnetic Induction," Annual International Conference of the IEEE Engineering in Medicine and Biology Society 2009:622-625, IEEE, United States (2009).
Zhi-De, D., "Electromagnetic Field Modeling of Transcranial Electric and Magnetic Stimulation: Targeting, Individualization, and Safety of Convulsive and Subconvulsive Applications," Academic Commons (2013).
Zhu, Y., et al., "Magnetic Stimulation of Muscle Evokes Cerebral Potentials by Direct Activation of Nerve Afferents: A Study During Muscle Paralysis," Muscle & Nerve 19(12):1570-1575, John Wiley & Sons, United Sates (Dec. 1996).
Kotz, Y., "Theory and Practice of Physical Culture," Training of Skeletal Muscle With Method of Electrostimulation, 64-67 (Mar. 1971).
Kotz, Y., "Theory and Practice of Physical Culture," Training of Skeletal Muscle With Method of Electrostimulation, 66-72 (Apr. 1971).
Werner, R., Magnetotherapy, Pulsating energy resonance therapy, 107 pages (Jun. 2007).
*BTL Industries, Inc.* v. *Allergan PLC et al.* DDE-1-19-cv-02356, Complaint for Patent Infringement and Exhibits 1-34, 375 pages (Dec. 2019).
*BTL Industries, Inc.* v. *Allergan PLC et al.* DDE-1-19-cv-02356, Order Granting Stipulation to Stay, Oct. 1, 2020, 1 page.
Prouza, O., "Ex-Post Analyza Spot Rebnich Dani," All pages, (2008).
Rutkove, S., "Effects of Temperature on Neuromuscular Electrophysiology," Muscle & Nerve 24(7):867-882, John Wiley & Sons, United States (Jul. 2001).
*Lumenis Be LTD.* v. *BTL Healthcare Technologies A.S.*, PTAB-IPR2022-00126, U.S. Pat. No. 10,695,576 Petition for Inter Partes Review, Nov. 10, 2021, 83 pages.
*Lumenis Be LTD.* v. *BTL Healthcare Technologies A.S.*, PTAB-IPR2022-00126, Declaration of Dr. Marom Bikson (EX1002), Nov. 10, 2021, 263 pages.
*Lumenis Be LTD.* v. *BTL Healthcare Technologies A.S.*, PTAB-IPR2022-00127, U.S. Pat. No. 10,695,576 Petition for Inter Partes Review, Nov. 10, 2021, 84 pages.
*Lumenis Be LTD.* v. *BTL Healthcare Technologies A.S.*, PTAB-IPR2022-00127, Declaration of Dr. Marom Bikson (EX1002), Nov. 10, 2021, 269 pages.
Agilent Technologies, Inc., "Agilent 33500 Series 30 MHz Function /Arbitrary Waveform Generator User's Guide," Publication No. 33520-90001 (Dec. 2010), 278 pages.
Agilent Technologies, Inc., "Agilent Announces 30 MHz Function/ Arbitrary Waveform Generators," Microwave J., URL: <https://www.microwavejournal.com/articles/9851-agilent-announces-30-mhz-function-arbitrary-waveform-generators> (Aug. 3, 2010), 8 pages.
Krueger, N. et al., "Safety and Efficacy of a New Device Combining Radiofrequency and Low-Frequency Pulsed Electromagnetic Fields for the Treatment of Facial Rhytides," J Drugs Dematol., 11(11):1306-1309 (Nov. 2012).
*Lumenis Be Ltd.* v. *BTL Healthcare Technologies A.S.*, PTAB-IPR2021-01402, U.S. Pat. No. 10,821,295 Petition for Inter Partes Review, Sep. 13, 2021, 81 pages.
*Lumenis Be Ltd.* v. *BTL Healthcare Technologies A.S.*, PTAB-IPR2021-01402, Declaration of Dr. Marom Bikson (EX1002), Sep. 13, 2021, 244 pages.
*Lumenis Be Ltd.* v. *BTL Healthcare Technologies A.S.*, PTAB-IPR2021-01403, U.S. Pat. No. 10,821,295 Petition for Inter Partes Review, Sep. 13, 2021, 84 pages.
*Lumenis Be Ltd.* v. *BTL Healthcare Technologies A.S.*, PTAB-IPR2021-01403, Declaration of Dr. Marom Bikson (EX1002), Sep. 13, 2021, 243 pages.
*Lumenis Be Ltd.* v. *BTL Healthcare Technologies A.S.*, PTAB-IPR2021-01404, U.S. Pat. No. 10,124,187 Petition for Inter Partes Review, Sep. 13, 2021, 82 pages.
*Lumenis Be Ltd.* v. *BTL Healthcare Technologies A.S.*, PTAB-IPR2021-01404, Declaration of Dr. Marom Bikson (EX1002), Sep. 13, 2021, 245 pages.
*Lumenis Be Ltd.* v. *BTL Healthcare Technologies A.S.*, PTAB-IPR2021-01405, U.S. Pat. No. 10,124,187 Petition for Inter Partes Review, Sep. 13, 2021, 86 pages.
*Lumenis Be Ltd.* v. *BTL Healthcare Technologies A.S.*, PTAB-IPR2021-01405, Declaration of Dr. Marom Bikson (EX 1002), Sep. 13, 2021, 247 pages.
Ruiz-Esparza, J. & J. Barba Gomez, "The Medical Face Lift: A Noninvasive, Nonsurgical Approach to Tissue Tightening in Facial Skin Using Nonablative Radiofrequency," Dermatol Surg, 29(4):325-32 (Apr. 2003).
Turley, J., "Agilent Technologies Announces 30 MHz Function/ Arbitrary Waveform Generators with Unparalleled Signal Accuracy," Elec. Eng'g J., URL: <https://www.eejournal.com/article/20100804-03/> (Aug. 4, 2010), 8 pages.
*Allergan, Inc et al.* v. *BTL Healthcare Technologies A.S.*, PTAB-PGR2021-00015, Paper 16 (Decision Denying Institution of Post-Grant Review), Jun. 17, 2021, 20 pages.
*Allergan, Inc et al.* v. *BTL Healthcare Technologies A.S.*, PTAB-PGR2021-00016, Paper 16 (Decision Denying Institution of Post-Grant Review), Jun. 17, 2021, 20 pages.
*Allergan, Inc et al.* v. *BTL Healthcare Technologies A.S.*, PTAB-PGR2021-00017, Paper 16 (Decision Denying Institution of Post-Grant Review), Jun. 16, 2021, 33 pages.
*Allergan, Inc et al.* v. *BTL Healthcare Technologies A.S.*, PTAB-PGR2021-00018, Paper 16 (Decision Denying Institution of Post-Grant Review), Jun. 16, 2021, 42 pages.
*Allergan, Inc et al.* v. *BTL Healthcare Technologies A.S.*, PTAB-PGR2021-00020, Paper 16 (Decision Denying Institution of Post-Grant Review), Jun. 16, 2021, 35 pages.
*Allergan, Inc et al.* v. *BTL Healthcare Technologies A.S.*, PTAB-PGR2021-00021, Paper 17 (Decision Denying Institution of Post-Grant Review), Jun. 16, 2021, 33 pages.
*Allergan, Inc et al.* v. *BTL Healthcare Technologies A.S.*, PTAB-PGR2021-00022; PTAB-PGR2021-00023; PTAB-PGR2021-00024; PTAB-PGR2021-00025; PTAB-IPR2021-00296; PTAB-IPR2021-00312, Paper 11 (Decision Settlement Prior to Institution of Trial), Jul. 6, 2021, 4 pages.
*BTL Industries, Inc.* v. *Allergan USA, Inc et al.*, DDE-1-19-cv-02356, Order Administratively Closing Case, Jul. 26, 2021, 1 page.
*BTL Industries, Inc.* v. *Allergan Ltd et al.*, DDE-1-20-cv-01046, Order Administratively Closing Case, Jul. 26, 2021, 1 page.
*Certain Non-Invasive Aesthetic Body-Contouring Devices, Components Thereof and Methods of Using the Same*, Inv. No. 337-TA-1219, Order No. 30 (Order Concerning the Procedural Schedule), Aug. 4, 2021, 3 pages.
Doucet, B., et al., "Neuromuscular Electrical Stimulation for Skeletal Muscle Function," Yale Journal of Biology & Medicine 85:201-215 (2012).
Gorgey, A., et al., "Effects of Electrical Stimulation Parameters on Fatigue in Skeletal Muscle," J. Orthop. & Sports Phys. Therapy vol. 39(9):684-92 (Sep. 2009).

(56) References Cited

OTHER PUBLICATIONS

Iskra Medical, "IESLA Stym Website," URL: <https://web.archive.org/web/20131106123126/http:/www.iskramedical.eu:80/magneto-therapy-medical/tesla-stym (Nov. 6, 2013).
*Lumenis Ltd. v. BTL Healthcare Technologies A.S.*, PTAB-IPR2021-01273, U.S. Pat. No. 10,478,634, Petition for Inter Partes Review, Aug. 13, 2021, 70 pages.
*Lumenis Ltd. v. BTL Healthcare Technologies A.S.*, PTAB-IPR2021-01273, Declaration of Dr. MaromBikson (EX1002), Aug. 13, 2021, 225 pages.
*Lumenis Ltd. v. BTL Healthcare Technologies A.S.*, PTAB-IPR2021-01275, U.S. Pat. No. 10,632,321, Petition for Inter Partes Review, Aug. 5, 2021, 92 pages.
*Lumenis Ltd. v. BTL Healthcare Technologies A.S.*, PTAB-IPR2021-01275, Declaration of Dr. MaromBikson (EX1002), Aug. 5, 2021, 282 pages.
*Lumenis Ltd. v. BTL Healthcare Technologies A.S.*, PTAB-IPR2021-01276, U.S. Pat. No. 10,965,575, Petition for Inter Partes Review, Aug. 5, 2021, 79 pages.
*Lumenis Ltd. v. BTL Healthcare Technologies A.S.*, PTAB-IPR2021-01276, Declaration of Dr. MaromBikson (EX1002), Aug. 5, 2021, 241 pages.
*Lumenis Ltd. v. BTL Healthcare Technologies A.S.*, PTAB-IPR2021-01278, U.S. Pat. No. 10,709,894, Petition for Inter Partes Review, Aug. 13, 2021, 85 pages.
*Lumenis Ltd. v. BTL Healthcare Technologies A.S.*, PTAB-IPR2021-01278, Declaration of Dr. MaromBikson (EX1002), Aug. 13, 2021, 255 pages.
*Lumenis Ltd. v. BTL Healthcare Technologies A.S.*, PTAB-IPR2021-01279, U.S. Pat. No. 10,709,895, Petition for Inter Partes Review, Aug. 5, 2021, 88 pages.
*Lumenis Ltd. v. BTL Healthcare Technologies A.S.*, PTAB-IPR2021-01279, Declaration of Dr. Marom Bikson (EX1002), Aug. 5, 2021, 258 pages.
*Lumenis Ltd. v. BTL Healthcare Technologies A.S.*, PTAB-IPR2021-01280, U.S. Pat. No. 10,478,634, Petition for Inter Partes Review, Aug. 13, 2021, 69 pages.
*Lumenis Ltd. v. BTL Healthcare Technologies A.S.*, PTAB-IPR2021-01280, Declaration of Dr. Marom Bikson (EX1002), Aug. 13, 2021, 235 pages.
*Lumenis Ltd. v. BTL Healthcare Technologies A.S.*, PTAB-IPR2021-01282, U.S. Pat. No. 10,632,321, Petition for Inter Partes Review, Aug. 5, 2021, 89 pages.
*Lumenis Ltd. v. BTL Healthcare Technologies A.S.*, PTAB-IPR2021-01282, Declaration of Dr. Marom Bikson (EX1002), Aug. 5, 2021, 267 pages.
*Lumenis Ltd. v. BTL Healthcare Technologies A.S.*, PTAB-IPR2021-01283, U.S. Pat. No. 10,695,575, Petition for Inter Partes Review, Aug. 5, 2021, 84 pages.
*Lumenis Ltd. v. BTL Healthcare Technologies A.S.*, PTAB-IPR2021-01283, Declaration of Dr. Marom Bikson (EX1002), Aug. 5, 2021, 241 pages.
*Lumenis Ltd. v. BTL Healthcare Technologies A.S.*, PTAB-IPR2021-01284, U.S. Pat. No. 10,709,895, Petition for Inter Partes Review, Aug. 5, 2021, 93 pages.
*Lumenis Ltd. v. BTL Healthcare Technologies A.S.*, PTAB-IPR2021-01284, Declaration of Dr. Marom Bikson (EX1002), Aug. 5, 2021, 279 pages.
*Lumenis Ltd. v. BTL Healthcare Technologies A.S.*, PTAB-IPR2021-01285, U.S. Pat. No. 10,709,894, Petition for Inter Partes Review, Aug. 13, 2021, 79 pages.
*Lumenis Ltd. v. BTL Healthcare Technologies A.S.*, PTAB-IPR2021-01285, Declaration of Dr. Marom Bikson (EX1002), Aug. 13, 2021, 249 pages.
Stevens, J., et al., "Neuromuscular Electrical Stimulation for Quadriceps Muscle Strengthening After Bilateral Total Knee Arthroplasty: A Case Series," Journal of Orthopaedic & Sports Physical Therapy, 34(1):21-29 (Jan. 2004).
U.S. Appl. No. 60/848,720, inventor Burnett, D., filed Sep. 30, 2006 (Not Published).
Woehrle, J., et al., "Dry Needling and its Use in Health Care—A Treatment Modality and Adjunct for Pain Management," J. Pain & Relief, 4(5): 1-3 (Aug. 2015).
Mantis, The non-invasive solution that restores natural beauty, improves health, and offers a renewed psychophysical sense of balance, MR991 theramagnetic, 2020, 8 pages.
Mantis Theramagnetic Compact: the compact that guarantees utmost efficiency and maximum performance, theramagnetic, 2020, 8 pages.
Pollegen, K200545, Legend Pro DMA, Indications for use, dated Oct. 20, 2021, 11 pages.
Jalinous, R., "Technical and Practical Aspects of Magnetic Nerve Stimulation," Journal of Clinical Neurophysiology 8(1):10-25, Lippincott Williams & Wilkins, United States (Jan. 1991).
*Lumenis Ltd. v. BTL Healthcare Technologies A.S.*, PTAB-IPR2022-00451, Declaration of Dr. Marom Bikson (EX1002), Jan. 24, 2022, 236 pages.
*Lumenis Ltd. v. BTL Healthcare Technologies A.S.*, PTAB-IPR2022-00451, U.S. Pat. No. 10,806,943 Petition for Inter Partes Review, Jan. 24, 2022, 87 pages.
*Lumenis Ltd. v. BTL Healthcare Technologies A.S.*, PTAB-IPR2022-00452, Declaration of Dr. Marom Bikson (EX1002), Jan. 24, 2022, 229 pages.
*Lumenis Ltd. v. BTL Healthcare Technologies A.S.*, PTAB-IPR2022-00452, U.S. Pat. No. 10,806,943 Petition for Inter Partes Review, Jan. 24, 2022, 81 pages.
Operating Manual: Magstim ® 2002, P/N 3001-23-04, The Magstim Company Limited, Mar. 18, 2005, 34 pages.
Stallknecht, B., et al., "Are Blood Flow and Lipolysis in Subcutaneous Adipose Tissue Influenced by Contractions in Adject Muscles in Humans?," American Journal of Physiology. Endocrinology and Metabolism 292(2):E394-E399, American Physiological Society, United States (Feb. 2007).
Weyh, T., et al., "Marked Differences in the Thermal Characteristics of Figure-of-eight Shaped Coils Used for Repetitive Transcranial Magnetic Stimulation," Clinical Neurophysiology 116(6):1477-1486, Elsevier, Netherlands (Mar. 2005).
Pascual-Leone, Alvaro et al. "Handbook of Transcranial Magnetic Stimulation" 2002 Arnold Publishers, Chapters 1-4, 58 pages.
Cutera, truSculptflex, Brochure, dated 2019, 2 pages.
Depatment of Health and Human Services, 501 (k) Letter and Summary for K092476 Body Control System 4M Powered Muscle Stimulator, dated May 7, 2010, 5 pages.
Depatment of Health and Human Services, 501 (k) Letter and Summary for K160992 HPM-6000 Powered Muscle Stimulator, dated Oct. 21, 2016, 9 pages.
Depatment of Health and Human Services, 501 (k) Letter and Summary for K163415 SlimShape System Powered Muscle Stimulator, dated Apr. 20, 2017, 8 pages.
Depatment of Health and Human Services, 501 (k) Letter and Summary for K182106 BTL 799-2T Powered Muscle Stimulator, dated Oct. 23, 2018, 9 pages.
Depatment of Health and Human Services, 501 (k) Letter and Summary for K190456 BTL 799-2L Powered Muscle Stimulator, dated Jul. 5, 2019, 9 pages.
Depatment of Health and Human Services, 501 (k) Letter and Summary for K192224 BTL 899 Powered Muscle Stimulator, dated Dec. 5, 2019, 11 pages.
Kocbach et al., "A Simulation Approach to Optimizing Perfermance of Equipment for Thermostimulation of Muscle Tissue using COMSOL Multiphysics" Article in Biophysics & Bioeng. dated 2011, 26 pages.
Mekawy et al., "Influence of Electro-lipolysis on Lipid Profile and Central Obesity in Obese Premenopausal Women" Bull. Fac. Ph. Th. Cairo Univ., vol. 17, No. (1), dated Jan. 2012, pp. 59-68.
Pollogen, Maximus Non-invasive body shaping System, User Manual, dated May 1, 2012, 44 pages.
Pollogen, TriFractional FAQs, User Manual, dated Aug. 2011, 4 pages.
Pollogen, TriLipo MED Procedure, Brochure, dated Apr. 7, 2021, 76 pages.
Publication of Medical Device Manufacturing Approval of Salus-TALENT-Pro, approval date Mar. 11, 2014, 39 pages.

(56) References Cited

OTHER PUBLICATIONS

Venus Concept Ltd., VenusFreeze MP2, User Manual, dated Jun. 2012, 46 pages.
Venus Concept Ltd., VenusViva, User Manual, dated Aug. 2013, 51 pages.
Wanitphakdeedecha et al., "Treatment of abdominal cellulite and circumference reduction with radiofrequency and dynamic muscle activation" Article in Journal of Cosmetic and Laser Therapy, dated Apr. 6, 2015, 7 pages.

* cited by examiner

AESTHETIC METHOD OF BIOLOGICAL STRUCTURE TREATMENT BY MAGNETIC FIELD

CROSS-REFERENCE

This application is a continuation of U.S. patent application Ser. No. 16/827,330, filed Mar. 23, 2020, which is a continuation of U.S. patent application Ser. No. 15/601,719, filed May 22, 2017, which claims priority to each of U.S. Provisional Patent Application Nos. 62/357,679, filed Jul. 1, 2016, 62/440,905, filed Dec. 30, 2016, and 62/440,922, filed Dec. 30, 2016. Each of these applications is incorporated herein in its entirety by reference thereto.

FIELD OF THE INVENTION

The present invention generally relates to methods using the influence of magnetic and induced electric field on biological structure. The magnetic field is time-varying and high powered therefore the method is based on a value of magnetic flux density sufficient to induce at least partial muscle contraction.

BACKGROUND OF THE INVENTION

Aesthetic medicine includes all treatments resulting in enhancing a visual appearance and satisfaction of the patient. Patients want to minimize all imperfections including body shape and effects of natural aging. Indeed, patients request quick, non-invasive procedures providing satisfactory results with minimal risks.

The most common methods used for non-invasive aesthetic applications are based on application of mechanical waves, e.g. ultrasound or shock wave therapy; or electromagnetic waves, e.g. radiofrequency treatment or light treatment, such as intense pulsed light or laser treatment. The effect of mechanical waves on tissue is based especially on cavitation, vibration and/or heat inducing effects. The effect of applications using electromagnetic waves is based especially on heat production in the biological structure.

Skin tissue is composed of three basic elements: epidermis, dermis and hypodermis or so called subcutis. The outer and also the thinnest layer of skin is the epidermis. The dermis consists of collagen, elastic tissue and reticular fibers. The hypodermis is the lowest layer of the skin and contains hair follicle roots, lymphatic vessels, collagen tissue, nerves and also fat forming a subcutaneous white adipose tissue (SWAT). The adipose cells create lobules which are bounded by connective tissue, fibrous septa (reticulum cutis).

Another part of adipose tissue, so called visceral fat, is located in the peritoneal cavity and forms visceral white adipose tissue (VWAT) located between parietal peritoneum and visceral peritoneum, closely below muscle fibers adjoining the hypodermis layer.

Existing devices have low efficiency and they waste energy, which limits their use. Eddy currents induced within the coil create engineering challenges. Existing devices contain coils which are made of metallic strips, electric wires or hollow conductors. Since the therapy requires large currents, significant losses are caused by induced eddy currents within the coil. Eddy currents lead to production of unwanted heat and therefore there is need to sufficiently cool the coil. Also, the energy source must be protected during reverse polarity of resonance. This requires using protective circuits which consume significant amounts of energy.

The currently used magnetic stimulation devices mostly consist of one magnetic field generating device, a capacitor parallel to a power source and a switching device in series to the power source. Further such topology requires a snubbering device, such as diode or RC snubbering circuit, for protecting the energy source during the reverse polarity of resonance. The use of a snubbering device causes high energy losses. The magnetic stimulation device wastes a lot of energy because of low efficiency due to significant electric losses while generating the time-varying magnetic field. Therefore these devices generate magnetic impulses ineffectively.

Current magnetic aesthetic methods are limited in key parameters which are repetition rate and/or magnetic flux density. All known methods use low values of magnetic flux density and/or low repetition rates which does not allow satisfactory enhancement of visual appearance. As a result, new methods are needed to enhance the visual appearance of the patient.

Magnet therapy uses the influence of magnetic flux on biological tissue. Electric current is induced in the tissue due to voltage change which causes a polarization of the cell membrane. One of fundamental phenomenon of electric current in biological tissue is a transfer of neural excitation or muscle contraction. The intensity of the effect is dependent on the magnetic flux density, repetition rate of the pulses, pulse time duration or envelope of the stimulation signal.

The currently used aesthetic applications don't provide any treatment combining the effect of time-varying magnetic field treatment and conventional treatment, e.g. treatment by electromagnetic field such as radiofrequency treatment. The currently used radiofrequency treatment includes many adverse events such as non-homogenous thermal temperature, insufficient blood and/or lymph flow during and/or after the treatment. Additionally several adverse event such as panniculitis may occur after the treatment.

SUMMARY OF THE INVENTION

The present methods and devices as described below produce a time varying magnetic field for patient treatment which better optimizes energy use, increases the effectiveness of the treatments and provide a new treatment. The magnetic pulses may be generated in monophasic, biphasic or polyphasic regimes. In a first aspect, the device has one or more coils; a switch; an energy storage device and a connection to an energy source. The coil may be made of insulated wires with a conductor diameter less than 3 mm even more preferably less than 0.5 mm and most preferably less than 0.05 mm. Smaller diameter and individual insulation of the wires significantly reduces self-heating of the coil and therefore increase efficiency of magnetic stimulation device. The coil may be flexibly attached in a casing of device. The casing may comprise a blower or blowers which ensure cooling of the coil.

The present methods provide new aesthetic applications for focused remodeling of the patient's body. The coil of the magnetic stimulation device may be flexibly attached to casing of the device. The blower or blowers may be arranged to blow air on both sides of coil. Optionally, the coil may be a flat type coil.

The method may provide a non-invasive transfer of a stimulation signal from an applicator to biological structure to evoke the action potential of biological structure.

The method of treating a biological structure uses a combination of non-invasive methods for enhancing human appearance. The invention utilizes electromagnetic field. Methods may be used for targeted remodeling of adipose tissue, focused treatment of cellulite, body contouring, skin tightening or skin rejuvenation. The invention relates to focused heating of the target tissue by electromagnetic waves, whereas the effect of focused heating of the target tissue is amplified by the effect of a magnetic treatment.

In a first aspect, a method provides stimulation of biological structure using magnetic field at repetition rates exceeding 50 Hz for purpose of at least a partial muscle contraction.

In further aspect, a neuromuscular plate and/or the nerve innervating the neuromuscular plate is stimulated and at least partial muscle contraction is provided.

The magnetic treatment induces the muscle contraction at higher repetition rates and the contraction is stronger. Therefore the treatment is more efficient for reducing the number and/or volume of adipocytes and enhancing the visual appearance of the treated body region via targeted muscle contraction. Further the temperature homogeneity of is improved. Additionally, strong muscle contractions at higher repetition rates cause mechanical movement of all the layers in proximity of the contracted muscle. The methods therefore cause remodeling and/or neogenesis of the collagen and elastin fibers.

In another aspect, the stimulation utilizes non-invasive and/or contactless transfer of the stimulation signal from an applicator to biological structure to evoke the action potential of the biological structure to induce at least partial muscle contraction. The applicator may include a source of magnetic field e.g. a coil.

In another aspect of the invention the repetition rate may exceed the frequency resolution of the structure. The magnetic flux density of the stimulation signal may increase over time. Therefore the envelope of resulting stimulation signal is increasing and it is perceived by the stimulated biological structure as a continuous stimulation signal instead of plurality of discrete stimuli. The envelope may be preferably triangular and other shapes may be used as well. This method is effective for stimulation of denervated muscle.

The envelope may be generated by time-varying magnetic flux density and/or repetition rate and/or impulse duration.

The muscle tissue is selectively stimulated and the magnetic flux density of the stimulation may be adjusted based on the patient's feeling and/or needs. Treatment time is shortened due to selective stimulation of muscles. Additionally, the treatment may be non-invasive or even contactless due to the high value of magnetic flux density. Invasive methods may be used as well. The patient may be treated without the necessity of taking clothes off. The method reduces patient discomfort.

The present methods may be used for enhancing visual appearance of body areas including adipose tissue reduction, muscle toning, muscle shaping, body contouring, body shaping, skin tightening, cellulite treatment, circumferential reduction, breast enhancement and/or lip enhancement.

The methods enable new treatments by magnetic and/or electromagnetic field. The repetition rate of the magnetic field is in the range of 1 to 300 Hz with high magnetic flux density up to 7 Tesla (equivalent to 70000 Gauss). The frequency of the electromagnetic field is 13.56 or 40.68 or 27.12 MHz or 2.45 GHz.

The present invention provides a new approach in determining the parameters of biological structure treatment.

According to the first aspect of the invention the magnetic stimulation device monitors the stimulation energy based on the current value of an operation parameter and/or the operation parameter waveform of one period.

According to still another aspect of the invention the control unit may calculate optimal flow of the cooling medium based on the treatment parameters, transition thermal characteristic of the magnetic stimulation device and/or the cooling medium temperature and significantly reduce the noise of the cooling system.

According to still another aspect of the invention the control unit may optimize the treatment parameters based on the current value of operation parameters and a transition thermal characteristic of the magnetic stimulation device.

The present invention relates to device and methods for treating a patient by a magnetic and/or electromagnetic field. The application of the magnetic and/or electromagnetic field is provided by at least one energy delivery element. The device may be used for treatment or focused remodeling of adipose tissue by reducing number and/or value of lipid-rich cells.

The present device and methods as described below provide combined treatment by high power magnetic and/or electromagnetic field, particularly radiofrequency treatment. The combined treatment may be provided by one device using at least one coil for providing both treatments, the magnetic and even the electromagnetic treatment.

The device may include a plurality of energy delivery elements. The positioning of the plurality of the energy delivery elements may be controlled by a mathematic method including monitoring a characteristic quantity of an operation parameter.

The energy delivery element may be used as an energy source for another functional part of an applicator, e.g. a blower, or for providing energy to light emitting device providing still another treatment.

Glossary

Conventional non-invasive and/or invasive aesthetic medicine treatment methods refer to aesthetic applications based on application of mechanical waves, e.g. acoustic wave, ultrasound or shock wave therapy; or electromagnetic waves, e.g. radiofrequency or diathermy treatment or light treatment, such as intense pulsed light or laser treatment; or mechanical stimulation, e.g. positive or negative pressure, rollerball, massage etc.; or thermal treatment, e.g. cryotherapy; or electrotherapy method; or mesotherapy method and or any combination thereof.

Thermal treatment refers to treatment by heating or cooling, e.g. a cryotherapy treatment.

Biological structure is at least one neuron, neuromuscular plate, muscle fiber, adipose cell or tissue, collagen, elastin, pigment or skin.

Remodeling target biological structure refers to reducing the number and/or volume of the adipocytes by apoptosis and/or necrosis, cellulite treatment, body shaping and/or contouring, muscle toning, skin tightening, collagen treatment, skin rejuvenation, wrinkle removing, reducing stretchmarks, breast lifting, lip enhancement, treatment of vascular or pigmented lesions of the skin or hair removing.

Stimulation signal refers to a magnetic flux density inducing an electric current in the biological structure.

Body region includes muscle or muscle group, buttocks, saddlebags, love handles, abdomen, hips, thighs, arms, limb and/or any other tissue.

Muscle includes at least one of muscle fiber, muscle tissue or group, neuromuscular plate or nerve innervating the at least one muscle fiber.

Deep muscle refers to a muscle that is at least partly below superficial muscles and/or to the muscle that is covered by a thick layer of other tissue, e.g. mostly adipose tissue and/or the skin, with thickness 0.5, 1, 2, 3, 4, 5 or more centimetres.

Adipose tissue refers to at least one lipid rich cell, e.g. adipocyte.

Bolus refers to a layer of fluid material, e.g. water or fluid solution of ceramic particles, preferably enclosed in a flexible sac made of biocompatible material.

Impulse refers to a single magnetic stimulus.

Pulse refers to a period of treatment by a magnetic field of at least one magnetic stimulus and time duration of no stimulation, i.e. time duration between two impulses from rise/fall edge to next rise/fall edge.

Repetition rate refers to frequency of firing the pulses; it is derived from the time duration of a pulse.

Envelope refers to shape of curve created by connection of induced energy amplitudes stimulating the target biological structure.

Neural structure includes at least one neural cell, a neuron, a neuroglia, a Schwann cell, a nerve, a neural tissue, spine or brain.

Operation parameter refers to voltage, current or magnetic flux density.

Induced energy refers to energy stimulating the target neural structure, the amount of induced energy corresponds to repetition rate, magnetic flux density and impulse duration.

Hardware panel refers to at least one hardware component used for controlling the optical and/or magnetic treatment. The hardware panel includes at least one of input interface for inputting treatment parameters by an operator and processing unit for controlling the optical and/or magnetic treatment.

Treatment parameters refer to one or more of: magnetic flux density, repetition rate, impulse duration, wavelength, power flux density and/or energy flux density of the optical waves, pulse width, modulation, treatment protocol or treatment duration.

Optical waves include electromagnetic waves from ultraviolet, visible and infrared spectrum ranges, i.e. the waves of wavelength in the range of 190 to 13000 nm.

Optical waves generating device refers to laser or laser diode, light emitting diode (LED), electric discharge source, incandescent source, fluorescent source, luminescent source, electroluminescent source etc.

Optical treatment refers to treatment by optical waves.

DETAILED DESCRIPTION

Figure 1:
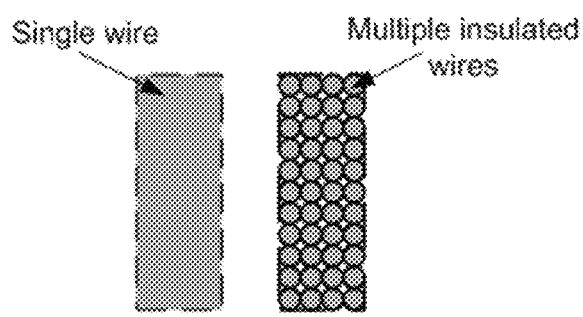
FIG. 1 is a cross section view of a coil winding.

The present invention provides a magnetic stimulation device and method of controlling the magnetic stimulation device using a plurality of magnetic field generating devices.

The magnetic stimulation device may include the at least one applicator, the at least one energy source and at least two magnetic field generating devices. However, in an alternative embodiment the magnetic stimulation device may include a plurality of applicators and/or plurality of energy sources. The plurality of applicators may be used for treatment of at least two cooperating muscle groups with different treatment effects. In an exemplary application e.g. the triceps brachii muscle may be treated to achieve myostimulation effects and the biceps brachii muscle may be treated to achieve myorelaxation effects.

The magnetic stimulation device may include a plurality of applicators. The applicator includes at least one magnetic field generating device which may be movable. The benefit of this embodiment is that the movement and/or positioning of the plurality of the applicators may be independent. Hence different parts of the patient's body may be treated simultaneously. Therefore the total treatment time is reduced and patient's downtimes are reduced as well. The movement of the at least one applicator may be automatic so that manual manipulation may not be needed. The movement of the at least one applicator may follow a predetermined trajectory or it may be random. In an alternative embodiment the movement of the plurality of applicators may be synchronized.

The plurality of applicators may be positioned with respect to each other in one plane; in at least two mutually tilted planes defined by convex or concave angles, or perpendicular to each other; or in at least two parallel planes. The angles of the planes may be adjusted by an operator following the patient's needs. In an alternative embodiment the patient may be positioned in the intersection of the magnetic fields generated by the plurality of magnetic field generating devices.

The benefit of this application may be treatment of a plurality of cooperating muscles, such as agonist and antagonists, e.g. one muscle may be stimulated to achieve strengthening effect and on the other side the other muscle may be stimulated to achieve myorelaxation effect.

Using a plurality of magnetic field generating devices provides faster treatment. Large and/or different areas may be treated in shorter time. Using a plurality of applicators allows different areas and/or target biological structures to be stimulated at the same time. The movement of the at least one applicator may automatically follow a predetermined trajectory. Hence manual manipulation is not needed. Furthermore the shape of the generated magnetic field may be adjusted by an operator.

The applicator including a coil which is preferably flat for magnet therapy is placed proximate to the patient's body. The magnetic flux is applied into the biological structure. The electric current is induced and stimulates the neuromuscular plate. Due to the stimulation at least a partial muscle contraction is caused.

In one aspect of the invention a magnetic stimulation device includes at least one applicator and a plurality of magnetic field generating devices. The magnetic field generating device may be air-cooled or cooled by any other fluid media.

Repetition rate and/or magnetic flux density may vary during the treatment protocol. Further the magnetic stimulation signal may include several periods of stimulation signal of different repetition rates, therefore the modulation of the signal is in repetition rate domain. The stimulation signal may include several periods of stimulation signal of different magnetic flux densities, therefore the modulation of the signal is in magnetic flux density domain. In yet another approach the envelope of the stimulation signal may be modulated by combinations of repetition rate domain, magnetic flux density domain or impulse duration domain.

Various envelopes of the stimulation signal and waveform, e.g. pulse, sinusoidal, rectangular, square, triangular, saw-tooth, trapezoidal, exponential etc. for the purpose of muscle stimulation may also be used, and is not limited to recited shapes of stimulation signals.

A magnetic treatment device may include at least one energy source and/or connection to the energy source, at least one switching device, at least one energy storage device, e.g. a capacitor, and at least one magnetic field generating device e.g. a coil.

The magnetic stimulation device may include at least one energy source, at least one energy storage device (e.g. a capacitor), at least one magnetic field generating device (e.g. a coil) and at least one switching device. The magnetic field generating device may include a core, however in a preferred embodiment the magnetic field generating device includes no core. The switching device may be any kind of switch such as diode, MOSFET, JFET, IGBT, BJT, thyristor or a combination of them.

The at least one magnetic generating device may be in various shapes to enhance a variability of magnetic field profile. The shape of the magnetic field generating device may be circular, semicircular, rectangular, "FIG. 8", V-shape, Y shape or a butterfly shape. The magnetic field generating device may be flat (2-D shape). In an alternative embodiment the magnetic field generating device may correspond to various 3-D bodies, e.g. a hemisphere. In another alternative embodiment the magnetic field generating device may be flexible to be better fitted to the patient. The magnetic field generating device may or may not include a core for the field shaping.

Large areas may be stimulated by the plurality of the magnetic field generating devices. The plurality of magnetic field generating devices may generate a plurality of independent magnetic fields, e.g. two magnetic field generating devices may generate two magnetic fields with two peaks of magnitude of magnetic flux density.

The plurality of magnetic field generating devices may be operated at various treatment parameters and/or operation modes to provide various treatment effects for the patient during the treatment, e.g. myostimulation, myorelaxation, analgesic effect or aesthetic effects such as adipose tissue reduction, muscle toning, muscle shaping, body contouring, body shaping, skin tightening, cellulite treatment, circumferential reduction, breast enhancement and/or lip enhancement.

FIG. 1 illustrates a cross section of winding of a coil for a magnetic stimulation device. The coil may be constructed from litz-wire, wherein each wire is insulated separately. Each individual conductor is coated with non-conductive material so the coil constitutes multiple insulated wires. Unlike existing magnetic coil conductors, the present coil is not made of bare wire e.g. litz-wire without insulation, or conductive tapes, conductive strips, or copper pipe with hollow inductors. The insulation of wires separately is a substantial improvement, since this leads to a significant reduction of the induced eddy currents. Power loss due to eddy currents, per single wire, is described by Equation 1 below. The small diameter of wires significantly reduces self-heating of the coil and therefore increases efficiency of the present magnetic stimulation device.

$$P_{EDDY} = \frac{\pi^2 \cdot B_P^2 \cdot d^2 \cdot f^2}{6 \cdot k \cdot \rho \cdot D}, \qquad \text{Eq. 1}$$

where: $P_{EDDY}$ is power loss per unit mass (W kg$^{-1}$); $B_P$ is the peak of magnetic field (T); f is frequency (Hz); d is the thickness of the sheet or diameter of the wire (m); k is constant equal to 1 for a thin sheet and 2 for a thin wire; ρ is the resistivity of material (Ω·m); D is the density of material (kg·m$^3$).

The individual insulation of each wire reduces eddy currents. The individually insulated wires may be wound either one by one or in a bundle of individually insulated wires so as to form a coil, which will serve as a magnetic field generator. The coil provides an improvement in the efficiency of energy transfer in the LC resonant circuit and also reduces or eliminates unwanted thermal effects.

The coil may have a planar coil shape where the individually insulated wires may have cross-section wires with conductor diameter less than 3 mm even more preferably less than 0.5 mm and most preferably less than 0.05 mm. The wires are preferably made of materials with higher density and higher resistivity e.g. gold, platinum or copper. The diameters of the single wires should be minimal. On the other hand the total diameter should be maximal because of inverse proportion between the cross-section of all wires forming the coil and the electrical resistance. Therefore the ohmic part of the heat is then lower. Eq. 2 describes power loss of the coil:

$$P_R = \frac{\rho \cdot \frac{l}{S} \cdot I^2}{m} \qquad \text{Eq. 2}$$

Where: $P_R$ is the power loss heat dissipation (W); ρ is the resistance (Ω·m); l is the length of wire (m); S is the surface area (m$^2$); I is the current (A) and m is 1 kg of wire material.

Total power loss is (Eq.3):

$$P_{TOT} = P_{EDDY} + P_R, \qquad \text{Eq. 3}$$

Where: $P_{TOT}$ is the total power losses (W·kg$^{-1}$); $P_{EDDY}$ is the power dissipation of eddy currents (W·kg$^{-1}$); $P_R$ is the power loss heat dissipation (W·kg$^{-1}$).

Dynamic forces produced by current pulses passing through the wires of the coil cause vibrations and unwanted noise. The individual insulated wires of the coil may be impregnated under pressure so as to eliminate air bubbles between the individual insulated wires. The space between wires can be filled with suitable material which causes unification, preservation and electric insulation of the system. Suitable rigid impregnation materials like resin, and elastic materials like PTE can be also used. With the coil provided as a solid mass, the vibrations and resonance caused by movements of the individual insulated wires are suppressed. Therefore noise is reduced.

The coil may be attached to the case of the applicator, such as a hand held applicator of the magnetic stimulation device; build-in applicator in e.g. chair, bed; or stand-alone applicator e.g. on mechanical fixture. The attachment may be provided by an elastic material e.g., silicone, gum; or other flexible manner. Connection with the coil of the applicator's case can be ensured by several points. The several fastening points ensure the connection of the coil to the casing by flexible material so that the main part of the coil and the main part of the casing of applicator are spaced apart. The spacing should be at least 0.1 mm so that air can easily flow. The gap between the coil and the casing can be used either for spontaneous or controlled cooling. The coil may optionally be connected to the case of the applicator by only one fastening point. The fastening points eliminate vibrations of wires which could be transferred to housing of the applicator and therefore reduce noise of the magnetic stimulation device.

The magnetic stimulation device may be cooled by a fluid, e.g. by a liquid or a gas. In the preferred embodiment the magnetic stimulation device is cooled by air.

Figure 2A:
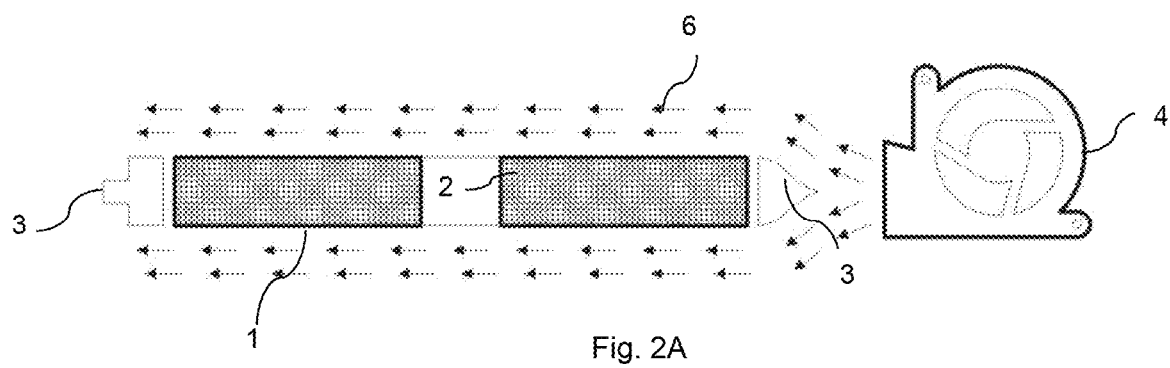
FIG. 2A is a cross-section of a magnetic applicator.

FIG. 2A is a cross-section of the magnetic applicator which allows better flow on the lower and upper sides of the coil and thus more efficient heat dissipation. The magnetic stimulation device includes a coil 1, the circuit wires 2 and the fastening points 3 for connection of the coil to the casing of the applicator (not shown). The fastening points 3 are preferably made of flexible material however the rigid material may be used as well. The fastening points 3 may be located on the outer circumferential side of the coil. However, alternatively it is possible to put these fastening points to a lower or upper side of the coil.

The fastening points 3 connect the coil to the case of the applicator in at least one point. The fastening points 3 maintain the coil and the main part of the case of the applicator spaced apart so that fluid (which may be air or any liquid) can flow between them. At least one blower 4 can be placed around the circumference of the coil, or perpendicular to the coil. The blower can be any known kind of device for directing the fluid e.g. outer air directed into the case of the applicator. This arrangement of the blower allows air to bypass the coil from upper and lower (patient's) sides. In still another embodiment the outer air can be cooled before directing into the case. The blower can have an inlet placed around the circumference of the coil for injecting air, to remove heat from the coil. A connecting tube (not shown) can ensure connection of the applicator 5 with the energy source and/or control unit of magnetic stimulation device. The connecting tube may also contain a conduit of the fluid.

The arrows 6 indicate the air flow through the applicator. This arrangement of the blower allows the air to bypass the coil from upper and lower (patient's) side. Outlet may be preferably placed on upper side of the casing. By placing the blower around the circumference of the coil instead of on the top/below the coil, the blower 4 does not interfere with the magnetic flux peak and therefore its lifespan and reliability is increased.

Figure 2B:
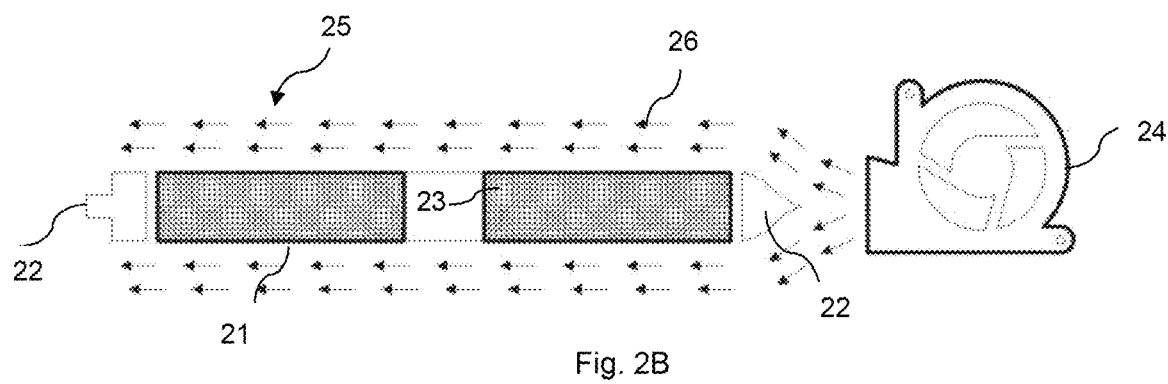
FIG. 2B is an illustrative embodiment of cross-section of the magnetic applicator.

FIG. 2B is a cross-section of the magnetic applicator which allows better flow on the lower and upper sides of the coil and thus more efficient heat dissipation. The magnetic stimulation device includes a coil 21, the circuit wires 23 and the fastening points 22 for connection of the coil to the casing of the applicator (not shown). The fastening points 22 are preferably made of flexible material however the rigid material may be used as well. The fastening points 22 may be located on the outer circumferential side of the coil. However, alternatively it is possible to put these fastening points to a lower or upper side of the coil.

The fastening points 22 connect the coil to the case of the applicator in at least one point. The fastening points 22 maintain the coil and the main part of the case of the applicator spaced apart so that fluid (which may be air or any liquid) can flow between them. At least one blower 24 can be placed around the circumference of the coil, or perpendicular to the coil. The blower can be any known kind of device for directing the fluid e.g. outer air directed into the case of the applicator. This arrangement of the blower allows air to bypass the coil from upper and lower (patient's) sides. In still another embodiment the outer air can be cooled before directing into the case. The blower can have an inlet placed around the circumference of the coil for injecting air, to remove heat from the coil. A connecting tube (not shown)

can ensure connection of the applicator 25 with the energy source and/or control unit of magnetic stimulation device. The connecting tube may also contain a conduit of the fluid.

The arrows 26 indicate the air flow through the applicator 25. This arrangement of the blower allows the air to bypass the coil from upper and lower (patient's) side. Outlet may be preferably placed on upper side of the casing. By placing the blower around the circumference of the coil instead of on the top/below the coil, the blower 24 does not interfere with the magnetic flux peak and therefore its lifespan and reliability is increased.

Figure 3:
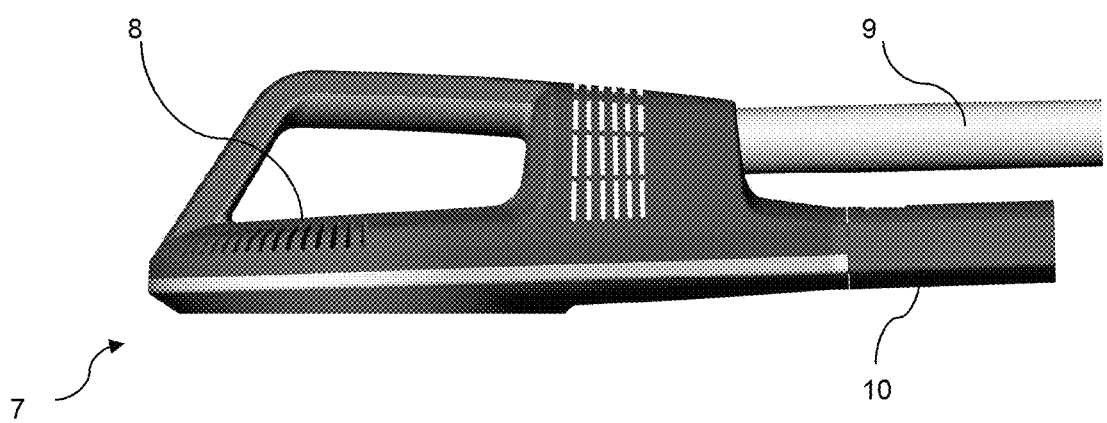
FIG. 3 is a side view of a casing of a magnetic applicator.

FIG. 3 is an illustrative embodiment of a casing of the magnetic applicator. The overview drawing contains casing itself 7, which might contain an outlet 8 preferably placed on upper side of the casing 7. A connecting tube 9 may not only ensure connection of the applicator with the energy source and/or control unit of magnetic stimulation device, but also connection to a source of the fluid; however the conduit of the fluid 10 may also be connected separately.

In an alternative embodiment cooling may be provided by a member using thermoelectric effect, e.g. a Peltier cooler. Alternatively, cooling may be provided by Stirling engine cooling system.

Figure 4A:
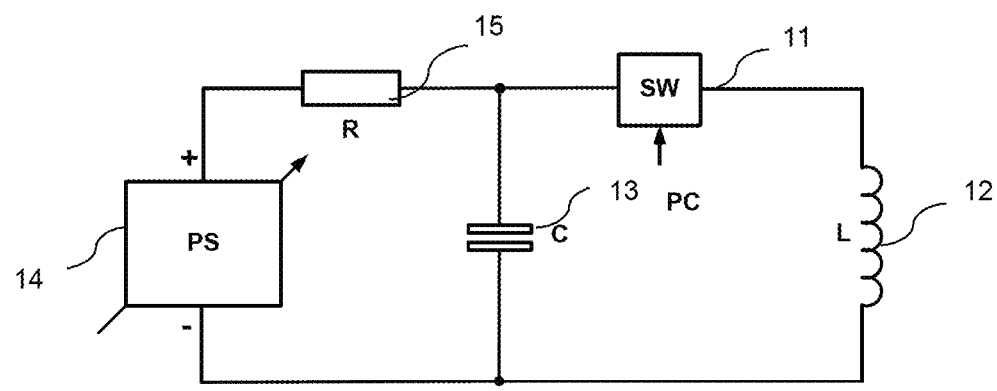
FIGS. 4A and 4B illustrate circuits for providing high power pulses to a stimulating coil.
Figure 4B:
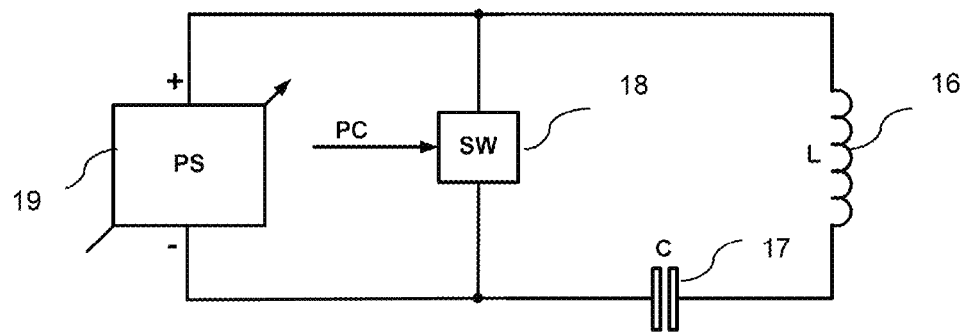

FIG. 4A and FIG. 4B illustrate circuits for providing high power pulses to the stimulating coil. FIG. 4A shows a circuit for providing high power magnetic pulses. FIG. 4B shows a circuit for providing high power pulses.

The state of art magnetic stimulation device achieves magnetic flux density of a few tenths to several ones of Tesla (1 Tesla is equivalent to 10000 Gauss). To achieve this level of magnetic flux density, the energy source used generates sufficient voltage. This voltage can reach thousands of volts. In FIG. 4A the circuits for providing high power pulses to the stimulating coil contain a series connection to the switch 11 and the coil 12. The switch 11 and the coil 12 together are connected in parallel with an energy storage device 13. The energy storage device 13 is charged by the energy source 14 and the energy storage device 13 then discharges through the switching device 11 to the coil 12.

During second half-period of LC resonance, the polarity on the energy storage device 13 is reversed in comparison with the energy source 14. In this second half-period, there is a conflict between energy source 14, where voltage on positive and negative terminals is typically thousands of Volts. The energy storage device 13 is also charged to the positive and negative voltage generally to thousands of Volts. As a result, there is in the circuit, consequently, twice the voltage of the energy source 14. Hence the energy source 14 and all parts connected in the circuit are designed for a high voltage load. Therefore, the protective resistors and/or protection circuitry 15 must be placed between energy source 14 and energy storage device 13. Disadvantage of state of art solution is large amount of energy transformed to undesired heat in protective resistors and/or protection circuitry 15.

FIG. 4B shows a circuit for providing high power pulses for improved function of the magnet stimulation device. The coil 16 and an energy storage device 17 are connected in series and disposed in parallel to the switch 18. The energy storage device 17 is charged through the coil 16. To provide an energy pulse, controlled shorting of energy source 19 takes place through the switch 18. In this way the high voltage load at the terminals of the energy source 19 during the second half-period of LC resonance associated with known devices is avoided. The voltage on the terminals of energy source 19 during second half-period of LC resonance is a voltage equal to the voltage drop on the switch 18.

The switch 18 can be any kind of switch such as diode, MOSFET, JFET, IGBT, BJT, thyristor or their combination. Depending on the type of component the load of energy source 19 is reduced to a few Volts, e.g., 1-10 volts. Consequently, it is not necessary to protect the energy source 19 from a high voltage load, e.g., thousands of Volts. The use of protective resistors and/or protection circuits is reduced or eliminated. The present designs simplify the circuits used, increase efficiency of energy usage and provide higher safety.

Figure 5A:
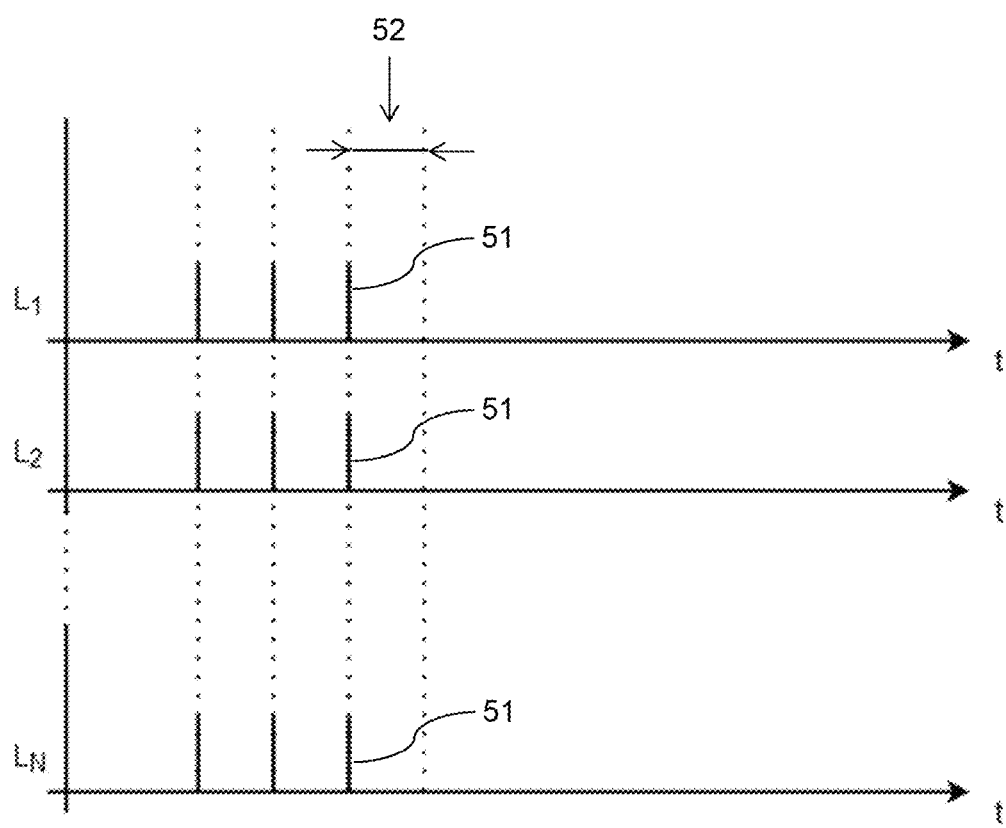
FIG. 5A illustrates an operation mode when impulses are generated by the plurality of magnetic field generating devices at one time within a pulse.
Figure 5B:
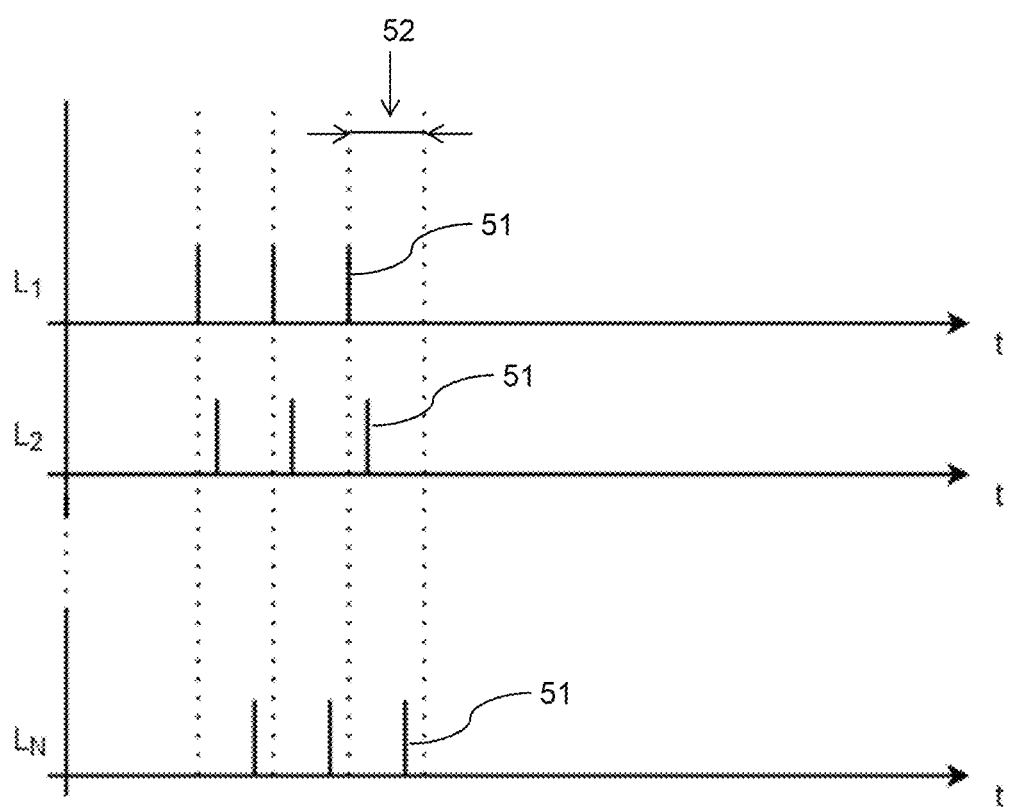
FIG. 5B illustrates an operation mode when impulses are generated by the plurality of magnetic field generating devices at plurality of different times within a pulse.

The treatment by the magnetic stimulation device may be in different operation modes. One operation mode may generate a plurality of impulses 51 at one time within the pulse 52 as illustrated in FIG. 5A. Another operation mode may generate a plurality of the impulses 51 at different times within the pulse 52 as illustrated in FIG. 5B. Both operation modes may be combined.

Figure 6:
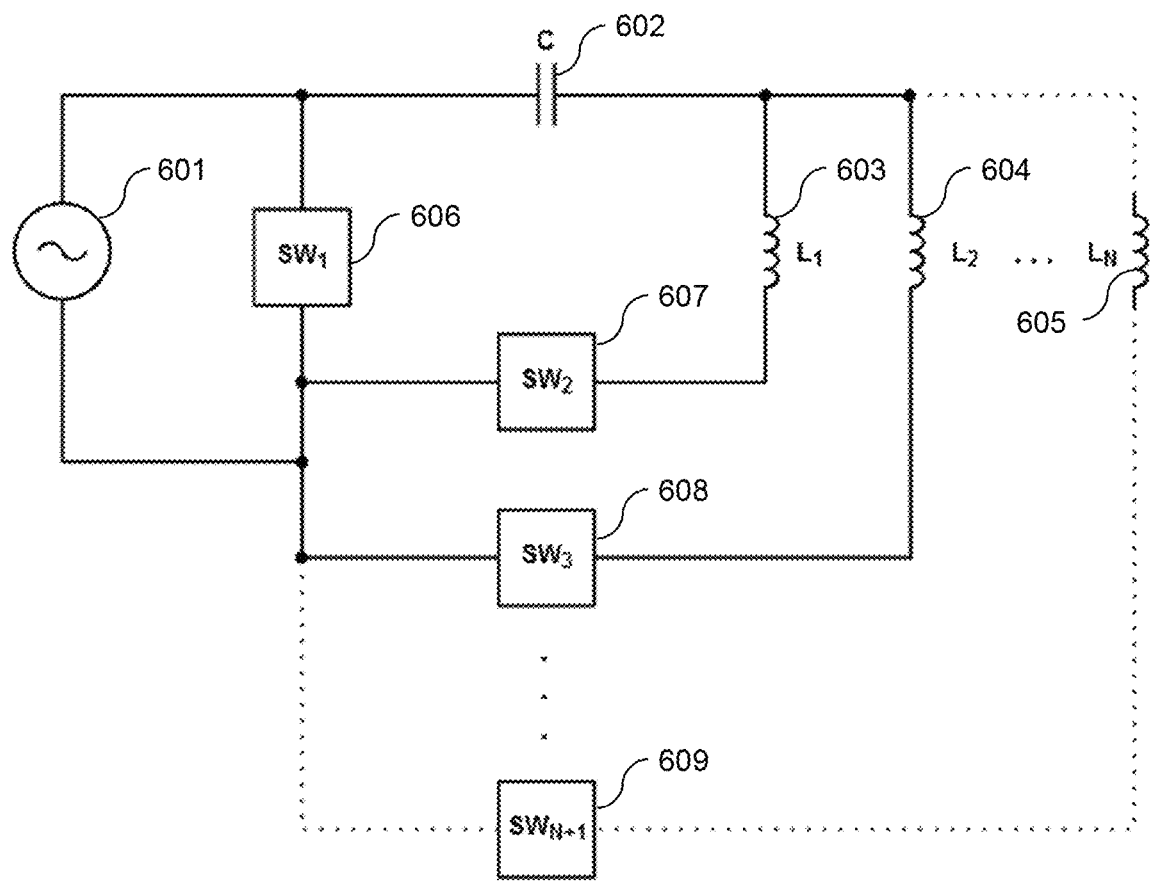
FIG. 6 illustrates an exemplary embodiment of a magnetic stimulation device including a plurality of magnetic field generating devices generating time-dependent impulses.

The magnetic stimulation device may generate a plurality of the impulses 51 by the magnetic field generation devices $L_1, L_2, \ldots L_N$ at one time within the pulse 52. This operation mode is illustrated in FIG. 5A. As shown in FIG. 6, a magnetic stimulation device may include at least one energy source 601, one energy storage device 602, N magnetic field generating devices 603-605 and N+1 switching devices 606-609, wherein N is positive integer greater than 1. This exemplary embodiment includes a minimum of hardware components. The value of inductance of each magnetic field generating device may be constant, however in an alternative embodiment different values of inductance may be used.

The switching device 607-609 may be switched separately, with the magnetic field generated by separate magnetic field generating devices.

In an alternative embodiment any switching device may be switched in combination with at least one other switching device.

The active magnetic field generating devices are the magnetic field generating device in the closed loop of the electric circuit. For example if the number of active magnetic field generating devices is 2 and the inductances of the magnetic field generating devices are the same, then the value of magnetic flux density for each magnetic field generating device is one-half of the magnetic flux density which would be reached by one active magnetic field generating device with the same parameters and conditions, e.g. inductance, resistance, frequency, voltage. The total equivalent inductance of the magnetic stimulation device may be changed by switching a plurality of switching devices into a closed electric circuit. Therefore the impulse duration may be adjusted by adjusting the inductance. The value of total equivalent inductance ($L_{total}$) may be determined by Equation 4.

$$\frac{1}{L_{totl}} = \frac{1}{L_1} + \frac{1}{L_2} + \cdots + \frac{1}{L_N} \qquad \text{Eq. 4}$$

The magnetic stimulation device may generate a plurality of impulses 51 generated by the magnetic field generation devices $L_1, L_2, \ldots L_N$ at different times within the pulse 52. This operation mode is illustrated in FIG. 5B. This operation mode may multiply the repetition rate perceived by the patient, e.g. when the number of magnetic field generation device is 3 and the repetition rate of each magnetic field generating device is 100 Hz, then the patient may perceive the repetition rate 300 Hz. In an alternative example, this operation mode may be used for treatments of high repetition rate when the magnetic stimulation devices are switched to reach such repetition rates which may be sufficiently cooled.

Figure 7:
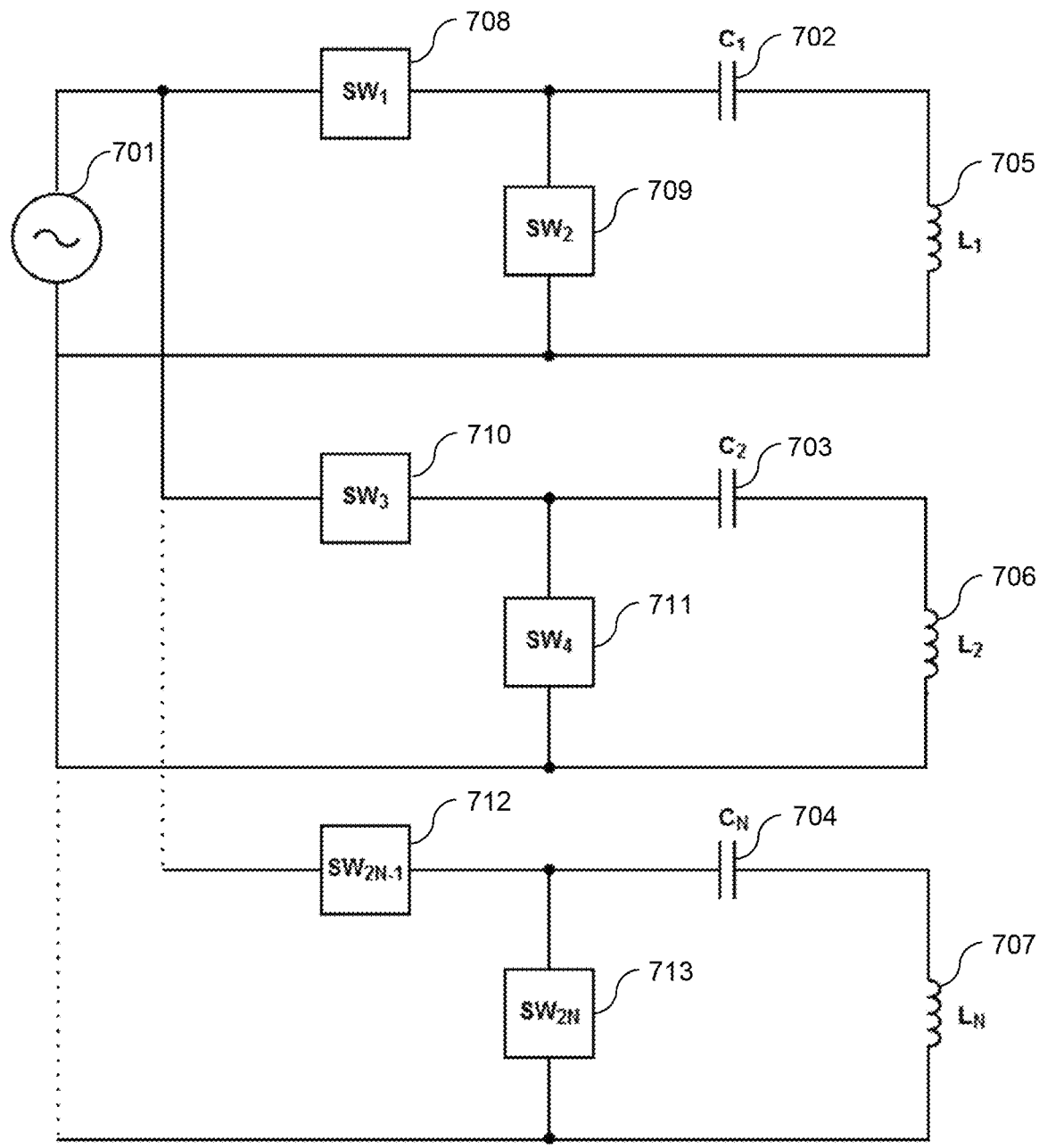
FIG. 7 illustrates an exemplary embodiment of a magnetic stimulation device including a plurality of magnetic field generating devices generating time-independent impulses.

In the example of FIG. 7 a magnetic stimulation device includes at least one energy source 701, N energy storage devices 702-704, N magnetic field generating devices 705-707 and 2×N switching devices 708-713, wherein N is positive integer greater than 1. The at least one energy storage device 702-704 may be selectively charged by the energy source 701 by selectively switching the switching devices 708, 710, 712 and the impulses may be selectively generated by selectively switching the switching devices 709, 711, 713.

The benefit of this exemplary embodiment is the time independency of the impulses generated by the separate magnetic field generating devices. However, the switching devices may be synchronized to generate the impulses at one fixed time within the pulse or both operation modes may be combined using this embodiment. Another benefit of this embodiment is the possibility of providing various treatments by a plurality of magnetic field generating devices. Various treatments may provide various effects for the patient, e.g. stimulation, such as myostimulation, pain alleviation or myorelaxation.

Figure 8:
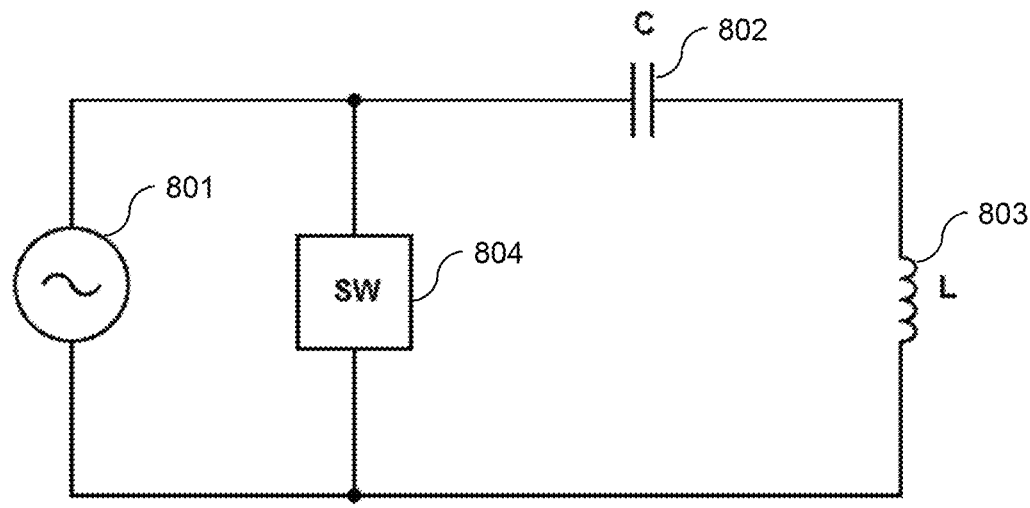
FIG. 8 illustrates an exemplary embodiment of a magnetic stimulation device including a plurality of magnetic field generating devices generating time-independent impulses.

FIG. 8 illustrates an example where the magnetic stimulation device includes N energy sources 801, N energy storage device 802, N magnetic field generating devices 803 and N switching devices 804, wherein N is positive integer greater than 1. The at least one energy storage device 802 may be selectively charged by the energy source 801 and the impulses may be selectively generated by selectively switching the switching devices 804.

The impulses generated by the separate magnetic field generating devices are time independent. However, the switching devices may be synchronized to generate the impulses at one time within the pulse or both operation modes may be combined.

The inductance of magnetic field generating devices in each embodiment may vary. The capacitance of the energy storage devices in each embodiment may vary as well. The impulse duration may be variable and/or the magnetic flux density generated by different magnetic field generating devices may vary as well.

Figure 9:
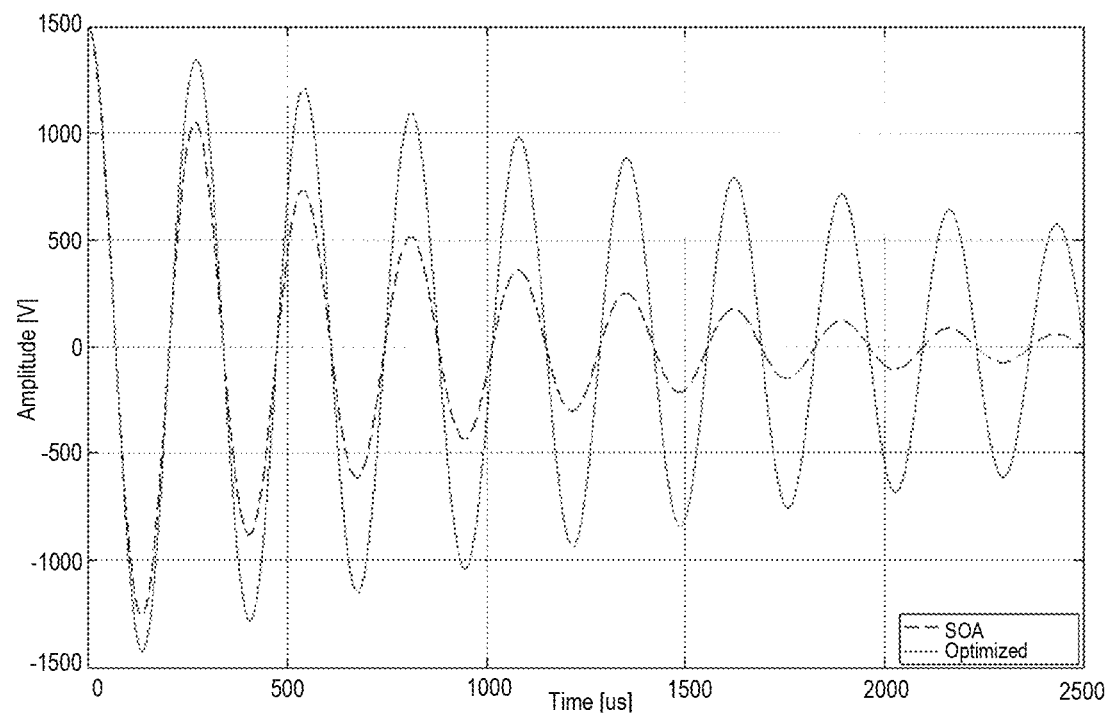
FIG. 9 is a graph showing voltage drop in the energy storage device.

FIG. 9 shows an exponential voltage drop in the energy storage device. Energy savings during time-varying magnetic therapy may be characterized by reduced voltage drop in the energy storage device between the first, second and subsequent maximums of the resonant oscillation. The magnitude of the individual voltage oscillations is exponentially dampened up to establishing the energy balance. This allows increasing the maximum possible frequency/repetition rate of magnetic pulses, since the frequency/repetition rate is dependent on the speed with which it is possible to recharge the energy storage device. Since the energy storage device is recharged by the amount of energy loss during the previous pulse, it is possible to increase the frequency/repetition rate of the device up to hundreds of magnetic pulses per second without the need to increase the input power. The voltage drop between any of the successive amplitudes is not higher than 21%, even more preferably not higher than 14% and most preferably not higher than 7%.

The device can be used for treatment/successive treatments in continual, interrupted or various duty cycle regime. The duty cycle may be higher than 10%, which means interrupted regime with the ratio up to 1 active to 9 passive time units. The ratio may possibly change during the therapy. The device enables operation defined by the peak to peak magnetic flux density on the coil surface at least 3 T, more preferably at least 2.25 T, most preferably at least 1.5 T at repetition rates above 50 Hz, more preferably at repetition rates above 60 Hz, even more preferably at repetition rates above 70, most preferably at repetition rates above 80 Hz with treatment/successive treatments lasting several seconds or longer, for example, for at least 5, 10, 30, 60, 120 or 240 seconds, or longer. The total power consumption is below 1.3 kW and the width of pulses is in the range of hundreds of μs.

The device enables achieving repetition rates above 100 Hz, more preferably repetition rates above 150 Hz, most preferably repetition rates above 200 Hz with the magnetic flux density providing a therapeutic effect on neurons and/or muscle fibers and/or endocrine cells (e.g. at least partial muscle contraction, action potential in cell). Based on achievement of repetition rates in order of few hundreds the device also enables assembling the magnetic pulses into the various shapes (e.g. triangular, rectangular, exponential), with the shape widths from 6 ms to several seconds or longer.

Alternatively the magnetic field generating device may generate a static magnetic field. The magnetic field generating device generating the static magnetic field may be e.g. a permanent magnet or electromagnet. The coil may be powered by a power source, a transformer and/or an energy storage device. The magnetic field may be applied as time-varying magnetic field by movement of the magnetic field generating device. Alternatively the magnetic field generating device may be switched on and off.

During last few decades patient have not only wanted to be in good health, they have also wanted to look well, i.e. to be well shaped, without any unattractive fat and to have a young appearance, without wrinkles, stretchmarks or sagging breasts. This has resulted in a progressive evolution of invasive aesthetic methods such as surgical removing of fat and remodeling the human body by invasive and potentially dangerous methods, e.g. liposuction or inserting implants into human body. The side effects of invasive methods may be scars, swelling or bruising. The side effects resulted in the rapid progress in non-invasive method, e.g. lipolysis or removing skin imperfections. One example of the last few years may is rapid increase of patients' demand for enhancing the visual appearance of buttocks. This has resulted in a higher percentage of these operations by plastic surgeons.

Electric current may be induced in the treated biological structure during pulsed magnetic treatment. Due to the high value of magnetic flux density the biological structure may be targeted and treated more specifically. A distribution of magnetic field is uniform in the biological structure. Particles (e.g. atoms, ions, molecules etc.) in the biological structures are influenced by the magnetic field and permeability of a cell membrane may also increase.

Due to increased permeability of the cell membrane, the pulsed magnetic treatment may induce following effects: at least partial muscle contraction; reduction of adipose tissue-volume and/or number of the adipose cells; neogenesis and/or remodeling of collagen and/or elastin fibers. Further magnetic treatment may improve circulation of blood and/or lymph and improve local and/or adipose tissue metabolism.

With the present methods, factors for enhancing visual appearance of the body include: treatment of major muscle, e.g. gluteus maximus; treatment of deep muscle which may be enabled by high value of magnetic flux density; non-contact application of magnetic flux density, it may be applied even through clothing; stronger muscle contraction due to higher value of magnetic flux density; higher-quality of muscle targeting; treatment may not be influenced by small movements during treatment; treatment time duration may be shortened due to high value of magnetic flux density and/or higher repetition rate; no delays may occur.

It is to be understood that the method is not limited to the particular applications and that the method may be practiced or carried out in various ways.

Present method may be applied for enhancing the visual appearance of body parts including or proximate to major muscle structures. Further the method may be applicable for enhancing the visual appearance of patients with high value of BMI. A patient with BMI of at least 18, preferably at least 25, more preferably at least 30, most preferably at least 35 or more may be preferably treated by the recited methods. The thickness of patient's SWAT and/or VWAT may be at least 0.1, 0.5, 10, 15, 25, 50, 75, 100 or more. The patient may be preferably healthy without any life-threatening conditions such as circulatory system disease, e.g. deep vein thrombosis. The present method is not limited to the application of the treatment to major muscle. Muscles other than major muscles may be treated as well.

The applicator of magnetic treatment may be placed proximate to the patient's body. As used here, proximate to includes both contactless and in actual contact with the skin of the patient. The muscles may be selectively treated and the magnetic flux density may be adjusted following the patient's feeling or needs. The treatment time may be shortened due to selective treatment of the correct muscles. Additionally, due to the high value of magnetic flux density, the muscle may be treated more effectively. Further, the treatment may be non-invasive or even preferably contactless due to the high value of magnetic flux density. The patient may be treated without removing clothing, reducing patient discomfort. Additionally, following the high efficiency of the muscle contraction the collagen and/or elastin fibers above the muscle structure may be remodeled, hence the visual appearance may be enhanced.

The collagen constitutes around 30% of proteins. Treatment by time-varying magnetic field may induce the neocollagenesis. The collagen may be treated by various repetition rates, e.g. in the range of 1 to 250 Hz, more preferably in the range of 10 to 100 Hz, or up to 700 Hz. However, the repetition rate of 25 Hz may be preferably used because the results achieved by stimulation of repetition rate of 25 Hz were the most significant. High value of magnetic flux density may improve the neocollagenesis more than low value of magnetic flux density. Hence the magnetic flux density may be at least 0.5 T, more preferably 1 T, most preferably at least 2 T, or up to 7 T.

The position of the patient may correspond to treated biological structure and/or body region. The patient may be treated in seated position. Alternatively, the patient may be treated in lying position, e.g. in supine position. Treatment in lateral recumbent position may be also applicable. Patient may be in prone position as well.

In the preferred application the treatment method may be applied to body regions prone to cellulite and/or prone to adipose accumulation, such as thighs, saddlebags, buttocks, abdomen, region of love handles, region of bra fat or arm. The adipose accumulation may be influenced by number and/or volume of adipose cells.

The magnetic treatment of the biological structure may have various applications for enhancing visual appearance of the contour of a body region. High density magnetic field reaching such values which may be used for: adipose tissue reduction, wherein the adipose tissue reduction may be achieved by reduction of number and/or volume of adipose cells; muscle toning, wherein the muscle appearance enhancement may be achieved by adipose tissue reduction with no muscle bulking; muscle shaping, wherein the muscle appearance enhancement may be achieved by adipose tissue reduction and/or muscle bulking; body contouring, wherein the silhouette appearance enhancement may be achieved by adipose tissue reduction with no muscle bulking; body shaping, wherein the silhouette appearance enhancement may be achieved by adipose tissue reduction and/or muscle bulking; skin tightening, wherein the skin appearance enhancement may be achieved by obtaining smoother and younger appearance, including wrinkles reduction; cellulite treatment, wherein the appearance enhancement may be achieved by adipose tissue reduction, muscle contraction and/or elastic fibers neogenesis; circumferential reduction, wherein the reduction may be achieved by adipose tissue reduction and/or the muscle bulking; breast enhancement, wherein the appearance enhancement effect may be achieved by elevation or shape modification; lip enhancement, wherein the lip appearance enhancement may be achieved by obtaining fuller and firmer appearance. The body region may be reduced in overall size. Further aesthetic effects may be achieved, e.g. connective tissue improvement, fat disruption, muscle volumization, muscle forming, muscle toning, muscle remodeling, contouring, sculpting or body sculpting.

The one approach is stimulating central neural system or peripheral neural structure and determining the feedback, e.g. muscle contraction.

Neural system includes central neural system and/or peripheral neural system.

In still another application of the invention, the time-varying magnetic field may be used for stimulation of neural structure to cause muscle stimulation. The muscle stimulation may occur during stimulation by envelopes of repetition frequencies below 100 Hz.

In the methods described, the magnetic stimulation device may or may not include a magnetic core. The magnetic stimulation device may be cooled by fluid, e.g. by air, water or oil. Total power consumption of the magnetic stimulation device may be below 1.3 kW. The power of the magnetic stimulation device may be at least 150, 250 or 500 W to generate a magnetic flux density sufficient to induce at least muscle contraction. A magnetic stimulation device as described in the U.S. patent application Ser. No. 14/789,156 or U.S. patent application Ser. No. 14/789,658, incorporated herein by reference, may be used.

The applicator for magnetic treatment may be placed proximate to the patient's body. The magnetic flux density may be applied into the target biological structure. Electric current may be induced and treat the neuromuscular plate and/or the nerve innervating the at least one muscle fiber. The treatment may cause at least a partial muscle contraction.

Figure 10:
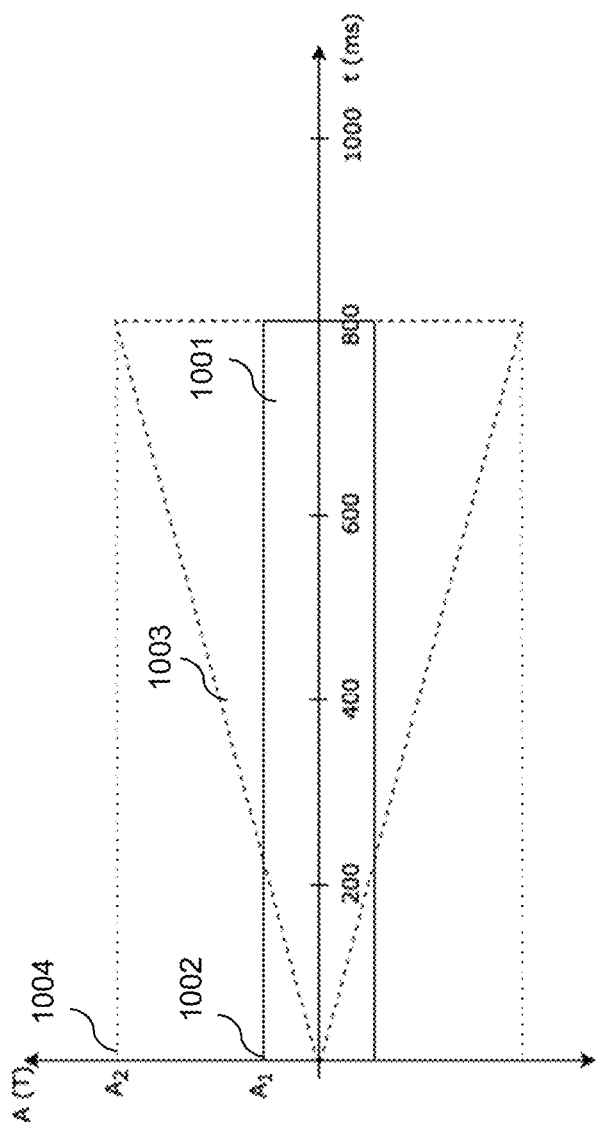
FIG. 10 illustrates a threshold value corresponding to different envelopes of the stimulation signal.

FIG. 10 illustrates the different shapes of the envelope of the stimulation signal and corresponding different threshold values of a healthy muscle. When the healthy muscle is stimulated by a rectangular envelope 1001 of stimulation signal the muscle contraction occurs at magnetic flux density $A_1$ 1002. When the healthy muscles is stimulated by increasing envelope 1003 of stimulation signal the muscle contraction occurs at magnetic flux density value $A_2$ 1004. However, when the denervated muscle is stimulated by increasing envelope 1003 of stimulation signal the denervated muscle contraction occurs at magnetic flux densities below $A_2$ 1004. Magnetic flux density value $A_2$ 1004 is a multiplication of magnetic flux density value $A_1$ 1002, wherein the multiplication coefficient is positive number greater than 1.

The envelope may be generated on the basis that the biological structure, e.g. a nerve or at least one muscle fiber, is not able to distinct single pulses during the stimulation at higher repetition rates, e.g. exceeding 100 Hz, more preferably at least 150 Hz, even more preferably at least 200 Hz, most preferably at least 250 Hz, or up to 700 Hz.

Generally, at least two pulses are necessary to create a simple shape of the envelope, e.g. rectangular or trapezoid. However, the more complex envelope shape is the more pulses are needed. The induced energy (IE) stimulating the target neural structure is a function of repetition rate, magnetic flux density and/or impulse duration.

The envelope may consists of several impulses 51 called train. The number of pulses in one train varies in a range of at least 2 pulses to thousands of pulses. The repetition frequency of envelope is given by the envelope period, i.e. the envelope may include time with no stimulation as well. The envelope may consist of stimulation signals with various burst frequencies, e.g. 5, 10, 20, 50, or more Hz. The envelope may be generated by several modulation approaches.

Figure 11A:
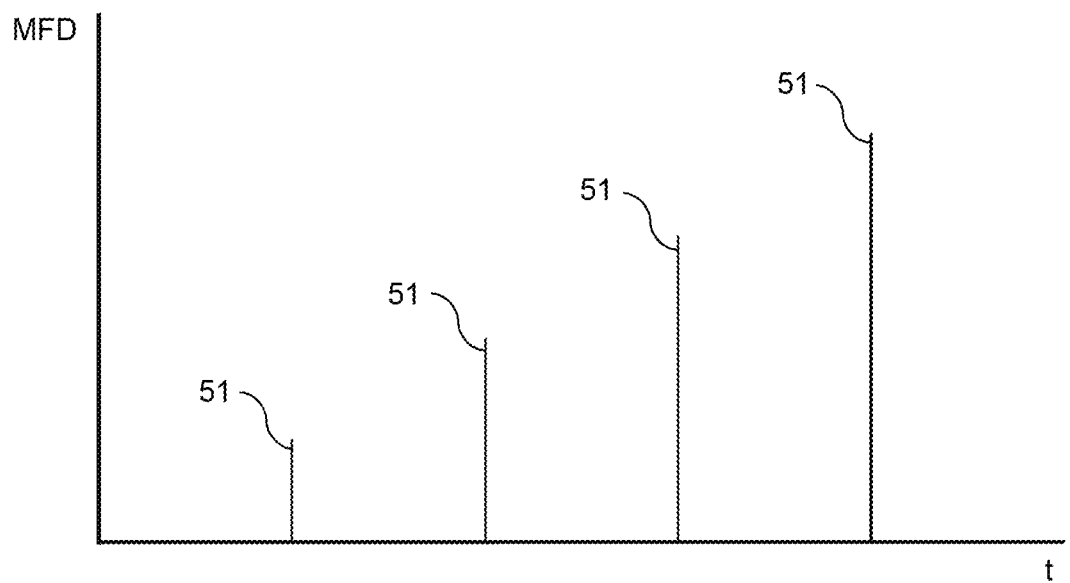
FIGS. 11A and 11B illustrate a detail of a stimulation signal with increasing envelope.
Figure 11B:
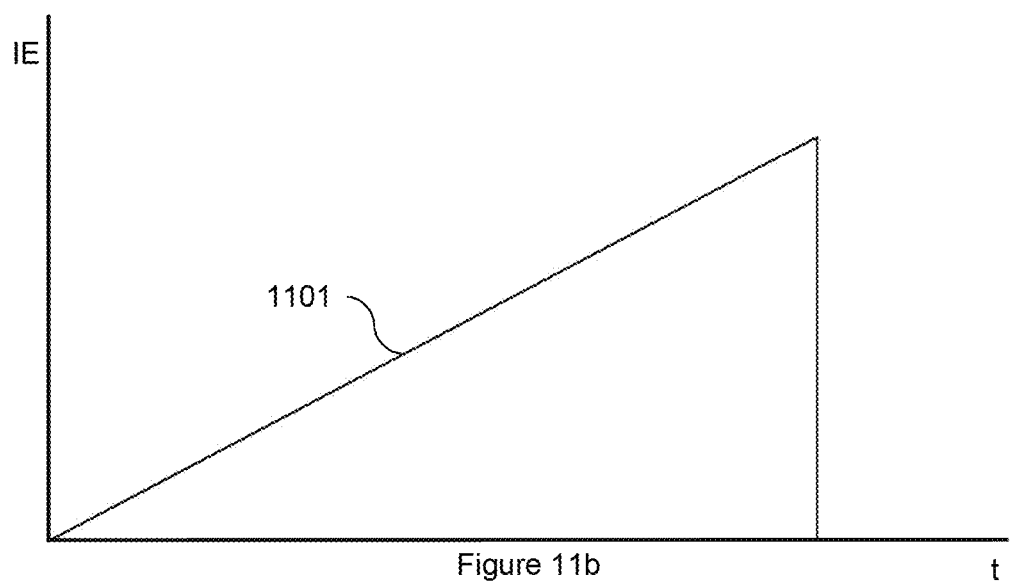

Envelope may be generated by time-varying magnetic field of varying peak magnetic flux density hence the process is called magnetic flux density modulation (MFDM). The principle of MFDM is described in FIGS. 11A and 11B. The repetition rate of the time-varying magnetic field is constant hence the period of the pulse is constant. The impulse duration remains constant as well. However, the magnetic flux density of each impulse 51 varies with respect to the preceding impulse 51, as in FIG. 11A. Therefore each impulse magnetic flux density is different from magnetic flux density of the preceding impulse. The principle is explained by triangular shaped envelope 1101 as shown in FIG. 11B.

Figure 12A:
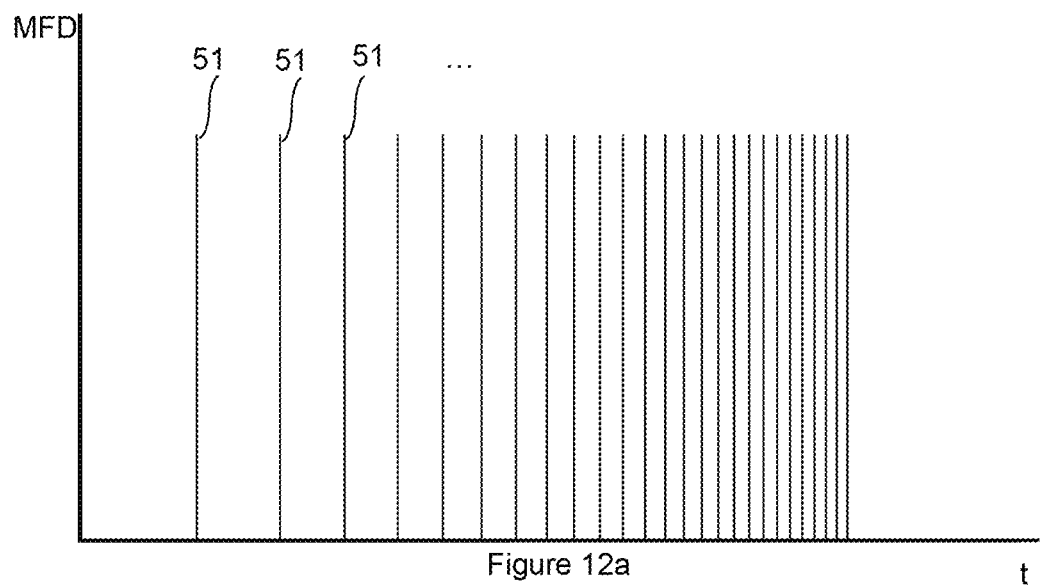
FIGS. 12A and 12B illustrate a detail of a stimulation signal with increasing envelope.
Figure 12B:
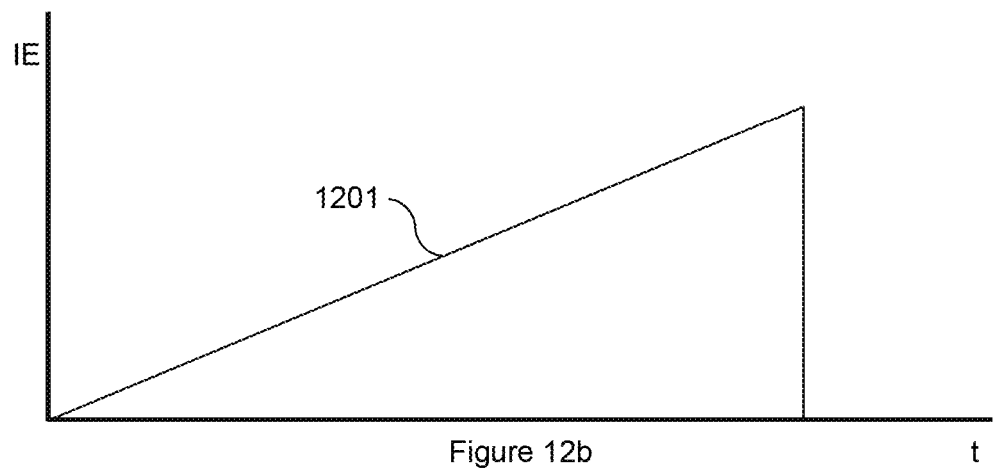

Alternatively the envelope may be generated in repetition rate domain hence the process is called repetition rate modulation (RRM). The principle of RRM is described in FIGS. 12A and 12B. The magnetic flux density of each impulse 51 remains constants. The impulse duration remains constant as well. Therefore the induced energy for one pulse is constant. However, the repetition rate varies hence the time duration of each pulse varies with respect to the preceding pulse, see FIG. 12A. The actual value of induced energy corresponds to the actual repetition rate of the time-varying magnetic field. When the repetition rate increases the value of induced energy increases or vice versa. The principle is explained by triangular shaped envelope 1201, see FIG. 12B.

Figure 13A:
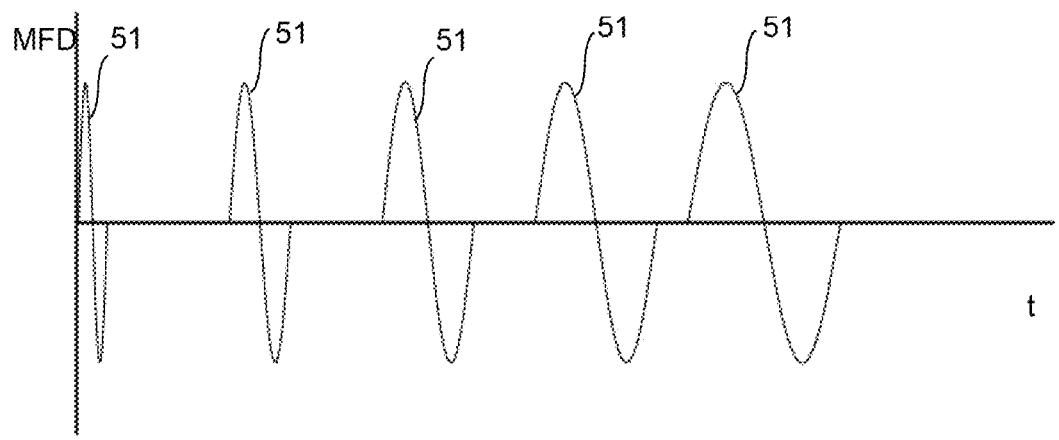
FIGS. 13A and 13B illustrate a detail of a stimulation signal with increasing envelope.
Figure 13B:
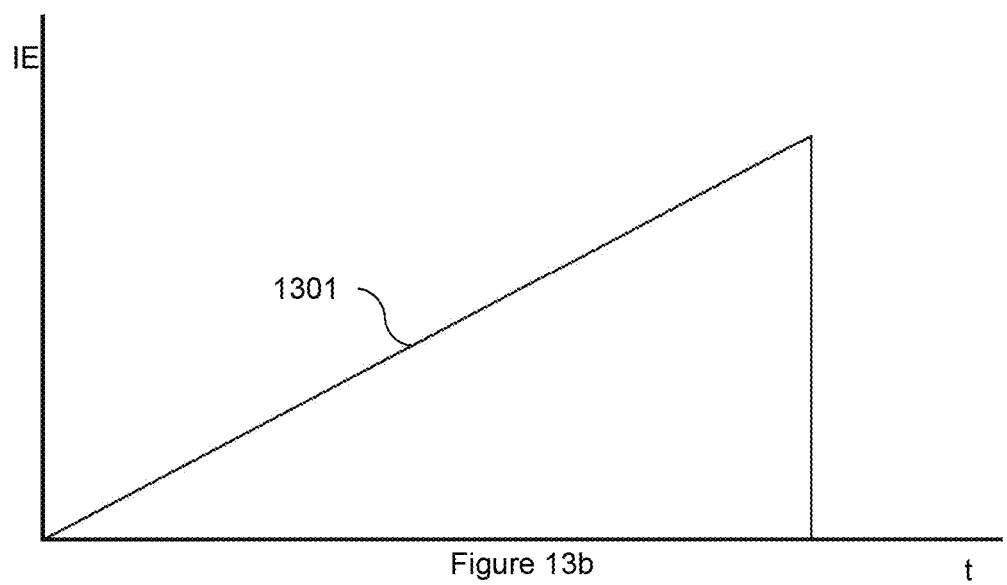

According to still another aspect of the application, envelope may be generated in impulse duration domain. The principle of impulse duration modulation is shown in FIGS. 13A and 13B where the magnetic flux density and the repetition rate of time-varying magnetic field remains constant. However, the impulse 51 duration of each pulse varies as shown FIG. 13A. The principle is explained by triangular shaped envelope 1301 in FIG. 13B.

The modulation approaches are not limited by exemplary waveform. Therefore the envelope may be rectangular, square, saw-tooth, trapezoidal, sinusoidal, exponential etc.

All the mentioned applications may be applied in constant repetition rate and/or repetition frequency manner. The envelope modulation or combination thereof is applicable as well.

Furthermore, the present invention discloses the advanced approaches in aesthetic applications, e.g. for cellulite treatment and/or body shaping. Combined methods of treatment by electromagnetic field and treatment by magnetic field are used. The electromagnetic field may include treatment by radiofrequency, infrared or optical waves. The magnetic treatment may be provided by permanent magnets, electromagnetic devices generating a static magnetic field or time-varying magnetic devices. In the preferred application the treatment by a pulsed magnetic field and radiofrequency treatment may be combined. However the application is not limited by the recited combination so the combined method may include magnetic treatment and any treatment by electromagnetic field, e.g. light treatment, IR treatment or treatment by radiofrequency waves, e.g. microwaves, short waves or long waves. The magnetic treatment may also be provided with thermal treatment, e.g. heating and/or cooling.

A device described in U.S. patent application Ser. No. 14/278,756 incorporated herein by reference may be used for application of the present methods. The device may exclude the balun transformer, or the balun transformer may be included in transmatch. The possible methods of treatment by combined methods are described below.

Magnetic treatment in combination with radiofrequency treatment may be applied by two independent treatment devices, e.g. one device for treating the biological structure by radiofrequency waves and second device for treating the biological structure by magnetic field. Both devices may have a separate applicator for treating the biological structure, or one applicator may be used by at least two devices, i.e. the applicator may be modular for a plurality of devices.

The device may include at least one HF frequency generator for providing energy for radiofrequency treatment and for providing energy for magnetic treatment. In an alternative embodiment, the device may include at least one HF frequency generator for providing energy for radiofrequency treatment and at least one other independent frequency generator for providing energy for magnetic treatment. The device may include plurality of applicators for providing separate radiofrequency or magnetic treatments to the patient.

In alternative embodiment the applicator may provide a combination of radiofrequency and magnetic treatment. In one embodiment, the applicator may include at least one radiofrequency electrode for providing radiofrequency treatment and at least one magnetic field generating device, e.g. a coil, for providing magnetic treatment. In another embodiment, the applicator may include at least one electrode for providing radiofrequency treatment and at least one magnetic field generating device providing magnetic treatment, wherein the at least one RF source provides energy for both at least one electrode and at least one magnetic field generating device.

In still another embodiment the at least one RF source may provide the energy for the at least one magnetic field generating device providing magnetic treatment wherein the at least one magnetic field generating device may be used as the at least one electrode. The essence is the far different stimulation frequencies which are used for RF treatment and magnetic treatment. The magnetic field generating device in the high frequency field is similar to the electrode. This enables the magnetic field generating device to be the electrode for radiofrequency treatment. In the preferred embodiment a flat coil may be used as the electrode.

The frequencies for the radiofrequency treatment may be in the range of ones of MHz to hundreds of GHz, more preferably in the range of 13 MHz to 3 GHz, most preferably around 13.56 or 40.68 or 27.12 MHz or 2.45 GHz. The term "around" should be interpreted as in the range of 5% of the recited value. The impulse frequencies for the magnetic treatment may be in the range of hundreds of Hz to hundreds of kHz, more preferably in the range of ones of kHz to tens of kHz, most preferably up to 10 kHz. However the repetition rate of the magnetic impulses may reach up to 700 Hz, more preferably up to 500 Hz, most preferably in the range of 1 to 300 Hz, e.g. at least 1, 5, 20, 30, 50, 100, 140 or 180 Hz. The magnetic flux density of the magnetic treatment may be at least 0.1, 0.8, 1, 1.5, 2, 2.4 or up to 7 Tesla on the coil surface (equivalent to 70000 Gauss). The treatment/successive treatments may last several seconds, e.g. at least 5, 10, 30, 60, 120 or 240 seconds, or longer, e.g. at least 20, 30, 45, 60 minutes. The impulse duration may be in the range of 3 μs to 10 ms or more, or alternatively 3 μs to 3 ms or alternatively 3 μs to 1 ms. The impulse duration may be e.g. 3, 10, 50, 200, 300, 400, 500, 625, 1000, 2000 or 3000 μs. The duty cycle of the stimulation may be at least 1:50, more preferably at least 1:40, even more preferably at least 1:20, most preferably at least 1:8 or up to 1:4. The magnetic stimulation device may emit no radiation.

A derivative of the magnetic flux density is defined by Equation 5.

$$\frac{dB}{dt}, \qquad \text{Eq. 5}$$

where: dB is magnetic flux density derivative [T]; dt is time derivative [s].

The maximal value of the magnetic flux density derivative may be up to 5 MT/s, preferably in the ranges of 0.3 to 800 kT/s, 0.5 to 400 kT/s, 1 to 300 kT/s, 1.5 to 250 kT/s, 2 to 200 kT/s, 2.5 to 150 kT/s. In exemplary applications the maximal value of the magnetic flux density derivative may be at least 0.3, 0.5, 1, 2.5, 3.2, 5, 8, 10, 17, 30 or 60 kT/s. The value of magnetic flux density derivative may correspond to induced current within the tissue.

The magnetic flux density derivative may be determined within the entire period of the magnetic signal and/or in any segment of the magnetic signal.

Alternatively the treatment device may include no deep muscle diathermy device for heating the target biological structure. The treatment preferably may include no electrode which may enable heating the biological structure in contact mode.

Cellulite is an effect of skin change resulting in orange peel appearance. The cause of the cellulite is orientation of collagen fibers in so called "fibrous" septae. The fibrous septae contract and harden over time creating a dimple effect. Additionally, blood and lymphatic vessels lack circulation due to the contraction and hardening of the septae. The lymph flow may be blocked resulting in swelling. Another cause of cellulite may be adipose cells protruding to dermis. Cellulite may be treated by the recited methods.

One application of time-varying magnetic field for enhancing the visual appearance of body region may be treatment of a muscle by magnetic flux density for reducing the cellulite. The magnetic flux density may be delivered through the skin to the neuromuscular plate and/or nerve innervating at least one muscle fiber. The electric current may be induced in the target biological structure causing at least partial muscle contraction. The at least partial muscle contraction may cause the movement of the skin and all the biological structures subtending epidermis. Additionally, the at least partial muscle contraction may improve blood circulation by itself, or via the movement of the muscle in the vicinity including fibrous septae. Additionally, blood and/or lymph circulation may be improved in the layers subtending epidermis since the muscle contraction may move the fibrous septae. Also local and/or adipose tissue metabolism may be improved.

The magnetic treatment may be used for improving the lymph flow.

The lymph flow may be improved by at least partial muscle contraction which may provide effect similar to manual massage. The improved lymph flow may improve local metabolism and/or immune system. The improved lymph flow may contribute to purer lymph due to faster delivery of the lymph to the lymph nodes where the lymph may be cleared.

The present method may provide a massage effect via the treatment which may be caused by the at least partial muscle contraction. Therefore the massage effect may be achieved by contactless methods instead of manual massage techniques or soft tissue techniques. The massage effect may improve lymph circulation.

In another aspect, improvement of functionality and/or the appearance of the muscle may be achieved with results similar to body exercise. The results may be achieved by application of high magnetic flux density to the body region and inducing at least partial muscle contraction. Higher values of magnetic flux density applied may result in a stronger muscle contraction. The patient may feel firmer and tighter.

With the present method muscle contractions induced by the applied magnetic flux density may help to tone the muscle providing a more attractive appearance. As the muscle structure is treated by time-varying magnetic field the entire limb may be moved due to the high power of the magnetic treatment. Nevertheless, the method is not limited to the applications to the limbs and the method is able to treat any muscle, e.g. gluteus maximus or any muscle/deep muscle to induce body contouring and/or body shaping effect and fat burn. Additionally, shortened and/or flabby muscles may be stretched. The physical fitness of the patient may be improved as well.

The magnetic field may treat various body regions, e.g. thighs, buttocks, hips, abdomen or arms. The muscles may be shaped to enhance visual appearance of the treated body region. The body part may obtain enhanced visual appearance of its contour.

The magnetic field may treat at least one muscle of lower limb, particularly the parts which are prone to cellulite such as thighs or saddlebags. The time-varying magnetic field may induce at least partial muscle contraction in different muscle and/or muscle group. Following the position and/or orientation of the magnetic field generating device the anterior, posterior and/or medial compartment of the thigh may be treated. The anterior compartment includes sartorius muscle, rectus femoris muscle, vastus lateralis muscle, vastus intermedius muscle, vastus medialis muscle. Posterior compartment includes biceps femoris muscle, semitendinosus muscle and semimembranosus muscle. Medial compartment includes pectineus muscle, external obturator muscle, gracilis muscle, adductor longus muscle, adductor brevis muscle and adductor magnus muscle.

The treatment may cause circumferential reduction of thighs. Further the muscle may obtain enhanced visual appearance, thigh may be well-shaped. Thigh contour may be enhanced as well.

The at least one surrounding body region may be treated as well, e.g. buttocks.

The ocular muscles may be treated by focused treatment of magnetic flux density exceeding 0.1 T. The treatment may induce the at least partial muscle contraction of the ocular muscle which may be exercised to be strengthened.

The applicator may be placed within proximity of the patient's treated area. The applicator may be fixed to the patient. Alternatively the correct position may be provided by a mechanical arm and/or adjustable applicator. The applicator may be made of adhesive and/or high friction material at least on contact surface with the patient.

The magnetic field may be generated with a low repetition rate such as 1 Hz for a predetermined period of time, e.g. 30 seconds, sufficient for setting the applicator to a correct position where the treatment is most effective. During the period the magnetic flux density may be adjusted following the patient's needs to induce muscle contraction sufficiently strong and comfortable for the patient.

The treatment may start a treatment protocol. The treatment protocol may include a set of predetermined treatment sequences of predetermined repetition rates applied for predetermined time periods. The sequences may be repeated and/or adjusted following the patient's need. The sequence may include a repetition rate in the range of 1 to 100 Hz, preferably in the range of 2 to 90 Hz, more preferably in the range of 5 to 50 Hz, most preferably in the range of 10 to 45 Hz. The sequences may last at least 30, 45, 60, 90, 120 or up to 300 seconds.

Alternatively the treatment may include the only the treatment protocol without applying the magnetic field of low repetition rate. The correct position of the applicator and/or adjusting the magnetic flux density may be adjusted during the first sequence of the treatment protocol.

Repetition rate and/or magnetic flux density may vary during the treatment protocol. Further the magnetic stimulation signal may include several periods of stimulation signal of different repetition rates, therefore the modulation of the signal is in repetition rate domain. The stimulation signal may include several periods of stimulation signal of different magnetic flux densities, therefore the modulation of the signal is in magnetic flux density domain. In yet another approach the envelope of the stimulation signal may be modulated by combinations of repetition rate domain and magnetic flux density domain.

In one application, the treatment may induce the same effect as muscle exercising of buttocks. During the treatment of buttocks the magnetic field may be targeted to treat of muscles shaping the buttocks, e.g. tensor fasciae latae muscle or at least one of gluteal muscles: maximus, medius or minimus. In one preferred application all three gluteal muscles may be treated. Further other muscles may be treated, e.g. abdominal muscles, spinal muscles and/or thoracic muscles. By the complex treatment and muscle contraction in the body region the treated muscles may be strengthened, toned, the cellulite may be reduced and dimples may be removed. Buttocks and even the patient's figure may be enhanced in visual shape appearance and may become more attractive. Buttocks become well-shaped, round, firm, well-trained, toned, smoother, tight and lifted. The complex treatment may reduce hips, make perfect round and lifted buttocks, increasing the self-confidence of the patient.

The treatment may be more efficient than standard workout in fitness since the fitness machines strengthen only the isolated muscles. The results may be achieved in very short-time periods with minimal time of treatment. Without being limited, it is believed that the exercising of the gluteus medius may reduce the volume of the buttocks; exercising of the gluteus maximus may shape and/or lift the buttocks; exercising of the gluteus minimus may lift the buttocks.

The magnetic treatment may also treat at least one surrounding body region, e.g. thighs and/or saddlebags.

In the preferred application the magnetic treatment may be combined with other treatment methods using different approaches, e.g. conventional non-invasive treatments. The combined treatment may be applied to the surroundings tissues around buttocks to reduce the cellulite around the buttocks and enhance the shape of the enhanced appearance of the buttocks. The surrounding tissues may be represented by e.g. abdomen, love handles, thighs or saddle bags.

The magnetic field may treat at least one muscle responsible for silhouette of the body. The time-varying magnetic field may induce at least partial muscle contraction in different muscle and/or muscle group responsible for silhouette in the region of abdomen, love handles and/or bra fat. Following the position and/or orientation of the magnetic field generating device rectus abdominis muscle may be treated. Alternatively latissimus dorsi muscle, abdominal internal oblique muscle, abdominal external oblique muscle, transverse abdominal muscle and/or pyramidalis muscle may be treated by the time-varying magnetic field.

The treatment may cause circumferential reduction in the region of belly, hips and/or love handles. Alternatively the treatment may tighten at least one of these body parts. Further the muscles may obtain enhanced visual appearance, belly may be well-shaped. Repetitive application may even reach in a six-pack look. The at least one surrounding body region may be treated as well, e.g. buttocks.

The magnetic field may treat at least one muscle of upper limb, particularly the parts which may be prone to cellulite such as arm. The time-varying magnetic field may induce at least partial muscle contraction. Following the position and/or orientation of the magnetic field generating device the at least partial muscle contraction may occur in biceps brachii muscle, *brachialis* muscle, coracobrachialis muscle and/or triceps brachii muscle.

The treatment may cause circumferential reduction of the arm. Further the muscle may obtain enhanced visual appearance, arm may be well-shaped. Arm contour may be enhanced as well.

The at least partial muscle contraction may be more efficient for adipose tissue metabolism as the value of magnetic flux density increases since the muscle contraction may be stronger. The higher magnetic flux density may treat the higher number of muscle fibers contraction and the more adipose tissue may be reduced. Therefore the visual appearance of regions prone to cellulite may be enhanced.

Treatment by time-varying magnetic field may induce lipolysis. Adipose tissue may be reduced by decreasing the number and/or volume of adipose cells. Promoted adipose cell metabolism may increase as the value of magnetic flux density increases. The treatment may release free fatty acids (FFA) from at least one adipose cell. The increased concentration of FFA may influence a homeostasis of the adipose cell. A disruption of the homeostasis may cause a dysfunction of the adipose cell. The dysfunction may be followed by stress for endoplasmic reticulum (ER stress). ER stress may cause additional lipolysis and/or apoptosis of the at least one adipose cell.

Furthermore, ER stress may cause increase of intracellular calcium ions (Ca2+) which may promote an apoptotic process and may continue into controlled cell death of the adipose cell. The apoptosis may be induced by Ca– dependent effectors, e.g. calpain or caspase-12. Endogenous ligands or pharmacological agents, such as vitamin D, may induce prolonged cytosolic calcium increase. Vitamin D may influence release of Ca2+ from endoplasmic reticulum. Hence the effect of treatment may be enhanced by application of vitamin D and/or Ca2+ prior, during and/or after the treatment. The most significant effect may be achieved by application of both, Ca2+ and vitamin D, prior the treatment to provide all factors influencing adipose cell apoptosis.

Alternatively, increased level of Ca2+ may induce autophagy within adipose cell as well. Autophagy is self-eating process of cellular organelles to produce energy and it may proceed into cell death. Autophagy may be induced by ER stress or it may be induced via Ca2+ signaling.

Figure 14:
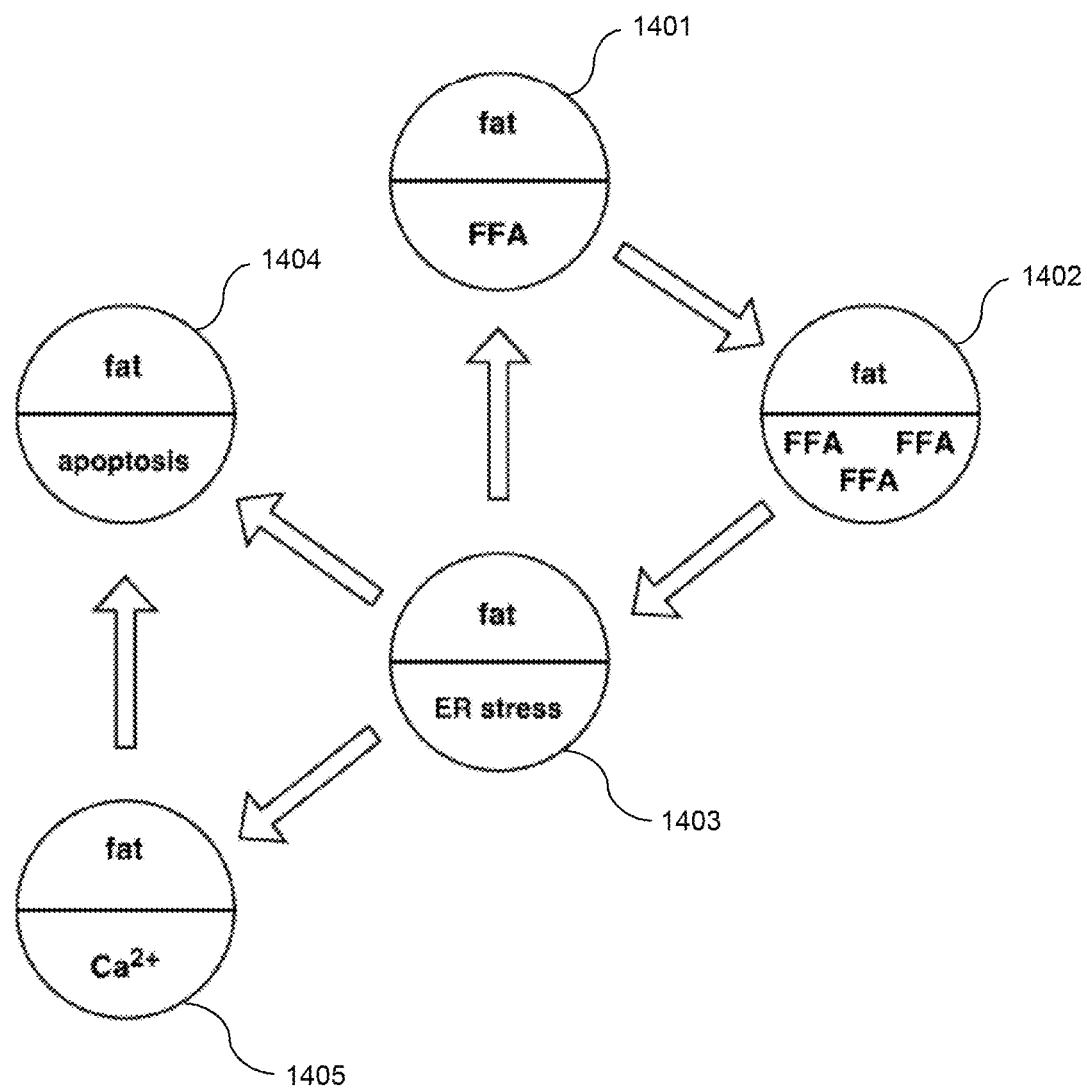
FIG. 14 is a diagram of a biological effect.

FIG. 14 illustrates pathways which may induce apoptosis of the at least one adipose cell. FFA may accumulate in the at least one adipose cell (1401). The magnetic field may induce lipolysis (1402), i.e. a release of FFA from adipose tissue. Accumulated FFA may reach a threshold when adipose cell is unable to utilize FFA. A dysfunction of the adipose cell may occur. The adipose cell may react on the dysfunction by ER stress (1403). ER stress may induce lipolysis hence additional release of FFA may occur (1401). ER stress may cause apoptosis of the adipose cell (1404). Furthermore, the ER stress may release Ca2+(1405) which may contribute the apoptosis (1404).

The effect of the treatment by magnetic field for adipose tissue reduction may be influenced by various biological processes and/or pathways as recited above. The processes and/or pathways may be synergic hence the adipose tissue reduction may be accelerated and/or more efficient.

The method may cause the circumferential reduction i.e. a reduction of the size of the treated body region. The method may be mostly indicated for the regions with cellulite, particularly for thighs, buttocks, saddlebags, love handles, abdomen, hips and/or arms. However, the indication is not limited to the mentioned regions and the method may be used for treatment of any other body region.

Furthermore, the method may change BMI index of the patient. In a preferred application the BMI of the patient may be reduced. Alternatively, the BMI of the patient may increase.

Heating/Cooling

The magnetic field may be combined with application of heat and/or cold. The body region may be heated/cooled. The target biological structures may be selectively treated due to different tolerance of various biological structures to heating/cooling. Applying of heat/cold may improve metabolism of the biological structure, alternatively a reduction of the biological structure may occur.

Various biological structures have a different tolerance to heating/cooling. Hence target biological structures may be remodeled, e.g. adipose cells may be selectively reduced. The cells different from adipose cells such as epidermal cells, are not reduced by the heating/cooling. The selective reduction of adipose cell may be caused by e.g. crystallization within adipose cells. The heating/cooling of the adipose cell may reduce the number and/or volume of adipose cells by lipolysis, apoptosis and/or necrosis.

Cooling

Although the following exemplary treatment describes applying cold to the patient, the treatment method is not limited to the exemplary application. The method may include heating the patient instead of cooling the patient.

The cooling may be provided in a contact, indirect contact and/or non-contact manner. Contact cooling may be provided by a cooling element placed to the proximity of the treated body region, e.g. a thermally conductive material such as metal, gel or ice may be used. Indirect contact may be provided by a flow of cooling media within a layer of flexible and/or rigid material, e.g. cooling media such as glycerol, saline or water solution may be used. The cooling element may include a plurality of passages which the cooling media may flow in. Non-contact cooling may be provided by radiant cooling. Alternatively cooling media may be applied directly on the body region. The cooling media used for non-contact heating/cooling may be preferably a fluid, e.g. a gas or liquid. The gas may be applied in form of a spray, e.g. cold air, $CO_2$ or $N_2$ may be used. The cooling media may be at a predetermined temperature which may be controlled by the device to induce selective treatment of the target biological structure.

In an exemplary application the adipose cells may be selectively treated by cooling. A cooling media may be applied to the body region. A reduction of adipose cell may be induced by cooling the adipose cell. The cells different from adipose cells are not reduced by the cooling.

Temperature Ranges

The temperature of the cooling media and/or element may be less than the temperature of the patient's body. The temperature of cooling media may be at least −196° C. The temperature of the cooling element may be preferably in the range of 40 to −40° C., more preferably in the range of 20 to −20° C., even more preferably in the range of 10 to −15° C. or in the range of 5 to −10° C. A temperature of the adipose cells may be above a freezing point of water to prevent a reduction of cells including water. The temperature of the adipose cells may be preferably in the range of 37 to −10° C., more preferably in the range of 20 to −4° C., even more preferably in the range of 15 to −2° C. or around 4° C. The temperature of epidermis may be at least −40, −20, −10, 15, 20, 35° C., more preferably the temperature of epidermis may be in the range of around 5 to −5° C. The term around may be interpreted to mean in the range of 10% of the particular value.

Alternatively the body may be heated by application of various treatment methods, e.g. radiofrequency, diathermy or optical waves. The temperature in the target tissue may be up to 80° C., more preferably in the range of 37 to 60° C., even more preferably in the range of 39 to 50° C., most preferably in the range of 42 to 47° C. The temperature may be adjusted based on the intended use, e.g. adipose tissue reduction or collagen production.

The temperature of adipose cells may vary during the treatment. The temperature of the adipose cells may oscillate around a predetermined temperature. The temperature of the adipose cells may also follow a temperature profile in a predefined temperature range. The temperature and/or the temperature range may be adjusted following the patient's needs.

Cycles

Alternatively the adipose cells may be heated prior, during and/or after cooling. The term "heat prior" refers to preheating the adipose cells before cooling treatment. The term "heat during" refers to cyclically changing periods of cooling and heating the adipose cells during the treatment. The treatment may also include passive periods between heating and/or cooling. The term "passive period" refers to applying neither heating nor cooling. The term "heat after" refers to applying heat after the cooling treatment. The periods of heating/cooling and/or passive periods may be adjusted following by the patient's need.

Treatment Duration

The cooling may be applied for at least 10 seconds. Time duration of cooling the body region may be in the range of 1 to 240 minutes, more preferably in the range of 5 to 120 minutes, even more preferably 10 to 60 minutes, most preferably up to 30 minutes.

The cooling element and/or media may be applied continuously and/or in pulses. Continuous application may be used for a cooling element and/or media at a temperature above 0° C. Pulsed mode may be used for application of fluids below 0° C. The cooling may be provided cyclically for short periods in order of milliseconds, e.g. $N_2$ may be applied cyclically to prevent damage to epidermis/dermis. The cooling element and/or media may be applied preferably non-invasively, e.g. by topical application. Alternatively the cooling element and/or media may be applied subcutaneously, e.g. injected.

Adjustable Applicator

The cooling element may correspond with the body region. The cooling element may be adjustable in shape to fit the body region. The cooling element may be made of flexible material to be modified in shape to follow the shape and/or contour of the body region. A fitting of the cooling element may provide homogenous treatment and/or temperature distribution. Further the heat exchange may be optimized at the contacted surface.

Pressure

A treatment may induce a thermal gradient in the body region, i.e. the shallow layer of the skin such as epidermis and/or dermis may have a lower temperature than the deeper layer such as adipose tissue. The effect of cooling may be improved by limiting and/or eliminating dermal blood flow. The dermal blood flow may be limited by applying vasoconstrictive medicine, preferably topically administered.

Positive

The dermal blood flow may also be limited and/or eliminated by applying a pressure. The pressure greater than systolic blood pressure may be used for pushing the blood out of the dermal and/or subcutaneous veins. The deeper adipose cells may be cooled and/or the cooling of the adipose cells to the temperature sufficient to reducing the adipose cells may be reached in shorter time period. Furthermore appropriate contact of the cooling element may be provided by the pressure in case of contact treatment.

Negative

The treatment effect may also be enhanced by applying negative pressure to the skin below the applicator, e.g. a convex cooling element may be used. The skin may be pulled towards the inner surface of the cooling element. Hence the contact may be enabled by applying negative pressure. Alternatively, the folded tissue may be pinched by two or more cooling elements and the cooling may be applied to the tissue, particularly to adipose cells. Further the skin may be stretched and a thickness of the skin may decrease. Skin thickness decrease may promote improved heat transfer to/from adipose cells.

Miscellaneous

The cooling may be applied with application mechanical treatment such as acoustic, ultrasound, and/or shockwave treatment to enable more homogenous treatment effect. The adipose cells reduction may also be promoted by physical movement of the body region by e.g. massaging, or vibrations. The pressure applied to the body region may vary to improve the results.

Protocols

An apoptotic index may increase after cooling the body region. The apoptotic index refers to a percentage of apoptotic cells in specimen. The apoptotic index may increase due to cooling up to ten times greater value compared with the value prior the cooling.

Based on the apoptotic index a treatment combining various methods may be designed as a tailor-made solution following the patient's need. The cooling may be applied to the body region of the patient prior, during and/or after applying a magnetic field to the patient.

Pain Relief

A pain relieving medicament may be provided during the treatment if the patient is more sensitive to decreased temperature. A topical application may be preferred. The pain relief effect may be provided by a magnetic field of repetition rate at least 100 Hz, more preferably 120 Hz, even more preferably at least 140 Hz or at least 180 Hz. The pain relieving effect may be provided before, during or after the treatment.

Precooling

Cooling the body region prior to applying the magnetic field may influence a metabolism of adipose cells. Alternatively, the cooling of the adipose cells may induce apoptosis, lipolysis, autophagy and/or disruption of the adipose cells. A release of FFA from adipose cells may induce ER stress as recited above. The application of the magnetic field may cause at least partial muscle contraction reducing the adipose cells. Furthermore the released FFA from adipose cells influenced by cooling may be used as energy source for muscle work. Hence the cooling may be followed by treating a patient by magnetic field inducing at least partial muscle contraction. Due to the combined effect of cooling and magnetic treatment the adipose cells may be reduced in number and/or volume. Moreover the muscles may be shaped, tightened, strengthened and/or the volume of the muscle may increase. Additionally, the cellulite appearance may be reduced due to muscle work.

The magnetic treatment may provide a massage effect. Hence blood and/or lymph flow may be improved. Additionally frozen tissue may be relaxed.

The combined magnetic treatment may be applied immediately after cooling, more preferably around 1 to 24 hours after cooling, e.g. 1, 2, 8 or 20 hours after cooling. The combined treatment may be applied periodically. Alternatively, the treatment by cooling and/or magnetic field may be applied separately, e.g. treatments may alternate in appropriate periods. The period may last from 12 hours to 1 month, more preferably from 1 day to 2 weeks, most preferably from 3 days to 1 week.

In an exemplary application of the treatment method a patient's body region may be cooled by a cooling element for e.g. at least 20 minutes up to 1 hour. After stopping the cooling the body region may be treated by magnetic field for e.g. 15 to 45 minutes.

Cooling

Cooling the body region may be applied simultaneously while the body region is treated by magnetic field within one treatment.

The magnetic cooling may be provided to the patient while the patient is being treated by magnetic field.

Alternatively, cooling may alternate with treatment by magnetic field, i.e. the magnetic field is applied when cooling is not provided to the patient or vice versa. Periods of alternating cooling and magnetic treatment may vary.

The magnetic field may be preferably applied in burst mode. Each burst contains train of magnetic impulses and a period of no magnetic treatment. The train may include a plurality of magnetic impulses. A number of magnetic impulses may vary in the range of at least 1 to 10000 impulses, more preferably in the range of at least 10 to 1000 impulses. The time duration of the train and/or the period of no magnetic treatment may vary in order of milliseconds to order of seconds, e.g. in the range of 100 milliseconds to 100 seconds, more preferably in the range of 1 to 30 seconds, most preferably in the range of 5 to 15 seconds.

An essential principle of magnet therapy used for biological structure stimulation is the influence of the magnetic field on the cell. The cell membrane is polarized due to the induced electric current. One of fundamental phenomenon of electric current in biological tissue may be an action potential occurrence, a transfer of neural excitation and/or a partial or full muscle contraction may be induced. Additionally, the effect of the generated action potential may modulate a painful stimulus transmission, providing a pain management effect.

According to still another application of the invention, the neural structure stimulation by time-varying magnetic field may be used for pain management.

According to one approach of the aspect of the application in pain management, the neural structure may be stimulated by an envelope created by higher repetition values e.g. exceeding 100 Hz, more preferably at least 150 Hz, even more preferably at least 200 Hz, most preferably at least 250 Hz, or up to 700 Hz. The envelope may be generated with predefined repetition frequency and/or shape.

According to still another approach of the aspect of the application in pain management, the neural structure may be stimulated by trains 1501 of several pulses 1502 and time with no stimulation after the train 1501. The group of several pulses 1502 and the time with no stimulation is called burst 1504. Therefore one burst 1504 consists of the only one train 1501 and time with no stimulation 1503. The train 1501 preferably consists of at least 2 pulses, more preferably 5 pulses, even more preferably tens pulses or up to hundreds pulses; repetition rate of the pulses 1502 is at least 100 Hz. The burst repetition rate may vary following the patient's needs. In the preferred application the burst repetition rate vary from 1 to 10 Hz. The number of pulses 1502 in train 1501 and/or the time with no stimulation may vary following the patient needs.

Figure 15:
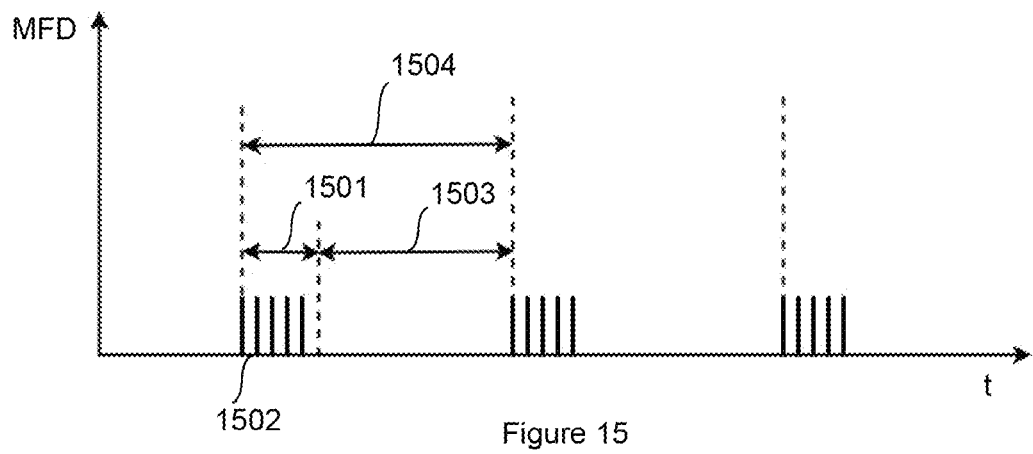
FIG. 15 illustrated a stimulation by exemplary clusters.

FIG. 15 shows an example of application of the stimulation by time-varying magnetic field with a repetition rate of 125 Hz in clusters 1501 consisting of 5 pulses 1502, with a burst 1504 repetition rate 10 Hz. Total time duration of one burst 20 is 100 ms. Total stimulation time of one cluster 1501 is 40 ms, hence the time with no stimulation 1503 is 60 ms. The most important advantage of this approach is analgesic effect and almost no adaptation of the neural structure to the stimulation. The approach may be used e.g. for alleviating the acute pain.

In an alternative application the neural structure may be stimulated by rectangular or increasing shaped envelope as well.

According to another aspect of the application in neural system diagnostics, the neural structure may be stimulated by single pulses or rectangular shaped envelope, and by increasing shaped envelope. Both envelopes are used for determination of minimal magnetic flux density value sufficient to induce at least partial muscle contraction. The envelope duration may last 1 second. After the determination of both magnetic flux densities values, the level of muscle denervation may be calculated.

According to still another aspect of the invention, the magnetic treatment may be used for treatment of diabetes, e.g. function of pancreas and/or liver may be improved. The magnetic field may influence hyperglycemia. Hence the treatment may reduce diabetic neuropathy which is caused by hyperglycemia.

Furthermore, the magnetic treatment may relieve the consequences of the neuropathy by locally improved blood, perfusion, metabolism or lymph circulation. The progress of the neuropathy may be inhibited, e.g. foot infection may be treated and/or reduced hence amputation may be prevented. Moreover, the magnetic treatment may be used for inducing pain relieving effect. The diabetes may be associated with venous ulcers which may be treated by magnetic treatment as well. The treatment of venous ulcer may be treated by similar effects as the consequences of the neuropathy.

In one exemplary application the body region may be cooled for a period of e.g. at least 5 minutes. After stopping the cooling the body region may be treated by a magnetic field for a period of e.g. at least 5 minutes. After stopping the magnetic treatment the body region may be cooled.

Post Cooling

The cooling may also be applied after magnetic treatment. The treatment by magnetic field may provide stimulation, pain relief and/or a myorelaxation effect for the treated body area before cooling. The cooling applied with pressure may be better accepted by the adipose tissue when the muscle below the adipose cells is relaxed. Alternatively the magnetic treatment may provide a temporary pain relief effect hence a patient suffering from a lower pain threshold, e.g. cool sensitivity, may be treated.

In an exemplary application the body region may be treated by a magnetic field for a period of e.g. at least 15, 20 or 30 minutes. After stopping the magnetic treatment the body region may be cooled.

The cooling may be applied immediately after magnetic treatment, more preferably around 1 to 24 hours after magnetic treatment, e.g. 1, 2, 8 or 20 hours after magnetic treatment. The combined treatment may be applied periodically.

In an exemplary application of the treatment method a patient's body region may be treated by magnetic field for e.g. at least 20 minutes up to 1 hour. After stopping the magnetic treatment the body region may be treated by cooling for e.g. 15 to 45 minutes.

In the previously described exemplary treatment methods the cooling of the patient may be replaced by heating the patient.

Figure 16A:
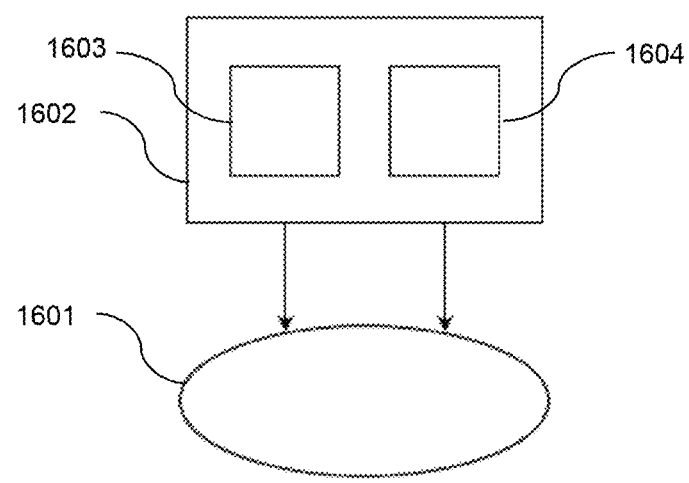
FIGS. 16A and 16B illustrate diagrams of a treatment device.
Figure 16B:
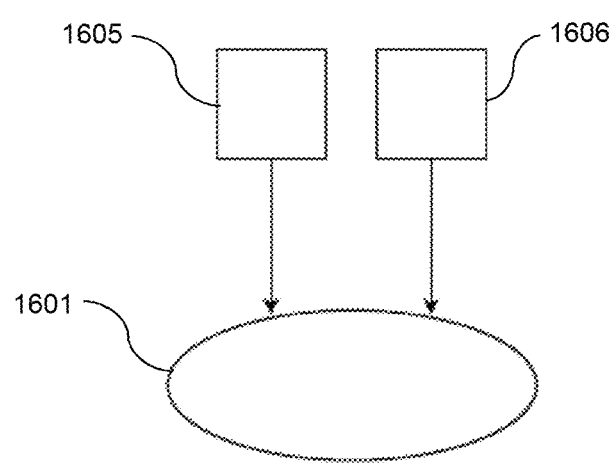

FIGS. 16A and 16B illustrate an application of the treatment by a device providing heating/cooling to the body region of the patient 1601. FIG. 16A illustrates a treatment device 1602 including a connection to power source, a magnetic field generating device 1603 and means for providing heating/cooling 1604, e.g. RF source or cooling element. FIG. 16B illustrates alternative treatment applied by two separate treatment devices, i.e. by a device providing magnetic treatment 1605 and a device providing heating/cooling 1606.

All the recited combined treatment methods may be provided by at least one applicator. The applicator may provide cooling and magnetic treatment. Alternatively one applicator may provide cooling and second applicator may provide magnetic treatment.

Combined Magnetic and Radiofrequency

The target structure may be treated by combined methods which may be used for remodeling the adipose tissue, body shaping and/or contouring, muscle toning, skin tightening, skin rejuvenation, wrinkle removing, reducing stretchmarks, breast lifting, lip enhancement or treatment of cellulite in general by application of electromagnetic radiation to target structure to selectively heat the target tissue to remove and/or remodel adipose tissue from the target tissue. The second approach is to transmit a magnetic treatment to the target structure, inducing at least partial muscle contraction within the target structure to remodel the adipose tissue by natural adipose tissue catabolism. Adipose tissue catabolism may be caused by apoptosis or necrosis of the adipocytes. The muscle contraction caused by induced eddy current is the same as a natural contraction. The adipose tissue may be reduced in natural way. Additionally, the muscle may be shredded in a natural way. Therefore the effect resulting in body shaping and/or contouring may be significantly improved.

The combination of the recited method may improve currently used applications in various aspects and the effect of the treatments may be significantly enhanced. The application of a radiofrequency electromagnetic field may be combined with application of a magnetic field applied before, simultaneously or after the radiofrequency treatment. The application of a magnetic field may induce many benefits for radiofrequency treatment, such as applications inducing at least partial muscle contraction, myorelaxation effect or analgesic effect. The perfusion or metabolism may be improved as well.

The at least partial muscle contraction may induce enhanced effects on adipose tissue reduction by catabolism of the adipose tissue and burning energy from adipose tissue. The total adipose tissue reduction effect may be enhanced by radiofrequency treatment.

Additionally, the at least partial muscle contraction may improve a blood flow and/or perfusion in the treated body region. The improved blood flow may be caused by activation of muscle pump and/or by the muscle necessity of more oxygen due to the at least partial contraction. The blood flow may increase rapidly and it may last temporarily, preferably up to 1 hour, more preferably up to 45 minutes, most preferably up to 30 minutes. Due to increased blood flow and/or local perfusion, the risk of overheated muscle may be limited or even eliminated. Further the homogeneity of the thermal field induced by thermal effect of radiofrequency treatment may be significantly enhanced and/or the temperatures may be well-balanced/compensated in the target body region. Still another benefit may be prevention of creation any hot spot caused by steep thermal gradient.

Due to improved blood flow, perfusion and/or lymph flow the metabolism may be improved. Additionally, the effect of radiofrequency treatment may be enhanced by improved metabolism, e.g. cellulite treatment, body shaping and/or contouring, skin tightening or skin rejuvenation. Further benefit may be reducing or eliminating the risk of panniculitis or local skin inflammation since any clustering of the treated adipocytes may be prevented by the improved metabolism. The improved blood and/or lymph flow may contribute the removing of the adipocytes. The removing of the adipocytes may be promoted by higher number of cells phagocytosing the adipocytes as well. Synergic effects of magnetic and RF treatment may significantly improve metabolism. Therefore the possibility of adverse event occurrence may be limited and treatment results induced by the present invention may be reached in shorter time period.

Further the at least partial muscle contraction may improve the movement of lymphatic vessel and the lymph flow may be improved.

In the preferred application the RF and/or magnetic field may be modulated. In the most preferred application both treatments are modulated. The magnetic treatment may be modulated in the magnetic flux density domain, repetition rate domain, or impulse duration domain, to provide different treatment effects and to prevent adaptation of the target biological structure. The radiofrequency treatment may be modulated in the frequency domain, intensity domain and/or time domain to reach the most complexity and/or efficiency of the target treated biological structure. The modulation in the time domain may be changing the active and passive periods of stimulation, e.g. the radiofrequency treatment may include period with no stimulation, i.e. the radiofrequency treatment may be not continual but the treatment may be provided in pulses. The periods of no stimulation may vary and may be adjusted by the operator. Due to modulation during the treatment, different target biological structures may be treated in the different depth.

The application may be contact or in the preferred application the treatment may be applied contactless. Contactless application may avoid all biocompatibility factors which may occur during contact treatment. In the most preferred application the treatment may be provided by self-operated device. Hence the applicator and/or magnetic field generating device need not be guided by the operator. The applicator may be fixed at a sufficient distance from the patient's skin enabling safe treatment for the patient. Self-operated treatment may be provided by a hand-held applicator or the applicator may be fixed to stand-alone device. The self-operated treatment may be also enabled using various types of sensors in communication with the device for monitoring the treatment and/or the patient. The at least one sensor may be e.g. reactive sensor, electrochemical sensor, biosensor, biochemical sensor, temperature sensor, sorption sensor, pH sensor, voltage sensor, sensor for measuring distance of applicator from the patient surface and/or from the treated area, position sensor, motion detector, photo sensor, camera, sound detector, current sensor, sensor for measuring of specific human/animal tissue and/or any suitable sensors measuring biological parameters and/or combination thereof such as sensor for measuring dermal tensile forces, sensor for measuring the activity of the muscle, muscle contraction forces, tissue impedance or skin elasticity.

Further the homogeneity of the treatment may be improved by several approaches. A first approach may be represented by a moveable applicator providing the dynamic treatment to a large target area. The dynamic treatment may improve the homogeneity of applied treatment energy and additionally due to large area the effect is uniform and/or well balanced. Static positioning of the applicator may be used as well. Another approach of improving homogeneity may be represented by using a bolus. The bolus may provide improved transmittance of the electromagnetic energy to the treated biological structures. Additionally, the bolus may prevent occurrence of hot spots within the treated area; the bolus may provide constant temperature to the target treated surface area; or the bolus may increase the homogeneity of the radiofrequency waves application by providing a homogenous medium for electromagnetic waves propagation not being influenced by the interface of the target treated area and an air. The bolus may profile the electromagnetic field to enhance the effect of the treatment. In still another approach an air gap may be between the applicator and the patient.

The treatment by magnetic and/or electromagnetic field may be in continuous or discrete mode. In one application the magnetic treatment may be applied in continual mode with no pauses and the electromagnetic treatment may be applied in pulsed mode to provide improved adipose tissue reduction caused by natural process and by the increased temperature. In another application the electromagnetic treatment may be applied continuously with no pauses and the magnetic treatment may be applied in pulsed mode to provide improved thermal reduction of adipose tissue and by improved metabolism due to improved blood flow. Both modes may be combined in various treatment sequences.

In the preferred application the treatment may be started at the moment when the target biological structure reaches the predetermined temperature. The temperature in the target tissue may be up to 80° C., more preferably in the range of 37 to 60° C., even more preferably in the range of 40 to 45° C. The temperature may be adjusted based on the intended use, e.g. adipose tissue reduction, collagen production or muscle contraction. In an alternative application the intended use may be coagulation and/or ablation. The temperature in the target biological structure may be measured by invasive method, e.g. using an invasive probe; or by contact method, e.g. using thermocouple sensor; or by contactless method, e.g. using infrared sensor or camera. The temperature of the target biological structure may be determined by a mathematic method. The sensor for measuring the temperature in the target biological structure may be attached to the applicator.

The applicator may include at least one sensor for detecting the temperature of the skin. The sensor may be preferably contactless. Alternatively the sensor may measure the temperature in contact manner. Alternatively, the skin impedance may be determined as well.

A benefit of the application of magnetic treatment and electromagnetic treatment may be causing an analgesic effect of the application and providing a possibility of treating a patient with higher sensitivity for thermal effects induced by electromagnetic treatment, i.e. patients with any predisposition inducing increased thermal sensitivity. The analgesic effect may be induced by magnetic treatment by suitable repetition rates and it may be induced immediately during the magnetic treatment. The analgesic effect may last up to several hours after magnetic treatment. The magnetic flux density of the magnetic treatment may preferably reach at least motor-threshold intensity inducing at least partial muscle contraction therefore the homogeneity of the thermal field may be significantly enhanced.

Another benefit of application the magnetic treatment may be causing a myorelaxation effect. The magnetic treatment may be applied on spastic muscle structures to relieve the hypertonus of the muscle and improving the blood and/or lymph flow. Therefore relieving the hypertoned muscle may contribute to the analgesic effect and contribute to the acceptability of the treatment by the patient.

The blood and/or lymph flow may be limited in the spastic muscles and the metabolism may be limited as well, meaning that the risk of clustering the treated target structures may be higher and possible adverse events may occur. The recited risks may be eliminated by the used of magnetic treatment.

In one aspect of the invention, the treatment by magnetic field may be applied to the target structure before the radiofrequency treatment to prepare the target structure for following treatment by radiofrequency field. The effect of magnetic treatment may be to induce at least partial muscle contraction or to treat a muscle structure to increase a muscular tonus of the target structure. Both effects may provide a massage effect for the structure within the proximity of the target structure hence the blood and/or lymph circulation may be improved to promote local metabolism. The temperature may be locally increased by the improved blood flow and the target structure may accept the following radiofrequency treatment at significantly higher quality. Additionally, the collagen and/or elastin fibers may be remodeled or restored and/or its neogenesis may be improved to provide a younger, smoother, firmer and enhanced skin appearance.

Additionally, previous application may improve acceptability of the electromagnetic field by increasing the temperature of the skin and the transmittance of the electromagnetic field may be improved due to less value of skin impedance. Further the radiofrequency may penetrate deeper target structures relative to treatment without a preceding magnetic treatment of the target structure and/or area.

Another benefit may be releasing the adipose tissue in the muscle by muscle contraction and/or by temperature increase causing better liquidity of adipose tissue. Still another benefit of the at least partial muscle contraction may be mechanical breaking large adipose tissue bulks into smaller bulks which may be easier metabolized and/or the smaller adipose tissue bulks may be removed faster by the lymphatic and/or blood flow. Due to improved metabolism and/or circulation the cellulite may be treated in a short time and the visual effect on skin appearance may be significantly enhanced.

In another aspect of the invention, the treatment by magnetic field may be applied to the target structure simultaneously with the radiofrequency treatment to improve effects of the electromagnetic treatment inducing heat in the target structure.

The simultaneous application of magnetic treatment and radiofrequency treatment may be in two modes: a first mode may generate the magnetic impulses while radiofrequency treatment is active or another mode may generate radiofrequency treatment while the magnetic treatment is not in an active stimulation period, i.e. the period of magnetic treatment and radiofrequency treatment alternates. Both modes amplify the resulting effect of the treatment. Therefore the results may be achieved in significantly shorter time than the same results achieved by separate applications of the radio frequency and magnetic treatments.

The simultaneous method of magnetic treatment and radiofrequency treatment of the target tissue may increase the peak magnetic component of the entire treatment resulting in improved heating of the target structure including containing higher water volume, e.g. skin. Due to increased temperature of skin, the production and/or remodeling of collagen and/or elastin fibers may be improved and the skin may be provided with a younger, smoother, firmer and enhanced appearance. The effect of overheating the muscle may be reduced by the improved blood flow.

In still another aspect of the invention, the treatment by magnetic field may be applied to the target structure after the treatment by electromagnetic field to enhance and/or contribute to the effects of radiofrequency treatment by influencing the target structure by magnetic field.

The magnetic field may treat the target structure to cause at least partial muscle contraction proximate to the target structure to improve blood flow and provide homogenous temperature distribution at high quality after creating a temperature distribution at lower quality by radiofrequency treatment.

All of the methods may be provided by the above recited technical solutions. The above mentioned methods may be used separately or in any combination.

The method may cause the circumferential reduction i.e. a reduction of the size of the treated body region. The method may be mostly indicated for the regions with cellulite, especially for buttocks, saddlebags, love handles, abdomen, hips, thighs or arms. However, the indication is not limited to the mentioned regions and the method may be used for treatment of any other body region.

The at least one applicator may include at least one magnetic field generating device. The plurality of magnetic field generating devices may be positioned in isolated locations of the at least one applicator. Alternatively, the magnetic field generating devices may be positioned next to each other, in an array or matrix, in a pattern or in randomized locations of the at least applicator.

The magnetic field generating devices may be positioned and/or moved in the at least one applicator in one plane; in at least two mutually tilted planes defined by a convex or concave angle, or perpendicular to each other; or in at least two parallel planes with the at least one magnetic field generating device in each parallel plane. The movement of the at least one magnetic field generating device may be translational and/or rotational, constant or accelerated. The movement may follow a predetermined, random or predefined trajectory, such as a pattern, array or matrix. The movement of the at least one applicator may be handled in similar manner as the movement of the at least one magnetic field generating device. The angles of the planes and/or the movement of the at least one magnetic field generating device may be adjusted by an operator following the patient's needs. The positioning may be provided by mechanical holder, enabling tilting, distancing and positioning magnetic field generating device in various planes. In an alternative embodiment the patient may be positioned in the intersection of the magnetic fields generated by the plurality of magnetic field generating devices. In the preferred application the at least one applicator may be movable and the movement may be circular.

The plurality of magnetic field generating devices may be positioned within one applicator having form of mechanical holder. The shape of the applicator having form of mechanical holder may be adjustable, e.g. the applicator may include at least one moveable part. In a preferred embodiment the applicator having form of mechanical holder may provide spatial arrangement of the energy delivery elements in one axis, two axes or three axes and/or provide tilting and/or rotation. The applicator having form of mechanical holder may provide fixation of the at least one magnetic field generating device in one position. The moveable parts may be connected by sliding mechanism and/or by a joint mechanism. An exemplary embodiment of such an applicator may be found in U.S. Pat. No. 9,468,774, incorporated herein by reference. The applicator may be adjustable following the body region and/or biological structure.

The static position of the at least one applicator may be provided by a positioning member. The positioning member may be e.g. an arm or an adjustable flexible belt. The positioning member may include a buckle for adjusting the length of the belt. The applicator may be placed within predefined locations of the belt. Alternatively the applicator may be shaped to be moveable along the positioning member, e.g. the shape of the applicator may be preferably concave, e.g. V-shaped or U-shaped. The positioning member may be inserted itself into the concavity of the applicator. The position of the applicator may be adjusted by limited movement along the positioning member because the positioning member may be used as guiding member. However, the applicator may not be fixed to a particular static position. The position of the applicator may be dynamically adjusted during the treatment following the patient's needs. The position of the applicator may be adjusted manually by the operator, or automatically by the treatment device. In one exemplary embodiment a plurality of applicators may be used for treating larger body regions, e.g. buttocks, abdomen or thigh.

The present methods may also induce muscle contraction to reduce effect of skin laxity. Skin laxity may be caused by e.g. aging process or increasing number and/or volume of adipose cells which pulls down the skin by gravity, rapid weight loss or skin stretching during the pregnancy. The muscles may be treated by the induced electric current to contract. Repetitive contractions may cause the muscles to obtain the tonus and flexibility. Therefore the skin appearance may be enhanced by treating the flabby muscles. The effect of skin tightening may be achieved. The method also may promote the collagen and elastin fibers in the layers subtending the epidermis hence the skin may obtain enhanced visual appearance. The method may be widely applied but not limited to application to the regions of neck, breasts, arms or abdomen. The method may provide the smoother and younger appearance of the skin to the patient.

Similar methods of the muscle structure treatment by time-varying magnetic field for inducing the at least partial muscle contraction may be used for treatment of wrinkles as well. Wrinkles are results of extrinsic and intrinsic factors. Nowadays, wrinkles are considered to be negative effect of natural aging process which decreases the production of collagen and elastin fibers and weakens the skin which becomes thinner. As the muscle treatment by the magnetic flux density may induce at least partial muscle contraction, the collagen and elastin fibers neogenesis may be improved. Additionally, the muscles subtending the treated region may be toned and the skin may obtain a younger and enhanced visual appearance. Therefore, the effect of skin tightening may be achieved.

Wrinkles may be prevented or reduced by practicing facial exercises which may cause a massage effect to the facial tissues, improving blood and lymph circulation. Additionally, the facial muscles may be relaxed and toned after the exercise. A similar effect as facial exercise may be achieved by non-invasive and/or contactless method of treating the facial muscles by magnetic flux density. Further additional advantage of the present method may be the improvement of restoration of the collagen and elastin fibers, more effective toning and strengthening of the facial muscles.

The present methods may improve the neogenesis and remodeling of collagen fibers in the lips to reach a full, plump and firmer appearance. The magnetic flux density may be applied to the lips by an applicator. Therefore the lips may become fuller and firmer without any need of invasive method such as injection of the synthetic fillers, permanent makeup or the facial implants. The present method may promote the remodeling and/or neogenesis of collagen fibers in a natural way. Additionally, the collagen is natural substance of the human body which may provide the elasticity to the structure.

The present methods may be used for enhancing the visual appearance of breasts. Cooper's ligament may be treated, improved and/or firmed by the at least partial muscle contraction. The treatment may induce the elevation of the breast tissue. Additionally, the breast tissue may be treated to be modified in a shape, wherein the shape includes the size and/or the contour of the breast tissue. Therefore the visual appearance may be enhanced and breasts may be more attractive for the patient. The present method may be a non-invasive alternative for current aesthetic surgery method for the treatment of sagging breast tissue. The present method may provide a patient a method of breast visual appearance enhancement without surgery. Therefore the method lacks post-surgery complications such as scars, postoperative pain or long recovery period. Various treatment protocols may be used.

Following the recited methods the treatment may be but is not limited to continuous, pulsed, randomized or burst. The impulse may be but not limited to monophasic, polyphasic, biphasic and/or static magnetic field. In the preferred application the magnetic impulse may be in biphasic regime, i.e. it is consisted of two phases, preferably positive and negative.

In the preferred application of the present method the trains of pulses, called bursts are used.

Repetition rate and/or magnetic flux density may vary during the treatment protocol. Further the treatment may include several periods of different repetition rates, therefore the modulation may be in repetition rate domain. The treatment may include several periods of different magnetic flux densities, therefore the modulation may be in magnetic flux density domain. Alternatively the treatment may include different impulse durations, therefore the modulation may be in impulse duration domain. In yet another approach the treatment may be modulated by any combinations thereof.

Various envelopes and/or waveforms, e.g. pulse, sinusoidal, rectangular, square, triangular, saw-tooth, trapezoidal, exponential etc. for the purpose of muscle treatment may also be used, and are not limited to recited shapes.

The values of magnetic flux density and repetition rate are cited in several preferred applications since the perception of the treatment is subjective. Nevertheless, the magnetic flux density and repetition rates are not limited by the recited values. A person skilled in the physical therapy is able to repeat and apply the treatment methods adjusting the magnetic flux density and/or repetition rate following the patient's sensitivity or needs.

The present method is not limited to be used independently. For enhancing the result the method may be used in combination with other conventional non-invasive and/or invasive aesthetic treatment method.

All the recited methods may be applied to a patient in a non-invasive and/or contactless way. Therefore the present methods provide an effective alternative approach of enhancing the visual appearance with no need of invasive treatment or surgery. Further, the visual results are appreciable after several treatments. Additionally, the results include not only the visual appearance enhancement but even the improvement of the muscle structures, hence the patient feels firmer and tighter. The muscle structures become toned with no need of any diet or spending time by exercising in fitness.

The patient may feel firmer and/or tighter. The skin may be also tighter. Additionally, adipose tissue reduction may occur. Furthermore, cellulite may be reduced as well.

A method of treating a biological structure uses a combination of non-invasive methods for enhancing human appearance. The invention utilizes electromagnetic radiation. Methods may be used for targeted remodeling adipose tissue, focused treatment of cellulite, body contouring, skin tightening or skin rejuvenation. The invention relates to focused heating of the target tissue by electromagnetic waves, whereas the effect of focused heating of the target tissue is amplified by the effect of a pulsed magnetic field treatment.

The present invention discloses the advanced approaches in aesthetic applications, e.g. for cellulite treatment and/or body shaping. Combined methods of treatment by electromagnetic field and treatment by magnetic field are used. The electromagnetic field may include treatment by radiofrequency, infrared or optical waves. The magnet treatment may be provided by permanent magnets, electromagnetic devices generating a static magnetic field or time-varying magnetic devices. In the preferred application the treatment by a pulsed magnetic field and radiofrequency treatment may be combined. However the application is not limited by the recited combination so the combined method may include magnet treatment and any treatment by electromagnetic field, e.g. light treatment, IR treatment or treatment by radiofrequency waves, e.g. microwaves, short waves or long waves.

Magnet treatment in combination with radiofrequency treatment may be represented by two independent treatment devices, e.g. one treating the target structure by radiofrequency waves and the second treating the target structure by magnetic field. Both devices may have a separate applicator for treating the target structure, or one applicator may be used by at least two devices, i.e. the applicator may be modular for a plurality of devices.

The aesthetic treatment device may include at least one HF frequency generator for providing energy for radiofrequency treatment and for providing energy for magnet treatment. In an alternative embodiment, the device may include at least one HF frequency generator for providing energy for radiofrequency treatment and at least one other independent frequency generator for providing energy for magnet treatment. The device may include plurality of applicators for providing separate radiofrequency or magnet treatments to the patient.

In alternative embodiment the applicator may provide a combination of radiofrequency and magnet treatment. In one embodiment, the applicator may include at least one radiofrequency electrode for providing radiofrequency treatment and at least one coil for providing magnet treatment. In another embodiment, the applicator may include at least one electrode for providing radiofrequency treatment and at least one coil providing magnet treatment, wherein the at least one RF source provides energy for both at least one electrode and at least one coil.

In still another embodiment the at least one RF source may provide the energy for the at least one coil providing magnet treatment wherein the at least one coil may be used as the at least one electrode. The essence is the far different stimulation frequencies which are used for RF treatment and magnet treatment. The coil in the high frequency field is similar to the electrode. This enables the coil to be the electrode for radiofrequency treatment. In the preferred embodiment a flat coil may be used as the electrode.

The frequencies for the radiofrequency treatment may be in the range of ones of MHz to hundreds of GHz, more preferably in the range of 13 MHz to 3 GHz, most preferably around 13.56 or 40.68 or 27.12 MHz or 2.45 GHz. The term "around" should be interpreted as in the range of 5% of the recited value.

The combination of the recited method may improve currently used applications in various aspects and the effect of the treatments may be significantly enhanced. The application of a radiofrequency electromagnetic field is combined with application of a magnetic field applied before, simultaneously or after the radiofrequency treatment. The magnetic field may be generated by a permanent magnet or electromagnet. The magnetic field may be constant in time or in the preferred application the magnetic field may be time-varying, more preferably a pulsed magnetic field may be used. The application of a magnetic field induces many benefits for radiofrequency treatment, such as applications inducing at least partial muscle contraction, myorelaxation effect or analgesic effect. The perfusion or metabolism may be improved as well.

The at least partial muscle contraction may induce enhanced effects on adipose tissue reduction by catabolism of the adipose tissue and burning energy from adipose tissue. The total adipose tissue reduction effect is enhanced by radiofrequency treatment.

Additionally, the at least partial muscle contraction may improve a blood flow and/or perfusion in the treated area. The improved blood flow may be caused by activation of muscle pump and/or by the muscle necessity of more oxygen due to the at least partial contraction. Due to increased blood flow and/or local perfusion, the risk of overheated muscle is limited or even eliminated. Further the homogeneity of the thermal field induced by thermal effect of radiofrequency treatment may be significantly enhanced and/or the temperatures may be well-balanced/compensated in the target treatment area. Still another benefit is prevention of creation any hot spot caused by steep thermal gradient.

Further the at least partial muscle contraction may improve the movement of lymphatic vessel and the lymph flow may be improved.

Due to improved blood flow, perfusion and/or lymph flow the metabolism may be improved. Additionally, the effect of radiofrequency treatment may be enhanced by improved metabolism, e.g. cellulite treatment, body shaping and/or contouring, skin tightening or skin rejuvenation. Further benefit may be reducing or eliminating the risk of panniculitis or local skin inflammation since any clustering of the treated adipocytes may be prevented by the improved metabolism. The improved blood and/or lymph flow may contribute the removing of the adipocytes. The removing of the adipocytes may be promoted by higher number of cells phagocytosing the adipocytes as well. Synergic effects of magnet and RF treatment significantly improves metabolism. Therefore the possibility of adverse event occurrence is limited and treatment results induced by the present invention are reached in shorter time period.

In the preferred application the RF and/or magnetic field may be modulated. In the most preferred application both stimulation signals are modulated. The magnetic stimulation may be modulated in the magnetic flux density domain, repetition rate domain, or impulse duration domain, to provide different treatment effects and to prevent adaptation of the target biological structure. The radiofrequency treatment may be modulated in the frequency domain, intensity domain and/or time domain to reach the most complexity and/or efficiency of the target treated biological structure. The modulation in the time domain may be changing the active and passive periods of stimulation, e.g. the radiofrequency treatment may include period with no stimulation, i.e. the radiofrequency treatment is not continual but the treatment is provided in pulses. The periods of no stimulation may vary and may be adjusted by the operator. Due to modulation during the treatment, different target biological structures may be treated in the different depth.

The application may be contact or the preferred application of the invention the treatment may be applied contactless. Contactless application may avoid all biocompatibility factors which may occur during contact treatment. In the most preferred application the treatment may be provided by self-operated device. Hence the continual surveillance and/or control by the operator is not essential for correct and/or safe operation of the treatment device. Self-operated treatment may be provided by a hand-held applicator or the applicator may be fixed to stand-alone device. The self-operated treatment may be also enabled using various types of sensors in communication with the device for monitoring the treatment and/or the patient. The at least one sensor may be e.g. reactive sensor, electrochemical sensor, biosensor, biochemical sensor, temperature sensor, sorption sensor, pH sensor, voltage sensor, sensor for measuring distance of applicator from the patient surface and/or from the treated area, position sensor, motion detector, photo sensor, camera, sound detector, current sensor, sensor for measuring of specific human/animal tissue and/or any suitable sensors measuring biological parameters and/or combination thereof such as sensor for measuring dermal tensile forces, sensor for measuring the activity of the muscle, muscle contraction forces, tissue impedance or skin elasticity.

Further the homogeneity of the treatment may be improved by several approaches. A first approach may be represented by a moveable applicator providing the dynamic treatment to a larger target area. The dynamic treatment improves the homogeneity of applied treatment energy and additionally due to larger area the effect is uniform and/or well balanced. Static positioning of the applicator may be used as well. Another approach of improving homogeneity may be represented by using a bolus. The bolus may provide improved transmittance of the electromagnetic energy to the treated biological structures. Additionally, the bolus may prevent occurrence of hot spots within the treated area; the bolus may provide constant temperature to the target treated surface area; or the bolus may increase the homogeneity of the radiofrequency waves application by providing a homogenous medium for electromagnetic waves propagation not being influenced by the interface of the target treated area and an air. The bolus may profile the electromagnetic field to enhance the effect of the treatment. In still another approach an air gap may be between the applicator and the patient.

The treatment by magnetic and/or electromagnetic field may be in continuous or discrete modes. In one application the magnetic treatment may be applied in continual mode with no pauses and the electromagnetic treatment may be applied in pulsed mode to provide improved adipose tissue reduction caused by natural process and by the increased temperature. In another application the electromagnetic treatment may be applied continuously with no pauses and the magnetic treatment may be applied in pulsed mode to provide improved thermal reduction of adipose tissue and by improved metabolism due to improved blood flow. Both modes may be combined in various treatment sequences.

In the preferred application the treatment is started at the moment when the target biological structure reaches the predetermined temperature. The temperature in the target tissue may be up to 80° C., more preferably in the range of 37 to 60° C., even more preferably in the range of 40 to 45° C. The temperature may be adjusted based on the intended use, e.g. adipose tissue reduction, collagen production or muscle contraction. In an alternative application the intended use may be coagulation and/or ablation. The temperature in the target biological structure may be measured by invasive method, e.g. using an invasive probe; or by contact method, e.g. using thermocouple sensor; or by contactless method, e.g. using infrared sensor or camera. The temperature of the target biological structure may be determined by a mathematic method. The sensor for measuring the temperature in the target biological structure may be attached to the applicator.

A benefit of the application of magnet treatment and electromagnetic treatment may be causing an analgesic effect of the application and providing a possibility of treating a patient with higher sensitivity for thermal effects induced by electromagnetic treatment, i.e. patients with any predisposition inducing increased thermal sensitivity. The analgesic effect may be induced by magnet treatment by suitable repetition rates and it may be induced immediately during the magnet treatment. The analgesic effect may last up to several hours after magnet treatment. The magnetic flux density of the magnetic stimulation may preferably reach at least motor-threshold intensity inducing at least partial muscle contraction therefore the homogeneity of the thermal field is significantly enhanced.

In one aspect of the invention, the treatment by magnetic field may be applied to the target structure before the radiofrequency treatment to prepare the target structure for following treatment by radiofrequency field. The effect of magnet treatment is to induce at least partial muscle contraction or to stimulate a muscle structure to increase a muscular tonus of the target structure. Both effects may provide a massage effect for the structure within the proximity of the target structure hence the blood and/or lymph circulation may be improved to promote local metabolism. The temperature may be locally increased by the improved blood flow and the target structure may accept the following radiofrequency treatment at significantly higher quality. Additionally, the collagen and/or elastin fibers may be remodeled or restored and/or its neogenesis may be improved to provide a younger, smoother and enhanced skin appearance.

Additionally, previous application may improve acceptability of the electromagnetic field by increasing the temperature of the skin and the transmittance of the electromagnetic field may be improved due to less value of skin impedance. Further the radiofrequency may penetrate deeper target structures relative to treatment without a preceding magnet treatment of the target structure and/or area.

Another benefit may be releasing the adipose tissue in the muscle by muscle contraction and/or by temperature increase causing better liquidity of adipose tissue. Still another benefit of the at least partial muscle contraction may be mechanical breaking large adipose tissue bulks into smaller bulks which may be easier metabolism of the adipose tissue and/or the smaller adipose tissue bulks may be removed faster by the lymphatic and/or blood flow. Due to improved metabolism and/or circulation the cellulite may be treated in a short time and the visual effect on skin appearance may be significantly enhanced.

In another aspect of the invention, the treatment by magnetic field may be applied to the target structure simultaneously with the radiofrequency treatment to improve effects of the electromagnetic treatment inducing heat in the target structure.

The simultaneous application of magnet treatment and radiofrequency treatment may be in two modes: a first mode may generate the magnet impulses while radiofrequency treatment is active or another mode may generate radiofrequency treatment while the magnet treatment is not in an active stimulation period, i.e. the period of magnet treatment and radiofrequency treatment alternates. Both modes amplify the resulting effect of the treatment. Therefore the results are achieved in significantly shorter time than the same results achieved by separate applications of the radio frequency and magnet treatments.

The simultaneous method of magnet treatment and radiofrequency treatment of the target tissue may increase the peak magnetic component of the entire treatment resulting in improved heating of the target structure including containing higher water volume, e.g. skin. Due to increased temperature of skin, the production and/or remodeling of collagen and/or elastin fibers may be improved and the skin may be provided with a younger, smoother and enhanced appearance. The effect of overheating the muscle is reduced by the improved blood flow.

In still another aspect of the invention, the treatment by magnetic field may be applied to the target structure after the treatment by electromagnetic field to enhance and/or contribute to the effects of radiofrequency treatment by influencing the target structure by magnetic field.

The magnetic field may treat the target structure to cause at least partial muscle contraction proximate to the target structure to improve blood flow and provide homogenous temperature distribution at high quality after creating a temperature distribution at lower quality by radiofrequency treatment.

The present device and methods of its operation are related to treatment of a patient by magnetic and/or electromagnetic treatment. The electromagnetic treatment may be particularly radiofrequency treatment. The application of the magnetic and/or electromagnetic treatment may be provided by at least one energy delivery element. The device may be used for treatment or focused remodeling of subcutaneous tissue by reducing number and/or value of lipid-rich cells, cellulite treatment, body shaping and/or contouring, muscle toning, skin tightening, collagen treatment, skin rejuvenation, wrinkle removing, reducing stretchmarks, breast lifting, lip enhancement, treatment of vascular or pigmented lesions of the skin or hair removing.

The essential principle for this device is a fact that the energy delivery element, e.g. a magnetic field generating device such as a flat coil which may be preferably circular shaped, may administer the same function as an electrode if it is provided by the high-frequency signal. Hence the coil may be used to generate a radiofrequency treatment. The reason is that the frequency spectra of low-frequency signal used for generating the magnetic field is far different from frequency spectra of high-frequency signal used for generating the electromagnetic field. The signals from at least one or more preferably two generators may be provided successively, with some overlay or simultaneously due to difference of the frequency spectra. The frequency spectra of high-frequency signal used for generating the electromagnetic field may be in the range of ones of kHz to hundreds of GHz, more preferably in the range of 500 kHz to 3 GHz, most preferably above 1 MHz around 3.4 or 6.7 or 13.56 or 40.68 or 27.12 MHz or 434 MHz or 915 MHz or 2.45 GHz. The frequency spectra of low-frequency signal used for generating the magnetic field impulses may be in the range of 1 to 100 kHz, more preferably in the range of 1.25 to 10 kHz, even more preferably in the range of 2 to 5 kHz, most preferably in the range of 3 to 4 kHz. The low-frequency signal is used for generating impulses of time-varying magnetic field. The repetition rate of the pulses may reach up to 700 Hz, more preferably up to 500 Hz, most preferably in the range of 1 to 300 Hz. The magnetic flux density of the magnet treatment is at least 0.1 T, more preferably at least 0.5 T, even more preferably at least 1 T, even more preferably at least 1.5 T, most preferably at least 2 T, or up to 7 T on the surface of the energy delivery element. The energy delivery element may be integrated within an applicator, such as patient support for maintaining the patient in sufficiently sitting or recumbent position, e.g. a chair or a bed. The energy delivery element may be moveable within the patient support. Alternatively the applicator may be moveable, e.g. it may be attached to an articulated arm or it may be preferably hand-held.

Figure 17:
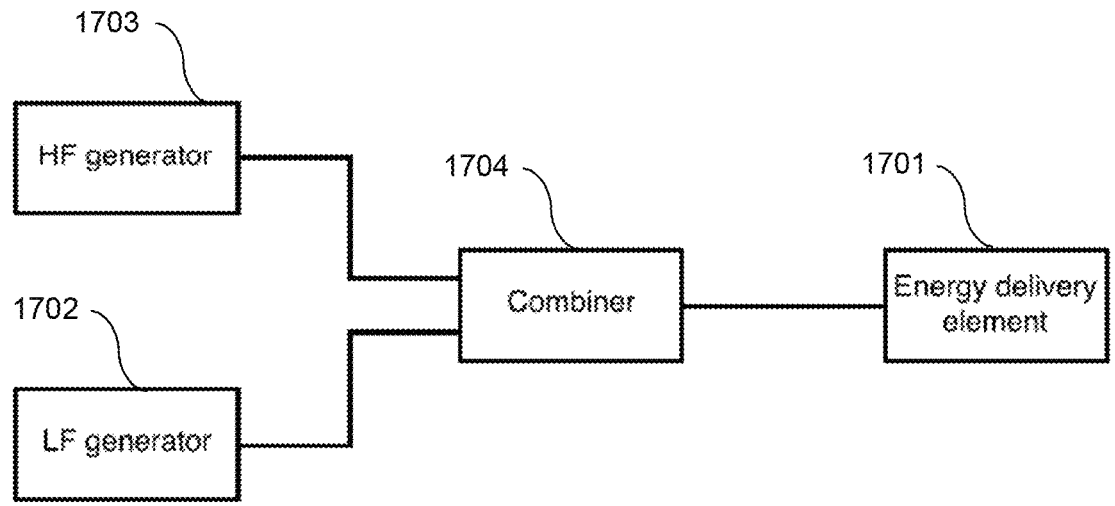
FIG. 17 illustrates a general principle of a treatment device.

FIG. 17 illustrates a general design of a treatment device. The treatment device may include at least one energy delivery element 1701, e.g. a coil, preferably a flat coil; a low-frequency generator 1702 for generating a signal for generating a magnetic field by the energy delivery element 1701. The low-frequency generator may be a connection of a switching device and an energy storage device. The switching device may be in serial connection with the energy storage device, preferably a parallel connection may be used. The treatment device further includes at least one high-frequency generator 1703 for generating a signal for generating an electromagnetic field. According to alternative embodiment only one generator providing low and high frequency may be used. Additionally a combiner 1704 for transmitting the signals to the energy delivery element 1701 may optionally but not necessarily be used. The combiner 1704 may transmit the signals from generators 1702, 1703 to the energy delivery element 1701. Furthermore the combiner may protect the high-frequency generator 1703 from the signal generated by the low-frequency generator 1702 or vice versa. Hence the combiner may prevent the signal from low-frequency generator to affect the high-frequency generator. The combiner may include at least one filtering device, e.g. capacitive and/or inductive coupling, high-pass, low-pass, band-pass or band-stop such as notch filter; at least one switching device, e.g. a switch, a diode, MOSFET, JFET, IGBT, BIT or a thyristor; or any combination thereof. Alternatively the combiner may include a relay. In an exemplary embodiment the combiner 1704 may include at least one coil and/or at least one capacitor, preferably a plurality of coils and/or a plurality of capacitors may be used as well.

The side of the energy delivery element closer to the patient may be covered by a layer of insulating material such as ceramic or epoxy coating, or bolus. The insulating material may provide electrical insulation of the patient and mechanical protection of the energy delivery element.

In an alternative embodiment the treatment device may include a plurality of HF generators and/or a plurality of LF generators.

In an alternative embodiment the treatment device may include a human machine interface for the patient. The patient may control the power in the treatment hence the patient may control e.g. temperature of the target biological structure or strength of the at least partial muscle contraction. Furthermore the patient may interrupt the treatment before any discomfort feeling may occur.

Figure 18:
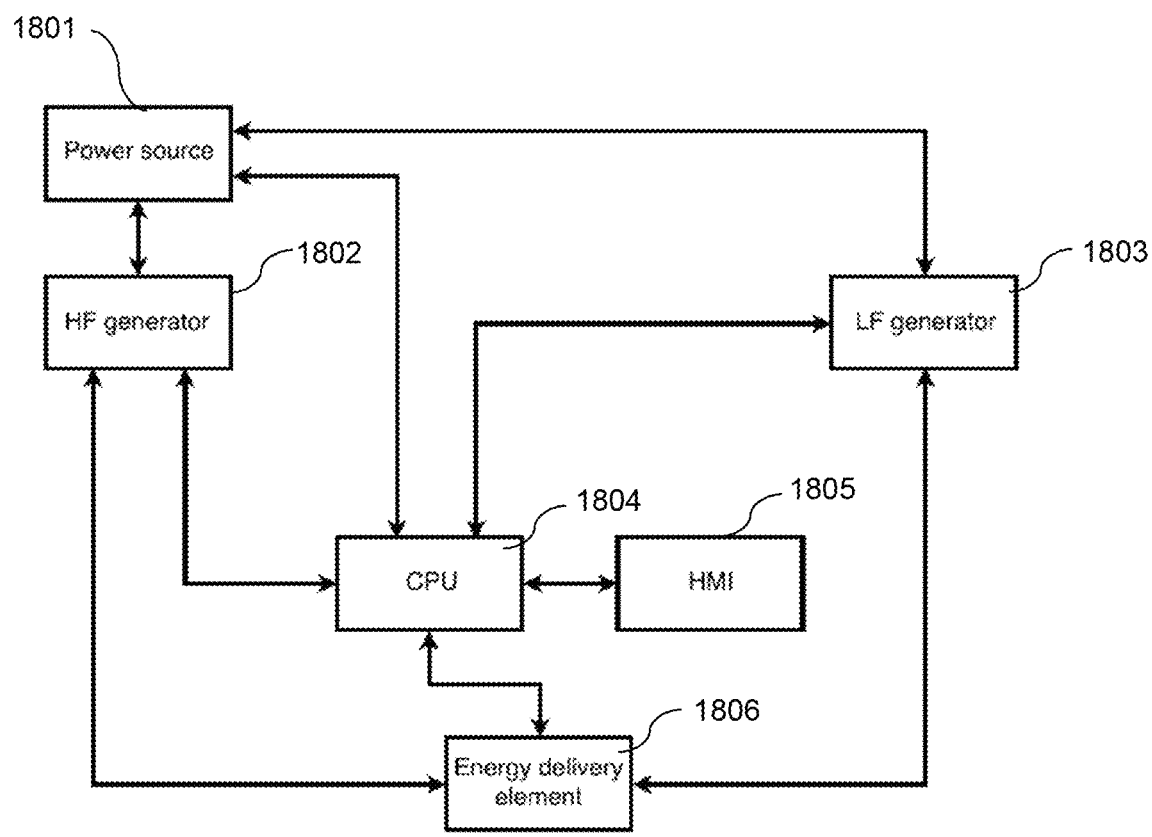
FIG. 18 illustrates a block diagram of treatment device including one energy delivery element.

FIG. 18 illustrates the treatment device which may include a connection to a power supply, a power source 1801, high-frequency generator 1802, low-frequency generator 1803, control unit 1804, human machine interface 1805 and at least one energy delivery element 1806. According to alternative embodiment only one generator providing low and high frequency may be used. The arrows illustrate the direction of communication.

The power supply may provide energy for the treatment device via the power source 1801. The power supply may be external, e.g. a plug, or it may be integrally included within the treatment device, e.g. a battery. The power source 1801 may communicate with generators 1802, 1803. The power source 1801 may provide energy to electric components of the treatment device, particularly to generators 1802, 1803 or to control unit 1804. The power source 1801 may communicate with control unit 1804 which may provide information about power necessary for the treatment. The power source 1801 may adjust the power for generators 1802, 1803 following the information from control unit 1804 or alternatively based on direct information from generator 1802 or generator 1803.

The control unit 1804 may communicate with LF generator. LF generator may provide LF signal to energy delivery element 1806 to generate magnetic treatment. The LF generator 1803 may provide information referred to treatment process to the control unit 1804, e.g. energy loss from one impulse. In an exemplary embodiment the control unit 1804 may send instruction to power source 1801 to provide the LF generator 1803 by the energy amount equaling the energy loss. Alternatively the control unit 1804 may control recharge of the LF generator.

The energy delivery element 1806 may include at least one sensor, e.g. a temperature sensor. The energy delivery element may provide information to control unit 1804, HF generator 1802 and/or to LF generator 1803.

The control unit 1804 may communicate with HF generator 1802 to provide instructions for HF generator 1802. HF generator may provide HF signal for energy delivery element 1806 to generate RF treatment. The HF generator 1802 may provide information referred to treatment process to the control unit 1804, e.g. temperature of the energy delivery element 1806. In one exemplary embodiment RF energy transfer may be optimized prior to the treatment. In an exemplary embodiment the HF generator 1802 may include an internal power source for adjusting energy for energy delivery element 1806. Alternatively, more than one energy delivery element 1806 may be used. When using two or more energy delivery elements, the at least one energy delivery element may deliver magnetic field, the at least one energy delivery element may deliver electromagnetic field (e.g. radiofrequency field); in still another embodiment each energy delivery element may provide both magnetic field and electromagnetic field (e.g. radiofrequency field) for magnetic and electromagnetic treatment.

The control unit 1804 may be in communication with human machine interface 1805. The human machine interface 1805 may include outputting interface for providing information for the operator and/or the patient. The outputting interface may include audio output, e.g. a speaker; visual output, e.g. a display or any combination. The outputting interface may provide a notification for the operator and/or the patient in a human perceptible form such as beep, flashing light, color change or mechanical signal.

The human machine interface 1805 may include at least one input element, e.g. touch member such as touchscreen, keyboard, control member for adjusting the treatment, for providing the information from operator. The operator may adjust e.g. a treatment protocol or may adjust treatment parameters following the patient's need.

In an alternative embodiment the treatment device may include at least two control units. One control unit may administer HF generator. Second control unit may administer LF generator. In this exemplary embodiment a communication link between both control units may be established.

Figure 19A:
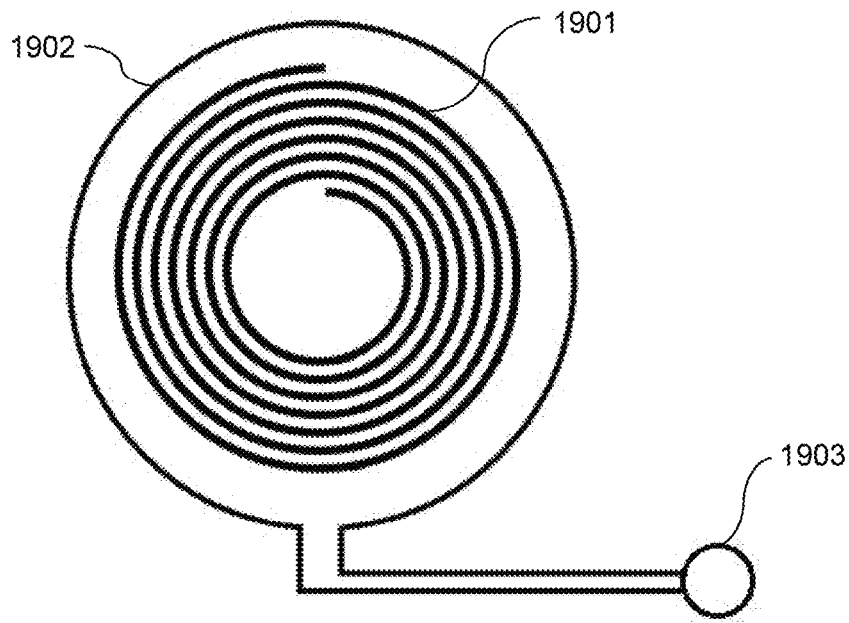
FIGS. 19A and 19B illustrate an energy delivery element used as a power supply for at least one electric component.
Figure 19B:
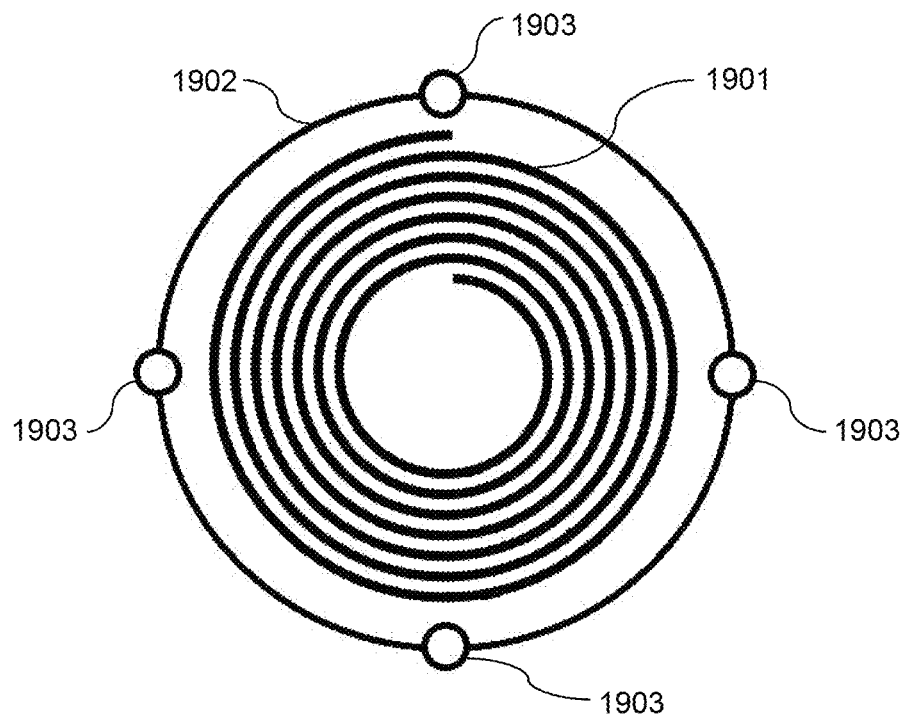

The energy delivery element may be used as an energy source for another part and/or electric member of the treatment device. The energy delivery element may be used as a part of transformer or antenna. In an exemplary embodiment illustrated in FIG. 19A the energy delivery element 1901 may be surrounded by a loop of conductor 1902 for inducing a voltage for proving power for the other electric member 1903. The loop may induce the voltage in order of tens Volts, e.g. 50 V. The induced voltage may be used for powering of electric member, e.g. a cooling device such as fan, blower or pump used for moving a cooling media, or Peltier cooler; or any electric member providing an additional treatment such as LED. FIG. 19B illustrates an exemplary embodiment of using induced voltage for powering a plurality of light sources providing optical treatment. The energy delivery element 1901 may be encircled by a loop of conductor 1902 for inducing a voltage to provide energy for the plurality of LED 1903 providing optical treatment for the patient. Alternatively at least one LED may be used for generating a light from visible spectra to be used for targeting the treatment. The power loss of the coil may be up to ones of Watts, more preferably up to 5 W, most preferably around 1 W.

Figure 20:
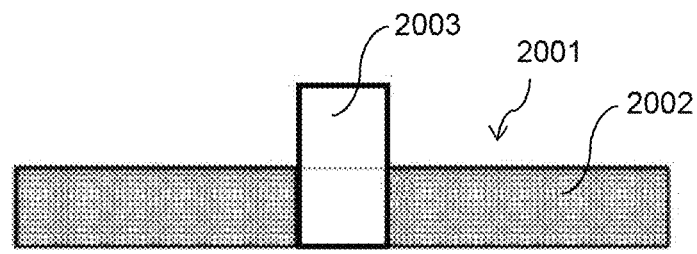
FIG. 20 illustrates an energy delivery element including a magnetic core.

FIG. 20 illustrates a cross section of an exemplary embodiment of energy delivery element 2001, particularly a flat coil comprising a plurality of insulated wires 2002. The coil may be wound around a magnetic core 2003 which may be protruded out from the coil up to several centimeters, more preferably in the range of 0.1 to 10 cm, even more preferably in the range of 0.5 to 7 cm, most preferably in the range of 1 to 5 cm. In an alternative embodiment the magnetic core may be around the coil. The magnetic field may be profiled, saturated and/or delivered to closer proximity of the patient by the protruding magnetic core.

In an exemplary embodiment the treatment device may include one energy delivery element. The energy delivery element, e.g. a flat coil, may be used for providing magnetic treatment and RF treatment. The energy delivery element may be provided by high-frequency and by low-frequency signal. The RF treatment may be unipolar. The high-frequency electromagnetic field may be radiated to the target biological structure. The applicator may be moveable to increase the homogeneity of the treatment. The scanning movement may be preferably used. Alternatively the movement of the applicator may follow a predetermined pattern corresponding to a treated body part. The movement of the applicator may be manual and/or automatically provided by a manipulating device, e.g. robotic arm or scanning mechanism.

The radiofrequency treatment may be applied by the energy delivery element to the target biological structure in three modes. One mode may be simultaneous application of RF treatment and magnetic treatment. Another mode may be separate RF treatment and magnetic treatment, RF and/or magnetic treatment may be applied in various sequences or it may alternate. Still another mode may be application of RF and magnetic treatment with some overlay. In an exemplary application the RF treatment may be applied prior a magnetic treatment. In another exemplary application the RF treatment may be applied after magnetic treatment.

In an alternative embodiment the treatment device may include a reference electrode to provide a monopolar application of RF treatment by the energy delivery element.

Figure 21A:
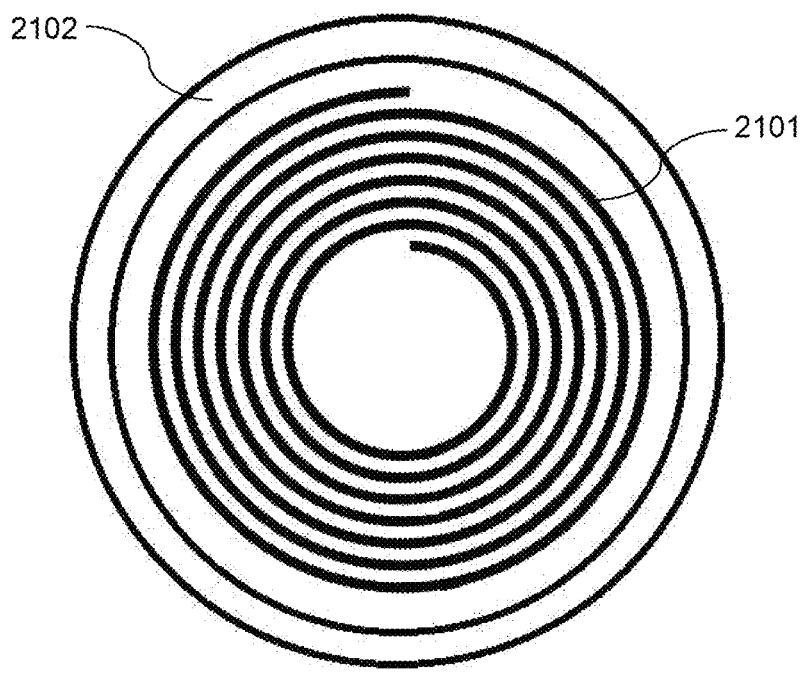
FIGS. 21A and 21B illustrate an energy delivery element encircled by at least one electrode.
Figure 21B:
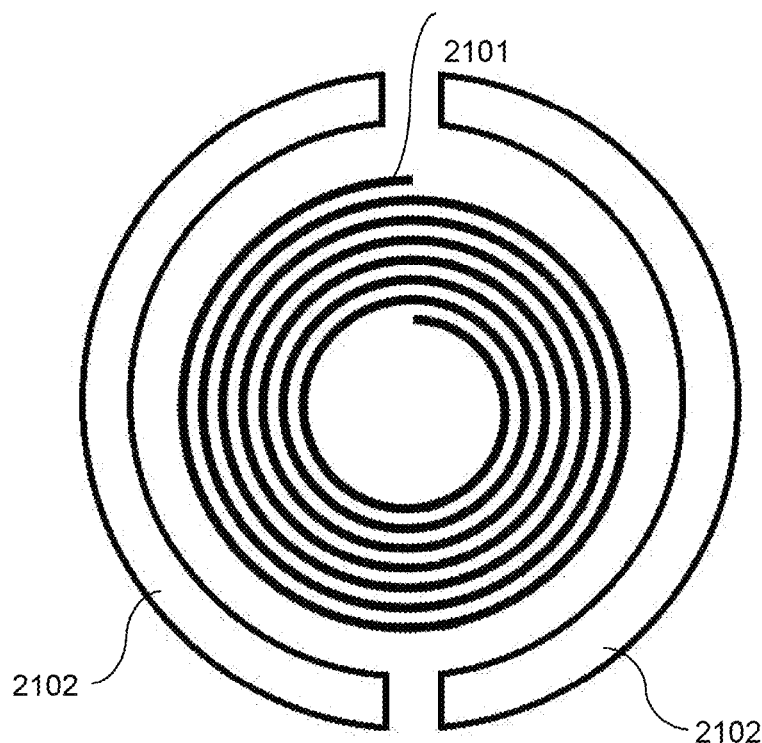

FIG. 21A illustrates an exemplary embodiment of the magnetic field generating device 2101 powered by LF generator which is encircled by an electrode 2102 for providing RF treatment. In an alternative embodiment illustrated in FIG. 21B the magnetic field generating device 2101 powered by LF generator may be encircled by a plurality of electrodes 2102 powered by HF generator to provide RF treatment. In this particular exemplary embodiment two electrodes are semicircular shaped. Still another exemplary embodiment including the magnetic field generating device powered by LF generator encircled by a plurality of round-shaped electrodes powered by at least one HF generator to provide RF treatment. Alternatively the plurality of electrodes may be powered by a plurality of HF generators. These exemplary embodiments may exclude combiner. The separation of the HF and LF signals may be provided by mechanical layout of the energy delivery elements, e.g. magnetic field generating device or electrode.

The treatment may be provided by contactless application. Alternatively the treatment may be administered in contact way or by indirect contact way by using a bolus/spacing object. The spacing object may be preferably transparent for high power magnetic field and it may include inner space filled with at least one substance. The spacing object may provide optimal distribution RF field used for treatment it may provide a cooling of the skin which it contacts.

Figure 22A:
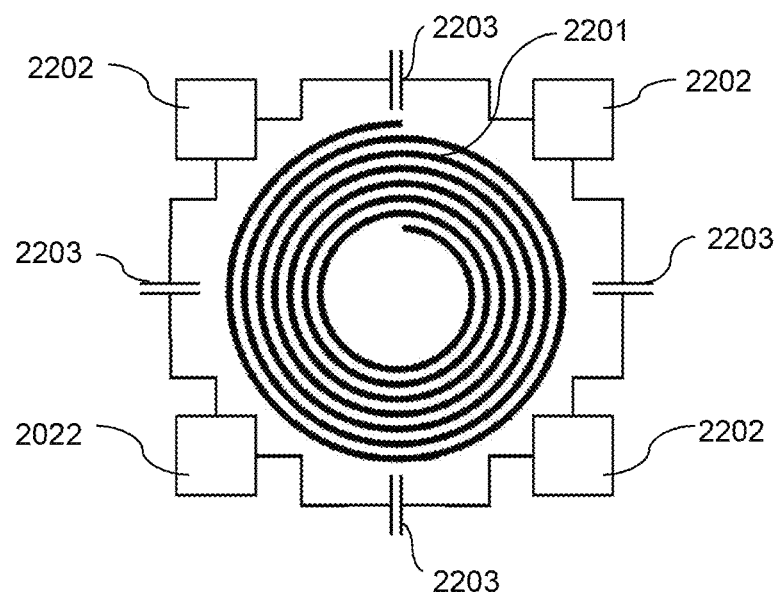
FIGS. 22A and 22B illustrate exemplary embodiments connected by coil or capacitor.

The at least two electrodes may be connected by at least one capacitor which may provide a capacitive connection between the electrodes. FIG. 22A illustrates an exemplary embodiment of the magnetic field generating device 2201 powered by LF generator. The magnetic field generating device 2201 may be encircled by a plurality of electrodes 2202 which are powered by one HF generator. The electrodes may be of various shapes, e.g. angular such as square or rectangle; or round such as circular or oval. The plurality of electrodes 2202 may be connected by a plurality of capacitors 2203. The at least one capacitor provides a capacitive coupling between electrodes hence the plurality of electrodes may provide a treatment as a plurality of unipolar electrodes. On the other hand the electrodes may not be influenced by a magnetic field generated by magnetic field generating device.

Figure 22B:
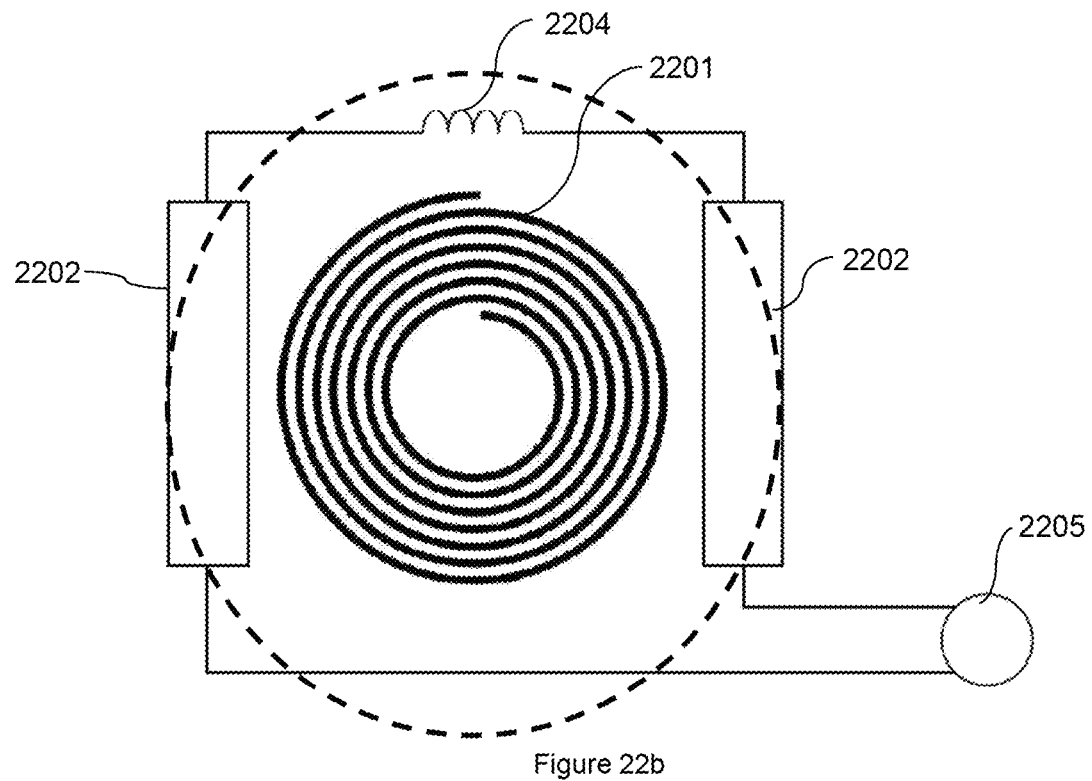

The at least two electrodes may be connected by at least one inductive member, e.g. a coil. FIG. 22B illustrates an exemplary embodiment of the magnetic field generating device 2201 powered by LF generator which is encircled by two electrodes 2202 which are powered by one HF generator. The electrodes 2202 may be connected by a coil 2204 which may provide separation of the electrodes 2202 powered by HF generator hence the RF treatment may be bipolar. On the other hand the coil 2204 provides connection of the electrodes 2202 for magnetic field generated by magnetic field generating device 2201 hence the coil and the electrodes 2202 may cause the same effect as a conductor loop (dotted line) around the magnetic field generating device 2201. The voltage induced in the loop may be use for powering of electric member 2205 as mentioned above.

Figure 23A:
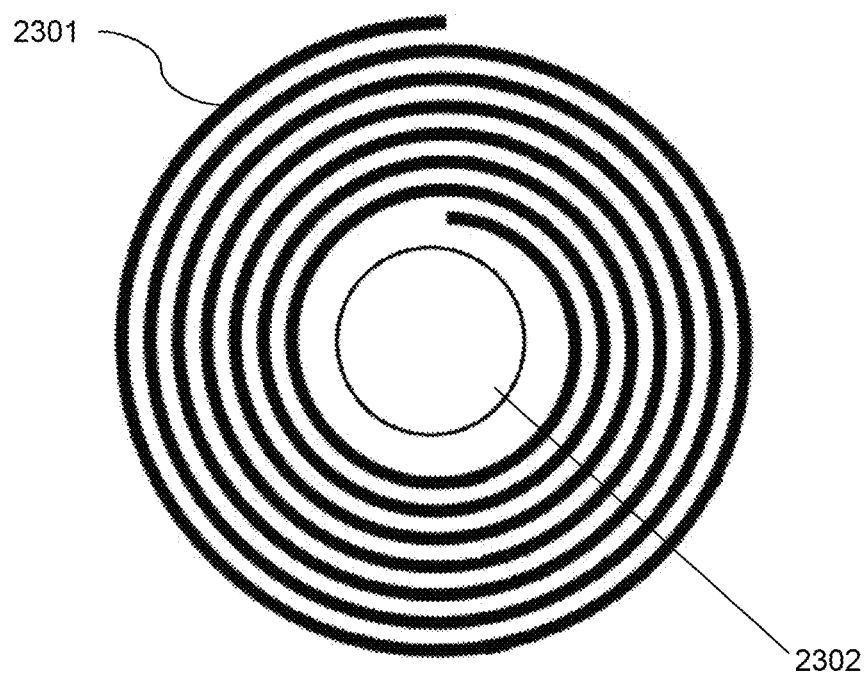
FIGS. 23A and 23B illustrate at least one electrode encircled by an energy delivery element.
Figure 23B:
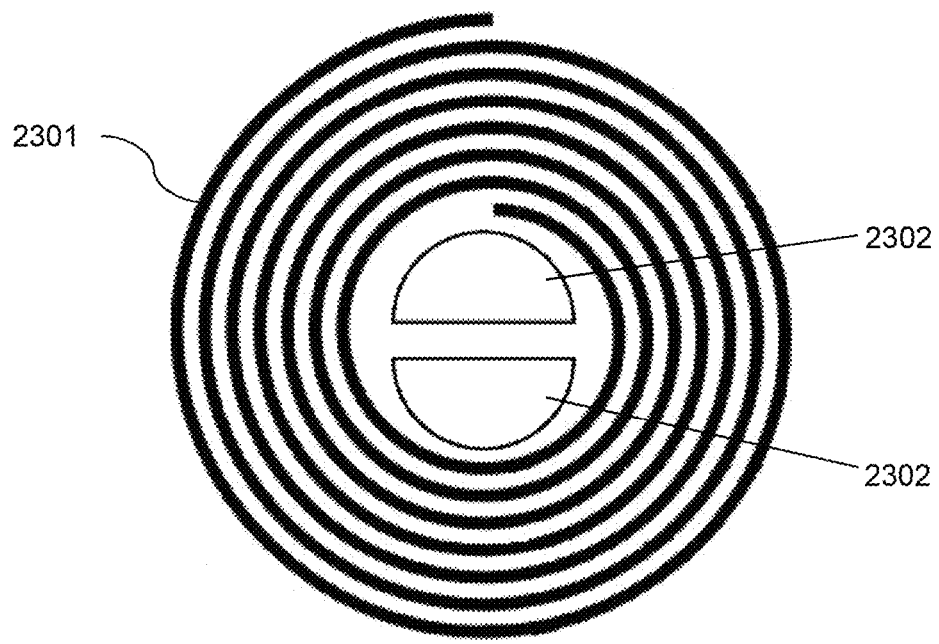

FIG. 23A illustrates an exemplary embodiment of the energy delivery element 2301 powered by LF generator. The energy delivery element 2301 may be wound around an electrode 2302 providing RF treatment. Preferably the energy delivery element may be wound around a plurality of electrodes. FIG. 23B illustrates an exemplary embodiment of the treatment device including two electrodes 2302 in the energy delivery element 2301 which is powered by LF generator. Alternatively at least two electrodes within the energy delivery element may be connected by an energy storage device. The energy storage device may be designed to be of low resistance value when high-frequency signal (frequency of RF signal) is provided and/or to be of high resistance when the low-frequency signal (frequency of magnetic signal) is provided. In the preferred embodiment the energy storage device may conduct as short-circuit when powered by high-frequency signal and as infinite resistor when power by low-frequency signal.

The treatment device may include a mathematic method including at least one of calculation and/or statistic method for monitoring correctness of the treatment and/or for monitoring the heat produced by the treatment device. The mathematic method may monitor at least one characteristic quantity of at least one operation parameter. The mathematic method may be used for determining heat generated by the energy delivery element. The generated heat may be used for additional heating biological structures in proximity. Alternatively, the energy delivery element may be less cooled to reach higher temperature for improved heating of the patient.

The applicator may be statically positioned to a predefined position to treat the target biological structure. Alternatively the applicator may be moveable during the treatment to treat larger area of the patient compared to treatment in static position. The RF energy transfer may be optimized prior to the treatment if the applicator is statically positioned and/or the treatment is provided in contact way. However, the continual optimizing of the energy transfer may be preferred for providing optimal and/or highly effective treatment to shorten the treatment duration, to improve the treatment effect and/or to achieve the desired results in shorter time period. Moreover the continual energy transfer optimizing may eliminate incorrect energy transfer caused by patient movement, e.g. caused by breath, and/or change of physiological conditions, e.g. caused by sweat, improved blood perfusion or increased temperature.

The treatment device may include a plurality of energy delivery elements, e.g. two, three, four or more. However, the even number of energy delivery elements may be used in the preferred embodiment. The at least two magnetic field device may provide a bipolar RF treatment, alternatively monopolar treatment may be provided as well. The bipolar treatment may provide homogenized temperature distribution in the target biological structure.

Figure 24:
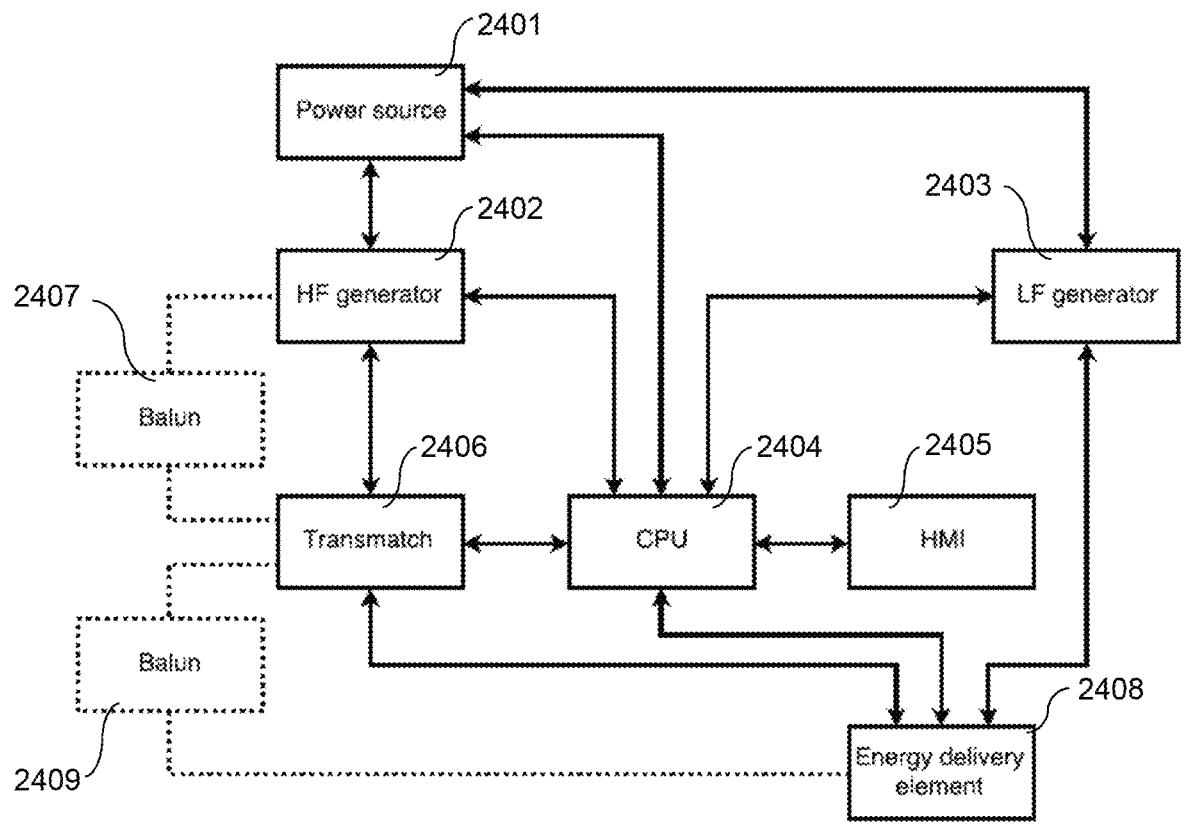
FIG. 24 illustrates a block diagram of treatment device including transmatch.

FIG. 24 illustrates the treatment device which may include a connection to a power supply, a power source 2401, high-frequency generator 2402, low-frequency generator 2403, control unit 2404, human machine interface 2405, transmatch 2406, balun 2407 and at least one energy delivery element 2408. The components illustrated by dotted line may be optional and may be excluded from the treatment device. According to alternative embodiment only one generator providing low and high frequency may be used. The arrows illustrate the direction of possible communication.

Transmatch may optimize the energy transfer to the patient. A function of balun is to transform unbalanced signal to balanced signal.

The power supply may provide energy for the treatment device via the power source 2401. The power supply may be external, e.g. a plug, or it may be integrally included within the treatment device, e.g. a battery. The power source 2401 may provide energy to electric components of the treatment device, particularly to both generators 2402, 2403 or to control unit 2404. The power source 2401 may communicate with control unit 2404 which may provide information about power necessary for the treatment. The power source 2401 may adjust the power for generators 2402, 2403 following the information from control unit 2404 or alternatively based on direct information from generator 2402 or generator 2403.

The control unit 2404 may communicate with LF generator 2403. LF generator 2403 may provide LF signal to at least one energy delivery element 2408 to generate magnetic treatment. The LF generator 2403 may provide information referred to treatment process to the control unit 2404, e.g. energy loss from one impulse. In an exemplary embodiment the control unit 2404 may send instruction to power source 2401 to provide the LF generator 2403 by the energy amount equaling the energy loss. Alternatively the control unit 2404 may control recharge of the LF generator.

The energy delivery element 2408 may include at least one sensor, e.g. a temperature sensor. The energy delivery element may provide information to control unit 2404, HF generator 2402 and/or to LF generator 2403.

The control unit 2404 may communicate with HF generator 2402 to provide instructions for HF generator 2402. HF generator 2402 may provide HF signal for at least one energy delivery element 2408 to generate RF treatment. The HF signal may be transferred via transmatch 2406. The HF generator 2402 may provide information referred to treatment process to the control unit 2404, e.g. temperature of the at least one energy delivery element 2408 and/or information provided by transmatch 2406. In exemplary embodiment RF energy transfer may be optimized prior to the treatment. However, the continual optimizing of the energy transfer may be preferred for providing optimal and/or highly effective treatment to shorten the treatment duration, to improve the treatment effect and/or to achieve the desired results in shorter time period. Moreover the continual energy transfer optimizing may eliminate incorrect energy transfer caused by patient movement, e.g. caused by breath, and/or change of physiological conditions, e.g. caused by sweat, improved blood perfusion or increased temperature. In an exemplary embodiment the HF generator 2402 may include an internal power source for adjusting energy for at least one energy delivery element 2408.

Alternatively, more than one energy delivery element 2408 may be used. When using two or more energy delivery elements, the at least one energy delivery element may deliver magnetic field, the at least one energy delivery element may deliver electromagnetic field (e.g. radiofrequency field); in still another embodiment each energy delivery element may provide both magnetic field and electromagnetic field (e.g. radiofrequency field) for magnetic and electromagnetic treatment.

The control unit 2404 may be in communication with human machine interface 2405. The human machine interface 2405 may include outputting interface for providing information for the operator and/or the patient. The outputting interface may include audio output, e.g. a speaker; visual output, e.g. a display or any combination. The outputting interface may provide a notification for the operator and/or the patient in a human perceptible form such as beep, flashing light, color change or mechanical signal.

The human machine interface 2405 may include at least one input element, e.g. touch member such as touchscreen, keyboard, control member for adjusting the treatment, for providing the information from operator. The operator may adjust e.g. a treatment protocol or may adjust treatment parameters following the patient's need.

The control unit 2404 may be in communication with transmatch 2406. The control unit 2404 may control the function of transmatch 2406. Transmatch 2406 may be provided by instructions from control unit 2404 to optimize the energy transfer to the patient. The transmatch 2406 may include an energy source to be able to adjust the energy provided to the at least one energy delivery element 2408.

In an alternative embodiment the transmatch 2406 may be excluded from the treatment device. The embodiment may be used for contact treatment or alternatively for contactless treatment. The energy transfer may be optimized prior the treatment.

In an alternative exemplary embodiment the transmatch may be the energy delivery element. The energy transfer may be optimized by adjusting e.g. transformation ratio.

The treatment device may include balun in various locations. In one exemplary embodiment unbalanced signal from HF generator 2402 may be transformed in the balun 2407 to balanced signal which further continues to transmatch 2406 and further to at least one energy delivery element 2408.

In an alternative exemplary embodiment the balun 2409 may be located in the transmatch 2406 or between transmatch 2406 and energy delivery element.

In alternative embodiment the balun may be excluded.

Figure 25A:
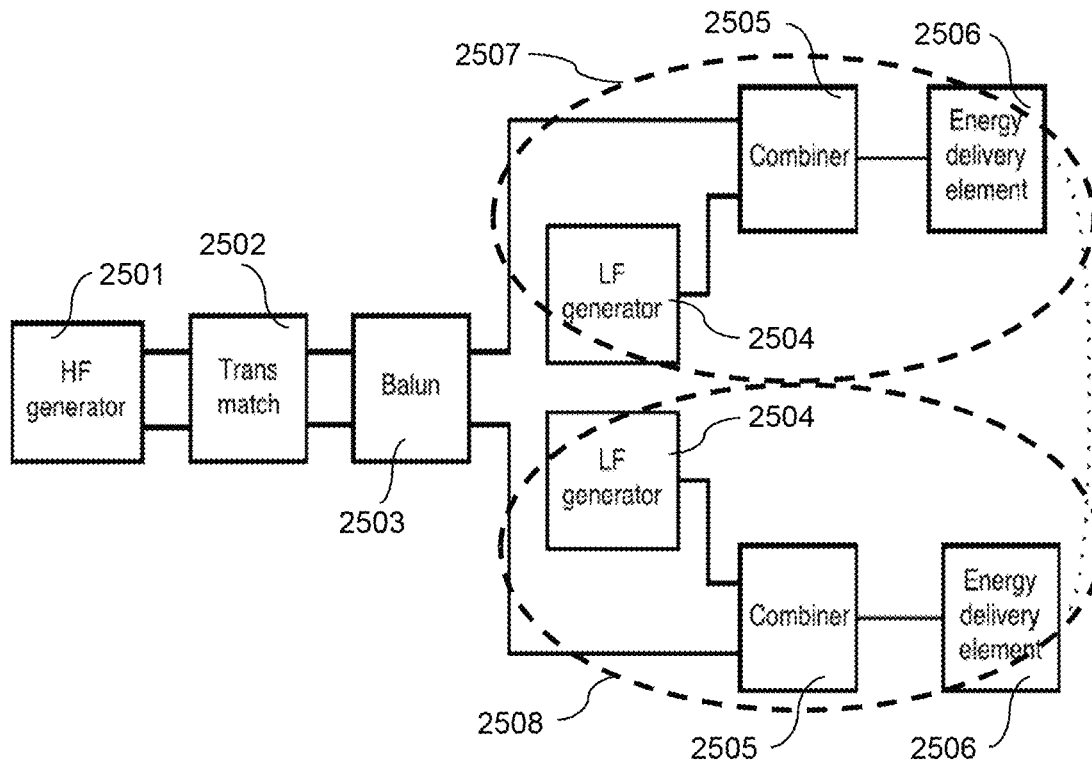
FIGS. 25A and 25B illustrate a block diagram of exemplary embodiments including a plurality of energy delivery elements.
Figure 25B:
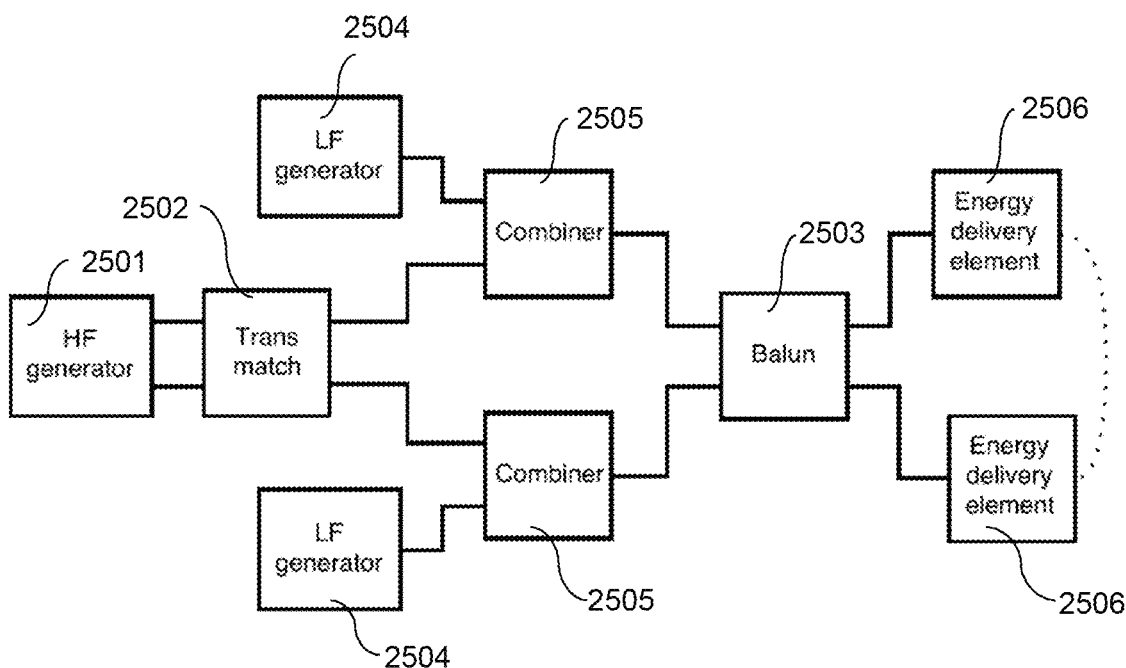

FIG. 25A illustrates an exemplary embodiment of the treatment device using a plurality of energy delivery elements. In this particular exemplary embodiment, two energy delivery elements may provide both magnetic field and electromagnetic field (e.g. radiofrequency field) for magnetic and electromagnetic treatment. The treatment device includes high frequency generator 2501, transmatch 2502, balun 2503, low frequency generator 2504, combiner 2505, at least two energy delivery elements 2506.

The HF generator 2501 may provide HF signal to transmatch 2502 which may adjust the HF signal to optimize the energy transfer between the treatment device and the patient. The optimized HF signal may be directed to balun 2503 and to combiner 2505. In an alternative embodiment the balun 2503 may be incorporated in transmatch 2502 or may be between HF generator 2501 and transmatch 2502.

The at least one LF generator 2504 may provide LF signal to at least one combiner 2505. The combiner 2505 may provide both signals, from HF generator 2501 and from LF generator 2504, to energy delivery element 2506. The energy delivery element 2506 may provide energy to treat the target biological structure. In the particular embodiment the energy transfer (illustrated by dotted line) is defined by position of the energy delivery elements 2506. The energy transfer may be capacitive and/or inductive.

In the exemplary embodiment illustrated in FIG. 25A the treatment device includes two loops 2507, 2508 each including HF signal, LF signal, energy delivery element. In an alternative embodiment the treatment device may include one common LF generator for both loops 2507, 2508. According to alternative embodiment only one generator providing low and high frequency may be used.

The HF generator 2501 may provide HF signal to transmatch 2502 which may adjust the HF signal to optimize the energy transfer between the treatment device and the patient. The optimized HF signal may be directed to combiner 2505. LF generator 2504 may provide LF signal to combiner 2505. The combiner 2505 may provide both signals, from HF generator 2501 and from LF generator 2504, via balun 2503 to energy delivery element 2506. The energy delivery element 2506 may provide energy to treat the target biological structure. In the particular embodiment the energy transfer (illustrated by dotted line) is defined by position of the energy delivery elements 2506. The energy transfer may be capacitive and/or inductive.

In an alternative embodiment the exemplary treatment device may include one LF generator. According to alternative embodiment only one generator providing low and high frequency may be used.

Alternatively, the transmatch may be a incorporated in balun. The energy transfer may be optimized by e.g. adjusting transformation ratio.

In still another exemplary embodiment with respect to 25A and 25B the combiners may be coupled. The coupling may be capacitive and/or inductive. Alternatively one combiner may be used. In another alternative embodiment the combiner may be excluded. The separation of the signals may be provided by mechanical layout of the energy delivery elements as described above.

The plurality of energy delivery elements may be positioned independently to each other to provide a treatment for the patient following the patient's needs. The position of the energy delivery element may be placed by the operator. The plurality of energy delivery elements may be in a plurality of applicators, e.g. each applicator includes at least one energy delivery element.

Figure 26A:
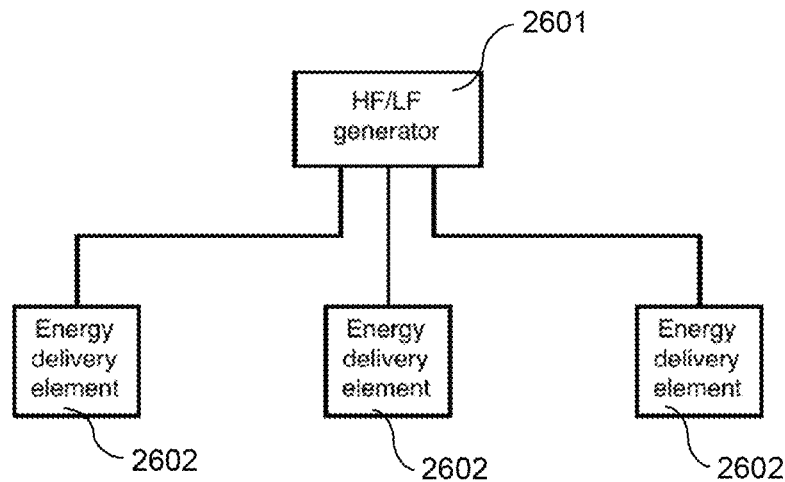
FIGS. 26A and 26B illustrate exemplary embodiments including a plurality of energy delivery elements with phase shift.
Figure 26B:
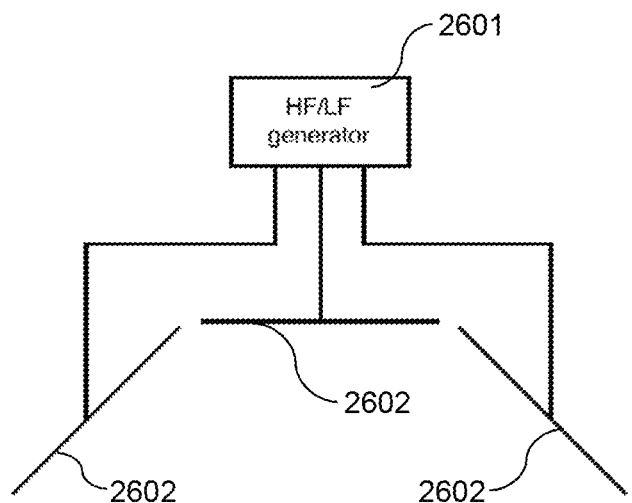

Alternatively the plurality of energy delivery elements may be positioned dependent to each other, preferably in a predefined pattern. The position of the plurality of the energy delivering elements may provide a treatment characterized by a phase shift. FIG. 26A illustrates an exemplary embodiment of the treatment with phase shift. The treatment device includes HF/LF generator 2601 for providing a signal for a plurality of energy delivery elements 2602. The signal for each energy delivery element may be phase shifted with respect to each other to generate a specific treatment profile which may be adjusted following the patient's needs. FIG. 26B illustrates an exemplary application. The HF/LF generator 2601 provides the signal for three energy delivery elements 2602 which may be preferably flat coils. The energy delivery elements are oriented with respect to each other. The HF signal may be provided to the energy delivery elements phase shifted to create a specific profile of the treatment. The phase shift may be e.g. 60°. The phase shift may be adjusted by the operator and/or by the patient following the patient's needs. In another alternative embodiment the phase shift may be dependent on the number of energy delivery elements.

The treatment device may include a plurality of applicators. Each applicator may include at least one energy delivery element. The applicator may be moveable during the treatment, the energy delivery element may be movable within the at least one applicator as well.

Alternatively the plurality of energy delivery elements may be positioned within one applicator having form of mechanical holder. The shape of the applicator having form of mechanical holder may be adjustable, e.g. the applicator may include at least one moveable part. In a preferred embodiment the applicator having form of mechanical holder may provide spatial arrangement of the energy delivery elements in one axis, two axes or three axes and/or provide tilting and/or rotation. The applicator having form of mechanical holder may provide fixation of the at least one energy delivery element in one position. The moveable parts may be connected by sliding mechanism and/or by a joint mechanism. The at least one part of the applicator may include at least one energy delivery element. The applicator may be adjustable following the treated area and/or biological structure.

The static position of the at least one applicator may be provided by a positioning member. The positioning member may be e.g. an arm or an adjustable flexible belt. The positioning member may include a buckle for adjusting the length of the belt. The applicator may be placed within predefined locations of the belt. Alternatively the applicator may be shaped to be moveable along the positioning member, e.g. the shape of the applicator may be preferably concave, e.g. V-shaped or U-shaped. The positioning member may be inserted itself into the concavity of the applicator. The position of the applicator may be adjusted by limited movement along the positioning member because the positioning member may be used as guiding member. However, the applicator may not be fixed to a particular static position. The position of the applicator may be dynamically adjusted during the treatment following the patient's needs. The position of the applicator may be adjusted manually by the operator, or automatically by the treatment device. In one exemplary embodiment a plurality of applicators may be used for treating larger body part, e.g. buttocks, abdomen or thigh.

Alternatively, the at least one energy delivery element, e.g. a coil, may be positioned below the at least one electrode. The energy delivery element may be positioned in between the electrode and the patient.

The at least one energy delivery element may influence at least one another energy delivery element while using the plurality of energy delivery elements. The correct treatment may be controlled via the mathematic method used for monitoring the at least one characteristic quantity of the operation parameter. The mutual positon of the energy delivery elements may be evaluated by the mathematic method as well. Hence the mathematic method may prevent providing the patient with incorrect treatment caused by incorrect position and/or orientation of at least two energy delivery elements. Furthermore the mathematic method may prevent the treatment device from affecting any conductive parts by the generated treatment, e.g. an additional heat may be generated.

The mathematic method may be further used for determining temperature and/or heat generated by at least one energy delivery element. Hence the mathematic method may be used for controlling a cooling of the energy delivery element, e.g. flow of the cooling media may be regulated. The heat generated by the energy delivery element may be further used for heating the patient.

The treatment system for creating the electromagnetic field can use bipolar electrodes, where electrodes alternates between active and return function and where the thermal gradient beneath electrodes is during treatment almost the same. The system may alternatively use monopolar electrodes, where the return electrode has sufficiently large area in contact with skin of patient and is typically positioned a relative larger distance from the active electrode. A unipolar electrode may also optionally be used.

Figure 27:
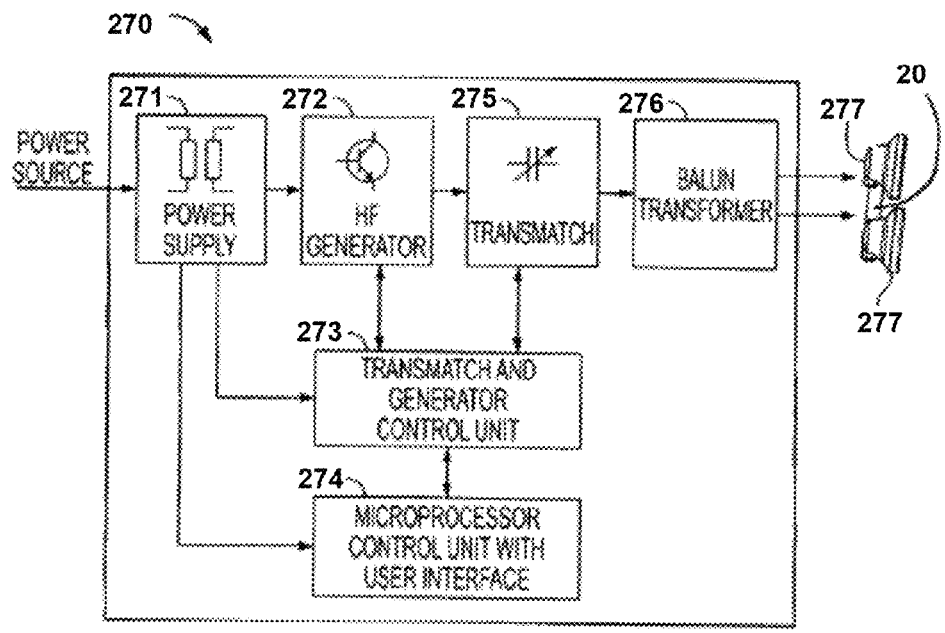
FIG. 27 is a schematic diagram of a system for controlled deep heating of sub dermal tissues.

Referring now to FIG. 27, a system 270 applies electromagnetic energy through a skin layer, such as the epidermis, and to the underlying dermal and/or sub dermal tissue, and underlying collagen tissue, causing acceleration of lipolysis and collagen remodeling. The system may include 6 blocks. The power supply 271 is connected to a power source. An HF generator (high frequency generator) 272 and a transmatch and generator control unit 273, and a microprocessor control unit with user interface 274, are connected to the power supply 271. The HF generator 272 may generate an electromagnetic field at 13.56 or 40.68 or 27.12 MHz, or 2.45 GHz or optionally at other frequencies as well. The 13.56, 27.12 and 40.68 MHz and 2.45 GHz frequencies avoid creating radio interference, as these frequencies are exclusively assigned as free or open frequencies.

The microprocessor control unit with user interface 274 provides communication between the transmatch and generator control unit 273 and user interface, which may be a touch screen on the device display.

The transmatch and generator control unit 273 receives information from the operator via the control unit and regulates the operation of the HF generator 272 and the transmatch 275. The transmatch transmits HF to a balun transformer 276, which converts unbalanced impedance to balanced impedance. This processed signal goes to two capacitive applicators 277, which may be positioned 0.5 cm or higher above the surface of the skin or applied on dielectric or insulating, non-conductive material which is in contact with the skin surface.

Figure 28:
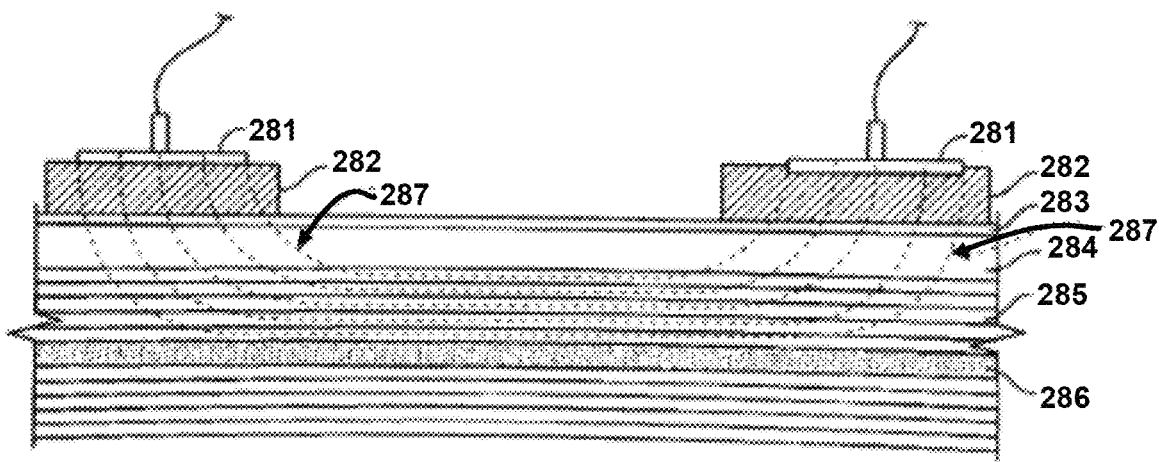
FIG. 28 is a schematic view of a trans-regional course of electromagnetic field.

FIG. 28 is a schematic representation of a heat distribution under the skin. One or more applicators 281 create an electromagnetic field. This electromagnetic field crosses through the skin 283, subcutaneous fat 284 and muscle 285 or the bone 286. Capacitive applicators 281 provide deep heating, which heats selectively only structures with low volume, of water. A spacer 282 such as a towel, gauze pad, foam pad, cloth pad and another porous or air permeable materials may be placed on the skin, with the applicator then placed on top of the spacer 282. The spacer may be made from three-dimensional material with high air permeability formed by two square fabrics with preferably low square densities connected by tough filaments. This automatically sets the separation distance between the applicator and the skin, and prevents the applicator from touching the skin. The spacer 282 may be made of various dielectric or electrically non-conductive materials. The spacer 282 is typically dry in use. Alternatively, a reusable or a disposable spacer may be attached to the applicator. For example, the spacer may comprise posts, a frame, or other structure on the applicator that contacts the skin, while keeping the active surface of the applicator spaced apart from the skin. As described and claimed here, such spacing elements are additional elements and not part of applicator. The methods may be performed with no part or surface of the actuator in contact with the skin.

Dielectric loss is created, as part of an AC electromagnetic field power is converted to heat in the dielectric. During this process, ions accelerate and collide, polar molecules rotate, non-polar molecules undergo distortion and these movements produce thermal energy. Skin and muscle are largely not affected by electromagnetic field 287 as they contain water and the blood, circulartion provides for cooling. Bone 286 gets little if any heating because the applicators 281 are positioned to create a field only on the upper structures. The lipid cells of the adipose tissue contain less water than any surrounding tissue and are therefore heated at higher level than any surrounding tissue.

An air gap or material with high air permeability may be placed between the skin and the applicator. This arrangement uses the human thermoregulatory system for cooling and avoids the need of artificial cooling of the skin. Additionally to enhance evaporation, airflow circulation between patient's skin and the applicator may be increased using a stream of chilled or room temperature air.

If more than one applicator is used, applicators may be positioned on opposite sides of the patient. A spacer may be positioned between one or more applicator and the skin of the patient. The electromagnetic waves may be transmitted in the range of 13.553-13.567 or 26.927-27.283 or 40.66-40.70 MHz or 2.4-2.5 GHz from the applicator into the subcutaneous tissue. The temperature of the skin surface may be increased to about 32-45° C.

One or more of the applicators may have a temperature sensor which measures and monitors the temperature of the treated tissue. Temperature can be analyzed by a microprocessor control unit. The temperature sensor may be a contactless sensor (e.g. infrared temperature sensor), contact sensor (e.g. resistance temperature detector) or invasive sensor (e.g. a thermocouple) for exact temperature measuring of deep or shallow tissue of human skin. The microprocessor controller may use algorithms to calculate the deep or shallow temperature based on the surface temperature of the skin. A feedback system may be used to measure and control temperatures on the skin surface or below the skin surface.

The feedback system may control the temperature to a predetermined level, for example by adjusting power, airflow circulation, phase shifting, supplemental magnetic field, and perhaps other parameters, or combinations of them.

The present device and method use a combination of non-invasive, preferably contactless, applications of different methods for enhancing human appearance. Particularly, the present invention uses a combined treatment by time-varying magnetic field and optical waves.

The treatment is defined by application of electromagnetic waves of wavelength in the range of 635 to 1100 nm, with maximal power flux density up to 100 W/cm². Alternatively, in the case of pulse light, the power flux density may be up to 100 W/cm² with light pulses lasting up to 300 ms, however, preferably in the range of 1 to 20 ms. Optical treatment may be used for inducing heat generation within the adipose cells over physiological temperature.

The treatment by optical waves may be combined with application of magnetic treatment inducing at least partial muscle contraction.

The presented methods enable aesthetic applications providing significant reduction of number and/or volume of adipose cells and cause circumferential reduction i.e. a reduction of the size of the treated body area. Furthermore, the treatment method induces at least partial muscle contraction to provide muscle toning, muscle shaping, body contouring, body shaping or skin tightening effect. Additionally, strong muscle contractions at high repetition rate may cause mechanical movement of all the layers in proximity of the contracted muscle. The method therefore may cause remodeling and/or neogenesis of the collagen and elastin fibers.

Optical treatment may selectively heat the target biological structure. Hence optical treatment may remove and/or remodel adipose tissue. Before/after, with some overlap or simultaneously the magnetic treatment of the target biological structure may induce at least partial muscle contraction within the target biological structure to remodel the adipose tissue by natural adipose tissue catabolism. Adipose tissue catabolism may be caused by apoptosis and/or necrosis of the adipocytes. The muscle contraction caused by induced eddy current is equivalent to a natural contraction. The adipose tissue may be reduced in natural way. Additionally, the muscle may be toned and/or shaped in a natural way. Therefore the effect resulting in body shaping and/or contouring may be significantly improved.

The present methods provide advanced approaches in aesthetic applications. Combined methods of treatment by optical treatment and treatment by magnetic field are used. The optical treatment may include treatment by optical waves. The magnet treatment may be provided by permanent magnets, electromagnetic devices generating a static magnetic field or preferably by magnetic devices generating time-varying magnetic field. In the preferred application the method may combine treatment by a pulsed magnetic field and optical treatment. The application is not limited by the recited combination so the combined method may include magnetic treatment and any treatment by electromagnetic field such as radiofrequency waves, e.g. microwaves, short waves or long waves.

The basic parts of the optical irradiation system include a hardware panel and an optical waves generating device or multiple optical waves generating devices. The optical waves generating device may be arranged in an array. The optical waves generating devices may be attached to each other or alternatively be individually mounted on dedicated supports. A scanning system may also be one of the options.

At least one optical wave generating device and a magnetic field generating device are provided. An optical treatment device may include at least one energy source and/or connection to the energy source, a hardware panel for controlling the optical treatment device and an optical waves generating device. Non limiting examples of optical waves generating device that may be used include light emitting diodes, lasers, laser diodes, different types of lamps and filtered lamps or combinations thereof. The treatment device may include at least one optical waves generating device, more preferably a plurality of optical waves generating devices of wavelength from ultraviolet, visible and infrared spectrum ranges. The wavelength may be in the range of 190 to 13000 nm, preferably in the range of 290 to 3000 nm, more preferably in the range of 400 to 1500 nm, even more preferably in the range of 550 to 1450 nm, particularly wavelengths about 915, 1064, 1208 and 1715 nm may be used.

The plurality of optical waves generating devices may generate optical waves simultaneously. The plurality of generated optical waves may interfere. Alternatively the plurality of optical waves generating devices may generate a plurality of independent optical waves at different times, preferably in sequences. The plurality of optical waves generating devices may be arranged in a predefined pattern within an applicator, e.g. in an array or a matrix.

The optical treatment applicator may be preferably external (e.g. hand-held). Alternatively, the optical treatment applicator may be an integral part of the optical treatment device (e.g. chair/bed implemented). Additionally, optical delivery elements, such as optical waveguides, light tubes or optical gel, may be used.

The magnetic treatment applicator may be an integral part of the treatment device, or it may be preferably external part of the treatment device (e.g. hand-held), alternatively the magnetic treatment applicator may be an integral part of the magnetic treatment device (e.g. chair/bed implemented).

According to one embodiment the magnetic treatment and optical treatment may be provided by at least two separate devices, i.e. at least one device for administering the magnetic treatment and at least one device for administering the optical treatment. The optical treatment may be applied to target biological structure prior, after or with some overlay with magnetic treatment. Alternatively optical treatment may be applied simultaneously with magnetic treatment. The time consequences of the treatment are described below.

Figure 29:
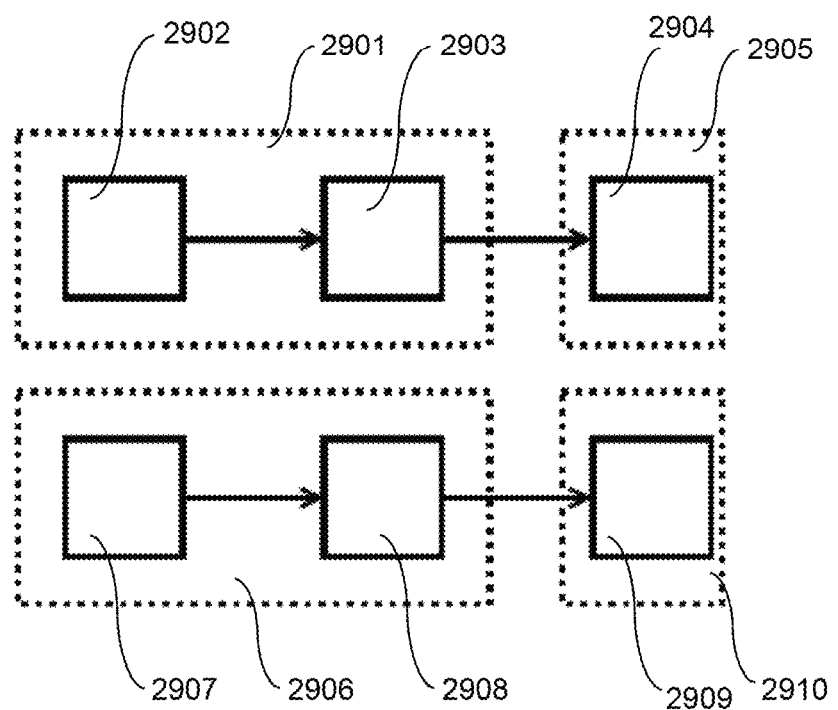
FIG. 29 illustrates a combined treatment administered by two separate devices.

FIG. 29 illustrates an exemplary embodiment providing combined treatment by magnetic field and optical treatment. The optical treatment is administered by optical treatment device 2901 (dotted line) including a connection to an energy source 2902 and a hardware panel 2903 for controlling the optical treatment. The hardware panel 2903 is connected with optical waves generating device 2904 within an optical treatment applicator 2905 (dotted line). The magnetic treatment is administered by magnetic treatment device 2906 (dotted line) including a connection to an energy source 2907 and a hardware panel 2908 for controlling the treatment by magnetic field. The hardware panel 2908 is connected with magnetic field generating device 2909 within a magnetic treatment applicator 2910 (dotted line).

In an alternative embodiment the at least one optical waves generating device may be in the treatment device. The optical waves may be delivered to the applicator and/or to the target biological structure by a waveguide.

Figure 30A:
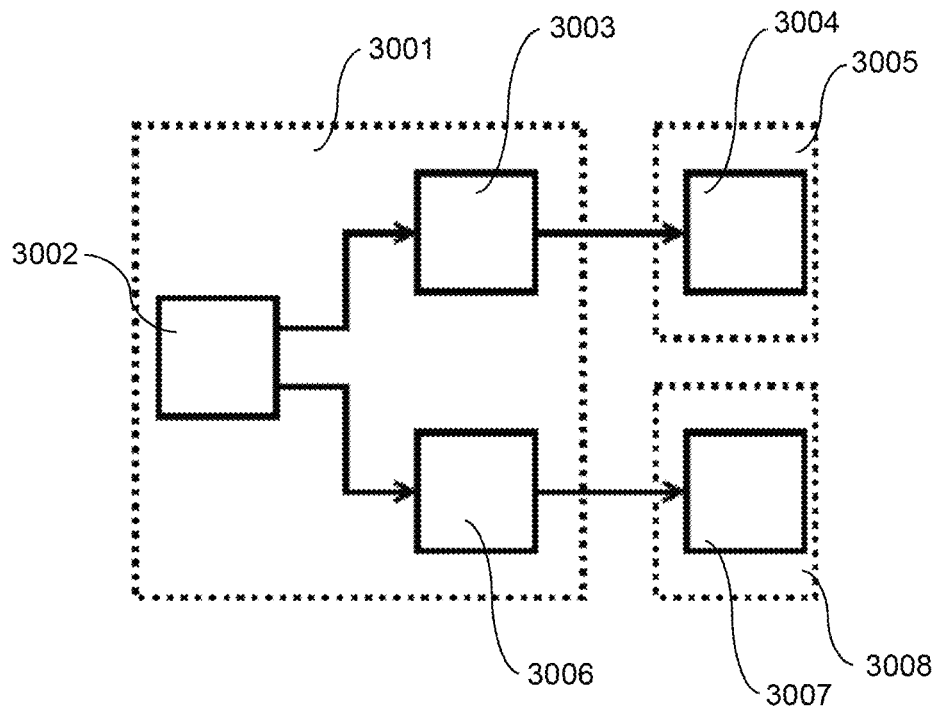
FIGS. 30A and 30B illustrate a combined treatment administered by one device including a plurality of applicators comprising magnetic field generating device or optical waves generating device.
Figure 30B:
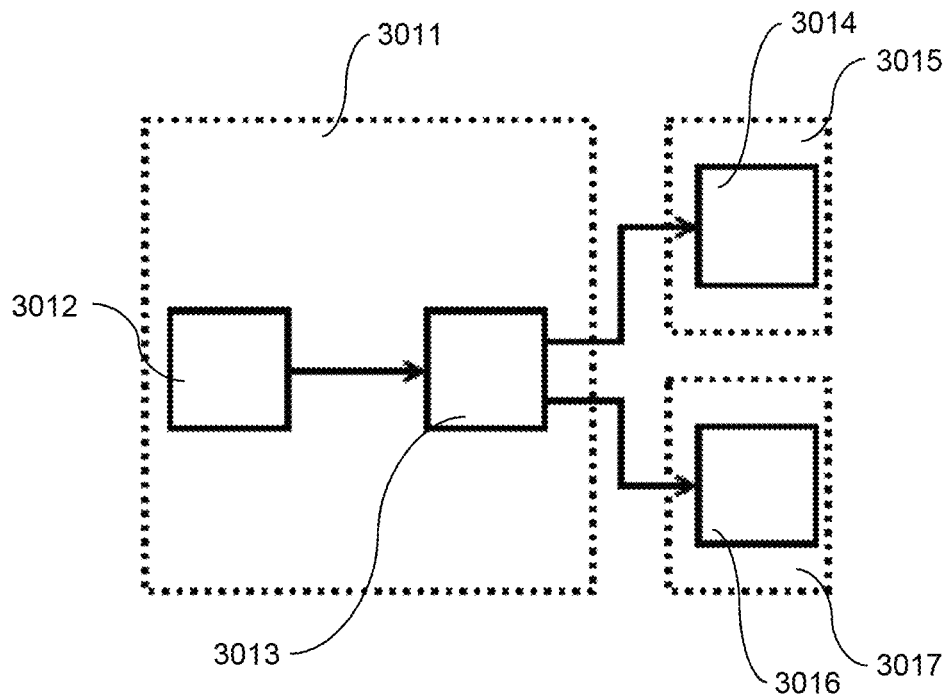
Figure 31A:
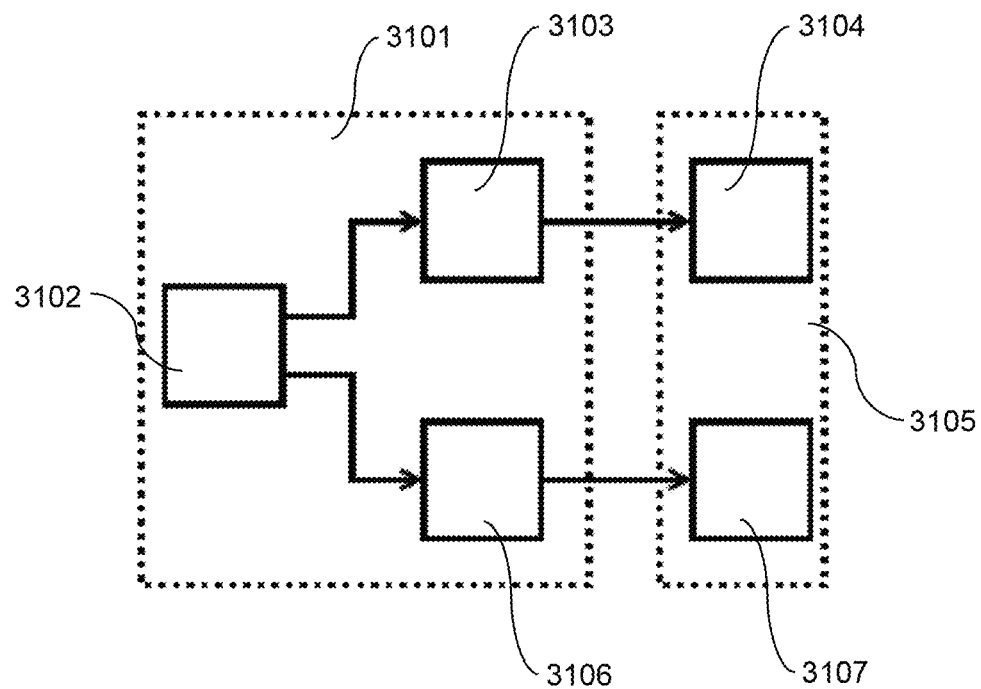
FIGS. 31A and 31B illustrate a combined treatment by one device including one applicator comprising at least one magnetic field generating device and at least one optical waves generating device.
Figure 31B:
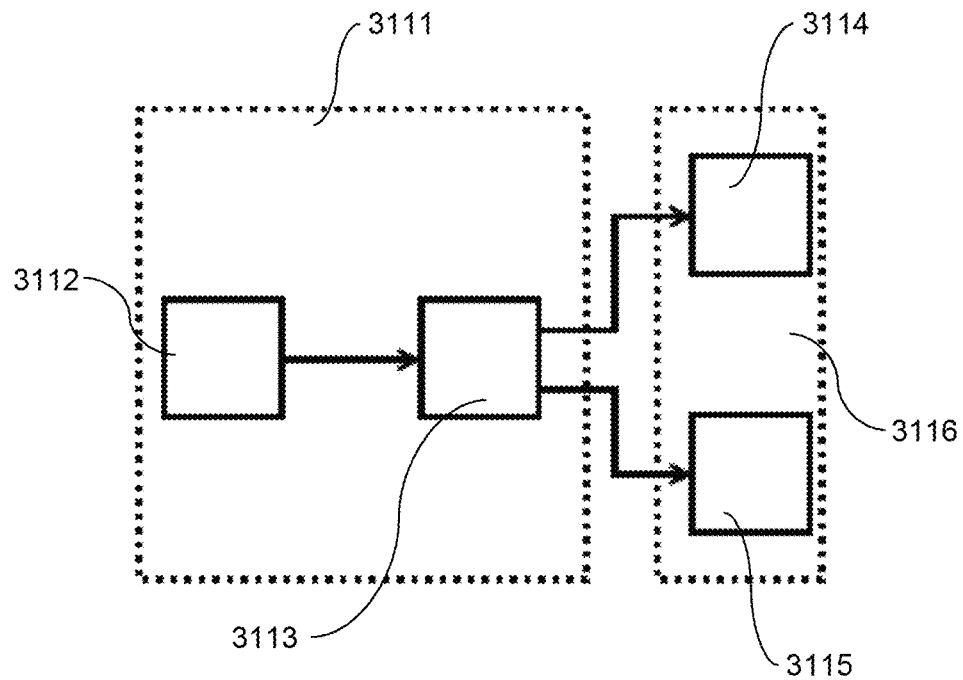

According to another embodiment the magnetic treatment and optical treatment may be provided by one device. The combined treatment provided by one device may be administered by at least one applicator. FIGS. 30A and 30B illustrate exemplary embodiments providing the combined treatment by two applicators providing different types of treatment, i.e. magnetic and optical treatment, to the target biological structure. FIGS. 31A and 31B illustrate exemplary embodiments providing the combined treatment by one applicator providing magnetic and/or optical treatment to the target biological structure.

FIG. 30A illustrates one exemplary embodiment of a combined treatment device providing magnetic and/or optical treatment by at least two applicators. The combined treatment device 3001 (dotted line) includes a connection to an energy source 3002 providing energy for a magnetic treatment and for an optical treatment. The optical treatment is controlled by a hardware panel for optical treatment 3003 which controls an optical waves generating device 3004 within an optical treatment applicator 3005 (dotted line). The magnetic treatment is controlled by a hardware panel for magnetic treatment 3006 which controls a magnetic field generating device 3007 within a magnetic treatment applicator 3008 (dotted line).

In an alternative embodiment the at least one optical waves generating device may be in the treatment device. The optical waves may be delivered to the applicator and/or to the target biological structure by a waveguide.

FIG. 30B illustrates another exemplary embodiment of a treatment device providing magnetic and/or optical treatment by at least two applicators. The combined treatment device 3011 (dotted line) includes a connection to an energy source 3012 providing energy for the magnetic treatment and/or for the optical treatment. Optical and/or magnetic treatments are controlled by a hardware panel 3013. The hardware panel 3013 controls an optical waves generating device 3014 within an optical treatment applicator 3015 (dotted line). Further the hardware panel 3013 controls a magnetic field generating device 3016 within a magnetic treatment applicator 3017 (dotted line).

In an alternative embodiment the optical waves generating devices may be in the treatment device. The optical waves may be delivered to the applicator and/or to the target biological structure by a waveguide.

FIG. 31A illustrates still another exemplary embodiment of a treatment device providing magnetic and/or optical treatment by at least one applicator. The combined treatment device 3101 (dotted line) includes a connection to an energy source 3102 providing energy for the magnetic treatment and/or for the optical treatment. The optical treatment is controlled by a hardware panel for optical treatment 3103 which controls an optical waves generating device 3104 within an applicator 3105 (dotted line). The magnetic treatment is controlled by a hardware panel for magnetic treatment 3106 which controls a magnetic field generating device 3107 within the applicator 3105 (dotted line). The applicator provides combined treatment.

In an alternative embodiment the optical waves generating devices may be in the treatment device. The optical waves may be delivered to the applicator and/or to the target biological structure by a waveguide.

FIG. 31B illustrates still another exemplary embodiment of a treatment device providing magnetic and/or optical treatment by at least one applicator. The combined treatment device 3111 (dotted line) includes a connection to an energy source 3112 providing energy for the magnetic treatment and/or for the optical treatment. Optical and/or magnetic treatment is controlled by a hardware panel 3113. The hardware panel 3113 controls an optical waves generating device 3114 and magnetic field generating device 3115 within an applicator 3116 (dotted line).

In an alternative embodiment the at least one optical waves generating device may be in the treatment device. The optical waves may be delivered to the applicator and/or to the target biological structure by a waveguide.

Figure 32A:
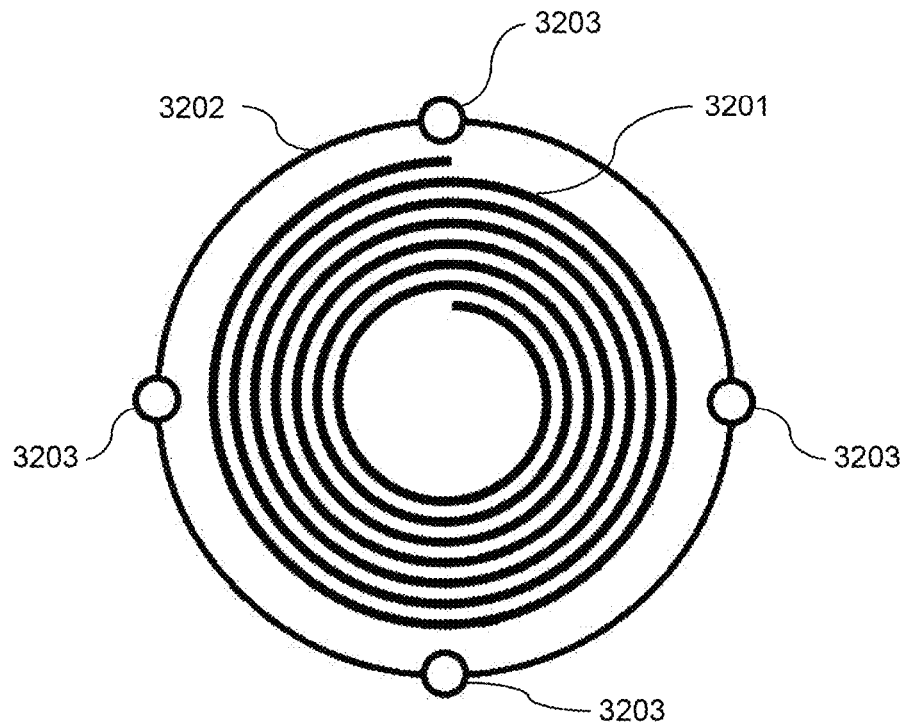
FIGS. 32A and 32B illustrate a combined treatment with optical waves generating device powered by magnetic field generated by magnetic field generating device.
Figure 32B:
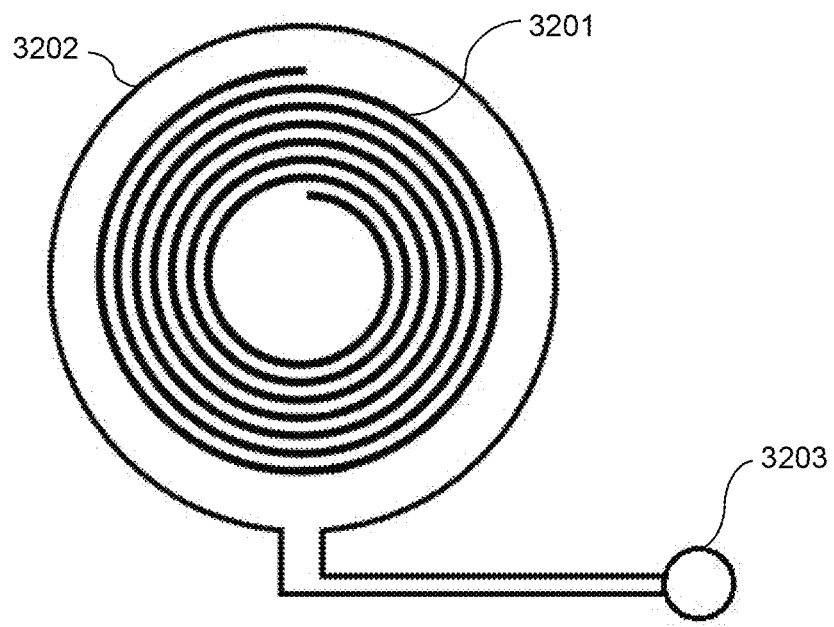

According to still another embodiment the magnetic field generating device may be used as an energy source for providing energy to another part of the treatment device, e.g. an optical waves generating device such as light-emitting diode (LED). FIGS. 32A and 32B illustrate exemplary embodiments of the magnetic field generating device which may be used as power supply. The magnetic field generating device 3201 may be surrounded by a conductor loop 3202. The time-varying magnetic field generated by magnetic field generating device 3201 induces eddy currents in the conductor loop 3202 within proximity of the magnetic field generating device 3201. The induced current in the conductor loop 3202 may be used for providing energy to another powered part of the treatment device, particularly in the applicator, or another treatment device, such as at least one optical waves generating device. FIG. 32A illustrates an exemplary embodiment of magnetic field generating device 3201 surrounded by a conductor loop 3202. The conductor loop 3202 may be connected to a plurality of optical waves generating devices 3203. FIG. 32B illustrates another exemplary embodiment of the magnetic field generating device 3201 surrounded by the conductor loop 3202. The conductor loop 3202 provides the energy to the optical waves generating device 3203. The optical waves generating device may be distanced from the conductor loop and may be external to the applicator including the magnetic field generating device 3201 and the conductor loop 3202.

Biocompatibility issues or hot spot generation may be overcome by transmitting electromagnetic energy into the target biological structure without physical contact with the patient. Contactless application of magnetic and/or optical treatments may provide sufficient passive cooling of the biological structure by circulating air.

In some indications, it may be advantageous to treat deeper adipose tissue by magnetic field simultaneously with the treatment of more superficial layers of the skin by optical waves.

An air gap or bolus material with high air permeability may be placed between the skin and the applicator. The material may be preferably transparent to the optical waves. This arrangement uses the human thermoregulatory system for cooling and avoids the need of artificial cooling of the skin. Optionally, the skin may be cooled via a stream of chilled or ambient temperature air. The human thermoregulatory system enables perspiration and other body fluids to evaporate and cool the surrounding skin. The application of electromagnetic waves is contactless. Therefore sweat accumulation and/or hot spot creation are avoided. Use of cooling fluids or gels is not necessary but may be optionally used. Cost of the treatment is reduced and patient comfort is improved. The applicator may be in direct or indirect contact with patient's skin. A bolus device may be used for providing indirect contact of the applicator with the target biological structure. A bolus may be filled with a material, preferably a fluid, influencing the propagation of the electromagnetic waves and/or homogenizing the temperature distribution of the patient's skin. Alternatively the bolus may deliver the electromagnetic waves to the target biological structure, e.g. a waveguide.

Cooling may be provided by positioning an air moving device proximate to the skin. The air moving device may be attached to or implemented into the applicator. Air moving device may be any kind of fan, ventilator or blower. The blower may include an air tube connected to air source for moving air through the air tube to the patient's skin. The air source may alternatively be cooled to provide cooled air. Alternatively, air suction may be also used as an active cooling method.

One or more applicators may move in the vicinity of the patient's body. The movement may be provided in various speed and/or acceleration. It may be moved in at least one direction, e.g. longitudinal, vertical, transversal or different axis and/or by rotational movement around any direction. Plurality of applicators may move in synchronized, randomized and/or independent manner. At least one applicator of the plurality of applicator may be static.

The homogeneity of treatment may be provided by the movement of the applicator. In one exemplary embodiment the applicator may move over and/or in different angle to the patient by rotational movement. In another exemplary embodiment the applicator may move in the vicinity of patient's skin. In still another exemplary embodiment the applicator may move to focus the treatment.

The movement of at least one applicator may provide a treatment pattern. The pattern may be, e.g. linear, wavy, circular, elliptical, zigzag, polygonal, oval, irregular and/or any combination thereof. In one exemplary application the at least one applicator may be positioned to the vicinity of thighs and the effect of treatment may be limited to these parts. In another exemplary application the at least one applicator may be positioned over the patient's abdomen to treat e.g. adipose cells.

The movement of the applicator may also provide a treatment to large body part, e.g. buttocks, abdomen or thigh.

The sensor may be connected with the hardware panel for controlling the optical treatment to adjust the power flux density applied to the biological structure to maintain the temperature of the target biological structure within treatment range. The temperature sensor also prevents the patient from any thermic damage.

Optical treatment may be used for remodeling, reducing the volume and/or number of adipose cells, body contouring or tightening skin, skin rejuvenation, wrinkles and/or stretch mark reduction, mole mark removal, tattoo removal, enhanced skin tightening, hair removal, treatment of vascular lesions, acne treatment, sweating reduction and other appearance improving and/or pain relief treatment without contacting the skin. The treatment may optionally be performed simultaneously or consecutively during the same session.

The commonly targeted skin chromophores are hemoglobin, melanin, carbon or tattoo ink. Alternatively water may absorb the optical waves. Each chromophore has unique absorption spectrum. The wavelength of the optical wave should match one of the absorption peaks of the targeted chromophore. The lasers or laser diodes work usually in pulse regime in these applications. The optical energy absorbed by the chromophore is converted to thermal energy thereby destroying the targeted cells. Selection of the best adapted wavelength, power and pulse duration allows achieving optimal effect on targeted biological structure with minimal effect on surrounding tissue.

The application of optical treatment may be improved by application of exogenous chromophores to the target biological structure. The exogenous chromophores may be applied in form of topical lotion, or may be delivered to the target biological structure by micro-invasive or invasive way such as injected.

According to the parameters of the optical waves used, different layers of the skin and different biological structures may be selectively treated. Various wavelengths, powers, pulse durations and repetition rates of electromagnetic radiation are applicable to provide the advantage of vast variability of penetration and absorption parameters. The operator may also adjust the optimum treatment time for each wavelength and the time sequences of treatments by different wavelengths, while some of them may overlap in time. In this way, a tailor-made solution for each patient and each indication is available. The treatment may be highly selective to reduce or avoid damage of the surrounding tissues.

Combinations of a plurality of optical waves generating devices allow performing the treatment of plurality of target biological structures at the same time and/or treating the same target tissue simultaneously by different means, which optimizes the doses of radiation applied. This diversification may also eliminate the risk of overheating, as the optical treatment with parameters leading to no or negligible thermic effect may be used. As a result, the risk of heat damage may be considerably reduced.

If the patient has more imperfections to be treated situated in the same body areas, it is also possible to treat them simultaneously by different types of electromagnetic waves. Each of the electromagnetic waves may be adjusted to optimum parameters for the target biological structure imperfection treatment. Thus the time of patient and of the operator is reduced, reducing the treatment cost.

The optical waves thermal effect may lead to temperature increase in the dermal and the sub dermal tissues also affects the triple-helix structure of collagen fibers contained in such tissues. This may result in remodeling and rejuvenation of collagen, increase of skin density and dermal thickening based on neocollagenesis. Skin tightening may also be achieved. In one aspect, the present methods selectively treat deep human tissue containing low volume of water, such as adipose tissue. Optical energy is provided to the skin by optical waves generating device. Remodeling and reducing the volume and/or number of adipocytes or skin tightening in the targeted areas may change the overall appearance of the body. Therefore it may be used for body contouring, body shaping and cellulite treatment.

Optical energy may be provided to the skin by at least one optical waves generating device in pulse or continuous mode. Optical energy is provided through the skin to the underlying dermal and/or subdermal tissue, without contacting the skin. The radiant energy may be converted inside the target tissue to heat. The radiant energy enables treating of the adipose tissue and/or collagen tissue, accelerating apoptosis and/or cell lysis (e.g. adipose cell), based on amount of energy transmitted to target biological structure. At the same time the triple helix structure of collagen fibers may result in remodeling and/or rejuvenation of collagen, increase of skin density and dermal thickening based on neocollagenesis. In an alternative embodiment the radiant energy enables treating of target tissue resulting e.g. in neocollagenesis without adipose tissue reduction. Target tissue may be remodeled and/or reduced and body contouring and/or skin tightening effect may occur.

Cooling may also be used to modify and to optimally adjust the depth of optical radiation penetration. Light penetration may be enhanced if cooling is used before phototherapy. The effects of heating in terms of light penetration are the opposite.

Optical treatment may treat the same or different skin layers as the magnetic treatment. As mentioned above, optical treatment may also be used for multiple rejuvenation and appearance enhancing applications. Another important indication is drug-free and addiction-free pain relief in many conditions.

Non-limiting examples of optical therapies that may be preferably used in combination with the treatment by magnetic field according to the present invention are: low level light therapy (LLLT), photodynamic therapy (PDT), high power laser therapy (HPLT) or intense pulsed light (IPL). However, the scope of the invention is not limited only to these particular optical irradiation methods. Other electromagnetic waves may be used, e.g. a radiofrequency treatment. The power flux density of the optical wave therapy may be in the range to $0.1\text{-}100 \text{ W/cm}^2$, more preferably in the range to $0.5\text{-}50 \text{ W/cm}^2$, most preferably $0.5\text{-}20 \text{ W/cm}^2$.

Low-level light therapy is one of the methods of non-invasive rejuvenation with no or a very small thermal effect. LLLT may be effective throughout the visible, infrared and near ultraviolet spectrum ranges. The term low level refers the fact that the levels of energy or power densities are low compared to other forms of light treatment such as by lasers, which are applicable for cutting, thermal coagulation or thermal damage, such as ablation. Treatment energies in LLLT are limited to $0.1\text{-}20$ or a few $\text{J/cm}^2$ and/or by a power of 1 mW to 500 mW per optical waves generating device. The depth of penetration of the low level light radiation depends on parameters of the optical waves generating device such as wavelength, operating mode, which may be pulse or continuous, the power output, the probe design and the treatment technique. The depth of penetration where the light still has therapeutic effects should match the depth of the desired zone to be treated. The penetration depth is lower than in HPTL, up to several tens of mm approximately. Due to the low levels of absorbed energy, the treated and surrounding biological structures are not heated and are not damaged. Although many wavelengths may be used, it is advantageous to use at least one beam in the visible spectrum so that the area of application on the patient's body may be easily determined by the operator.

LLLT uses either coherent optical waves generating devices such as lasers or laser diodes or non-coherent light sources including incandescent lamps, gas filled lamps, filtered lamps optimized for a particular wavelength, light-emitting diodes, etc. A combination of any types of optical waves generating devices may be also used, as well as a plurality of optical waves generating devices of the same type.

The photons emitted by the low level optical waves generating devices used in LLLT therapy may be absorbed by endogenous mitochondrial chromophores in skin. Consequently, many processes may be activated, e.g. electron transport, increased adenosine triphosphate (ATP) production, enhanced blood micro-circulation, collagen production increase, dermal matrix remodeling etc. LLLT may thus successfully treat a multitude of conditions that require stimulation of healing, acute/chronic pain relief or restoration of function. LLLT has beneficial effects on wrinkles, scars including acne scars, stimulating the scalp in hair treatment, healing of burns, skin tightening, anti-oedematous effects, regeneration after sport etc. Inflammatory skin diseases such as psoriasis or acne may be also treated by the proposed treatment. In pigmentation disorders such as vitiligo, LLLT may increase pigmentation by stimulating melanocyte proliferation.

LLLT may influence also reduction of number and/or volume of adipose cells. It is believed that the incident optical waves produce transient pores in adipose cells, allowing lipids to leak out into the interstitial space of adipose tissue. If the parameters are appropriate, the pores close upon cessation of the energy application and the cell membrane returns to contiguity. The adipose cells are not destroyed, but temporary opening within the cell's membrane induced by the optical waves may provide a pathway for lipid to exit the cell and in the end also the patient's body. It may leads to the reduction of number and/or volume of adipose cells. This adipose cell number and/or volume reduction may restore proper adipose cells function thereby acting as an anti-diabetes mechanism.

It is advantageous to combine LLLT and magnetic treatment for safe and efficient target biological structure treatment.

While in LLLT the light is absorbed by endogenous cellular chromophores, PDT may be based on introduction of exogenous photosensitizers into the cells which are then irradiated with wavelengths of visible or near infra-red light. Photosensitizer drugs may become activated by one or several types of optical waves. The optimal type of optical waves depends on the target biological structure and the absorption peak of the particular chromophore drug used. PDT optical waves generating devices include laser, intense pulsed light, light-emitting diodes or many visible lights including natural sunlight, etc.

Unlike LLLT HPLT has pronounced thermal effects on the skin. HPLT lasers having an output of 500 mW or greater may be used for this treatment, with energy densities greater than $10 \text{ J/cm}^2$. High power allows extremely high penetration of the optical waves, in order of ten centimeters or even more, ensuring that the right dose actually reaches the target biological structure localized deep in the tissue. Laser may be precisely adjusted due to its monochromacy and coherency. Therefore its propagation and targeted biological structure may be finely pre-defined. Research shows that biological structures treated by HPLT are stimulated to increase production of adenosine triphosphate (ATP). Similarly to LLLT, the biological responses to increased ATP production may include reduction of inflammation, reducing scars, increased cell metabolism, improved vascular activity, and accelerated healing. It may improve regeneration after sport. Significant improvements of many post-traumatic pathologies or osteoarthritis have been noted, as well as temporary relief of stiffness and muscle spasms. It is important to note that HPLT also may provide the patients with drug-free and addiction-free acute and/or chronic mediation of pain, by decreasing inflammation and/or swelling and by increasing the release of endorphins and enkephalins. Moreover, if a pulse regime is applied, the wavelength-specific photomechanical wave generated in the tissue may stimulate free nerve endings, thus blocking pain pathways in the nervous systems and bringing immediate pain relief.

High power lasers, laser diodes or intense pulse light sources (IPL) may be also used for treating pigmented targets in the skin by selective photothermolysis. Such high power lasers reaching sufficient power density to vaporize illuminated cells may be gas lasers such as $CO_2$ or excimer laser, solid-state lasers such as rubin, Nd:YAG or Er:YAG laser, semiconductor lasers, dye lasers such as Rhodamin 6G laser etc.

IPL may be used also for other skin treatments with therapeutic or rejuvenating effects, sharing some similarities with high power laser treatment. In both cases, optical waves are used to destroy the target. But unlike lasers that use a single wavelength of light which typically matches only one chromophore, and hence only one condition, IPL uses a broad spectrum of wavelengths. When used with filters, it may be adapted to treat various conditions. This may be achieved when the IPL operator selects the appropriate filter that matches a specific chromophore. Such filter may be represented by an optical material filtering e.g. 480 nm, 530 nm, 560 nm, 640 nm or 690 nm.

The optical energy flux density of the IPL treatment may be in the range of 1 and 50 $J/cm^2$, preferably in the range of 2 to 40 $J/cm^2$, more preferably at least 5 J/cm2, or up to 100 $J/cm^2$. The optical waves may be applied continually or in pulses. Pulse width is time duration that the target is exposed to the optical waves, it is measured in miliseconds. Pulse width is shorter than thermal relaxation time of the target, i.e. the pulse width is long enough to allow heating of the target but also short enough that the target is able to cool so that there is no heat buildup in surrounding skin and tissue. The pulse width may be in the range of 1 to 300 ms, preferably in the range of 5 to 50 ms, most preferably up to 30 ms.

Optical waves may penetrate the skin and increase the temperature of adipose cells and thermally damage the adipose cells. Hence the optical treatment may be used for reducing number and/or volume of adipose cells, remodeling treated body parts, or improving the skin appearance. The target biological structure, e.g. adipose cells, may be exposed to increased temperature. The temperature may be in the range of 37.5 to 60° C., more preferably in the range of 40 to 50° C., most preferably in the range of 42 to 47° C., or up 80° C. The damaged adipose cells may be removed by blood and/or lymphatic system to be metabolized. The heat generated in the target biological structure may induce a production of growth factors and/or fibroblasts which may improve collagen neogenesis and/or new vein formation to support the newly generated collagen formations.

Optimal wavelength should include low absorption within the skin, i.e. low absorption of water and/or melanin, and high absorption within the adipose cells. The optical waves may be in visible or in IR spectrum such as near-IR spectrum, e.g. in the range of 600 to 1500 nm in a plurality of applicable bands e.g. in the range of 635 to 680 nm, particularly 658 nm; or in the range of 780 to 980 nm, particularly 800 nm or 940 nm; or in the range of 1050 to 1100 nm, particularly 1060 nm due to relatively high penetration through the skin. Alternatively the optical waves may be in the range of 1300 to 1450 nm, particularly 1320 and 1440 nm may be applicable.

The optical treatment may last up to 120 minutes, preferably in the range of 1 to 60 minutes, more preferably in the range of 20 to 40 minutes. The treatment time may be dependent on BMI of the patient. The power flux density of the optical treatment may be up to 50 $W/cm^2$, preferably up to 25 $W/cm^2$, more preferably in the range of 1 to 15 $W/cm^2$, most preferably in the range of 2 to 10 $W/cm^2$ such as at least 5 W/cm2. In the preferred application power modulation may be used.

Optionally, active cooling may be included. However, in many cases, auto thermoregulation by sweating is sufficient. The active cooling may be administered in continual mode or in pulsed mode to maintain the skin temperature within physiologic temperature, i.e. around or below 37° C.

Alternatively, optical treatment by high power optical waves generating device may be used for treatment of incontinence or menorrhagia. One exemplary application may be inserting the optical wave generating device into the body cavity, e.g. a vagina, and treating the target biological structure by selectively heating. A suitable probe may be used for inserting the optical waves generating device. The target biological structure may be tightened due to increased temperature and/or improved collagenesis. Alternatively the optical wave generating device may be external to the body cavity and the optical waves may be delivered to target tissue by optical delivery element.

An exemplary application of application combined treatment by optical waves and magnetic treatment may be application to enhancing appearance of genitalia, e.g. external female genitalia such as labia minora, labia majora and/or clitoris. Furthermore collagenesis may be improved in vagina hence it may be smoother and/or firmer. Therefore the combined treatment may enhance physical pleasure during coitus.

Optimal wavelength of the optical waves may be in the range of 400 to 600 nm, particularly around 500 nm. Energy density may be up to 25 $J/cm^2$, more preferably up to 10 $J/cm^2$, most preferably in the range of 1 to 8 $J/cm^2$. Treatment may be administered in continual or preferably in pulsed mode.

Alternatively, the application of optical waves may provide disinfection effect. Such application may include application of UV light, e.g. UV-B and/or UV-C light. The wavelength of the optical waves may be in the range of 200 to 300 nm, most preferably in the range of 250 to 270 nm. The optical radiation may destroy the DNA of microorganisms such as bacteria, or virus. The nucleic acid in DNA may form a covalent bond (such as thymine dimer) preventing unzipping process during reproduction cycle. Hence the replication ability of the microorganism is disabled and the microorganism may die and the infection may be treated. The power density may be up to 300 mW/cm2, preferably up to 200 mW/cm2, or in the range of 1 to 50 mW/cm2, more preferably in the range of 5 to 25 mW/cm2 In one exemplary application the UV light may be in external flow-chamber to provide disinfected air to the treated area.

Similar application of optical waves may be used for cleaning the skin of the patient.

The treatment by a combination of magnetic field and optical waves significantly improves the treatment effect. Most preferably, the optical waves include wavelengths ranging from 405 to 1500 nm. At least one optical waves generating device and at least one magnetic field generating device may be used.

The methods described are more gentle and efficient in adipose cells treatment or skin tightening since the target biological structure is treated by magnetic and/or by electromagnetic field.

The application of magnetic and optical treatment may be used for treatment of pelvic floor area disorders, e.g. gynaecologic and/or urologic issues such as incontinence. The magnetic treatment may be targeted to the area of pelvic floor to treat pelvic floor muscles. The repetition rate of the magnetic pulses may be in the range of 1 to 150 Hz, preferably up to 100 Hz, more preferably in the range of 5 to 70 Hz, e.g. at least 30 Hz. The optical treatment may selectively raise a temperature in the vagina to provide tightening effect. Alternatively the optical treatment may provide biostimulation effect to promote neocollagenesis. The tightening effect may be also promoted by at least partial muscle contraction. Hence the treatment of incontinence may be provided by different energy types. The collagenesis may be improved by application of magnetic treatment improving local metabolism by improved blood flow and/or at least partial muscle contraction.

Another application of magnetic and optical treatment may be used for treating a pain. The pain relieving effect may be combined and significantly improved due to different applied energies and different approaches of relieving the pain. The pain relief is drug-free and may last up to several hours after the treatment. The pain relieving may be applied for treatment of chronic and/or acute pain. Alternatively, the pain relieving effect caused by magnetic and/or optical treatment may be used for improving acceptability of optical treatment provided by high power density optical radiation, e.g. high power laser or IPL.

Still another application of magnetic and optical treatment may be used for causing relaxing effect. High efficient relaxation may be caused by combined influence optical and magnetic treatment on the biological structure.

Still another application of magnetic and optical treatment may be used for treating the adipose cells. The adipose cells may be heated by the optical treatment above 37.5° C., more preferably above 40° C., most preferably in the range of 40 and 50° C., or up to 60° C. The temperature increase may induce apoptosis and/or necrosis of the adipose cells. The apoptosis of the adipose cells may be preferred effect due to reduced risk of inflammation and/or panniculitis occurrence. The temperature increase may also liquefy the adipose tissue. The magnetic treatment may contribute the optical treatment by inducing the at least partial muscle contraction which may improve the local blood and/or lymph circulation and/or local metabolism. Hence the death adipose cells may be removed faster from the human body. The apoptosis of the adipose cells may be also contributed by the influence of the magnetic treatment to metabolism of Ca ions as was described before. The optical waves may be in visible or in IR spectrum such as near-IR spectrum, e.g. in the range of 600 to 1500 nm in a plurality of applicable bands e.g. in the range of 635 to 680 nm, particularly 658 nm; or in the range of 780 to 980 nm, particularly 800 nm or 940 nm; or in the range of 1050 to 1100 nm, particularly 1060 nm due to relatively high penetration through the skin. Alternatively the optical waves may be in the range of 1300 to 1450 nm, particularly 1320 and 1440 nm may be applicable.

The optical treatment may last up to 120 minutes, preferably in the range of 1 to 60 minutes, more preferably in the range of 20 to 40 minutes. The treatment time may be dependent on BMI of the patient. The power flux density of the optical treatment may be up to 50 W/cm$^2$, preferably up to 25 W/cm2, more preferably in the range of 1 to 15 W/cm$^2$, most preferably in the range of 2 to 10 W/cm$^2$ such as at least 5 W/cm$^2$. In the preferred application power modulation may be used.

Still another application of magnetic and optical treatment may be used for treating the cellulite. As was mentioned above the adipose cells may be influenced by apoptosis and/or necrosis. Alternatively the adipose cells may be liquefied. The adipose cells metabolism may be contributed by the at least partial muscle contraction. Furthermore the application of optical treatment may heat the fibrous septae of the cellulite. The heated septae may be straightened by the at least partial muscle contraction caused by the magnetic treatment. Further the at least partial muscle contraction may remove the water from the cellulite tissue to reduce the cellulite. Therefore more significant results may be achieved in shorter time periods. The above mentioned methods may be combined hence the enhanced effect may be induced. Hence the results may be achieved in shorted time period and may be more significant.

Still another application of magnetic and optical treatment may be used for enhancing body shape and/or improving muscle tonus to enhance visual appearance of the body part. According to one application, the muscle may be treated by the optical treatment to increase the temperature of the muscle. Afterwards the heated muscle may be treated by magnetic treatment. The magnetic treatment may achieve more significant results due to increased temperature of the muscle. The muscle may be toned and/or strengthened more effectively. The toned and/or strengthened muscle may induce body shaping effect to enhance visual appearance of the treated body part. Moreover the results may be achieved without hours spent by exercising of the muscle which may achieve unpredictable results within different body parts. The effectiveness of the magnetic treatment may be enhanced by preheating of the muscle by optical treatment. Magnetic treatment may be provided at repetition rate of at least 0.1 Hz, more preferably at least 5 Hz, even more preferably at least 20 Hz, most preferably at least 50 Hz, or up to 700 Hz. The magnetic treatment may be preferably modulated.

Still another application of magnetic and optical treatment may be used for focused treating of specific muscle structures, e.g. buttocks. The demand for enhancing visual appearance of the buttocks has rapidly increased during last few years. The combined treatment may enhance the visual appearance of the buttocks by thermal effect caused by optical treatment and/or by muscle exercising effect by focus magnetic treatment. The magnetic treatment may be selectively focus to enhancing the visual appearance of the buttocks by shredding and/or toning of the buttock muscles such as gluteus maximus, medius and/or minimus.

Alternatively, the combined focused treatment may be used for causing breast lifting effect by preheating effect of the Cooper's ligament and following magnetic treatment with increased effectiveness. The treatment may lift the breasts up.

Still another application of magnetic and optical treatment may be used for skin rejuvenation. The optical treatment may be applied to cause micro-damages within the skin to promote the increase production and/or regeneration of collagen fibers. It may induce the enhanced visual appearance of the skin which may look well-toned, smoother and/or firmer. The optical treatment may be contributed by magnetic treatment causing at least partial muscle contraction which may induce the increase local metabolism and/or blood circulation. Hence the sufficiency of nutrients may be delivered to the target biological structure to promote its regeneration and/or production process.

Still another application of magnetic and optical treatment may be used for treating the wrinkles. The optical treatment may remove the wrinkles by resurfacing of the skin. Different wavelength may promote the growth of collagen and/or elastin fibers to provide the skin younger, firmer and/or smoother appearance. The optical treatment may be contributed by magnetic treatment causing at least partial muscle contraction which may induce the increase local metabolism and/or blood circulation. Hence the sufficiency of nutrients may be delivered to the target biological structure to promote its regeneration and/or production process.

The optical treatment may provide to the target biological structure the optical waves of wavelength in the range of 500 to 3000 nm, several wavelengths may be applicable for the treatment of wrinkles e.g. 590, 640, 695, 800, 1320 or 2940 nm. Alternatively other wavelengths may be also used. The energy delivered to the target biological structure may be up to 50 J/cm$^2$, more preferably up to 25 J/cm$^2$, most preferably in the range of 1 to 15 J/cm$^2$.

Still another application of magnetic and optical treatment may be used for treating the scars and/or stretchmarks. The optical treatment may enhance the visual appearance of scars and/or stretchmarks by providing improved the growth of collagen and/or elastin fibers to provide the skin younger, firmer and/or smoother appearance. The optical treatment may induce micro-damages to collagen and/or elastin fibers to promote their regeneration and/or production. The optical treatment may be contributed by magnetic treatment causing at least partial muscle contraction which may induce the increase local metabolism and/or blood circulation. Hence the sufficiency of nutrients may be delivered to the target biological structure to promote its regeneration and/or production process. Furthermore the at least partial muscle contraction may straighten the newly produced collagen and/or elastin fibers by massaging effect.

Still another application of magnetic and optical treatment may be used for lip visual appearance enhancing effect. The optical treatment may improve the growth of collagen and/or elastin fibers to provide younger, fuller, firmer and/or smoother appearance. The optical treatment may be contributed by magnetic treatment causing at least partial muscle contraction which may induce the increase local metabolism and/or blood circulation. Hence the sufficiency of nutrients may be delivered to the target biological structure to promote its regeneration and/or production process.

The above mentioned methods may be combined hence the enhanced effect may be induced. Hence the results may be achieved in shorted time period and may be more significant.

Optical treatment may be applied before the magnetic treatment. The effect of the optical treatment may be stimulating, e.g. increasing the temperature of the target biological structure to prepare a target biological structure to be treated by magnetic treatment inducing at least partial muscle contraction. To enhance the efficiency of the treatment in some indications, it may be advantageous to preheat the tissue by infrared radiation prior to magnetic treatment or combined magnetic and optical treatment.

Alternatively the effect caused by optical treatment may increase the temperature of the target biological structure, e.g. adipose cell or fibrous septae. It may be contributed by magnetic treatment causing at least partial muscle contraction. The at least partial muscle contraction may provide a massage effect for biological structures within proximity of the target biological structure, improve the blood and/or lymph circulation to improve local metabolism. Additionally the at least partial muscle contraction may reduce the number and/or volume of the adipose cells by energy used for the at least partial muscle contraction itself. Moreover, homogenous temperature distribution may be provided due to improved blood flow. Alternatively the at least partial muscle contraction may provide massage effect for promoting movement of fibrous septae.

Simultaneous application of combined magnetic and optical treatment may reach more significant results than separate use of these treatments.

Simultaneous application of magnetic treatment and optical treatment may be administered in two modes: a first mode may generate the magnetic pulses while optical treatment is active or second mode may generate magnetic pulses while the optical treatment is not in an active stimulation period, i.e. the period of magnetic treatment and optical treatment alternates.

The simultaneous application of magnetic treatment and optical treatment to the target biological structure may increase the peak magnetic component of the entire treatment resulting in improved heating of the target biological structure containing higher water volume, e.g. skin. Alternatively, the level of polarization of the optical radiation may be increased due to magnetic field, or a plane of polarization may rotate, e.g. Faraday's effect may occur. Due to increased temperature of skin, the production and/or remodeling of collagen and/or elastin fibers may be improved and the skin may be provided with a younger, smoother and enhanced appearance. The effect of overheating the muscle is reduced by the improved blood flow.

Optical treatment may also be used to attenuate the pain. Alternatively the repetition rate of the magnetic treatment may attenuate pain as well.

Optical treatment may be applied after the magnetic treatment to provide contributing effect such as analgesic effect or it may further improve local metabolism. The magnetic treatment may induce at least partial muscle contraction or to stimulate a muscle structure to increase a muscular tonus of the target biological structure. Both effects may provide a massage effect for biological structures within the proximity of the target biological structure hence the blood and/or lymph circulation may be improved to promote local metabolism. The temperature may be locally increased by the improved blood flow and the target biological structure may accept the following optical treatment at significantly higher efficiency. Hence the muscle may be heated at higher quality. Additionally, the collagen and/or elastin fibers may be remodeled or restored and/or its neogenesis may be improved to provide a younger, smoother and enhanced skin appearance.

Additionally, previous application of magnetic treatment may improve acceptability of the optical treatment. The magnetic treatment may provide pain relieving effect for the biological structure hence the thermic effect caused by the optical treatment may be more tolerable for the patient.

Another benefit may be releasing the adipose cells from the muscle by at least partial muscle contraction and/or by temperature increase causing improved metabolism of adipose cells. Still another benefit of the at least partial muscle contraction may be mechanic breaking large adipose cells bulks into smaller bulks which may be easier removed by the lymphatic and/or blood flow. The liquidity of the smaller adipose bulks may be contributed by application of optical treatment. Due to improved liquidity, improved metabolism and/or blood circulation the cellulite may be treated in a short time and the visual effect on skin appearance may be significantly enhanced.

Optical radiation may be also used to attenuate the pain after the magnetic treatment.

Combined treatments may be applied to one target biological structure to provide combined effect of magnetic and optical treatment. Alternatively the treatment may be applied to different target biological structures, e.g. optical treatment may be applied to at least adipose cell and magnetic treatment may be applied to at least one muscle fiber to improve local and/or adipose cell metabolism.

All applications of combined magnetic and optical treatment may amplify the resulting effect of the treatment. Therefore the results are achieved in significantly shorter time than the same results achieved by separate applications of the optical and magnet treatments. The treatment may be provided in various predefined treatment protocols focused on specific patient's needs, e.g. cellulite treatment, incontinence treatment, pain relieving etc. Each treatment parameter may be adjusted in the treatment protocol by the operator following the patient's needs. Alternatively the specific treatment may be designed by the operator for providing the most effective treatment following the patient's needs.

A treatment device including a high frequency generator, a low frequency generator, a combiner and an energy deliver element; wherein the at least one energy delivery element provides an electromagnetic treatment and a magnetic treatment for treating a biological structure.

A treatment device including a least one high frequency generator, at least one low frequency generator, a plurality of combiners and a plurality of energy deliver elements; wherein the plurality of energy delivery elements provides an electromagnetic treatment and a magnetic treatment for treating a biological structure.

A method of operating a treatment device comprising: generating a high frequency signal; and generating a low frequency signal; and delivering the high frequency signal and/or the low frequency signal to an energy delivering element; and providing by the least one energy delivery element an electromagnetic and/or a magnetic treatment.

Magnetic stimulation device producing time-varying magnetic field for treatment, wherein device comprises: a connection to an energy source, a switch, a coil, an energy storage device, at least one blower and a casing; wherein the coil and the casing are arranged in a manner that fluid can flow in-between and wherein the coil is cooled by fluid flow over at least upper and lower sides of the coil.

A method of patient's neural structure stimulation by time-varying magnetic field inducing an action potential and/or modulating the action potential, including: exposing the patient to a time-varying magnetic field with a repetition rate which exceeds a repetition rate resolution of the target stimulated biological structure and wherein the time-varying magnetic field generates an envelope including at least two pulses.

A method of operating a magnetic stimulation device including at least one applicator, at least one energy source, a plurality of switching devices, at least one energy storage device and a plurality of magnetic field generating devices, comprising: generating a plurality of peaks of magnitudes of magnetic flux density using a plurality of magnetic field generating devices.

A treatment method for enhancing a visual appearance of a patient's body region comprising: applying a time-varying magnetic field to a target biological structure in the body region to induce electric current in the target biological structure, wherein the body region is at least one of thighs, saddlebags, buttocks, abdomen, hips, torso, arms, breast, neck, face or lip of the patient.

Thus, novel systems and methods have been described. Various changes and substitutions may of course be made without departing from the spirit and scope of the invention. The invention, therefore, should not be limited, except by the following claims and their equivalents.

The following U.S. patent applications are incorporated herein by reference: Ser. Nos. 14/873,110; 14/926,365; 14/951,093; 15/073,318; 15/099,274; 15/151,012; 15/178, 455; 15/396,073; 15/446,951; 15/404,384 and 15/473,390.

Thus, novel apparatus and methods have been shown and described. Various changes and substitutions may of course be made without departing from the spirit and scope of the invention. The invention, therefore, should not be limited, except by the following claims and their equivalents.

What is claimed is:

1. A device for treating a patient comprising:
a high-frequency generator configured to generate a high-frequency signal for generating an electromagnetic field;
a low-frequency generator comprising a circuit configured to generate a low-frequency signal having a frequency in a range of 1 kHz to 100 kHz, for generating a time-varying magnetic field, the circuit comprising:
an energy storage device; and
a switching device;
a first energy delivery element connected to the circuit and configured to apply the time-varying magnetic field to the patient at a repetition rate in a range of 1 Hz to 300 Hz to cause a muscle contraction; and
a second energy delivery element connected to the high-frequency generator and configured to apply the electromagnetic field to the patient to heat a biological structure.

2. The device of claim 1, further comprising a first applicator and a second applicator, wherein the first applicator comprises the first energy delivery element, and wherein the second applicator comprises the second energy delivery element.

3. The device of claim 2, further comprising a belt, wherein the belt is configured to hold the first applicator in contact with the patient.

4. The device of claim 1, further comprising an applicator, wherein the applicator comprises the first energy delivery element and the second energy delivery element.

5. The device of claim 4, wherein the second energy delivery element comprises a coil.

6. The device of claim 4, wherein the second energy delivery element comprises a radiofrequency electrode.

7. The device of claim 6, wherein the applicator further comprises a filtering device, and wherein the filtering device comprises a capacitor.

8. The device of claim 6, wherein the applicator further comprises a filtering device, and wherein the filtering device comprises a coil.

9. A device for treating a patient comprising:
a first energy delivery element;
a second energy delivery element;
a high-frequency generator configured to generate a high-frequency signal for generating an electromagnetic field; and
a low-frequency generator comprising a circuit configured to generate a low-frequency signal for generating a time-varying magnetic field, the circuit comprising:
an energy storage device; and
a switching device,
wherein the first energy delivery element is configured to receive the high-frequency signal from the high-frequency generator and configured to provide the electromagnetic field for heating of the patient, and
wherein the second energy delivery element is configured to receive the low-frequency signal from the low-frequency generator and configured to provide the time-varying magnetic field to cause a muscle contraction.

10. The device of claim 9, wherein the first energy delivery element and the second energy delivery element are configured to provide the electromagnetic field and the time-varying magnetic field, respectively, within the same treatment session.

11. The device of claim 9, wherein the first energy delivery element comprises a radiofrequency electrode, and wherein the second energy delivery element comprises a magnetic coil.

12. The device of claim 11, wherein the magnetic coil is flat.

13. The device of claim 12, wherein the magnetic coil is configured to provide the time-varying magnetic field with a repetition rate in range of 1 Hz to 300 Hz and a magnetic flux density in a range of 0.1 T to 7 T on a surface of the magnetic coil.

14. The device of claim 11, wherein the device is configured to provide a first plurality of impulses having a first repetition rate and a second plurality of impulses having a second repetition rate, and wherein the first repetition rate is different than the second repetition.

15. The device of claim 11, wherein the device is configured to modulate an amplitude of magnetic flux density of impulses of the time-varying magnetic field such that a first plurality of impulses is modulated to trapezoidal shape.

16. A device for treating a patient comprising:
a high-frequency generator configured to generate a high-frequency signal for generating a radiofrequency field;
a low-frequency generator comprising a circuit configured to generate a low-frequency signal for generating a time-varying magnetic field, the circuit comprising:
an energy storage device; and
a switching device; and
a first applicator comprising:
a first energy delivery element; and
a second energy delivery element,
wherein the first energy delivery element is configured to receive the high-frequency signal from the high-frequency generator and configured to provide the radiofrequency field for heating of the patient, and
wherein the second energy delivery element is configured to receive the low-frequency signal from the low-frequency generator and configured to provide the time-varying magnetic field to cause a muscle contraction.

17. The device of claim 16, further comprising a belt configured to couple the first applicator to the patient.

18. The device of claim 17, wherein the first energy delivery element comprises a radiofrequency electrode.

19. The device of claim 18, wherein the second energy delivery element is a magnetic coil configured to provide a first plurality of impulses and a second plurality of impulses, wherein an amplitude of magnetic flux density of impulses of the first plurality of impulses is modulated to a rectangular shape, and wherein an amplitude of magnetic flux density of impulses of the second plurality of impulses is modulated to a rectangular shape.

20. The device of claim 17, wherein the second energy delivery element is a magnetic coil configured to provide a first plurality of impulses and a second plurality of impulses, wherein an amplitude of magnetic flux density of impulses of the first plurality of impulses is modulated to a trapezoidal shape, and wherein an amplitude of magnetic flux density of impulses of the second plurality of impulses is modulated to a trapezoidal shape.

21. The device of claim 17, further comprising a second applicator, the second applicator comprising a third energy delivery element configured to provide a radiofrequency field and a fourth energy delivery element configured to provide a time-varying magnetic field.

22. The device of claim 21, wherein one or both of the second applicator and the first applicator comprises a temperature sensor configured to measure a temperature of the patient.

23. The device of claim 21, wherein the device further comprises a human machine interface including an input configured for adjusting an amplitude of magnetic flux density during a treatment of the patient.

24. A device for treating a patient comprising:
a first energy delivery element;
a second energy delivery element;
a high-frequency generator configured to generate a high-frequency signal for generating a radiofrequency field; and
a low-frequency generator comprising a circuit configured to generate a low-frequency signal for generating a time-varying magnetic field, the circuit comprising:
an energy storage device; and
a switching device,
wherein the first energy delivery element is configured to receive the high-frequency signal from the high-frequency generator and configured to provide the radiofrequency field for heating of the patient, and
wherein the second energy delivery element is configured to receive the low-frequency signal from the low-frequency generator and configured to provide the time-varying magnetic field having a magnetic flux density in a range of 0.1 T to 7 T to cause a muscle contraction.

25. The device of claim 24, further comprising an applicator,
wherein the first energy delivery element and the second energy delivery element are disposed within the applicator,
wherein the first energy delivery element is a radiofrequency electrode,
wherein the second energy delivery element is a magnetic coil, and
wherein the radiofrequency electrode encircles the magnetic coil.

26. The device of claim 24, further comprising a first applicator, wherein the first energy delivery element comprises a first radiofrequency electrode located in the first applicator.

27. The device of claim 26, wherein the second energy delivery element is a magnetic coil configured to provide a first plurality of impulses having a first repetition rate and a second plurality of impulses having a second repetition rate, wherein an amplitude of magnetic flux density of impulses of the first plurality of impulses or the second plurality of impulses is modulated to a trapezoidal shape, and wherein the first repetition rate is different than the second repetition rate.

28. The device of claim 26, further comprising a second applicator, the second applicator comprising a magnetic coil and two radiofrequency electrodes.

29. The device of claim 26, wherein the first applicator is configured to be held in a position proximate the patient by an adjustable flexible belt.

30. The device of claim 26, wherein further comprising a spacing object configured to be placed between the patient and the first applicator.

* * * * *